US006680197B2

(12) United States Patent
Jiang et al.

(10) Patent No.: US 6,680,197 B2
(45) Date of Patent: Jan. 20, 2004

(54) COMPOSITIONS AND METHODS FOR THE THERAPY AND DIAGNOSIS OF BREAST CANCER

(75) Inventors: Yuqiu Jiang, Kent, WA (US); Davin C. Dillon, Issaquah, WA (US); Jennifer L. Mitcham, Redmond, WA (US); Jiangchun Xu, Bellevue, WA (US); Susan L. Harlocker, Seattle, WA (US); William T. Hepler, Seattle, WA (US); Robert A. Henderson, Edmonds, WA (US)

(73) Assignee: Corixa Corporation, Seattle, WA (US)

(*) Notice: Subject to any disclaimer, the term of this patent is extended or adjusted under 35 U.S.C. 154(b) by 121 days.

(21) Appl. No.: 09/834,759

(22) Filed: Apr. 13, 2001

(65) Prior Publication Data

US 2002/0085998 A1 Jul. 4, 2002

Related U.S. Application Data

(63) Continuation-in-part of application No. 09/620,405, filed on Jul. 20, 2000, now Pat. No. 6,528,054, which is a continuation-in-part of application No. 09/604,287, filed on Jun. 22, 2000, now Pat. No. 6,586,572, which is a continuation-in-part of application No. 09/590,751, filed on Jun. 8, 2000, which is a continuation-in-part of application No. 09/551, 621, filed on Apr. 17, 2000, which is a continuation-in-part of application No. 09/433,826, filed on Nov. 3, 1999, now Pat. No. 6,579,973, which is a continuation-in-part of application No. 09/389,681, filed on Sep. 2, 1999, now Pat. No. 6,518,237, which is a continuation-in-part of application No. 09/339,338, filed on Jun. 23, 1999, now Pat. No. 6,573,368, which is a continuation-in-part of application No. 09/285, 480, filed on Apr. 2, 1999, now Pat. No. 6,590,076, which is a continuation-in-part of application No. 09/222,575, filed on Dec. 28, 1998, now Pat. No. 6,387,697.

(51) Int. Cl.[7] .......................... C12N 5/08; C07H 21/04; C12Q 1/70

(52) U.S. Cl. .................. 435/325; 435/320.1; 536/24.3; 536/24.31; 536/24.33

(58) Field of Search .............................. 536/23.1, 24.3, 536/24.31, 24.33; 435/6, 320.1, 325

(56) References Cited

U.S. PATENT DOCUMENTS

| | | | |
|---|---|---|---|
| 5,215,926 | A | 6/1993 | Etchells, III et al. |
| 5,240,856 | A | 8/1993 | Goffe et al. |
| 5,668,267 | A | 9/1997 | Watson et al. |
| 5,855,889 | A | 1/1999 | Watson et al. |
| 5,891,857 | A | 4/1999 | Holt et al. |
| 5,922,836 | A | 7/1999 | Watson et al. |
| 5,968,754 | A | 10/1999 | Watson et al. |
| 5,986,170 | A | 11/1999 | Subjeck |
| 6,004,756 | A | 12/1999 | Watson et al. |

FOREIGN PATENT DOCUMENTS

| | | |
|---|---|---|
| WO | WO 89/06280 | 7/1989 |
| WO | WO 91/16116 | 10/1991 |
| WO | WO 92/07243 | 4/1992 |
| WO | WO 96/29430 | 9/1996 |
| WO | WO 98/21331 | 5/1998 |
| WO | WO 98/33915 | 8/1998 |
| WO | WO 98/54963 | 12/1998 |
| WO | WO 99/09155 | 2/1999 |
| WO | WO 00/08210 | 2/2000 |
| WO | WO 00/43420 | 7/2000 |
| WO | WO 00/60076 | 10/2000 |
| WO | WO 00/73801 | 12/2000 |
| WO | WO 01/37779 | 5/2001 |
| WO | WO 01/47959 | 7/2001 |

OTHER PUBLICATIONS

GenBank Accession No. AI687645, May 27, 1999.
GenBank Accession No. AQ280806, Nov. 22, 1998.
Genseq (Derwent) Accession No. AAV90219, Feb. 15, 1999.
GenBank Accession No. AF269087, Mar. 28, 2001.
GenBank Accession No. AAK27325, Mar. 28, 2001.
GenBank Accession No. AL157387, Feb. 18, 2000.
GenBank Accession No. AC036170, Apr. 9, 2000.
Jäger, D. et al, "Identification of a Tissue–specific Putative Transcription Factor in Breast Tissue by Serological Screening of a Breast Cancer Library," *Cancer Research 61*(5): 2055–2061, Mar. 1, 2001.
GenBank Accession No. AC069200, May 24, 2000.
Sulston et al., "Toward a complete human genome sequence," *Genome Research 8*(11):1097–1108, 1998.
Chang and Shu, "Current status of adoptive immunotherapy of cancer," *Critical Reviews in Oncology/Hematology 22*(3):213–228, Apr. 1996.
Cheever and Chen, "Therapy with cultured T cells: principles revisited," *Immunological Reviews, 157*: 177–194, 1997.
Cheever et al., "Potential uses of interleukin 2 in cancer therapy," *Immunobiol, 172*:365–382, 1986.
Chen et al., "T–cells for tumor therapy can be obtained from antigen–loaded sponge implants," *Cancer Research 54*(4): 1065–1070, Feb. 15, 1994.
Cole et al., "Characterization of the functional specificity of a cloned T–cell receptor heterodimer recognizing the MART–1 melanoma antigent," *Cancer Research, 55*:748–752, Feb. 15, 1995.
Durrant L., "Cancer vaccines," *Anti–Cancer Drugs, 8*:727–733, 1997.

(List continued on next page.)

*Primary Examiner*—Sean McGarry
*Assistant Examiner*—Janet L. Epps-Ford
(74) *Attorney, Agent, or Firm*—Seed IP Law Group PLLC

(57) ABSTRACT

Compositions and methods for the therapy and diagnosis of cancer, particularly breast cancer, are disclosed. Illustrative compositions comprise one or more breast tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly breast cancer.

6 Claims, 2 Drawing Sheets

OTHER PUBLICATIONS

Eshhar Z., "Tumor–specific T–bodies: toward clinical application," *Cancer Immunol Immnother, 45*:131–136, 1997.

GenBank Accession No. AA864891, Feb. 20, 1998.

GenBank Accession No. AA398925, Apr. 25, 1997.

Geneseq Accession No. V84525 (Dec. 10, 1998).

Hwu et al., "In vivo antitumor activity of T cells redirected with chimeric antibody/T–cell receptor genes," *Cancer Research, 55*:3369–3373, Aug. 1, 1995.

Porter–Jordan and Lippman, "Overview of the biologic markers of breast cancer," *Breast Cancer 8*:(1):73–100, Feb. 1994.

Prilliman et al., "HLA–B15 peptide ligands are preferentially anchored at their c termini," *The Journal of Immunology 162*(12):7277–7284, Jun. 15, 1999.

Stratagene 1991 product catalog, Prime–It™ Random Labeling Kit, catalog No. 300387, p. 66.

Wei et al., "Protection against mammary tumor growth by vaccination with full–length, modified human *ErbB–2* DNA," *Int. J. Cancer, 81*:748–754, 1999.

SYN18C6 Northern Blot

D207 B726P-specific CTL Clone 1-9Arecognize HTB 21 a breast tumor cell line that expresses HLA-B*1501 and B726P

COMPOSITIONS AND METHODS FOR THE THERAPY AND DIAGNOSIS OF BREAST CANCER

CROSS REFERENCE TO RELATED APPLICATIONS

This Application is a Continuation-In-Part of U.S. patent application Ser. No. 09/620,405, filed Jul. 20, 2000 now U.S. Pat. No. 6,528,054, which is a Continuation-In-Part of U.S. patent application Ser. No. 09/604,287, filed Jun. 22, 2000 now U.S. Pat. No. 6,586,572, which is a Continuation-In-Part of U.S. patent application Ser. No. 09/590,751, filed Jun. 8, 2000, which is a Continuation-In-Part Of U.S. patent application Ser. No. 09/551,621, filed Apr. 17, 2000, which is a Continuation-In-Part of U.S. patent application Ser. No. 09/433,826, filed on Nov. 3, 1999 now U.S. Pat. No. 6,579,973, which is a Continuation-In-Part of U.S. application Ser. No. 09/389,681, filed on Sep. 2, 1999 now U.S. Pat. No. 6,518,237, which is a Continuation-In-Part of U.S. application Ser. No. 09/339,338, filed on Jun. 23, 1999 now U.S. Pat. No. 6,573,368, which is a Continuation-In-Part of U.S. application Ser. No. 09/285,480, filed on Apr. 2, 1999 now U.S. Pat. No. 6,590,076, which is a Continuation-In-Part of U.S. application Ser. No. 09/222,575, filed Dec. 28, 1998 now U.S. Pat. No. 6,387,697.

TECHNICAL FIELD OF THE INVENTION

The present invention relates generally to therapy and diagnosis of cancer, such as breast cancer. The invention is more specifically related to polypeptides, comprising at least a portion of a breast tumor protein, and to polynucleotides encoding such polypeptides. Such polypeptides and polynucleotides are useful in pharmaceutical compositions, e.g., vaccines, and other compositions for the diagnosis and treatment of breast cancer.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

In one aspect, the present invention provides polynucleotide compositions comprising a sequence selected from the group consisting of:

(a) sequences provided in SEQ ID NO: 1–175, 178, 180, 182–468, 474, 476, 477 479, 484, 486, 489, 504–506, 510–513 and 520–533;

(b) complements of the sequences provided in SEQ ID NO: 1–175, 178, 180, 182–468, 474, 476, 477 479, 484, 486, 489, 504–506, 510–513 and 520–533;

(c) sequences consisting of at least 20 contiguous residues of a sequence provided in SEQ ID NO: 1–175, 178, 180, 182–468, 474, 476, 477 479, 484, 486, 489, 504–506, 510–513 and 520–533;

(d) sequences that hybridize to a sequence provided in SEQ ID NO: 1–175, 178, 180, 182–468, 474, 476, 477 479, 484, 486, 489, 504–506, 510–513 and 520–533, under moderately stringent conditions;

(e) sequences having at least 75% identity to a sequence of SEQ ID NO: 1–175, 178, 180, 182–468, 474, 476, 477 479, 484, 486, 489, 504–506, 510–513 and 520–533;

(f) sequences having at least 90% identity to a sequence of SEQ ID NO: 1–175, 178, 180, 182–468, 474, 476, 477 479, 484, 486, 489, 504–506, 510–513 and 520–533; and (g) degenerate variants of a sequence provided in SEQ ID NO: 1–175, 178, 180, 182–468, 474, 476, 477 479, 484, 486, 489, 504–506, 510–513 and 520–533.

In one preferred embodiment, the polynucleotide compositions of the invention are expressed in at least about 20%, more preferably in at least about 30%, and most preferably in at least about 50% of breast tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NO: 176, 179, 181, 469–473, 475, 485, 487, 488, 507–509, 514–519 and 534–547.

In certain preferred embodiments, the polypeptides and/or polynucleotides of the present invention are immunogenic, i. e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NOs: 176, 179, 181, 469–473, 475, 485, 487, 488, 507–509, 514–519 and 534–547 or a polypeptide sequence encoded by a polynucleotide sequence set forth in SEQ ID NOs: 1–175, 178, 180, 182–468, 474, 476, 477 479, 484, 486, 489, 504–506, 510–513 and 520–533.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

The present invention further provides, in other aspects, fusion proteins that comprise at least one polypeptide as described above, as well as polynucleotides encoding such fusion proteins. Exemplary fusion proteins according to the present invention comprise a first amino acid portion and a second amino acid portion wherein the first amino acid portion includes 9 or more contiguous amino acids from mammaglobin as depicted by amino acids 1–93 of SEQ ID NO: 493 (SEQ ID NO: 503); wherein the second amino acid portion includes 9 or more contiguous amino acids from B726P as depicted by SEQ ID NO: 475, SEQ ID NO: 469, or SEQ ID NO: 176; and wherein the first amino acid portion is connected to either the amino terminal or carboxy-terminal end of the second amino acid portion.

Still further embodiments of the present invention provide fusion proteins wherein said first amino acid portion is selected from the group consisting of: IDELKECFLNQTDETLSNVE (SEQ ID NO: 496; amino acids 59–78 of SEQ ID NO: 493); TTNAIDELKECFLNQ (SEQ ID NO: 497; amino acids 55–69 of SEQ ID NO: 493); SQHCYAGSGCPLLENVISKTI (SEQ ID NO: 498; amino acids 13–33 of SEQ ID NO: 493); EYKELLQEFIDDNATTNAID (SEQ ID NO: 499; amino acids 41–60 of SEQ ID NO: 493); KLLMVLMLA (SEQ ID NO: 500; amino acids 2–10 of SEQ ID NO: 493); QEFIDDNATTNAI (SEQ ID NO: 501; amino acids 47–59 of SEQ ID NO: 493); and LKECFLNQTDETL (SEQ ID NO: 502; amino acids 62–74 of SEQ ID NO: 493).

Alternative embodiments provide fusion proteins wherein the second amino acid portion includes 9 or more contiguous amino acids encoded by (1) the combined upstream and downstream open reading frame (ORF) of B726P as depicted in SEQ ID NO: 475; (2) the upstream ORF of B726P as depicted in SEQ ID NO: 469; and (3) the downstream ORF of B726P as depicted in SEQ ID NO: 176. Fusion proteins according to the present invention may also comprise a second amino acid portion that includes 9 or more contiguous amino acids from the amino acid sequence depicted by amino acids 1–129 of SEQ ID NO: 475. Still additional exemplary fusion proteins are depicted herein by SEQ ID NO: 493, SEQ ID NO: 494, and SEQ ID NO: 495.

Fusion proteins are provided wherein the mammaglobin amino acid portion is connected to the amino-terminus of the B726P amino acid portion while other fusion proteins are provided wherein the mammaglobin amino acid portion is connected to the carboxy-terminus of the B726P amino acid portion. The connection between the mammaglobin amino acid portion and the B726P portion may be a covalent bond. Additionally, a stretch of amino acids either unrelated or related to either mammaglobin and/or B726P may be incorporated between or either amino- or carboxy-terminal to either the mammaglobin and/or B726P amino acid portion.

The present invention also provides isolated polynucleotides that encode any of the fusion proteins that are specifically disclosed herein as well as those fusion proteins that may be accomplished with routine experimentation by the ordinarily skilled artisan.

Within further aspects, the present invention provides methods for stimulating an immune response in a patient, preferably a T cell response in a human patient, comprising administering a pharmaceutical composition described herein. The patient may be afflicted with breast cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with breast cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably a breast cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

Figure 1:
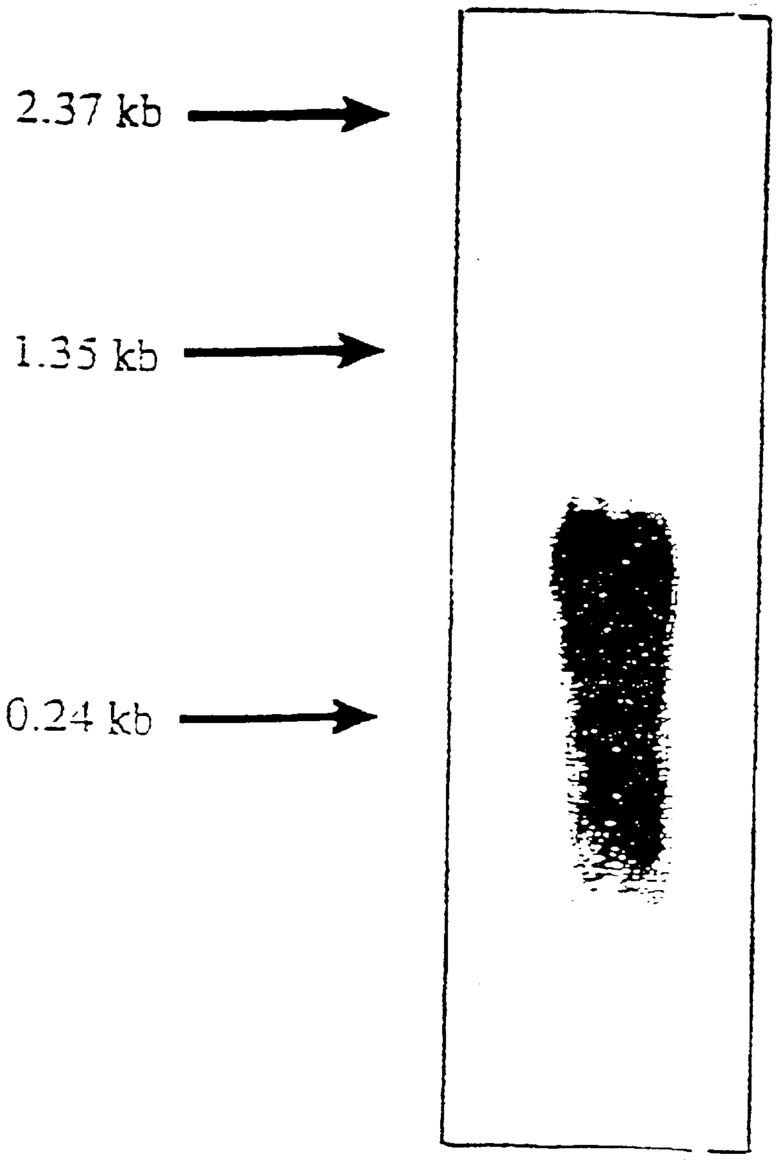
FIG. 1 shows the results of a Northern blot of the clone SYN18C6 (SEQ ID NO: 40).

SEQ ID NO: 1 is the determined cDNA sequence of JBT2.

SEQ ID NO: 2 is the determined cDNA sequence of JBT6.

SEQ ID NO: 3 is the determined cDNA sequence of JBT7.

SEQ ID NO: 4 is the determined cDNA sequence of JBT10.

SEQ ID NO: 5 is the determined cDNA sequence of JBT13.

SEQ ID NO: 6 is the determined cDNA sequence of JBT14.

SEQ ID NO: 7 is the determined cDNA sequence of JBT15.

SEQ ID NO: 8 is the determined cDNA sequence of JBT16.

SEQ ID NO: 9 is the determined cDNA sequence of JBT17.

SEQ ID NO: 10 is the determined cDNA sequence of JBT22.

SEQ ID NO: 11 is the determined cDNA sequence of JBT25.

SEQ ID NO: 12 is the determined cDNA sequence of JBT28.

SEQ ID NO: 13 is the determined cDNA sequence of JBT32.

SEQ ID NO: 14 is the determined cDNA sequence of JBT33.

SEQ ID NO: 15 is the determined cDNA sequence of JBT34.

SEQ ID NO: 16 is the determined cDNA sequence of JBT36.

SEQ ID NO: 17 is the determined cDNA sequence of JBT37.

SEQ ID NO: 18 is the determined cDNA sequence of JBT51.

SEQ ID NO: 19 is the determined cDNA sequence of JBTT1.

SEQ ID NO: 20 is the determined cDNA sequence of JBTT7.

SEQ ID NO: 21 is the determined cDNA sequence of JBTT11.

SEQ ID NO: 22 is the determined cDNA sequence of JBTT14.

SEQ ID NO: 23 is the determined cDNA sequence of JBTT18.

SEQ ID NO: 24 is the determined cDNA sequence of JBTT19.

SEQ ID NO: 25 is the determined cDNA sequence of JBTT20.

SEQ ID NO: 26 is the determined cDNA sequence of JBTT21.

SEQ ID NO: 27 is the determined cDNA sequence of JBTT22.

SEQ ID NO: 28 is the determined cDNA sequence of JBTT28.

SEQ ID NO: 29 is the determined cDNA sequence of JBTT29.

SEQ ID NO: 30 is the determined cDNA sequence of JBTT33.

SEQ ID NO: 31 is the determined cDNA sequence of JBTT37.

SEQ ID NO: 32 is the determined cDNA sequence of JBTT38.

SEQ ID NO: 33 is the determined cDNA sequence of JBTT47.

SEQ ID NO: 34 is the determined cDNA sequence of JBTT48.

SEQ ID NO: 35 is the determined cDNA sequence of JBTT50.

SEQ ID NO: 36 is the determined cDNA sequence of JBTT51.

SEQ ID NO: 37 is the determined cDNA sequence of JBTT52.

SEQ ID NO: 38 is the determined cDNA sequence of JBTT54.

SEQ ID NO: 39 is the determined cDNA sequence of SYN17F4.

SEQ ID NO: 40 is the determined cDNA sequence of SYN18C6 (also known as B709P).

SEQ ID NO: 41 is the determined cDNA sequence of SYN19A2.

SEQ ID NO: 42 is the determined cDNA sequence of SYN19C8.

SEQ ID NO: 43 is the determined cDNA sequence of SYN20A12.

SEQ ID NO: 44 is the determined cDNA sequence of SYN20G6.

SEQ ID NO: 45 is the determined cDNA sequence of SYN20G6-2.

SEQ ID NO: 46 is the determined cDNA sequence of SYN21B9.

SEQ ID NO: 47 is the determined cDNA sequence of SYN21B9-2.

SEQ ID NO: 48 is the determined cDNA sequence of SYN21C10.

SEQ ID NO: 49 is the determined cDNA sequence of SYN21G10.

SEQ ID NO: 50 is the determined cDNA sequence of SYN21G10-2.

SEQ ID NO: 51 is the determined cDNA sequence of SYN21G11.

SEQ ID NO: 52 is the determined cDNA sequence of SYN21G11-2.

SEQ ID NO: 53 is the determined cDNA sequence of SYN21H8.

SEQ ID NO: 54 is the determined cDNA sequence of SYN22A10.

SEQ ID NO: 55 is the determined cDNA sequence of SYN22A10-2.

SEQ ID NO: 56 is the determined cDNA sequence of SYN22A12.

SEQ ID NO: 57 is the determined cDNA sequence of SYN22A2 (also referred to as B718P).

SEQ ID NO: 58 is the determined cDNA sequence of SYN22B4.

SEQ ID NO: 59 is the determined cDNA sequence of SYN22C2.

SEQ ID NO: 60 is the determined cDNA sequence of SYN22E10.

SEQ ID NO: 61 is the determined cDNA sequence of SYN22F2.

SEQ ID NO: 62 is a predicted amino acid sequence for SYN18C6 (also known as B709P).

SEQ ID NO: 63 is the determined cDNA sequence of B723P.

SEQ ID NO: 64 is the determined cDNA sequence for B724P.

SEQ ID NO: 65 is the determined cDNA sequence of B770P.

SEQ ID NO: 66 is the determined cDNA sequence of B716P.

SEQ ID NO: 67 is the determined cDNA sequence of B725P.

SEQ ID NO: 68 is the determined cDNA sequence of B717P.

SEQ ID NO: 69 is the determined cDNA sequence of B771P.

SEQ ID NO: 70 is the determined cDNA sequence of B722P.

SEQ ID NO: 71 is the determined cDNA sequence of B726P.

SEQ ID NO: 72 is the determined cDNA sequence of B727P.

SEQ ID NO: 73 is the determined cDNA sequence of B728P.

SEQ ID NO: 74–87 are the determined cDNA sequences of isolated clones which show homology to known sequences.

SEQ ID NO: 88 is the determined cDNA sequence of 13053.

SEQ ID NO: 89 is the determined cDNA sequence of 13057.

SEQ ID NO: 90 is the determined cDNA sequence of 13059.

SEQ ID NO: 91 is the determined cDNA sequence of 13065.

SEQ ID NO: 92 is the determined cDNA sequence of 13067.

SEQ ID NO: 93 is the determined cDNA sequence of 13068.

SEQ ID NO: 94 is the determined cDNA sequence of 13071.

SEQ ID NO: 95 is the determined cDNA sequence of 13072.

SEQ ID NO: 96 is the determined cDNA sequence of 13073.

SEQ ID NO: 97 is the determined cDNA sequence of 13075.

SEQ ID NO: 98 is the determined cDNA sequence of 13078.

SEQ ID NO: 99 is the determined cDNA sequence of 13079.

SEQ ID NO: 100 is the determined cDNA sequence of 13081.

SEQ ID NO: 101 is the determined cDNA sequence of 13082.

SEQ ID NO: 102 is the determined cDNA sequence of 13092.

SEQ ID NO: 103 is the determined cDNA sequence of 13097.

SEQ ID NO: 104 is the determined cDNA sequence of 13101.

SEQ ID NO: 105 is the determined cDNA sequence of 13102.

SEQ ID NO: 106 is the determined cDNA sequence of 13119.

SEQ ID NO: 107 is the determined cDNA sequence of 13131.

SEQ ID NO: 108 is the determined cDNA sequence of 13133.

SEQ ID NO: 109 is the determined cDNA sequence of 13135.

SEQ ID NO: 110 is the determined cDNA sequence of 13139.

SEQ ID NO: 111 is the determined cDNA sequence of 13140.

SEQ ID NO: 112 is the determined cDNA sequence of 13146.

SEQ ID NO: 113 is the determined cDNA sequence of 13147.

SEQ ID NO: 114 is the determined cDNA sequence of 13148.

SEQ ID NO: 115 is the determined cDNA sequence of 13149.

SEQ ID NO: 116 is the determined cDNA sequence of 13151.

SEQ ID NO: 117 is the determined cDNA sequence of 13051

SEQ ID NO: 118 is the determined cDNA sequence of 13052

SEQ ID NO: 119 is the determined cDNA sequence of 13055

SEQ ID NO: 120 is the determined cDNA sequence of 13058

SEQ ID NO: 121 is the determined cDNA sequence of 13062

SEQ ID NO: 122 is the determined cDNA sequence of 13064

SEQ ID NO: 123 is the determined cDNA sequence of 13080

SEQ ID NO: 124 is the determined cDNA sequence of 13093

SEQ ID NO: 125 is the determined cDNA sequence of 13094

SEQ ID NO: 126 is the determined cDNA sequence of 13095

SEQ ID NO: 127 is the determined cDNA sequence of 13096

SEQ ID NO: 128 is the determined cDNA sequence of 13099

SEQ ID NO: 129 is the determined cDNA sequence of 13100

SEQ ID NO: 130 is the determined cDNA sequence of 13103

SEQ ID NO: 131 is the determined cDNA sequence of 13106

SEQ ID NO: 132 is the determined cDNA sequence of 13107

SEQ ID NO: 133 is the determined cDNA sequence of 13108

SEQ ID NO: 134 is the determined cDNA sequence of 13121

SEQ ID NO: 135 is the determined cDNA sequence of 13126

SEQ ID NO: 136 is the determined cDNA sequence of 13129

SEQ ID NO: 137 is the determined cDNA sequence of 13130

SEQ ID NO: 138 is the determined cDNA sequence of 13134

SEQ ID NO: 139 is the determined cDNA sequence of 13141

SEQ ID NO: 140 is the determined cDNA sequence of 13142

SEQ ID NO: 141 is the determined cDNA sequence of 14376

SEQ ID NO: 142 is the determined cDNA sequence of 14377

SEQ ID NO: 143 is the determined cDNA sequence of 14383

SEQ ID NO: 144 is the determined cDNA sequence of 14384

SEQ ID NO: 145 is the determined cDNA sequence of 14387

SEQ ID NO: 146 is the determined cDNA sequence of 14392

SEQ ID NO: 147 is the determined cDNA sequence of 14394

SEQ ID NO: 148 is the determined cDNA sequence of 14398

SEQ ID NO: 149 is the determined cDNA sequence of 14401

SEQ ID NO: 150 is the determined cDNA sequence of 14402

SEQ ID NO: 151 is the determined cDNA sequence of 14405

SEQ ID NO: 152 is the determined cDNA sequence of 14409

SEQ ID NO: 153 is the determined cDNA sequence of 14412

SEQ ID NO: 154 is the determined cDNA sequence of 14414

SEQ ID NO: 155 is the determined cDNA sequence of 14415

SEQ ID NO: 156 is the determined cDNA sequence of 14416

SEQ ID NO: 157 is the determined cDNA sequence of 14419

SEQ ID NO: 158 is the determined cDNA sequence of 14426

SEQ ID NO: 159 is the determined cDNA sequence of 14427

SEQ ID NO: 160 is the determined cDNA sequence of 14375

SEQ ID NO: 161 is the determined cDNA sequence of 14378

SEQ ID NO: 162 is the determined cDNA sequence of 14379

SEQ ID NO: 163 is the determined cDNA sequence of 14380

SEQ ID NO: 164 is the determined cDNA sequence of 14381

SEQ ID NO: 165 is the determined cDNA sequence of 14382

SEQ ID NO: 166 is the determined cDNA sequence of 14388

SEQ ID NO: 167 is the determined cDNA sequence of 14399

SEQ ID NO: 168 is the determined cDNA sequence of 14406

SEQ ID NO: 169 is the determined cDNA sequence of 14407

SEQ ID NO: 170 is the determined EDNA sequence of 14408

SEQ ID NO: 171 is the determined cDNA sequence of 14417

SEQ ID NO: 172 is the determined cDNA sequence of 14418

SEQ ID NO: 173 is the determined cDNA sequence of 14423

SEQ ID NO: 174 is the determined cDNA sequence of 14424

SEQ ID NO: 175 is the determined cDNA sequence of B726P-20

SEQ ID NO: 176 is the predicted amino acid sequence of B726P-20 (also referred to as B726P downstream ORF)

SEQ ID NO: 177 is a PCR primer

SEQ ID NO: 178 is the determined cDNA sequence of B726P-74

SEQ ID NO: 179 is the predicted amino acid sequence of B726P-74

SEQ ID NO: 180 is the determined cDNA sequence of B726P-79

SEQ ID NO: 181 is the predicted amino acid sequence of B726P-79

SEQ ID NO: 182 is the determined cDNA sequence of 19439.1, showing homology to the mammaglobin gene SEQ ID NO: 183 is the determined cDNA sequence of 19407.1, showing homology to the human keratin gene SEQ ID NO: 184 is the determined cDNA sequence of 19428.1, showing homology to human chromosome 17 clone SEQ ID NO: 185 is the determined cDNA sequence of B808P (19408), showing no significant homology to any known gene SEQ ID NO: 186 is the determined cDNA sequence of 19460.1, showing no significant homology to any known gene SEQ ID NO: 187 is the determined cDNA sequence of 19419.1, showing homology to Ig kappa light chain SEQ ID NO: 188 is the determined cDNA sequence of 19411.1, showing homology to human alpha-1 collagen SEQ ID NO: 189 is the determined cDNA sequence of 19420.1, showing homology to mus musculus proteinase-3

SEQ ID NO: 190 is the determined cDNA sequence of 19432.1, showing homology to human high motility group box SEQ ID NO: 191 is the determined cDNA sequence of 19412.1, showing homology to the human plasminogen activator gene SEQ ID NO: 192 is the determined cDNA sequence of 19415.1, showing homology to mitogen activated protein kinase SEQ ID NO: 193 is the determined cDNA sequence of 19409.1, showing homology to the chondroitin sulfate proteoglycan protein SEQ ID NO: 194 is the determined cDNA sequence of 19406.1, showing no significant homology to any known gene SEQ ID NO: 195 is the determined cDNA sequence of 19421.1, showing homology to human fibronectin SEQ ID NO: 196 is the determined cDNA sequence of 19426.1, showing homology to the retinoic acid receptor responder 3

SEQ ID NO: 197 is the determined cDNA sequence of 19425.1, showing homology to MyD88 mRNA SEQ ID NO: 198 is the determined cDNA sequence of 19424.1, showing homology to peptide transporter (TAP-1) mRNA SEQ ID NO: 199 is the determined cDNA sequence of 19429.1, showing no significant homology to any known gene SEQ ID NO: 200 is the determined cDNA sequence of 19435.1, showing homology to human polymorphic epithelial mucin SEQ ID NO: 201 is the determined cDNA sequence of B813P (19434.1), showing homology to human GATA-3 transcription factor SEQ ID NO: 202 is the determined cDNA sequence of 19461.1, showing homology to the human AP-2 gene SEQ ID NO: 203 is the determined cDNA sequence of 19450.1, showing homology to DNA binding regulatory factor SEQ ID NO: 204 is the determined cDNA sequence of 19451.1, showing homology to Na/H exchange regulatory co-factor SEQ ID NO: 205 is the determined cDNA sequence of 19462.1, showing no significant homology to any known gene SEQ ID NO: 206 is the determined cDNA sequence of 19455.1, showing homology to human mRNA for histone HAS.Z SEQ ID NO: 207 is the determined cDNA sequence of 19459.1, showing homology to PAC clone 179N16

SEQ ID NO: 208 is the determined cDNA sequence of 19464.1, showing no significant homology to any known gene SEQ ID NO: 209 is the determined cDNA sequence of 19414.1, showing homology to lipophilin B SEQ ID NO: 210 is the determined cDNA sequence of 19413.1, showing homology to chromosome 17 clone hRPK.209_J_20

SEQ ID NO: 211 is the determined cDNA sequence of 19416.1, showing no significant homology to any known gene SEQ ID NO: 212 is the determined cDNA sequence of 19437.1, showing homology to human clone 24976 mRNA SEQ ID NO: 213 is the determined cDNA sequence of 19449.1, showing homology to mouse DNA for PG-M core protein SEQ ID NO: 214 is the determined cDNA sequence of 19446.1, showing no significant homology to any known gene SEQ ID NO: 215 is the determined cDNA sequence of 19452.1, showing no significant homology to any known gene SEQ ID NO: 216 is the determined cDNA sequence of 19483.1, showing no significant homology to any known gene SEQ ID NO: 217 is the determined cDNA sequence of 19526.1, showing homology to human lipophilin C SEQ ID NO: 218 is the determined cDNA sequence of 19484.1, showing homology to the secreted cement gland protein XAG-2

SEQ ID NO: 219 is the determined cDNA sequence of 19470.1, showing no significant homology to any known gene SEQ ID NO: 220 is the determined cDNA sequence of 19469.1, showing homology to the human HLA-DM gene SEQ ID NO: 221 is the determined cDNA sequence of 19482.1, showing homology to the human pS2 protein gene SEQ ID NO: 222 is the determined cDNA sequence of B805P (19468.1), showing no significant homology to any known gene SEQ ID NO: 223 is the determined cDNA sequence of 19467.1, showing homology to human thrombospondin mRNA SEQ ID NO: 224 is the determined cDNA sequence of 19498.1, showing homology to the CDC2 gene involved in cell cycle control SEQ ID NO: 225 is the determined cDNA sequence of 19506.1, showing homology to human cDNA for TREB protein SEQ ID NO: 226 is the determined cDNA sequence of B806P (19505.1), showing no significant homology to any known gene SEQ ID NO: 227 is the determined cDNA sequence of 19486.1, showing homology to type I epidermal keratin SEQ ID NO: 228 is the determined cDNA sequence of 19510.1, showing homology to glucose transporter for glycoprotein SEQ ID NO: 229 is the determined cDNA sequence of 19512.1, showing homology to the human lysyl hydroxylase gene SEQ ID NO: 230 is the determined cDNA sequence of 19511.1, showing homology to human palimotoyl-protein thioesterase SEQ ID NO: 231 is the determined cDNA sequence of 19508.1, showing homology to human alpha enolase SEQ ID NO: 232 is the determined cDNA sequence of B807P (19509.1), showing no significant homology to any known gene SEQ ID NO: 233 is the determined cDNA sequence of B809P (19520.1), showing homology to clone 102D24 on chromosome 11q13.31

SEQ ID NO: 234 is the determined cDNA sequence of 19507.1, showing homology toprosome beta-subunit SEQ ID NO: 235 is the determined cDNA sequence of 19525.1, showing homology to human pro-urokinase precursor SEQ ID NO: 236 is the determined cDNA sequence of 19513.1, showing no significant homology to any known gene SEQ ID NO: 237 is the determined cDNA sequence of 19517.1, showing homology to human PAC 128M19 clone SEQ ID NO: 238 is the determined cDNA sequence of 19564.1, showing homology to human cytochrome P450-IIB SEQ ID NO: 239 is the determined cDNA sequence of 19553.1, showing homology to human GABA-A receptor pi subunit SEQ ID NO: 240 is the determined cDNA sequence of B811P (19575.1), showing no significant homology to any known gene SEQ ID NO: 241 is the determined cDNA sequence of B810P (19560.1), showing no significant homology to any known gene SEQ ID NO: 242 is the determined cDNA sequence of 19588.1, showing homology to aortic carboxypetidase-like protein SEQ ID NO: 243 is the determined cDNA sequence of 19551.1, showing homology to human BCL-1 gene SEQ ID NO: 244 is the determined cDNA sequence of 19567.1, showing homology to human proteasome-related mRNA SEQ ID NO: 245 is the determined cDNA sequence of B803P (19583.1), showing no significant homology to any known gene SEQ ID NO: 246 is the determined cDNA sequence of B812P (19587.1), showing no significant homology to any known gene SEQ ID NO: 247 is the determined cDNA sequence of B802P (19392.2), showing homology to human chromosome 17

SEQ ID NO: 248 is the determined cDNA sequence of 19393.2, showing homology to human nicein B2 chain SEQ ID NO: 249 is the determined cDNA sequence of 19398.2, human MHC class II DQ alpha mRNA SEQ ID NO: 250 is the determined cDNA sequence of B804P (19399.2), showing homology to human Xp22 BAC GSHB-184P14

SEQ ID NO: 251 is the determined cDNA sequence of 19401.2, showing homology to human ikB kinase-b gene SEQ ID NO: 252 is the determined cDNA sequence of 20266, showing no significant homology to any known gene SEQ ID NO: 253 is the determined cDNA sequence of B826P (20270), showing no significant homology to any known gene SEQ ID NO: 254 is the determined cDNA sequence of 20274, showing no significant homology to any known gene SEQ ID NO: 255 is the determined cDNA sequence of 20276, showing no significant homology to any known gene SEQ ID NO: 256 is the determined cDNA sequence of 20277, showing no significant homology to any known gene SEQ ID NO: 257 is the determined cDNA sequence of B823P (20280), showing no significant homology to any known gene SEQ ID NO: 258 is the determined cDNA sequence of B821P (20281), showing no significant homology to any known gene SEQ ID NO: 259 is the determined cDNA sequence of B824P (20294), showing no significant homology to any known gene SEQ ID NO: 260 is the determined cDNA sequence of 20303, showing no significant homology to any known gene SEQ ID NO: 261 is the determined cDNA sequence of B820P (20310), showing no significant homology to any known gene SEQ ID NO: 262 is the determined cDNA sequence of B825P (20336), showing no significant homology to any known gene SEQ ID NO: 263 is the determined cDNA sequence of B827P (20341), showing no significant homology to any known gene SEQ ID NO: 264 is the determined cDNA sequence of 20941, showing no significant homology to any known gene SEQ ID NO: 265 is the determined cDNA sequence of 20954, showing no significant homology to any known gene SEQ ID NO: 266 is the determined cDNA sequence of 20961, showing no significant homology to any known gene SEQ ID NO: 267 is the determined cDNA sequence of 20965, showing no significant homology to any known gene SEQ ID NO: 268 is the determined cDNA sequence of 20975, showing no significant homology to any known gene SEQ ID NO: 269 is the determined cDNA sequence of 20261, showing homology to Human p 120 catenin SEQ ID NO: 270 is the determined cDNA sequence of B822P (20262), showing homology to Human membrane glycoprotein 4F2

SEQ ID NO: 271 is the determined cDNA sequence of 20265, showing homology to Human Na, K-ATPase Alpha 1

SEQ ID NO: 272 is the determined cDNA sequence of 20267, showing homology to Human heart HS 90, partial cds SEQ ID NO: 273 is the determined cDNA sequence of 20268, showing homology to Human mRNA GPI-anchored protein p137

SEQ ID NO: 274 is the determined cDNA sequence of 20271, showing homology to Human cleavage stimulation factor 77 kDa subunit SEQ ID NO: 275 is the determined cDNA sequence of 20272, showing homology to Human p190-B SEQ ID NO: 276 is the determined cDNA sequence of 20273, showing homology to Human ribophorin SEQ ID NO: 277 is the determined cDNA sequence of 20278, showing homology to Human omithine amino transferase SEQ ID NO: 278 is the determined cDNA sequence of 20279, showing homology to Human S-adenosylmethionine synthetase SEQ ID NO: 279 is the determined cDNA sequence of 20293, showing homology to Human x inactivation transcript SEQ ID NO: 280 is the determined cDNA sequence of 20300, showing homology to Human cytochrome p450

SEQ ID NO: 281 is the determined cDNA sequence of 20305, showing homology to Human elongation factor-1 alpha SEQ ID NO: 282 is the determined cDNA sequence of 20306, showing homology to Human epithelial ets protein SEQ ID NO: 283 is the determined cDNA sequence of 20307, showing homology to Human signal transducer mRNA SEQ ID NO: 284 is the determined cDNA sequence of 20313, showing homology to Human GABA-A receptor pi subunit mRNA SEQ ID NO: 285 is the determined cDNA sequence of 20317, showing homology to Human tyrosine phosphatase SEQ ID NO: 286 is the determined cDNA sequence of 20318, showing homology to Human cathepsine B proteinase SEQ ID NO: 287 is the determined cDNA sequence of 20320, showing homology to Human 2-phosphopyruvate-hydratase-alpha-enolase SEQ ID NO: 288 is the determined cDNA sequence of 20321, showing homology to Human E-cadherin SEQ ID NO: 289 is the determined cDNA sequence of 20322, showing homology to Human hsp86

SEQ ID NO: 290 is the determined cDNA sequence of B828P (20326), showing homology to Human x inactivation transcript SEQ ID NO: 291 is the determined cDNA sequence of 20333, showing homology to Human chromatin regulator, SMARCA5

SEQ ID NO: 292 is the determined cDNA sequence of 20335, showing homology to Human sphingolipid activator protein 1

SEQ ID NO: 293 is the determined cDNA sequence of 20337, showing homology to Human hepatocyte growth factor activator inhibitor type 2

SEQ ID NO: 294 is the determined cDNA sequence of 20338, showing homology to Human cell adhesion molecule CD44

SEQ ID NO: 295 is the determined cDNA sequence of 20340, showing homology to Human nuclear factor (erythroid-derived)-like 1

SEQ ID NO: 296 is the determined cDNA sequence of 20938, showing homology to Human vinculin mRNA SEQ ID NO: 297 is the determined cDNA sequence of 20939, showing homology to Human elongation factor EF-1-alpha SEQ ID NO: 298 is the determined cDNA sequence of 20940, showing homology to Human nestin gene SEQ ID NO: 299 is the determined cDNA sequence of 20942, showing homology to Human pancreatic ribonuclease SEQ ID NO: 300 is the determined cDNA sequence of 20943, showing homology to Human transcobalamin I SEQ ID NO: 301 is the determined cDNA sequence of 20944, showing homology to Human beta-tubulin SEQ ID NO: 302 is the determined cDNA sequence of 20946, showing homology to Human HS 1 protein SEQ ID NO: 303 is the determined cDNA sequence of 20947, showing homology to Human cathepsin B SEQ ID NO: 304 is the determined cDNA sequence of 20948, showing homology to Human testis enhanced gene transcript SEQ ID NO: 305 is the determined cDNA sequence of 20949, showing homology to Human elongation factor EF-1-alpha SEQ ID NO: 306 is the determined cDNA sequence of 20950, showing homology to Human ADP-ribosylation factor 3

SEQ ID NO: 307 is the determined cDNA sequence of 20951, showing homology to Human IFP53 or WRS for tryptophanyl-tRNA synthetase SEQ ID NO: 308 is the determined cDNA sequence of 20952, showing homology to Human cyclin-dependent protein kinase SEQ ID NO: 309 is the determined cDNA sequence of 20957, showing homology to Human alpha-tubulin isoform 1

SEQ ID NO: 310 is the determined cDNA sequence of 20959, showing homology to Human tyrosine phosphatase-61 bp deletion SEQ ID NO: 311 is the determined cDNA sequence of 20966, showing homology to Human tyrosine phosphatase SEQ ID NO: 312 is the determined cDNA sequence of B830P (20976), showing homology to Human nuclear factor NF 45

SEQ ID NO: 313 is the determined cDNA sequence of B829P (20977), showing homology to Human delta-6 fatty acid desaturase SEQ ID NO: 314 is the determined cDNA sequence of 20978, showing homology to Human nuclear aconitase SEQ ID NO: 315 is the determined cDNA sequence of clone 23176.

SEQ ID NO: 316 is the determined cDNA sequence of clone 23140.

SEQ ID NO: 317 is the determined cDNA sequence of clone 23166.

SEQ ID NO: 318 is the determined cDNA sequence of clone 23167.

SEQ ID NO: 319 is the determined cDNA sequence of clone 23177.

SEQ ID NO: 320 is the determined cDNA sequence of clone 23217.

SEQ ID NO: 321 is the determined cDNA sequence of clone 23169.

SEQ ID NO: 322 is the determined cDNA sequence of clone 23160.

SEQ ID NO: 323 is the determined cDNA sequence of clone 23182.

SEQ ID NO: 324 is the determined cDNA sequence of clone 23232.

SEQ ID NO: 325 is the determined cDNA sequence of clone 23203.

SEQ ID NO: 326 is the determined cDNA sequence of clone 23198.

SEQ ID NO: 327 is the determined cDNA sequence of clone 23224.

SEQ ID NO: 328 is the determined cDNA sequence of clone 23142.

SEQ ID NO: 329 is the determined cDNA sequence of clone 23138.

SEQ ID NO: 330 is the determined cDNA sequence of clone 23147.

SEQ ID NO: 331 is the determined cDNA sequence of clone 23148.

SEQ ID NO: 332 is the determined cDNA sequence of clone 23149.

SEQ ID NO: 333 is the determined cDNA sequence of clone 23172.

SEQ ID NO: 334 is the determined cDNA sequence of clone 23158.

SEQ ID NO: 335 is the determined cDNA sequence of clone 23156.

SEQ ID NO: 336 is the determined cDNA sequence of clone 23221.

SEQ ID NO: 337 is the determined cDNA sequence of clone 23223.

SEQ ID NO: 338 is the determined cDNA sequence of clone 23155.

SEQ ID NO: 339 is the determined cDNA sequence of clone 23225.

SEQ ID NO: 340 is the determined cDNA sequence of clone 23226.

SEQ ID NO: 341 is the determined cDNA sequence of clone 23228.

SEQ ID NO: 342 is the determined cDNA sequence of clone 23229.

SEQ ID NO: 343 is the determined cDNA sequence of clone 23231.

SEQ ID NO: 344 is the determined cDNA sequence of clone 23154.

SEQ ID NO: 345 is the determined cDNA sequence of clone 23157.

SEQ ID NO: 346 is the determined cDNA sequence of clone 23153.

SEQ ID NO: 347 is the determined cDNA sequence of clone 23159.

SEQ ID NO: 348 is the determined cDNA sequence of clone 23152.

SEQ ID NO: 349 is the determined cDNA sequence of clone 23161.

SEQ ID NO: 350 is the determined cDNA sequence of clone 23162.

SEQ ID NO: 351 is the determined cDNA sequence of clone 23163.

SEQ ID NO: 352 is the determined cDNA sequence of clone 23164.

SEQ ID NO: 353 is the determined cDNA sequence of clone 23165.

SEQ ID NO: 354 is the determined cDNA sequence of clone 23151.

SEQ ID NO: 355 is the determined cDNA sequence of clone 23150.

SEQ ID NO: 356 is the determined cDNA sequence of clone 23168.

SEQ ID NO: 357 is the determined cDNA sequence of clone 23146.

SEQ ID NO: 358 is the determined cDNA sequence of clone 23170.

SEQ ID NO: 359 is the determined cDNA sequence of clone 23171.

SEQ ID NO: 360 is the determined cDNA sequence of clone 23145.

SEQ ID NO: 361 is the determined cDNA sequence of clone 23174.

SEQ ID NO: 362 is the determined cDNA sequence of clone 23175.

SEQ ID NO: 363 is the determined cDNA sequence of clone 23144.

SEQ ID NO: 364 is the determined cDNA sequence of clone 23178.

SEQ ID NO: 365 is the determined cDNA sequence of clone 23179.

SEQ ID NO: 366 is the determined cDNA sequence of clone 23180.

SEQ ID NO: 367 is the determined cDNA sequence of clone 23181.

SEQ ID NO: 368 is the determined cDNA sequence of clone 23143

SEQ ID NO: 369 is the determined cDNA sequence of clone 23183.

SEQ ID NO: 370 is the determined cDNA sequence of clone 23184.

SEQ ID NO: 371 is the determined cDNA sequence of clone 23185.

SEQ ID NO: 372 is the determined cDNA sequence of clone 23186.

SEQ ID NO: 373 is the determined cDNA sequence of clone 23187.

SEQ ID NO: 374 is the determined cDNA sequence of clone 23190.

SEQ ID NO: 375 is the determined cDNA sequence of clone 23189.

SEQ ID NO: 376 is the determined cDNA sequence of clone 23202.

SEQ ID NO: 378 is the determined cDNA sequence of clone 23191.

SEQ ID NO: 379 is the determined cDNA sequence of clone 23188.

SEQ ID NO: 380 is the determined cDNA sequence of clone 23194.

SEQ ID NO: 381 is the determined cDNA sequence of clone 23196.

SEQ ID NO: 382 is the determined cDNA sequence of clone 23195.

SEQ ID NO: 383 is the determined cDNA sequence of clone 23193.

SEQ ID NO: 384 is the determined cDNA sequence of clone 23199.

SEQ ID NO: 385 is the determined cDNA sequence of clone 23200.

SEQ ID NO: 386 is the determined cDNA sequence of clone 23192.

SEQ ID NO: 387 is the determined cDNA sequence of clone 23201.

SEQ ID NO: 388 is the determined cDNA sequence of clone 23141.

SEQ ID NO: 389 is the determined cDNA sequence of clone 23139.

SEQ ID NO: 390 is the determined cDNA sequence of clone 23204.

SEQ ID NO: 391 is the determined cDNA sequence of clone 23205.

SEQ ID NO: 392 is the determined cDNA sequence of clone 23206.

SEQ ID NO: 393 is the determined cDNA sequence of clone 23207.

SEQ ID NO: 394 is the determined cDNA sequence of clone 23208.

SEQ ID NO: 395 is the determined cDNA sequence of clone 23209.

SEQ ID NO: 396 is the determined cDNA sequence of clone 23210.

SEQ ID NO: 397 is the determined cDNA sequence of clone 23211.

SEQ ID NO: 398 is the determined cDNA sequence of clone 23212.

SEQ ID NO: 399 is the determined cDNA sequence of clone 23214.

SEQ ID NO: 400 is the determined cDNA sequence of clone 23215.

SEQ ID NO: 401 is the determined cDNA sequence of clone 23216.

SEQ ID NO: 402 is the determined cDNA sequence of clone 23137.

SEQ ID NO: 403 is the determined cDNA sequence of clone 23218.

SEQ ID NO: 404 is the determined cDNA sequence of clone 23220.

SEQ ID NO: 405 is the determined cDNA sequence of clone 19462.

SEQ ID NO: 406 is the determined cDNA sequence of clone 19430.

SEQ ID NO: 407 is the determined cDNA sequence of clone 19407.

SEQ ID NO: 408 is the determined cDNA sequence of clone 19448.

SEQ ID NO: 409 is the determined cDNA sequence of clone 19447.

SEQ ID NO: 410 is the determined cDNA sequence of clone 19426.

SEQ ID NO: 411 is the determined cDNA sequence of clone 19441.

SEQ ID NO: 412 is the determined cDNA sequence of clone 19454.

SEQ ID NO: 413 is the determined cDNA sequence of clone 19463.

SEQ ID NO: 414 is the determined cDNA sequence of clone 19419.

SEQ ID NO: 415 is the determined cDNA sequence of clone 19434.

SEQ ID NO: 416 is the determined extended cDNA sequence of B820P.

SEQ ID NO: 417 is the determined extended cDNA sequence of B821P.

SEQ ID NO: 418 is the determined extended cDNA sequence of B822P.

SEQ ID NO: 419 is the determined extended cDNA sequence of B823P.

SEQ ID NO: 420 is the determined extended cDNA sequence of B824P.

SEQ ID NO: 421 is the determined extended cDNA sequence of B825P.

SEQ ID NO: 422 is the determined extended cDNA sequence of B826P.

SEQ ID NO: 423 is the determined extended cDNA sequence of B827P.

SEQ ID NO: 424 is the determined extended cDNA sequence of B828P.

SEQ ID NO: 425 is the determined extended cDNA sequence of B829P.

SEQ ID NO: 426 is the determined extended cDNA sequence of B830P.

SEQ ID NO: 427 is the determined cDNA sequence of clone 266B4.

SEQ ID NO: 428 is the determined cDNA sequence of clone 22892.

SEQ ID NO: 429 is the determined cDNA sequence of clone 266G3.

SEQ ID NO: 430 is the determined cDNA sequence of clone 22890.

SEQ ID NO: 431 is the determined cDNA sequence of clone 264B4.

SEQ ID NO: 432 is the determined cDNA sequence of clone 22883.

SEQ ID NO: 433 is the determined cDNA sequence of clone 22882.

SEQ ID NO: 434 is the determined cDNA sequence of clone 22880.

SEQ ID NO: 435 is the determined cDNA sequence of clone 263G1.

SEQ ID NO: 436 is the determined cDNA sequence of clone 263G6.

SEQ ID NO: 437 is the determined cDNA sequence of clone 262B2.

SEQ ID NO: 438 is the determined cDNA sequence of clone 262B6.

SEQ ID NO: 439 is the determined cDNA sequence of clone 22869.

SEQ ID NO: 440 is the determined cDNA sequence of clone 21374.

SEQ ID NO: 441 is the determined cDNA sequence of clone 21362.

SEQ ID NO: 442 is the determined cDNA sequence of clone 21349.

SEQ ID NO: 443 is the determined cDNA sequence of clone 21309.

SEQ ID NO: 444 is the determined cDNA sequence of clone 21097.

SEQ ID NO: 445 is the determined cDNA sequence of clone 21096.

SEQ ID NO: 446 is the determined cDNA sequence of clone 21094.

SEQ ID NO: 447 is the determined cDNA sequence of clone 21093.

SEQ ID NO: 448 is the determined cDNA sequence of clone 21091.

SEQ ID NO: 449 is the determined cDNA sequence of clone 21089.

SEQ ID NO: 450 is the determined cDNA sequence of clone 21087.

SEQ ID NO: 451 is the determined cDNA sequence of clone 21085.

SEQ ID NO: 452 is the determined cDNA sequence of clone 21084.

SEQ ID NO: 453 is a first partial cDNA sequence of clone 2BT1-40.

SEQ ID NO: 454 is a second partial cDNA sequence of clone 2BT1-40.

SEQ ID NO: 455 is the determined cDNA sequence of clone 21063.

SEQ ID NO: 456 is the determined cDNA sequence of clone 21062.

SEQ ID NO: 457 is the determined cDNA sequence of clone 21060.

SEQ ID NO: 458 is the determined cDNA sequence of clone 21053.

SEQ ID NO: 459 is the determined cDNA sequence of clone 21050.

SEQ ID NO: 460 is the determined cDNA sequence of clone 21036.

SEQ ID NO: 461 is the determined cDNA sequence of clone 21037.

SEQ ID NO: 462 is the determined cDNA sequence of clone 21048.

SEQ ID NO: 463 is a consensus DNA sequence of B726P (referred to as B726P-spliced_seq_B726P).

SEQ ID NO: 464 is the determined cDNA sequence of a second splice form of B726P (referred to as 27490.seq_B726P).

SEQ ID NO: 465 is the determined cDNA sequence of a third splice form of B726P (referred to as 27068.seq_B726P).

SEQ ID NO: 466 is the determined cDNA sequence of a second splice form of B726P (referred to as 23113.seq_B726P).

SEQ ID NO: 467 is the determined cDNA sequence of a second splice form of B726P (referred to as 23103.seq_B726P).

SEQ ID NO: 468 is the determined cDNA sequence of a second splice form of B726P (referred to as 19310.seq_B726P).

SEQ ID NO: 469 is the predicted amino acid sequence encoded by the upstream ORF of SEQ ID NO: 463.

SEQ ID NO: 470 is the predicted amino acid sequence encoded by SEQ ID NO: 464.

SEQ ID NO: 471 is the predicted amino acid sequence encoded by SEQ ID NO: 465.

SEQ ID NO: 472 is the predicted amino acid sequence encoded by SEQ ID NO: 466.

SEQ ID NO: 473 is the predicted amino acid sequence encoded by SEQ ID NO: 467.

SEQ ID NO: 474 is the determined cDNA sequence for an alternative splice form of B726P.

SEQ ID NO: 475 is the amino acid sequence encoded by SEQ ID NO: 474.

SEQ ID NO: 476 is the isolated cDNA sequence of B720P.

SEQ ID NO: 477 is the cDNA sequence of a known keratin gene.

SEQ ID NO: 478 is the amino acid sequence encoded by SEQ ID NO: 477.

SEQ ID NO: 479 is the determined cDNA sequence for clone 19465.

SEQ ID NO: 480 and 481 are PCR primers.

SEQ ID NO: 482 is the cDNA sequence for the expressed downstream ORF of B726P.

SEQ ID NO: 483 is the amino acid sequence for the expressed recombinant downstream ORF of B726P.

SEQ ID NO: 484 is the determined full-length cDNA sequence for B720P.

SEQ ID NO: 485 is the amino acid sequence encoded by SEQ ID NO: 484.

SEQ ID NO: 486 is the determined cDNA sequence of a truncated form of B720P, referred to as B720P-tr.

SEQ ID NO: 487 is the amino acid sequence of B720P-tr.

SEQ ID NO: 488 is the amino acid sequence of a naturally processed epitope of B726P recognized by B726P-specific CTL.

SEQ ID NO: 489 is a DNA sequence encoding the B726P epitope set forth in

SEQ ID NO: 488.

SEQ ID NO: 490 is a DNA sequence encoding a fusion protein wherein mammaglobin is fused to the B726P combined upstream and downstream open reading frame (ORF) (the amino acid sequence of the B726P combined ORF is disclosed herein as SEQ ID NO: 475 which is encoded by the DNA sequence of SEQ ID NO: 474).

SEQ ID NO: 491 is a DNA sequence encoding a fusion protein wherein mammaglobin is fused to the B726P upstream ORF (the amino acid sequence of the B726P upstream ORF is disclosed herein as SEQ ID NO: 469 which is encoded by the DNA sequence of SEQ ID NO: 463).

SEQ ID NO: 492 is a DNA sequence encoding a fusion protein wherein mammaglobin is fused to the B726P downstream ORF (the amino acid sequence of the B726P downstream ORF is disclosed herein as SEQ ID NO: 176 which is encoded by the DNA sequence of SEQ ID NO: 175).

SEQ ID NO: 493 is the amino acid sequence encoded by the DNA sequence of SEQ ID NO: 490.

SEQ ID NO: 494 is the amino acid sequence encoded by the DNA sequence of SEQ ID NO: 491.

SEQ ID NO: 495 is the amino acid sequence encoded by the DNA sequence of SEQ ID NO: 492.

SEQ ID NO: 496 is amino acids 59–78 of SEQ ID NO: 493.

SEQ ID NO: 497 is amino acids 55–69 of SEQ ID NO: 493.

SEQ ID NO: 498 is amino acids 13–33 of SEQ ID NO: 493.

SEQ ID NO: 499 is amino acids 41–60 of SEQ ID NO: 493.

SEQ ID NO: 500 is amino acids 2–10 of SEQ ID NO: 493

SEQ ID NO: 501 is amino acids 47–59 of SEQ ID NO: 493.

SEQ ID NO: 502 is amino acids 62–74 of SEQ ID NO: 493.

SEQ ID NO: 503 is amino acids 1–93 of SEQ ID NO: 493.

SEQ ID NO: 504 is the full-length cDNA sequence for B718P.

SEQ ID NO: 505 is the cDNA sequence of the open reading frame of B718P including stop codon.

SEQ ID NO: 506 is the cDNA sequence of the open reading frame of B718P without stop codon.

SEQ ID NO: 507 is the full-length amino acid sequence of B718P.

SEQ ID NO: 508 represents amino acids 1–158 of SEQ ID NO: 507.

SEQ ID NO: 509 represents amino acids 159–243 of SEQ ID NO: 509.

SEQ ID NO: 510 is the entire cDNA sequence of the open reading frame, including stop codon, of a first variant of B723P, referred to as B723P-short.

SEQ ID NO: 511 is the entire cDNA sequence of the open reading frame, without stop codon, of a first variant of B723P, referred to as B723P-short.

SEQ ID NO: 512 is the entire cDNA sequence of the open reading frame, including stop codon, of a second variant of B723P, referred to as B723P-long.

SEQ ID NO: 513 is the entire cDNA sequence of the open reading frame, without stop codon, of a second variant of B723P, referred to as B723P-long.

SEQ ID NO: 514 is the amino acid sequence of B723P-short.

SEQ ID NO: 515 is the amino acid sequence of B723P-long.

SEQ ID NO: 516 is amino acids 1–197 of B723P-short.

SEQ ID NO: 517 is amino acids 1–232 of B723P-long.

SEQ ID NO: 518 is amino acids 198–243 of B723P-short.

SEQ ID NO: 519 is amino acids 218–243 of B723P-short.

SEQ ID NO: 520–533 are the DNA sequences of epitopes of B726P.

SEQ ID NO: 534–547 are the amino acid sequences of epitopes of B726P.

DETAILED DESCRIPTION OF THE INVENTION

The present invention is directed generally to compositions and their use in the therapy and diagnosis of cancer, particularly breast cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" "is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NOs: 1–175, 178, 180, 182–468, 474, 476, 477 479, 484, 486, 489, 504–506, 510–513 and 520–533, or a sequence that hybridizes under moderately stringent conditions, or, alternatively, under highly stringent conditions, to a polynucleotide sequence set forth in any one of SEQ ID NOs: 1–175, 178, 180, 182–468, 474, 476, 477 479, 484, 486, 489, 504–506, 510–513 and 520–533. Certain other illustrative polypeptides of the invention comprise amino acid sequences as set forth in any one of SEQ ID NOs: 176, 179, 181, 469–473, 475, 485, 487, 488, 507–509, 514–519 and 534–547.

The polypeptides of the present invention are sometimes herein referred to as breast tumor proteins or breast tumor polypeptides, as an indication that their identification has been based at least in part upon their increased levels of expression in breast tumor samples. Thus, a "breast tumor polypeptide" or "breast tumor protein," refers generally to a polypeptide sequence of the present invention, or a polynucleotide sequence encoding such a polypeptide, that is expressed in a substantial proportion of breast tumor samples, for example preferably greater than about 20%, more preferably greater than about 30%, and most preferably greater than about 50% or more of breast tumor samples tested, at a level that is at least two fold, and preferably at least five fold, greater than the level of expression in normal tissues, as determined using a representative assay provided herein. A breast tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with breast cancer. Screening for immunogenic activity can be performed using techniques well known to the skilled artisan. For example, such screens can be performed using methods such as those described in Harlow and Lane, *Antibodies: A Laboratory Manual,* Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1–30 amino acids, preferably 5–15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NOs: 176, 179, 181, 469–473, 475, 485, 487, 488, 507–509, 514–519 and 534–547, or those encoded by a polynucleotide sequence set forth in a sequence of SEQ ID NOs: 1–175, 178, 180, 182–468, 474, 476, 477 479, 484, 486, 489, 504–506, 510–513 and 520–533.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provide by the present invention are immunologically reactive with an antibody and/or T-cell that reacts with a full-length polypeptide specifically set for the herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1–30 amino acids, preferably 5–15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff M.o. (1978) A model of evolutionary change in proteins—Matrices for detecting distant relationships. In Dayhoff, M.o. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy-the Principles and Practice of Numerical Taxonomy,* Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86–91, 1997).

In one preferred embodiment, the immunological fusion partner is derived from a Mycobacterium sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. patent application Ser. No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis.* The nucleotide sequence and amino acid sequence of MTB32A have been described (for example, U.S. patent application Ser. No. 60/158,585; see also, Skeiky et al., *Infection and Immun.* (1999) 67:3998–4007, incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NSI (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NOs: 1–175, 178, 180, 182–468, 474, 476, 477 479, 484, 486, 489, 504–506, 510–513 and 520–533, complements of a polynucleotide sequence set forth in any one of SEQ ID NOs: 1–175, 178, 180, 182–468, 474, 476, 477 479, 484, 486, 489, 504–506, 510–513 and 520–533, and degenerate variants of a polynucleotide sequence set forth in any one of SEQ ID NOs: 1–175, 178, 180, 182–468, 474, 476, 477 479, 484, 486, 489, 504–506, 510–513 and 520–533. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NOs: 1–175, 178, 180, 182–468, 474, 476, 477 479, 484, 486, 489, 504–506, 510–513 and 520–533, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising various lengths of contiguous stretches of sequence identical to or complementary to one or more of the sequences disclosed herein. For example, polynucleotides are provided by this invention that comprise at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60–65° C. or 65–70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M.o. (1978) A model of evolutionary change in proteins—Matrices for detecting distant relationships. In Dayhoff, M.o. (ed.) Atlas of Protein Sequence and Structure, National Biomedical Research Foundation, Washington DC Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy-the Principles and Practice of Numerical Taxonomy,* Freeman Press, San Francisco, Calif.; Wilbur, W. J. and Lipman, D. J. (1983) *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389–3402 and Altschul et al. (1990) *J. Mol. Biol.* 215:403–410, respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., Science. 1988 Jun 10;240(4858):1544–6; Vasanthakumar and Ahmed, Cancer Commun. 1989;1(4):225–32; Peris et al., Brain Res Mol Brain Res. 1998 Jun 15;57(2):310–20; U.S. Pat. Nos. 5,801,154; 5,789,573; 5,718,709 and U.S. Pat. No. 5,610,288). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof In another embodiment, the oligonucleotides comprise R NA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v.4 of the OLIGO primer analysis software and/or the BLASTN 2.0.5 algorithm software (Altschul et al., Nucleic Acids Res. 1997, 25(17) :3389–402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. Jul. 15, 1997;25(14):2730–6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, Proc Natl Acad Sci USA. December, 1987;84(24):8788–92; Forster and Symons, Cell. Apr. 24, 1987;49(2):211–20). For example, a large number of ribozymes accelerate phosphoester transfer reactions with a high degree of specificity, often cleaving only one of several phosphoesters in an oligonucleotide substrate (Cech et al., Cell. December 1981;27(3 Pt 2):487–96; Michel and Westhof, J. Mol Biol. Dec. 5, 1990;216(3):585–610; Reinhold-Hurek and Shub, Nature. May 14, 1992;357(6374):173–6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., Proc Natl Acad Sci USA. Aug. 15, 1992;89(16):7305–9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. Sep. 11, 1992;20(17):4559–65. Examples of hairpin motifs are described by Hampel et al. (Eur. Pat. Appl. Publ. No. EP 0360257), Hampel and Tritz, Biochemistry Jun. 13, 1989;28 (12):4929–33; Hampel et al., Nucleic Acids Res. Jan. 25, 1990;18(2):299–304 and U.S. Pat. No. 5,631,359. An example of the hepatitis δ virus motif is described by Perrotta and Been, Biochemistry. Dec. 1, 1992;31(47) :11843–52; an example of the RNaseP motif is described by Guerrier-Takada et al., Cell. December 1983;35(3 Pt 2):849–57; Neurospora VS RNA ribozyme motif is described by Collins (Saville and Collins, Cell. May 18, 1990;61(4):685–96; Saville and Collins, Proc Natl Acad Sci USA. Oct. 1, 1991;88(19):8826–30; Collins and Olive, Biochemistry. Mar 23, 1993;32(11):2795–9); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. patent appl. Publ. No. WO 94/02595 and Int. patent appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431–37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* Jun. 15, 1997(6):224–9). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* Dec. 6, 1991;254(5037):1497–500; Hanvey et al., Science. Nov. 27, 1992;258(5087):1481–5; Hyrup and Nielsen, Bioorg Med Chem. Jan. 4, 1996(1):5–23). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., Bioorg Med Chem. Apr. 3, 1995(4):437–45). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., Bioorg Med Chem. Apr. 3, 1995(4):437–45; Petersen et al, J Pept Sci. May–Jun. 1, 1995(3):175–83; Orum et al., Biotechniques. Sep. 19, 1995(3):472–80; Footer et al., Biochemistry. Aug. 20, 1996;35(33):10673–9; Griffith et al Nucleic Acids Res. Aug. 11, 1995;23(15):3003–8; Pardridge et al., Proc Natl Acad Sci U S A. Jun. 6, 1995;92 (12):5592–6; Boffa et al., Proc Natl Acad Sci USA. Mar. 14, 1995;92(6):1901–5; Gambacorti-Passerini et al., Blood. Aug 15, 1996;88(4):1411–7; Armitage et al., Proc Natl Acad Sci USA. Nov. 11, 1997;94(23):12320–5; Seeger et al., Biotechniques. Sep. 23, 1997(3):512–7). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (Anal Chem. Dec 15, 1993;65(24):3545–9) and Jensen et al. (Biochemistry. Apr. 22, 1997;36(16):5072–7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual,* Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR ™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$p) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of beta-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or Trichoplusia larvae in which the polypeptide of interest may be expressed (Engelhard, E. K. et al. (1994) *Proc. Natl. Acad. Sci.* 91:3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) Annual Rev. Biochem. 59:439–473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as breast cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "$F(ab')_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) Proc. Nat. Acad. Sci. USA 69:2659–2662; Hochman et al. (1976) Biochem 15:2706–2710; and Ehrlich et al. (1980) Biochem 19:4091–4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) Proc. Nat. Acad. Sci. USA 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349:293–299; Lobuglio et al. (1989) Proc. Nat. Acad. Sci. USA 86:4220–4224; Shaw et al. (1987) J Immunol. 138:4534–4538; and Brown et al. (1987) Cancer Res. 47:3577–3583), rodent CDRs grafted into a human supporting FR prior to fusion with an appropriate human antibody constant domain (Riechmann et al. (1988) Nature 332:323–327; Verhoeyen et al. (1988) Science 239:1534–1536; and Jones et al. (1986) Nature 321:522–525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) Ann. Rev. Biochem. 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml–100 $\mu$g/ml, preferably 200 ng/ml–25 $\mu$g/ml) for 3–7 days will typically result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143–198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as Bacillus-Calmette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980–990; Miller, A. D. (1990) Human Gene Therapy 1:5–14; Scarpa et al. (1991) Virology 180:849–852; Burns et al. (1993) Proc. Natl. Acad. Sci. USA 90:8033–8037; and Boris-Lawrie and Temin (1993) Cur. Opin. Genet. Develop. 3:102–109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267–274; Bett et al. (1993) J. Virol. 67:5911–5921; Mittereder et al. (1994) Human Gene Therapy 5:717–729; Seth et al. (1994) J. Virol. 68:933–940; Barr et al. (1994) Gene Therapy 1:51–58; Berkner, K. L. (1988) BioTechniques 6:616–629; and Rich et al. (1993) Human Gene Therapy 4:461–476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; Kotin, R. M. (1994) Human Gene Therapy 5:793–801; Shelling and Smith (1994) Gene Therapy 1:165–169; and Zhou et al. (1994) J. Exp. Med. 179:1867–1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(-) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743–6747; Fuerst et al. Proc. Natl. Acad. Sci. USA (1986) 83:8122–8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866–6869 and Wagner et al. Proc. Natl. Acad. Sci. USA (1992) 89:6099–6103, can also be used for gene delivery under the invention.

Additional illustrative information on these and other known viral-based delivery systems can be found, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074, 720, the disclosures of which are incorporated herein by reference in their entireties, and polyoxyethylene ether adjuvants such as those described in WO 99/52549A1.

Other preferred adjuvants include adjuvant molecules of the general formula (I): $HO(CH_2CH_2O)_n$-A-R, wherein, n is 1–50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12_{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4–1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature Mar. 27, 1997;386(6623):410–4; Hwang et al., Crit Rev Ther Drug Carrier Syst 1998;15(3):243–84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release Mar. 2, 1998;52(1–2):81–7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol Jul. 16, 1998(7):307–21; Takakura, Nippon Rinsho Mar. 56, 1998(3):691–5; Chandran et al., Indian J Exp Biol. Aug. 35, 1997(8):801–9; Margalit, Crit Rev Ther Drug Carrier Syst. 1995;12(2–3):233–61; U.S. Pat. Nos. 5,567,434; 5,552,157; 5,565,213; 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. Sep. 25, 1990;265(27):16337–42; Muller et al., DNA Cell Biol. Apr. 9, 1990(3):221–9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. Dec. 24, 1998(12):1113–28). To avoid side effects due to intracellular polymeric overloading, such ultrafine particles (sized around 0.1 $\mu$m) may be designed using polymers able to be degraded in vivo. Such particles can be made as described, for example, by Couvreur et al., Crit Rev Ther Drug Carrier Syst. 1988;5(1)

:1–20; zur Muhlen et al., Eur J Pharm Biopharm. Mar; 45, 1998(2):149–55; Zambaux et al. J Controlled Release. Jan. 2, 1998; 50(1–3):31–40; and U.S. Pat. No. 5,145,684.

Cancer Therapeutic Methods

In further aspects of the present invention, the pharmaceutical compositions described herein may be used for the treatment of cancer, particularly for the immunotherapy of breast cancer. Within such methods, the pharmaceutical compositions described herein are administered to a patient, typically a warm-blooded animal, preferably a human. A patient may or may not be afflicted with cancer. Accordingly, the above pharmaceutical compositions may be used to prevent the development of a cancer or to treat a patient afflicted with a cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more breast tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual,* Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 $\mu$g/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis. Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.,* 51:263, 1987; Erlich ed., *PCR Technology,* Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLE 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+RNA was purified using an oligo(dT) cellulose column according to standard protocols. First strand cDNA was synthesized using the primer supplied in a Clontech PCR-Select cDNA Subtraction Kit (Clontech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH10B cells (Gibco BRL Life, Technologies) by electroporation. DNA was isolated from independent clones and sequenced using a Perkin Elmer/Applied Biosystems Division (Foster City, Calif.) Automated Sequencer Model 373A.

Sixty-three distinct cDNA clones were found in the subtracted breast tumor-specific cDNA library. The determined one strand (5' or 3') cDNA sequences for the clones are provided in SEQ ID NO: 1–61, 72 and 73, respectively. Comparison of these cDNA sequences with known sequences in the gene bank using the EMBL and GenBank databases (Release 97) revealed no significant homologies to the sequences provided in SEQ ID NO: 14, 21, 22, 27, 29, 30, 32, 38, 44, 45, 53, 57, 72 and 73. The sequences of SEQ ID NO: 1, 3, 16, 17, 34, 48, 60 and 61 were found to represent known human genes. The sequences of SEQ ID NO: 2, 4, 23, 39 and 50 were found to show some similarity to previously identified non-human genes. The remaining clones (SEQ ID NO: 5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

Further studies resulted in the isolation of the full-length cDNA sequence for the clone of SEQ ID NO: 57 (referred to as B718P). By computer analysis, the full-length sequence was found to contain a putative transmembrane domain at amino acids 137–158. The full-length cDNA sequence of B718P is provided in SEQ ID NO: 504, with the cDNA sequence of the open reading frame including stop codon being provided in SEQ ID NO: 505 and the eDNA sequence of the open reading frame without stop codon being provided in SEQ ID NO: 506. The full-length amino acid sequence of B718P is provided is SEQ ID NO: 507. SEQ ID NO: 508 represents amino acids 1–158 of B718P, and SEQ ID NO: 509 represents amino acids 159–243 of B718P.

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO: 40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO: 41 and 48 were found to be over-expressed in breast tumor and expressed at low levels in all other tissues tested, with the exception of bone marrow. The clone of SEQ ID NO: 42 was found to be over-expressed in breast tumor and expressed at low levels in all other tissues tested except bone marrow and spinal cord. The clone of SEQ ID NO: 43 was found to be over-expressed in breast tumor and expressed at low levels in all other tissues tested with the exception of spinal cord, heart and small intestine. The clone of SEQ ID NO: 51 was found to be over-expressed in breast tumor and expressed at low levels in all other tissues tested with the exception of large intestine. The clone of SEQ ID NO: 54 was found to be over-expressed in breast tumor and expressed at low levels in all other tissues tested with the exception of PBMC, stomach and small intestine. The clone of SEQ ID NO: 56 was found to be over-expressed in breast tumor and expressed at low levels in all other tissues tested with the exception of large and small intestine, human mammary epithelia cells and SCID mouse-passaged breast tumor. The clone of SEQ ID NO: 60 was found to be over-expressed in breast tumor and expressed at low levels in all other tissues tested with the exception of spinal cord and heart. The clone of SEQ ID NO: 61 was found to be over-expressed in breast tumor and expressed at low levels in all other tissues tested with the exception of small intestine. The clone of SEQ ID NO: 72 was found to be over-expressed in breast tumor and expressed at low levels in all other tissues tested with the exception of colon and salivary gland.

The results of a Northern blot analysis of the clone SYN18C6 (SEQ ID NO: 40) are shown in FIG. 1. A predicted protein sequence encoded by SYN18C6 is provided in SEQ ID NO: 62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined cDNA sequences for these clones are provided in SEQ ID NO: 63–87. Comparison of the sequences of SEQ ID NO: 74–87 with those in the gene bank as described above, revealed homology to previously identified human genes. No significant homologies were found to the sequences of SEQ ID NO: 63–73.

Three DNA isoforms for the clone B726P (partial sequence provided in SEQ ID NO: 71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [α-32P]dCTP. The sequence of the primer employed for this PCR is provided in SEQ ID NO: 177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO: 175, with the corresponding predicted amino acid sequence being provided in SEQ ID NO: 176. The determined cDNA sequence of the isoform B726P-74 is provided in SEQ ID NO: 178, with the corresponding predicted amino acid sequence being provided in SEQ ID NO: 179. The determined cDNA sequence of the isoform B726P-79 is provided in SEQ ID NO: 180, with the corresponding predicted amino acid sequence being provided in SEQ ID NO: 181.

Efforts to obtain a full-length clone of B726P using standard techniques led to the isolation of five additional clones that represent additional 5' sequence of B726P. These clones appear to be alternative splice forms of the same gene. The determined cDNA sequences of these clones are provided in SEQ ID NO:464–468, with the predicted amino acid sequences encoded by SEQ ID NO: 464–467 being provided in SEQ ID NO:470–473, respectively. Using standard computer techniques, a 3,681 bp consensus DNA sequence (SEQ ID NO:463) was created that contains two large open reading frames. The downstream ORF encodes the amino acid sequence of SEQ ID NO:176. The predicted amino acid sequence encoded by the upstream ORF is provided in SEQ ID NO:469. Subsequent studies led to the isolation of an additional splice form of B726P that has 184 bp insert relative to the other forms. This 184 bp insert causes a frameshift that brings the down stream and upstream ORFs together into a single ORF that is 1002 aa in length. The determined cDNA sequence of this alternative splice form is disclosed in SEQ ID NO:474, with the corresponding amino acid sequence being provided in SEQ ID NO:475.

Comparison of the cDNA sequence of SEQ ID NO: 63 (referred to as B723P) with the sequences in the GeneSeq™ DNA database showed matches to 5 DNA sequences (Accession nos. A26456, A37144, A26424, V84525 and T22133), 4 of which appear to represent the full-length sequence of the gene. Three of these sequences encode a 243 amino acid open reading frame (ORF), while one of the DNA sequences (Accession no. A37144) contains an extra C at position 35, resulting in a 278 amino acid ORF. The open reading frame, including stop codon, of the first variant of B723P (referred to as B723P-short) is provided in SEQ ID NO: 510, with the open reading frame without stop codon being provided in SEQ ID NO: 511. The open reading frame, including stop codon, of the second variant of B723P (referred to as B723P-long) is provided in SEQ ID NO: 512, with the open reading frame without stop codon being provided in SEQ ID NO: 513. The amino acid sequences of B723P-short and B723P-long are provided in SEQ ID NO: 514 and 515, respectively. Computer analysis of these sequences demonstrated the presence of putative transmembrane domains at amino acids 233–252 of the B723P-long ORF and amino acids 198–217 of the B723P-short ORF. SEQ ID NO: 516, 518 and 519 represent amino acids 1–197, 198–243 and 218–243, respectively of B723P-short. SEQ ID NO: 517 represents amino acids 1–232 of B723P-long.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO: 182–251 and 479 were 2 or more fold over-expressed in human breast tumor tissues over normal human tissues. No significant homologies were found for nineteen of these clones, including, SEQ ID NO: 185, 186, 194, 199, 205, 208, 211, 214–216, 219, 222, 226, 232, 236, 240, 241, 245, 246 and 479, with the exception of some previously identified expressed sequence tags (ESTs). The remaining clones share some homology to previously identified genes, specifically SEQ ID NO: 181–184, 187–193, 195–198, 200–204, 206, 207, 209, 210, 212, 213, 217, 218, 220, 221, 223–225, 227–231, 233–235, 237–239, 242–244 and 247–251.

One of the cDNA clones isolated by PCR subtraction as described above (SEQ ID NO: 476; referred to as B720P) which was shown by microarray to be over-expressed in breast tumor tissues, was found to be identical to a known keratin gene. The full-length cDNA sequence of the known keratin gene is provided in SEQ ID NO: 477, with the corresponding amino acid sequence being provided in SEQ ID NO: 478. Primers were generated based on the sequence of SEQ ID NO: 477 and used to clone full-length cDNA from mRNA which was obtained from total RNA showing high expression of B720P in real-time PCR analysis. Products were then cloned and sequenced. The determined full-length cDNA sequence for B720P is provided in SEQ ID NO: 484, with the corresponding amino acid sequence being provided in SEQ ID NO: 485.

In further studies, a truncated form of B720P (referred to as B720P-tr) was identified in breast carcinomas. This antigen was cloned from mRNA derived from total breast tumor RNA that showed high expression of B720P-tr in real-time PCR analysis. mRNA was used to generate a pool of cDNA which was then used as a template to amplify the cDNA corresponding to B720P-tr by PCR. The determined cDNA sequence for B720P-tr is provided in SEQ ID NO: 486. B720P-tr has an ORF of 708 base pairs which encodes a 236 amino acid protein (SEQ ID NO: 487). The size of the transcript was confirmed by northern analysis.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO: 185) was over-expressed in the majority of breast tumors and also in the SCID breast tumors tested (refer to Example 2); additionally, over-expression was found in a majority of normal breast tissues. Clone 19483.1 (SEQ ID NO: 216) was over-expressed in a few breast tumors, with no over-expression in any normal tissues tested. Clone 19470.1 (SEQ ID NO: 219) was found to be slightly over-expressed in some breast tumors. Clone 19468.1 (SEQ ID NO: 222) was found to be slightly over-expressed in the majority of breast tumors tested. Clone 19505.1 (SEQ ID NO: 226) was found to be slightly over-expressed in 50% of breast tumors, as well as in SCID tumor tissues, with some degree of over-expression in found in normal breast. Clone 1509.1 (SEQ ID NO: 232) was found to be over-expressed in very few breast tumors, but with a certain degree of over-expression in metastatic breast tumor tissues, as well as no significant over-expression found in normal tissues. Clone 19513.1 (SEQ ID NO: 236) was shown to be slightly over-expressed in few breast tumors, with no significant over-expression levels found in normal tissues. Clone 19575.1 (SEQ ID NO: 240) showed low level over-expression in some breast tumors and also in normal breast. Clone 19560.1 (SEQ ID NO: 241) was over-expressed in 50% of breast tumors tested, as well as in some normal breast tissues. Clone 19583.1 (SEQ ID NO: 245) was slightly over-expressed in some breast tumors, with very low levels of over-expression found in normal tissues. Clone 19587.1 (SEQ ID NO: 246) showed low level over-expression in some breast tumors and no significant over-expression in normal tissues. Clone 19520.1 (SEQ ID NO: 233), showing homology to clone 102D24 on chromosome 11 q 13.31, was found to be over-expressed in breast tumors and in SCID tumors. Clone 19517.1 (SEQ ID NO: 237), showing homology to human PAC 128M19 clone, was found to be slightly over-expressed in the majority of breast tumors tested. Clone 19392.2 (SEQ ID NO: 247), showing homology to human chromosome 17, was shown to be over-expressed in 50% of breast tumors tested. Clone 19399.2 (SEQ ID NO: 250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO: 405–415. Comparison of these sequences to those in the public database, as outlined above, revealed homologies between the sequences of SEQ ID NO: 408, 411, 413 and 414 and previously isolated ESTs. The sequences of SEQ ID NO: 405–407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO: 316–404. Comparison of these sequences with those in the public database, as described above, revealed no significant homologies to the sequence of SEQ ID NO: 366. The sequences of SEQ ID NO: 321–325, 343, 354, 368, 369, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues. A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO: 427–439. The determined cDNA sequences of 22 clones identified using the modified Gemtools analysis are provided in SEQ ID NO: 440–462, wherein SEQ ID NO: 453 and 454 represent two partial, non-overlapping, sequences of the same clone.

Comparison of the clone sequences of SEQ ID NO: 436 and 437 (referred to as 263G6 and 262B2) with those in the public databases, as described above, revealed no significant homologies to previously identified sequences. The sequences of SEQ ID NO: 427, 429, 431, 435, 438, 441, 443, 444, 445, 446, 450, 453 and 454 (referred to as 266B4, 266G3, 264B4, 263G1, 262B6, 2BT2-34, 2BT1-77, 2BT1-62, 2BT1-59, 2BT1-52 and 2BT1-40, respectively) showed some homology to previously isolated expressed sequences tags (ESTs). The sequences of SEQ ID NO: 428, 430, 432, 433, 434, 439, 440, 442, 447, 448, 449, 451, 452 and 455–462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

EXAMPLE 2

Isolation and Characterization of Breast Tumor Polypeptides Obtained by PCR-based Subtraction Using SCID-Passaged Tumor RNA Human breast tumor antigens were obtained by PCR-based subtraction using SCID mouse passaged breast tumor RNA as follows. Human breast tumor was implanted in SCID mice and harvested on the first or sixth serial passage, as described in patent application Ser. No. 08/556,659 filed 11/13/95, U.S. Pat. No. 5,986,170. Genes found to be differentially expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 13068, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for these clones are provided in SEQ ID NO: 88–116, respectively. The isolated cDNA sequences of SEQ ID NO: 117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 14398, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO: 141–159, respectively. The isolated cDNA sequences of SEQ ID NO: 160–174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO: 252–268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO: 269–314, respectively.

The clones 20310, 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis 10 indicated at least two- to three-fold overexpression of these clones in breast tumor RNA compared to normal tissues tested. Subsequent studies led to the determination of the complete insert sequence for the clones B820P, B821P, B822P, B823P, B824P, B825P, B826P, B827P, B828P and B829P. These extended cDNA sequences are provided in SEQ ID NO: 416–426, respectively.

EXAMPLE 3

Synthesis of Polypeptides

Polypeptides may be synthesized on an Perkin Elmer/Applied Biosystems Division 430A peptide synthesizer using FMOC chemistry with HPTU (0-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

EXAMPLE 4

Elicitation of Breast Antigen-Specific CTL Responses in Human Blood

This Example illustrates the ability of the breast-specific antigen B726P to elicit a cytotoxic T lymphocyte (CTL) response in peripheral blood lymphocytes from normal humans.

Autologous dendritic cells (DC) were differentiated from monocyte cultures derived from PBMC of a normal donor by growth for five days in RPMI medium containing 10% human serum, 30 ng/ml GM-CSF and 30 ng/ml IL-4. Following five days of culture, DC were infected overnight with adenovirus expressing recombinant B726P (downstream ORF; SEQ ID NO:176) at an M.O.I. of 2.5 and matured for 8 hours by the addition of 2 micrograms/ml CD40 ligand. CD8 positive cells were enriched for by the depletion of CD4 and CD 14-positive cells. Priming cultures were initiated in individual wells of several 96-well plates with the cytokines IL-6 and IL-12. These cultures were restimulated in the presence of IL-2 using autologous fibroblasts treated with IFN-gamma and transduced with B726P and CD80. Following three stimulation cycles, the presence of B726P-specific CTL activity was assessed in IFN-gamma Elispot assays (Lalvani et al., *J. Exp. Med.* 186:859–865, 1997) using IFN-gamma treated autologous fibroblasts transduced to express either B726P or an irrelevant, control, antigen as antigen presenting cells (APC). Of approximately 96 lines, one line (referred to as 6-2B) was identified that appeared to specifically recognize B726P-transduced APC but not control antigen-transduced APC. This microculture was cloned using standard protocols. B726P-specific CTL were identified by Elispot analysis and expanded for further analysis. These CTL clones were demonstrated to recognize B726P-expressing fibroblasts, but not the control antigen MART-1, using chromium-51 release assays. Furthermore, using a panel of allogeneic fibroblasts transduced with B726P in antibody blocking assays, the HLA restriction element for these B726P-specific CTL was identified as HLA-B*1501.

In order to define more accurately the location of the epitope recognized by the B726P-specific CTL clones, a deletion construct comprising only the N-terminal half (a.a. 1–129) of B726P (referred to as B726Pdelta3') was constructed in the pBIB retroviral expression plasmid. This plasmid, as well as other plasmids containing B726P, were transfected into COS-7 cells either alone or in combination with a plasmid expressing HLA-B*1501. Aproximately 48 hours after transfection, a B726P-specific CTL clone (1–9B) was added at approximately $10^4$ cells per well. The cells were harvested the next day and the amount of IFN-gamma released was measured by ELISA. The CTL responded above background (EGFP) to COS-7 cells that had been transfected with both B726P and HLA-B*1501. There was no response above background to COS-7 cells that had been transfected with either B726P or HLA-B*1501 alone. Importantly, a higher response was seen with COS-7 cells that had been transfected with both HLA-B*1501 and B726Pdelta3'. This result indicated that the epitope was likely to be located in the N-terminal region (a.a. 1–129) of B726P. This region was examined and amino acid sequences that corresponded to the HLA-B*1501 peptide binding motif (*J. Immunol.* 1999, 162:7277–84) were identified and synthesized. These peptides were pulsed at 10 μg/ml onto autologous B-LCL overnight. The next day, the cells were washed and the ability of the cells to stimulate the B726P-specific CTL clone 1–9B was assayed in a IFN-gamma ELISPOT assay. Of the eleven peptides tested, only one peptide, having the amino acid sequence SLTKRASQY (a.a. 76–84 of B726P; SEQ ID NO: 488) was recognized by the CTL clone. This result identifies this peptide as being a naturally-processed epitope recognized by this B726P-specific CTL clone.

Figure 2:
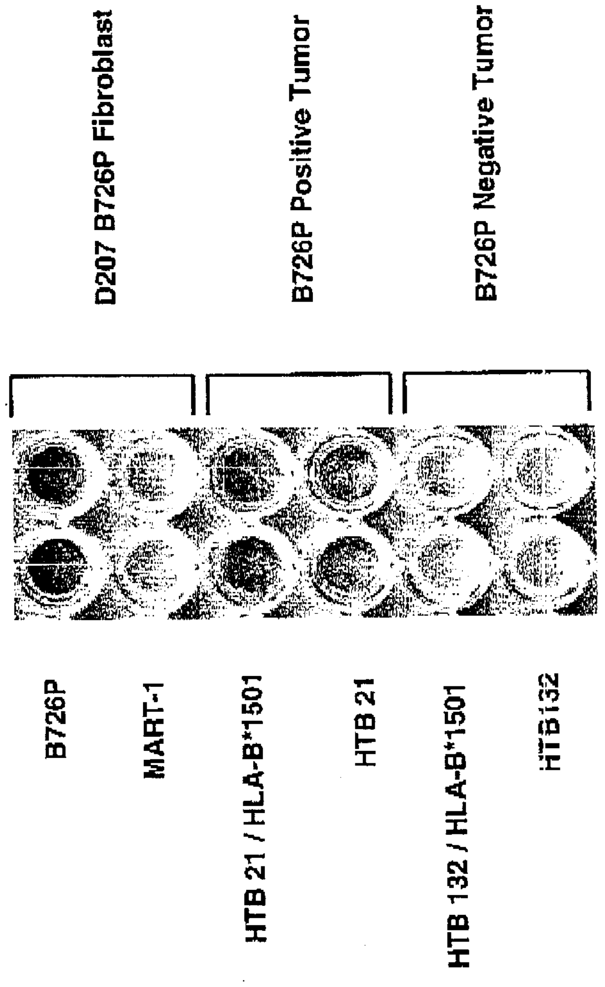
FIG. 2 shows the results of an IFN-gamma ELISPOT assay demonstrating that the B726P-specific CTL clone recognizes and lyses breast tumor cell lines expressing B726P.

In further studies, a panel of breast tumor cell lines obtained from the American Type Culture Collection (Manassas, Va.), was analyzed using real time PCR to determine their B726P message level. The cell line that expressed the highest level of B726P (referred to as HTB21) and a line that expressed no B726P (referred to as HTB132) were transduced with HLA-B*1501. These cell lines were grown up and analyzed using FACS to determine their B1501 expression. The line HTB 21 was found to endogenously express B1501. To determine if clone 1–9A would recognize the tumor cell line HTB21, an IFN-gamma ELISPOT assay was performed using 20,000 T cells, low dose IL-2 (5 ug/ml), and 20,000 of the following targets: autologous B726P or Mart-1 fibroblasts, untransduced or B1501-transduced HTB21; or untransduced or B1501-transduced HTB132. These were incubated overnight and the assay was developed the next day. The results of this assay are shown in FIG. 2. These studies demonstrate that B726P-specific CTL can recognize and lyse breast tumor cells expressing B726P.

EXAMPLE 5

Identification of Immunogenic CD4 T Cell Epitopes in Breast Antigens

Immunogenic CD4 T cell epitopes derived from the breast antigen B726P were identified as follows.

A total of thirty-five 20-mer peptides overlapping by 12 amino acids and derived from the downstream ORF of B726P (corresponding to amino acids 1–317 of SEQ ID NO: 176) were generated by standard procedure. Dendritic cells (DC) were derived from PBMC of a normal male donor using GMCSF and IL-4 by standard protocol. Purified CD4 T cells were generated from the same donor as the DC using MACS beads and negative selection of PBMCs. DC were pulsed overnight with pools of the 20-mer peptides, with each peptide at an individual concentration of 0.5 micrograms/mL. Pulsed DC were washed and plated at 10,000 cells/well of 96-well U bottom plates, and purified CD4 T cells were added at 100,000 cells/well. Cultures were supplemented with 10 ng/mL IL-6 and 5 ng/mL IL-12 and incubated at 37° C. Cultures were restimulated as above on a weekly basis using DC made and pulsed as above as the antigen presenting cell, supplemented with 10 u/mL IL-2 and 5 ng/mL IL-7. Following three in vitro stimulation cycles (the initial priming +two restimulations), cell lines (each corresponding to one well) were tested for specific proliferation and cytokine production in response to the stimulating pool versus an irrelevant pool of peptides derived from unrelated antigens. A number of individual CD4 T cell lines (36/672 by IFN-gamma and 64/672 by proliferation) demonstrated significant cytokine release (IFN-gamma) and proliferation in response to the B726P peptide pools but not to the control peptide pool. Twenty-five of these T cell lines were restimulated on the appropriate pool of B726P peptides and reassayed on autologous DC pulsed with either the individual peptides or recombinant B726P protein made in *E. coli.* Approximately 14 immunogenic peptides were recognized by the T cells from the entire set of peptide antigens tested. The amino acid sequences of these 14 peptides are provided in SEQ ID NO: 534–547, with the corresponding DNA sequences being provided in SEQ ID NO: 520–533, respectively. In some cases the peptide reactivity of the T cell line could be mapped to a single peptide but some could be mapped to more than one peptide in each pool. Thirteen of the fifteen T cell lines recognized the recombinant B726P protein. These results demonstrate that 13 of the 14 peptide sequences (SEQ ID NO: 534–542 and 544–547) may be naturally processed CD4 epitopes of the B726P protein.

EXAMPLE 6

Preparation and Characterization of Antibodies Against Breast Tumor Polypeptides Polyclonal antibodies against both the downstream (SEQ ID NO:176) and upstream (SEQ ID NO:469) ORF of the breast tumor antigen B726P were prepared as follows.

The downstream or upstream ORF of B726P expressed in an *E. coli* recombinant expression system was grown overnight in LB broth with the appropriate antibiotics at 37° C. in a shaking incubator. The next morning, 10 ml of the overnight culture was added to 500 ml to 2× YT plus appropriate antibiotics in a 2L-baffled Erlenmeyer flask. When the Optical Density (at 560 nm) of the culture reached 0.4–0.6, the cells were induced with IPTG (1 mM). Four hours after induction with IPTG, the cells were harvested by centrifugation. The cells were then washed with phosphate buffered saline and centrifuged again. The supernatant was discarded and the cells were either frozen for future use or immediately processed. Twenty ml of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For proteins that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM Tris pH 8.0 and 300 mM imidazole and collected in 3 ml fractions. A SDS-PAGE gel was run to determine which fractions to pool for further purification.

As a final purification step, a strong anion exchange resin, such as HiPrepQ (Biorad), was equilibrated with the appropriate buffer and the pooled fractions from above were loaded onto the column. Antigen was eluted off the column with a increasing salt gradient. Fractions were collected as the column was run and another SDS-PAGE gel was run to determine which fractions from the column to pool. The pooled fractions were dialyzed against 10 mM Tris pH 8.0. The protein was then vialed after filtration through a 0.22 micron filter and the antigens were frozen until needed for immunization.

Four hundred micrograms of the B726P antigen was combined with 100 micrograms of muramyldipeptide (MDP). Every four weeks rabbits were boosted with 100 micrograms mixed with an equal volume of Incomplete Freund's Adjuvant (IFA). Seven days following each boost, the animal was bled. Sera was generated by incubating the blood at 4° C. for 12–24 hours followed by centrifugation.

Ninety-six well plates were coated with B726P antigen by incubating with 50 microliters (typically 1 microgram) of recombinant protein at 4° C. for 20 hours. 250 Microliters of BSA blocking buffer was added to the wells and incubated at room temperature for 2 hours. Plates were washed 6 times with PBS/0.01% Tween. Rabbit sera was diluted in PBS. Fifty microliters of diluted sera was added to each well and incubated at room temperature for 30 min. Plates were washed as described above before 50 microliters of goat anti-rabbit horse radish peroxidase (HRP) at a 1:10000 dilution was added and incubated at room temperature for 30 min. Plates were again washed as described above and 100 microliters of TMB microwell peroxidase substrate was added to each well. Following a 15 min incubation in the dark at room temperature, the calorimetric reaction was stopped with 100 microliters of IN $H_2SO_4$ and read immediately at 450 nm. All the polyclonal antibodies showed immunoreactivity to the appropriate B726P antigen.

EXAMPLE 7

Protein Expression of Breast Tumor Antigens

The downstream ORF of B726P (SEQ ID NO:176), together with a C-terminal 6X His Tag, was expressed in insect cells using the baculovirus expression system as follows.

The cDNA for the full-length downstream ORF of B726P was PCR amplified using the primers of SEQ ID NO: 480 and 481. The PCR product with the expected size was recovered from agarose gel, restriction digested with EcoRI and Hind II, and ligated into the transfer plasmid pFastBac1, which was digested with the same restriction enzymes. The sequence of the insert was confirmed by DNA sequencing. The recombinant transfer plasmid pFBB726P was used to make recombinant bacmid DNA and virus using the Bac-To-Bac Baculovirus expression system (BRL Life Technologies, Gaithersburg, Md.). High Five cells were infected with the recombinant virus BVB726P to produce protein. The cDNA and amino acid sequences of the expressed B726P recombinant protein are provided in SEQ ID NO: 482 and 483, respectively.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. An isolated polynucleotide selected from the group consisting of (a) a polynucleotide sequence comprising SEQ ID NO:463, and (b) the complement of (a).

2. An oligonucleotide probe specific for a polynucleotide of claim 1, wherein the oligonucleotide probe consists of at least about 10 contiguous nucleotides of SEQ ID NO:463 or its complement.

3. A composition comprising a first component selected from the group consisting of physiologically acceptable carriers and immunostimulants, and a second component comprising SEQ ID NO:463.

4. An expression vector comprising a polynucleotide of claim 1 operably linked to an expression control sequence.

5. An isolated host cell transformed or transfected with an expression vector according to claim 4.

6. A diagnostic kit comprising at least one oligonucleotide probe according to claim 2.

* * * * *

SEQUENCE LISTING

<160> NUMBER OF SEQ ID NOS: 547

<210> SEQ ID NO 1
<211> LENGTH: 281
<212> TYPE: DNA
<213> ORGANISM: Homo sapien

<400> SEQUENCE: 1
caatgacagt caatctctat cgacagcctg cttcatattt agctattgtt cgtattgcct 60
tctgtcctag gaacagtcat atctcaagtt caaatgccac aacctgagaa gcggtgggct 120
aagataggtc ctactgcaaa ccacccctcc atatttccgt acgcaattac aattcagttt 180
ctgtgacatc tctttacacc actggaggaa aaatgagata ttctctgatt tattctacta 240
taacactcta catagagcta tggtgagtgc taaccacatc g 281

<210> SEQ ID NO 2
<211> LENGTH: 300
<212> TYPE: DNA
<213> ORGANISM: Homo sapien

<400> SEQUENCE: 2
gaggtcctgg gctaacctaa tggtttatta ttggtggaga gaaagatctg gaaatacttg 60
aggttattac atactagatt agcttctaat gtgaaccatt tttcttttaa cagtgataaa 120
ttattatttc cgaagttaac tgttcccttg gtcgtgatac acactcgatt aacaaacata 180
ctgttgtatt ttttccagtt ttgtttggct atgccaccac agtcatcccc agggtctata 240
catactatgt ctcaactgta ttatttgcca tttttggcat tagaatgctt cgggaaggct 300

<210> SEQ ID NO 3
<211> LENGTH: 302
<212> TYPE: DNA
<213> ORGANISM: Homo sapien

<400> SEQUENCE: 3
ggccgaggta attggttaag tctaaagaga ttattattcc ttgatgtttg ctttgtattg 60
gctacaaatg tgcagaggta atacatatgt gatgtcgatg tctctgtctt tttttttgtc 120
tttaaaaaat aattggcagc aactgtattt gaataaaatg atttcttagt atgattgtac 180
agtaatgaat gaaagtggaa catgtttctt tttgaaaggg agagaattga ccatttattg 240
ttgtgatgtt taagttataa cttatcgagc acttttagta gtgataactg tttttaaact 300
tg 302

<210> SEQ ID NO 4
<211> LENGTH: 293
<212> TYPE: DNA
<213> ORGANISM: Homo sapien

<400> SEQUENCE: 4
tgtaccaatc ctttggcaca agaatatgta agaactatag ttgtttttat tggtttttgt 60
tcttgagatt gttttcattc tgtttttgac tgtatctctt taggaggctg aggatggcat 120
tattgcttat gatgactgtg gggtgaaact gactattgct tttcaagcca aggatgtgga 180
aggatctact tctcctcaaa tacgagataa ggcaagataa ttctgctcat tcgagagagg 240
gttaagagtt gtcatcttaa tcataaatcc tgcaggatgg gttcttcaaa ttt 293

-continued

<210> SEQ ID NO 5
<211> LENGTH: 275
<212> TYPE: DNA
<213> ORGANISM: Homo sapien

<400> SEQUENCE: 5
cgaggtttgg aatcagactt ctgtgtccag taaaaaactc ctgcactgaa gtcattgtga 60
cttgagtagt tacagactga ttccagtgaa cttgatctaa tttcttttga tctaatgaat 120
gtgtctgctt accttgtctc cttttaattg ataagctcca agtagttgct aattttttga 180
caactttaaa tgagtttcat tcacttcttt tacttaatgt tttaagtata gtaccaataa 240
tttcattaac ctgttctcaa gtggtttagc tacca 275

<210> SEQ ID NO 6
<211> LENGTH: 301
<212> TYPE: DNA
<213> ORGANISM: Homo sapien

<400> SEQUENCE: 6
gaggtctggt ttcctgggta tgcctggact gttgcccagt gtaagatctg tgcaagccat 60
attggatgga agtttacggc caccaaaaaa gacatgtcac ctcaaaaatt ttggggctta 120
acgcgatctg ctctgttgcc cacgatccca gacactgaag atgaaataag tccagacaaa 180
gtaatacttt gcttgtaaac agatgtgata gagataaagt tatctaacaa attggttata 240
ttctaagatc tgctttggaa attattgcct ctgatacata cctaagtaaa cataacatta 300
a 301

<210> SEQ ID NO 7
<211> LENGTH: 301
<212> TYPE: DNA
<213> ORGANISM: Homo sapien

<400> SEQUENCE: 7
gtccagtttg tacacagtga ttccttatgc acgccgaaag ggtttccgta aaaatgacat 60
tatatacaaa tctgtacacc catccaccag agcgattctc cagctcccag agggagttat 120
caacttaaag caggatacct gaggtttcat gtctttagtt gccttatcat aatcccaaat 180
atacatttca gggtttgttt ttgtttttaa agacactttc ctggaatatg tgcactatgg 240
ttaaaattaa aaacaaaagt aataaaataa aatgatcgct ggaaggactg acctccccac 300
c 301

<210> SEQ ID NO 8
<211> LENGTH: 301
<212> TYPE: DNA
<213> ORGANISM: Homo sapien

<400> SEQUENCE: 8
ctgtcctcat ctctgcaaag ttcagcttcc ttccccaggt ctctgtgcac tctgtcttgg 60
atgctctggg gagctcatgg gtggaggagt ctccaccaga gggaggctca ggggactggt 120
tgggccaggg atgaatattt gagggataaa aattgtgtaa gagccaaaga attggtagta 180
gggggagaac agagaggagc tgggctatgg gaaatgattt gaataatgga gctgggaata 240
tggctggata tctggtacta aaaaagggtc tttaagaacc tacttcctaa tctcttcccc 300
a 301

<210> SEQ ID NO 9

-continued

<211> LENGTH: 301
<212> TYPE: DNA
<213> ORGANISM: Homo sapien

<400> SEQUENCE: 9
gaggtctgcc taagtagagg acaaagactt cctcctttca aaggagaact gagcccagga 60
ttggtaagtt taaggcactt aaccttgacc agctctgtag gtctggagca ttctggtccc 120
tggccgcttt caccaccagg cccttctcac ttatccacct cacatactgc cccagcattc 180
ctttggcatt gcgagctgtg acttgacaca ttttaatgac aagattgaag tagctacctt 240
gcaggataga ttttctgggg tataggggac aaaccaacag tgccatcagg tgtcttaaca 300
c 301

<210> SEQ ID NO 10
<211> LENGTH: 301
<212> TYPE: DNA
<213> ORGANISM: Homo sapien

<400> SEQUENCE: 10
ggcaggtcca acagttcttc cagttctggt cgagctttga atcgtccctt gaagtcttct 60
tcagtgtgct ccttcactga cagtctgact ccttcaggaa gactgctttg gattatttcc 120
aagaaaattt ctgcaaacgt agcactcaaa ccgctgatct gaaccactcg ctcatgggtg 180
gtaagcactg agtccaggag cattttgctg ccttggtcct gcaactgcaa cacttctatg 240
gttttggttg gcattgcata actttcctcg actttaatgg agagagattg cagaggttgt 300
g 301

<210> SEQ ID NO 11
<211> LENGTH: 301
<212> TYPE: DNA
<213> ORGANISM: Homo sapien

<400> SEQUENCE: 11
aggtctgtga ctttcaccca ggacccagga cgcagccctc cgtgggcact gccggcgcct 60
tgtctgcaca ctggaggtcc tccattacag aggcccagcg cacatcgctg gccccacaaa 120
cgttcagggg tacagccatg gcagctcctt cctctgccgt gagaaaagtg cttggagtac 180
ggtttgccac acacgtgact ggacagtgtc caattcaaat ctttcagggc agagtccgag 240
cagcgcttgg tgacagcctg tcctctcctg ctctccaaag gccctgctcc ctgtcctctc 300
t 301

<210> SEQ ID NO 12
<211> LENGTH: 301
<212> TYPE: DNA
<213> ORGANISM: Homo sapien

<400> SEQUENCE: 12
gaggtctggg attacaggca cgtgccacca cacctagcta atttttgagc atggggctca 60
aaggaactgc tctctggggc atgtcagatt tcggatttgg ggctgcacac tgatactctc 120
taagtggtgg aggaacttca tcccactgaa attcctttgg catttggggt tttgtttttc 180
tttttttcct tcttcatcct cctccttttt taaaagtcaa cgagagcctt cgctgactcc 240
accgaagaag tgcaccactg ggagccaccc cagtgccagg cgcccgtcca gggacacaca 300
c 301

-continued

<210> SEQ ID NO 13
<211> LENGTH: 256
<212> TYPE: DNA
<213> ORGANISM: Homo sapien

<400> SEQUENCE: 13 tttttggca taaaaaacac aatgatttaa tttctaaagc acttatatta ttatggcatg 60
gtttgggaaa caggttatta tattccacat aggtaattat gcagtgcttc tcatggaaaa 120
aatgcttagg tattggcctt ttctctggaa accatatttt tcctttttta ataatcaact 180
aaaatgtata tgttaaaaag cctcatcttt tgattttcaa tatacaaaat gctttcttta 240
aaagaacaag attcaa 256

<210> SEQ ID NO 14
<211> LENGTH: 301
<212> TYPE: DNA
<213> ORGANISM: Homo sapien

<400> SEQUENCE: 14
ggtccttgat agaggaagag gaatatccaa ggcaaagcca ccaccacgtc caacctcctc 60
atcctctacc tttcctgtcc ccagaggtat gagatagacc ccctggcctg gttcctgcac 120
tgtgctaggc ccacagtgga cacttccacc ttaatggaga ataggcccca tggagtggag 180
gtccctcctc catggcctgc aacccaatga ctatgggggt gacacaagtg acctctgccc 240
tgtgatggct caacaccatc acacgcaact gtccagacaa gccccctcaa cgggctgctg 300
t 301

<210> SEQ ID NO 15
<211> LENGTH: 259
<212> TYPE: DNA
<213> ORGANISM: Homo sapien

<400> SEQUENCE: 15
gtcttgaaag tatttattgt ttaataattc tttctcccct cagccccatc cggccactct 60
ctctttctgc ttttctgatc atcctaaagg ctgaatacat cctcctcctg tgtggaggac 120
acgaagcaat actaaaatca atacactcga tcaggtcttc atcagatacc acgtcactgt 180
gggtagagtg ctaattttca acaaatgtgg tgttcttagg gccccacaag gtagtccttt 240
ctcaaggtcg ctgggccac 259

<210> SEQ ID NO 16
<211> LENGTH: 301
<212> TYPE: DNA
<213> ORGANISM: Homo sapien

<400> SEQUENCE: 16
cgaggttgtt cacattttca aataaaataat actccccgta agtaataact gcaaccaatc 60
agtgttattc agtgctatgc ctccttgtaa tgggtagtta ttaattattt tcagagcttt 120
ctggaaatac tgtcctaact ggctatgttt aggatctttg ttatctctga agacaaagaa 180
agaactagga ctcttaattt tggggtgctt cttgactctt agttgggaaa ctgaaaatat 240
ttccaacctt ttacccacgt caatggcata ttctgggaat caccaccacc accaccacta 300
c 301

<210> SEQ ID NO 17
<211> LENGTH: 301
<212> TYPE: DNA

-continued

<213> ORGANISM: Homo sapien

<400> SEQUENCE: 17
gcccgggcag gtctggggcc tagggtggct ctttgcaaag ctgaggggca agctaaggaa 60
gccaggcagg tcaggggccc tttcggcctt ctcaagcctc cacctgagtt ctcgtcaatg 120
ccagtctccc tggtatgatt ggggacatta tcagagaaac atctaatagc gcacatctgg 180
gcacccacac tctgcttcag ttgcatccat cctcccaccc caaattcaac tcctgaccca 240
atacaaaaga ctttttttaac caggatttct tcttgcagga aagctgactt ggaaacacgg 300
g 301

<210> SEQ ID NO 18
<211> LENGTH: 301
<212> TYPE: DNA
<213> ORGANISM: Homo sapien

<400> SEQUENCE: 18
attacaggca cgtgccacca cacctagcta atttttgagc atggggctca aaggaactgc 60
tctctggggc atgtcagatt tcggatttgg ggctgcacac tgatactctc taagtggtgg 120
aggaacttca tcccactgaa attcctttgg catttggggt tttgtttttc tttttttcct 180
tcttcatcct cctccttttt taaaagtcaa cgagagcctt cgctgactcc accgaagaag 240
tgcaccactg ggaccaccc agtgccaggc gcccgtccag ggacacacac agtcttcact 300
g 301

<210> SEQ ID NO 19
<211> LENGTH: 301
<212> TYPE: DNA
<213> ORGANISM: Homo sapien

<400> SEQUENCE: 19
agaatctctg cactgtcatc aggtacaaca aaagatcaaa cccctgtccc gatgttaact 60
ttttaactta aaagaatgcc agaaaaccca gatcaacact ttccagctac gagccgtcca 120
caaaggccac ccaaaggcca gtcagactcg tgcagatctt attttttaat agtagtaacc 180
acaatacaca gctctttaaa gctgttcata ttcttccccc attaaacacc tgccccgggc 240
ggccaagggc gaattctgca gatatccatc acactggcgg ccgctcgagc atgcatctag 300
a 301

<210> SEQ ID NO 20
<211> LENGTH: 290
<212> TYPE: DNA
<213> ORGANISM: Homo sapien

<400> SEQUENCE: 20
aggttttttt tttttttttt tttttttttt tttttccctt tcaattcatt taatttcaac 60
aatctgtcaa aaaacagcca ataaacaaat actgaattac attctgctgg gttttttaaa 120
ggctctaaac tataaaaaca tcttgtgtct cccaccctga ccaccctgct acttttccat 180
ataccacagg ccacccataa acacaaagcc agggggtgaa gctgacatgg tctatttgga 240
gccagtaaac aggagggcga taagtcctga taagcactta tggacaatat 290

<210> SEQ ID NO 21
<211> LENGTH: 301
<212> TYPE: DNA
<213> ORGANISM: Homo sapien -continued

<400> SEQUENCE: 21
agaaaggtaa ctgccagcca ggcttgcatt gtttagccag aaattgctgc ttggttctag 60
actctttaaa aaaaaaaaat acccagggtt tgtcatcatt ttcagaggca gagtgccaaa 120
tatcacccaa agctcttgtg tcttttttttt accccttat tttattttta tttattaatt 180
ttttgtgcaa acatcaaatg tcactggtgt tcacagaagg cttttttgac tagccttaaa 240
ttcctgagtc aaaagattaa tcagattttc aggcagtgtt taatcaggtg ctttgtcctg 300
t 301

<210> SEQ ID NO 22
<211> LENGTH: 301
<212> TYPE: DNA
<213> ORGANISM: Homo sapien

<400> SEQUENCE: 22
gacgccatgc accctccggt aaccagcagc cgcctgtcca tcccccaaga ccggaaaggc 60
agcagcagcc cccgggagcc cagggctgtc ctcggtgcat ctggctgcag agggaaattg 120
atgaccttac acagcaacta gcggccatgc agtccttcac tgacaagttc caggaccttt 180
gaagttggag ccagcgtccg gagctgcagc caagcgagtt tcctccttat cctccttagc 240
cagggctttt tctcttccgc tgcatttgcc cccttcccaa cgcaattcaa agcagttgtg 300
a 301

<210> SEQ ID NO 23
<211> LENGTH: 381
<212> TYPE: DNA
<213> ORGANISM: Homo sapien

<400> SEQUENCE: 23
cgaggtccag acagtggacc aagagatacg ctacataaat tggggtttca caattcttac 60
attatttgtc tgtcacagaa gagagctgct tatgattttg aaggggtcag ggagggtggg 120
agttggtaaa gagtagggta tttctataac agatattatt cagtcttatt tcctaagatt 180
ttgttgtaac ttaaggtatc ttgctacagt agacagaatt ggtaatagca acttttaaaa 240
ttgtcattag ttctgcaata ttagctgaaa tgtagtacag aaaagaatgt acatttagac 300
atttgggttc agttgcttgt agtctgtaaa tttaaaacag cttaatttgg tacaggttac 360
acatatggac ctcccgggcg g 381

<210> SEQ ID NO 24
<211> LENGTH: 214
<212> TYPE: DNA
<213> ORGANISM: Homo sapien

<400> SEQUENCE: 24
aatgatgtaa aaattaatca acagggctgc cacttgcgaa tcccctccaa ggatgctgtg 60
caaagggtct cattggtcct gatgaataat cttgtgactg tacatattcc tgggtgcatg 120
tccacaaata ctgaggtata gcctgcatgc cactaaaaat aacaaaggtt tcaggggtgg 180
aaacattgtc caccacactg tcatgaccat cttt 214

<210> SEQ ID NO 25
<211> LENGTH: 302
<212> TYPE: DNA
<213> ORGANISM: Homo sapien -continued

<400> SEQUENCE: 25
gggggcactg agaactccct ctggaattct tggggggtgt tggggagaga ctgtgggcct 60
ggagataaaa cttgtctcct ctaccaccac cctgtaccct agcctgcacc tgtcctcatc 120
tctgcaaagt tcagcttcct tccccaggtc tctgtgcact ctgtcttgga tgctctgggg 180
agctcatggg tggaggagtc tccaccagag ggaggctcag gggactggtt gggccaggga 240
tgaatatttg agggataaaa attgtgtaag aagccaaaga aattggtagt agggggggaga 300 ac 302

<210> SEQ ID NO 26
<211> LENGTH: 301
<212> TYPE: DNA
<213> ORGANISM: Homo sapien

<400> SEQUENCE: 26
ttggagaacg cgctgacata ctgctcggcc acagtcagtg aagctgctgc atctccatta 60
tgttgtgtca gagctgcagc caggattcga atagcttcag ctttagcctt ggccttcgcc 120
agaactgcac tggcctctcc tgctgcctga tttatctgtg cagccttttc tgcttcggag 180
gccaggatct gggcctgttt cttcccttct gccacattga tggccgactc tcgggtcccc 240
tcagactcta gaactgtggc ccgtttccgc cgctctgcct ccacctgcat ctgcatagac 300
t 301

<210> SEQ ID NO 27
<211> LENGTH: 301
<212> TYPE: DNA
<213> ORGANISM: Homo sapien

<400> SEQUENCE: 27
aaatcagtca tcacatctgt gaaaagagtg ctagttataa caaatgagat cacaaatttg 60
accattttat tagacaccct ctattagtgt taacagacaa agatgaaggt taagttgaaa 120
tcaaattgaa atcatcttcc ctctgtacag attgcaatat ctgataatac cctcaacttt 180
cttggtgcaa attaattgcc tggtactcac agtccagtgt taacaggcaa taatggtgtg 240
attccagagg agaggactag gtggcaggaa aataaatgag attagcagta tttgacttgg 300
a 301

<210> SEQ ID NO 28
<211> LENGTH: 286
<212> TYPE: DNA
<213> ORGANISM: Homo sapien

<400> SEQUENCE: 28
tttttttttg cacaggatgc acttattcta ttcattctcc cccacccttc ccatatttac 60
atccttagag gaagagaggg gtaaggtgat aaagtaactg aaggaccgca agacgggtat 120
gtcccttgtt caccaaatgg tcaaagggtc aaagatcgga ggaggtcagg gggtaacgca 180
ggaacaggtg agggcgtttc gccctctctc cctctcccct tttcaacctc ttaatcactg 240
gctaactcgc gacctcatgg gttaattcgt aagcttacac gcgttg 286

<210> SEQ ID NO 29
<211> LENGTH: 301
<212> TYPE: DNA
<213> ORGANISM: Homo sapien

<400> SEQUENCE: 29

-continued

```
gtcatgttct tgctcttcct tctttacaca tttgagttgt gccttctgtt cttaaagaga     60

ttttcctttg ttcaaaggat ttattcctac catttcacaa atccgaaaat aattgaggaa    120

acaggttaca tcattccaat tttgccttgg gtttgaagag tctctcatgg tggcacagtc    180

ctccagggta gctatgttgt tgggctcccc tacatcccag aagctcagag actttgtcaa    240

aggtgtgccg tccacccatt gccactgacc ctcgacaacc tggtctgaca gtccaataaa    300

a                                                                    301


<210> SEQ ID NO 30
<211> LENGTH: 332
<212> TYPE: DNA
<213> ORGANISM: Homo sapien

<400> SEQUENCE: 30

gagcagaatt gatgcctatg gctccaagtc aaatactgct aatctcattt attttcctgc     60

cacctagtcc tctcctctgg aatcacacca ttattgcctg ttaacactgg actgtgagta    120

ccaggcaatt aatttgcacc aagaaagttg agggtattat cagatattgc aatctgtaca    180

gagggaagat gatttcaatt tgatttcaac ttaaccttca tctttgtctg ttaacactaa    240

tagagggtgt ctaataaaat ggtcaaattt gtgatctcat ttgttataac tagcactctt    300

ttcacagatg tgatgactga tttccagcag ac                                  332


<210> SEQ ID NO 31
<211> LENGTH: 141
<212> TYPE: DNA
<213> ORGANISM: Homo sapien

<400> SEQUENCE: 31

aaaggctatc aagtactttg aaggacagga aggaatgaac acacccaggt ggacgtttgg     60

tttcatttgc aggggttcag ggagggttgc aggggttcag ggagggctct tgtcccacaa    120

ccgggggaag ggagagggca c                                              141


<210> SEQ ID NO 32
<211> LENGTH: 201
<212> TYPE: DNA
<213> ORGANISM: Homo sapien

<400> SEQUENCE: 32

gagctgatct cacagcacat acagaatgat gctactatgt agaccctcac tcccttggga     60

aatctgtcat ctaccttaaa gagagaaaaa agatggaaca taggcccacc tagtttcatc    120

catccaccta cataaccaac atagatgtga ggtccactgc actgatagcc agactgcctg    180

gggtaaacct tttcagggag g                                              201


<210> SEQ ID NO 33
<211> LENGTH: 181
<212> TYPE: DNA
<213> ORGANISM: Homo sapien

<400> SEQUENCE: 33

tttcaaaaca ctcatatgtt gcaaaaaaca catagaaaaa taaagtttgg tgggggtgct     60

gactaaactt caagtcacag acttttatgt gacagattgg agcagggttt gttatgcatg    120

tagagaaccc aaactaattt attaaacagg atagaaacag gctgtctggg tgaaatggtt    180

c                                                                    181
```

-continued

<210> SEQ ID NO 34
<211> LENGTH: 151
<212> TYPE: DNA
<213> ORGANISM: Homo sapien

<400> SEQUENCE: 34
atgtcctgca cagtatagct tggacctctg ggcctgaacc agggtgagca tcaaggcccc 60
catttctcct caccacgggg tcgcttgtca gctccaagaa ccagtctggc cccactgaga 120
acttttcagt cgagggcctg atgaatcttg g 151

<210> SEQ ID NO 35
<211> LENGTH: 291
<212> TYPE: DNA
<213> ORGANISM: Homo sapien

<400> SEQUENCE: 35
tctttagggc aaaatcatgt ttctgtgtac ctagcaatgt gttcccattt tattaagaaa 60
agctttaaca cgtgtaatct gcagtcctta acagtggcgt aattgtacgt acctgttgtg 120
tttcagtttg tttttcacct ataatgaatt gtaaaaacaa acatacttgt ggggtctgat 180
agcaaacata gaaatgatgt atattgtttt ttgttatcta tttattttca tcaatacagt 240
attttgatgt attgcaaaaa tagataataa tttatataac aggttttctg t 291

<210> SEQ ID NO 36
<211> LENGTH: 201
<212> TYPE: DNA
<213> ORGANISM: Homo sapien

<400> SEQUENCE: 36
ctgatacaat tataataacg gttccctgaa ccttttagag tgcaattaag aacaaaaact 60
aaattttgtt tacatgaata tggaataaat acaataatca aaatatgact ctccctaaaa 120
gtgaaacaca caagccaatc cggaactgct gtgcgaaaga taaaatcgag aaaggcaagg 180
tttcggtagg aggacgcgat g 201

<210> SEQ ID NO 37
<211> LENGTH: 121
<212> TYPE: DNA
<213> ORGANISM: Homo sapien

<400> SEQUENCE: 37
catcacactg gcggccgctc gagcatgcat ctagagggcc caattcgccc tataatgagt 60
cgtattacaa ttcactggcc gtcgttttac aacgtcgtga ctgggaaaac cctggcgtta 120
c 121

<210> SEQ ID NO 38
<211> LENGTH: 200
<212> TYPE: DNA
<213> ORGANISM: Homo sapien

<400> SEQUENCE: 38
aaacatgtat tactctatat ccccaagtcc tagagcatga cctgcatgtt ggagatgttg 60
tacagcaatg tatttatcca gacatacata tatgatattt agagacacag tgattctttt 120
gataacacca cacatagaac attataatta cacacaaatt tatggtaaaa gaattaatat 180
gctgtctggt gctgctgtta 200

-continued

<210> SEQ ID NO 39
<211> LENGTH: 760
<212> TYPE: DNA
<213> ORGANISM: Homo sapien

<400> SEQUENCE: 39
gcgtggtcgt cggccgaggt cctgggctag acctaatggt ttattattgg tggagagaaa 60
gatctggaaa tacttgaggt tattacatac tagattagct tctaatgtga accatttttc 120
ttttaacagt gatcaaatta ttatttcgaa gttaatcgtt cccttggtgg ctgcatacac 180
atcgcattaa caaacatact gttgtatttt ttcccagttt tgtttggcta tgccaccaca 240
gtcatcccca gggtctatac atactatgtt tcaactgtat tatttgccat ttttggcatt 300
agaatgcttc gggaaggctt aaagatgagc cctgatgagg gtcaagagga actggaagaa 360
gttcaagctg aattaaagaa gaaagatgaa gaagtaagcc atggcactgt tgatctggac 420
caaaaaggca ctcaactagg aataaacact ctacagaggt ttctcagtgg ccccatctgt 480
gtgatatgcg gggctacaca aaaatagctt cttttgcttt gttctgttct tatacctgtc 540
tgtgatctga cttggggttg gtgtgaatgt agtagagaaa ggaagctgac agatgaatac 600
tgaacacagg taatcagttt ccttaattag gttgattata agctcctgaa aagcaggaac 660
tgtattttat aattttacct gtttctcccg tggtgtctag gatagtaagt gagcagagca 720
gtaaatactg tttggtttgt tcagacctgc ccgggcggcc 760

<210> SEQ ID NO 40
<211> LENGTH: 452
<212> TYPE: DNA
<213> ORGANISM: Homo sapien

<400> SEQUENCE: 40
aatcactaaa gatattgact agagaatgct gtgtgctatt tcaattacat ttgtttttct 60
tttattaaca ggaattttga ttcttcaagg aagtggctca atttcaattt caggtgacca 120
ggtttatcgt gacttttcct tcttgtttac ttttcgctag gaaggggagt tgtaggggca 180
gattcaggta ttggaatagg aaaattacgt ctaaaccatg gaaatcttgg aaatggaatt 240
ggtggaagtg ggcgaaatgg atatgggtaa gggaacacaa aaaaccctga agctaattca 300
tcgctgtcac tgatacttct tttttctcgt tcctggtctt gagagactgg gaaaccaaca 360
gccactgcca agatggctgt gatcaggagg agaactttct tcatctcaaa cgtttcagtc 420
agttctttct ctcacctcgg ccgcgaccac gc 452

<210> SEQ ID NO 41
<211> LENGTH: 676
<212> TYPE: DNA
<213> ORGANISM: Homo sapien

<400> SEQUENCE: 41
aatctttgaa tgccaagtct cttctgtact ttcttttatt aacatcatag tctttgcatc 60
aagatacata gcaatgatag caggtttctt tttaaagctt agtattaata ttaaatattt 120
ttccccattt aaattttaca ttacttgcca agaaaaaaaa aaaattaaaa ctcaagttac 180
ttgaagcctg gacacacttc catgattagc cgggctaggt aaaagttggt ggctttattc 240
ttcctgctct ataagcagat ccaggcccta gaaagatggg accagggtat ataattgttt 300
ttgaaaagtg tgctacaaaa atggatggcc tgttataagc caggatacaa agttaaggat 360
gggggtaagg gagggacatt ttcttccaga agaaaagaca gaatttctga agagtcccag 420

-continued tccataattt tcccaaaatg gttggaggag agggtaaaat ctcaacatga gtttcaaagt 480
actgtctctg tgaggggccg gtagatgcct tgctgaggag ggatggctaa tttggaccat 540
gccccatccc cagctaggag aatggaaatg gaaactttaa ttgcccagtg ggtgtgaaag 600
tgggctgaag cttggttggt actgaattct ctaagaggtt tcttctagaa acagacaact 660
cagacctgcc cgggcg 676

<210> SEQ ID NO 42
<211> LENGTH: 468
<212> TYPE: DNA
<213> ORGANISM: Homo sapien

<400> SEQUENCE: 42
agcgtggtcg cggccgaggt ttggccggga gcctgatcac ctgccctgct gagtcccagg 60
ctgagcctca gtctccctcc cttggggcct atgcagaggt ccacaacaca cagatttgag 120
ctcagccctg gtgggcagag aggtagggat ggggctgtgg ggatagtgag gcatcgcaat 180
gtaagactcg ggattagtac acacttgttg attaatggaa atgtttacag atccccaagc 240
ctggcaaggg aatttcttca actccctgcc ccccagccct ccttatcaaa ggacaccatt 300
ttggcaagct ctatgaccaa ggagccaaac atcctacaag acacagtgac catactaatt 360 aaaacccccct gcaaagccca gcttgaaacc ttcacttagg aacgtaatcg tgtcccctat 420
cctacttccc cttcctaatt ccacagacct gcccgggcgg ccgctcga 468

<210> SEQ ID NO 43
<211> LENGTH: 408
<212> TYPE: DNA
<213> ORGANISM: Homo sapien

<400> SEQUENCE: 43
atcatatcaa aacactatct tcccatctgt ttctcaatgc ctgctacttc ttgtagatat 60
ttcatttcag gagagcagca gttaaacccg tggattttgt agttaggaac ctgggttcaa 120
acctctttcc actaattggc tatgtctctg gacagttttt tttttttttt tttttttaa 180 accctttctg aactttcact ttctatggct acctcaaaga attgttgtga ggcttgagat 240
aatgcatttg taaagggtct gccagatagg aagatgctag ttatggattt acaaggttgt 300
taaggctgta agagtctaaa acctacagtg aatcacaatg catttacccc cactgacttg 360
gacataagtg aaaactagcc cgaagtctct ttttcaaatt acttacag 408

<210> SEQ ID NO 44
<211> LENGTH: 160
<212> TYPE: DNA
<213> ORGANISM: Homo sapien

<400> SEQUENCE: 44
tggtcgcggc cgaggtcttg tgtgccctgt ggtccagggg accaagaaca acaagatcca 60
ctctctgtgc tacaatgatt gcaccttctc acgcaacact ccaaccagga ctttcaacta 120
caacttctcc gctttggcaa acaccgtcac tcttgctgga 160

<210> SEQ ID NO 45
<211> LENGTH: 231
<212> TYPE: DNA
<213> ORGANISM: Homo sapien

<400> SEQUENCE: 45
cgagcggccg cccgggcagg tctggggagg tgattccatc cagagtcata tctgttgtca 60

-continued ccccaataag tcgatcagca aggctgacag gctgtgagga aaccccggcc ttgtagcctg 120
tcacctctgg ggggatgatg actgcctggc agacgtaggc tgtgatagat ttgggagaaa 180
acctgactca ccctcaggaa tccggaggtc ggtgacattg tcggtgcaca c 231

<210> SEQ ID NO 46
<211> LENGTH: 371
<212> TYPE: DNA
<213> ORGANISM: Homo sapien

<400> SEQUENCE: 46
cccgggcagg tctgtgtaac atgccaaggc tttgcacttt ctgcagagca gttttttatt 60
ttccttatca ggtacaggtt ttggtttttc ttgactatct ctgatgaatt tttcatgagt 120
ctgtatatgc agaatctttt ccctaaatac tgcttcgtcc catgtctgaa ggcgtaaaat 180
aaagtcattc atcatttttt ctttgtacat gtttatttgt tctttttcaa ttacaccaag 240
cattactagt cagaaggaag cacttgctac ctcttgctct tcctctgcct ctggtttgga 300
tcattttgat gacattgccc acattactca tgaaggatga caagattgca ctgtgcaatg 360
tcaattgcct t 371

<210> SEQ ID NO 47
<211> LENGTH: 261
<212> TYPE: DNA
<213> ORGANISM: Homo sapien

<400> SEQUENCE: 47
gccctgtttt tatacacttc acatttgcag aaatataatg atgccctcat tatcagtgag 60
catgcacgaa tgaaagatgc tctggattac ttgaaagact tcttcagcaa tgtccgagca 120
gcaggattcg atgagattga gcaagatctt actcagagat ttgaagaaaa gctgcaggaa 180
ctagaaagtg tttccaggga tcccagcaat gagaatccta aacttgaaga cctctgcttc 240
atcttacaag aagagtacca c 261

<210> SEQ ID NO 48
<211> LENGTH: 701
<212> TYPE: DNA
<213> ORGANISM: Homo sapien

<400> SEQUENCE: 48
cgagcggccc ccgggcaggt ccaattagta caagtctcat gatataatca ctgcctgcat 60
acatatgcac agatccagtt agtgagtttg tcaagcttaa tctaattggt taagtctcaa 120
agagattatt attcttgatg tttgctttgt attggctaac aaatgtgcag aggtaataca 180
tatgtgatgt ccgatgtctc tgtctttttt tttgtcttta aaaaataatt ggcagcaact 240
gtatttgaat aaaatgattt cttagtatga ttgtaccgta atgaatgaaa gtggaacatg 300
tttctttttg aaagggagag aattgaccat ttattattgt gatgtttaag ttataactta 360
ttgagcactt ttagtagtga taactgtttt taaacttgcc taataccttt cttgggtatt 420
gtttgtaatg tgacttattt aaccccccttt tttgtttgtt taagttgctg ctttaggtta 480
acagcgtgtt ttagaagatt taaatttttt tcctgtctgc acaattagtt attcagagca 540
agagggcctg attttataga agccccttga aaagaggtcc agatgagagc agagatacag 600
tgagaaatta tgtgatctgt gtgttgtggg aagagaattt tcaatatgta actacggagc 660
tgtagtgcca ttagaaactg tgaatttcca aataaatttg a 701

-continued

<210> SEQ ID NO 49
<211> LENGTH: 270
<212> TYPE: DNA
<213> ORGANISM: Homo sapien

<400> SEQUENCE: 49
agcggccgcc cgggcaggtc tgatattagt agctttgcaa ccctgataga gtaaataaat 60
tttatgggcg ggtgccaaat actgctgtga atctatttgt atagtatcca tgaatgaatt 120
tatggaaata gatatttgtg cagctcaatt tatgcagaga ttaaatgaca tcataatact 180
ggatgaaaac ttgcatagaa ttctgattaa atagtgggtc tgtttcacat gtgcagtttg 240
aagtatttaa attaaccact cctttcacag 270

<210> SEQ ID NO 50
<211> LENGTH: 271
<212> TYPE: DNA
<213> ORGANISM: Homo sapien

<400> SEQUENCE: 50
atgcatttat ccatatgaac ttgattattc tgaattactg actataaaaa ggctattgtg 60
aaagatatca cactttgaaa cagcaaatga attttcaatt ttacatttaa ttataagacc 120
acaataaaaa gttgaacatg cgcatatcta tgcatttcac agaagattag taaaactgat 180
ggcaacttca gaattatttc atgaagggta caaacagtct ttaccacaat tttcccatgg 240
tcttatcctt caaaataaaa ttccacacac t 271

<210> SEQ ID NO 51
<211> LENGTH: 241
<212> TYPE: DNA
<213> ORGANISM: Homo sapien

<400> SEQUENCE: 51
tggtcgcggc cgaggtgtga ggagatgaac tttgtgttaa tggggggcac tttaaatcga 60
aatggcttat ccccaccgcc atgtaagtta ccatgcctgt ctcctccctc ctacacattt 120
ccagctcctg ctgcagttat tcctacagaa gctgccattt accagccctc tgtgattttg 180
aatccacgag cactgcaggc cctccacagc gttactaccc agcaggcact cagctcttca 240
t 241

<210> SEQ ID NO 52
<211> LENGTH: 271
<212> TYPE: DNA
<213> ORGANISM: Homo sapien

<400> SEQUENCE: 52
tccaagactt aaaacttagg aaacacctat gatgccactt taactggaag taatggagac 60
atctgattcc aaattcacat tttaaatgcc tatttgcaat cagcaaagag ccaggtatgc 120
tgcatgctgc ttgctgtaag ttacgatttg gcttcactag ctcaaatttt ttcactccac 180
caaaagataa ggcacaggcc cgtttgtcca atcaagtttg ctgaaaatac tgcagcctga 240
gtgtagacaa acttcccctg aatttgctag a 271

<210> SEQ ID NO 53
<211> LENGTH: 493
<212> TYPE: DNA
<213> ORGANISM: Homo sapien

<400> SEQUENCE: 53

-continued

```
ttagcgtggt cgcggtccga ggtctggcct gactagctca ctctgaagag tgtctttcac     60

atggattaac caaaaaatgc attactgcct ttggcacact gtcttgaata ttctttctga    120

caatgagaaa atatgattta atggagtcgt tcaataacct cacaatctcg ctgttccgag    180

cagatagttt tcgtgccaac aggaactggc acatctagca ggttcacggc atgacctttt    240

tgtggactgg ctggcataat tggaatgggt tttgattttt cttctgctaa taactcttca    300

agcttttgaa gttttcaagc attcctctcc agttgcctgt ggttggttct tgaacaccat    360

ctccaacccc accacctcca gatgcaacct tgtctcgtga tacagacctg cccgggcggc    420

cctcaagggc gaattctgca gatatccatc acactggcgg ccgctcgagc atgcatctag    480

gggcccaat tcg                                                         493
```

<210> SEQ ID NO 54
<211> LENGTH: 321
<212> TYPE: DNA
<213> ORGANISM: Homo sapien

<400> SEQUENCE: 54

```
cgtggtcgcg gccgaggtct gtttgcttgt tggtgtgagt ttttcttctg gagactttgt     60

actgaatgtc aataaactct gtgattttgt taggaagtaa aactgggatc tatttagcca    120

ctggtaagct tctgaggtga aggattcagg gacatctcgt ggaacaaaca ctccccactg    180

gactttctct ctggagatac ccttttgaat atacaatggc cttggctcac taggtttaaa    240

tacaaacaag tctgaaaccc actgaagact gagagattgc agcaatattc tctgaattag    300

gatcgggttc cataactcta a                                               321
```

<210> SEQ ID NO 55
<211> LENGTH: 281
<212> TYPE: DNA
<213> ORGANISM: Homo sapien

<400> SEQUENCE: 55

```
ttgcaaatga aactgtggat gtataataag aaaacacaag ggtttattct taacactaaa     60

attaacatgc cacacgaaga ctgcattaca gctctctgtt tctgtaatgc agaaaaatct    120

gaacagccca ccttggttac agctagcaaa gatggttact tcaaagtatg gatattaaca    180

gatgactctg acatatacaa aaaagctgtt ggctggacct gtgactttgt tggtagttat    240

cacaagtatc aagcaactaa ctgttgtttc tccgaagatg g                         281
```

<210> SEQ ID NO 56
<211> LENGTH: 612
<212> TYPE: DNA
<213> ORGANISM: Homo sapien

<400> SEQUENCE: 56

```
gcgtggtcgc ggccgaggtc ctgtccgggg gcactgagaa ctccctctgg aattcttggg     60

gggtgttggg gagagactgt gggcctggag ataaaacttg tctcctctac caccaccctg    120

taccctagcc tgcacctgtc ctcatctctg caaagttcag cttccttccc caggtctctg    180

tgccactctg tcttggatgc tctggggagc tcatgggtgg aggagtctcc accagaggga    240

ggctcagggg actggttggg ccagggatga atatttgagg gataaaaatt gtgtaagagc    300

caaagaattg gtagtagggg gagaacagag aggagctggg ctatgggaaa tgatttgaat    360

aatggagctg ggaatatggc tggatatctg gtactaaaaa agggtcttta agaacctact    420
```

-continued

```
tcctaatctc ttccccaatc caaaccatag ctgtctgtcc agtgctctct tcctgcctcc    480

agctctgccc caggctcctc ctagactctg tccctgggct agggcagggg aggagggaga    540

gcagggttgg gggagaggct gaggagagtg tgacatgtgg ggagaggacc agacctgccc    600

gggcggccgt cg                                                        612
```

<210> SEQ ID NO 57
<211> LENGTH: 363
<212> TYPE: DNA
<213> ORGANISM: Homo sapien

<400> SEQUENCE: 57

```
gtcgcggccg aggtcctgag cgtcacccta gttctgcccc tttttagctg tgtagacttg     60

gacaagacat ttgacttccc tttctccttg tctataaaat gtggacagtg gacgtctgtc    120

acccaagaga gttgtgggag acaagatcac agctatgagc acctcgcacg gtgtccagga    180

tgcacagcac aatccatgat gcgttttctc cccttacgca ctttgaaacc catgctagaa    240

aagtgaatac atctgactgt gctccactcc aacctccagc gtggatgtcc ctgtctgggc    300

cctttttctg ttttttattc tatgttcagc accactggca ccaaatacat tttaattcac    360

cga                                                                  363
```

<210> SEQ ID NO 58
<211> LENGTH: 750
<212> TYPE: DNA
<213> ORGANISM: Homo sapien

<400> SEQUENCE: 58

```
cgtggtcgcg gccgaggtct aattccacct gactggcaga acctgcgccc ctcgcctaac     60

ctgcgccctt ctcccaactc gcgtgcctca cagaacccag gtgctgcaca gccccgagat    120

gtggcccttc ttcaggaaag agcaaataag ttggtccaag tacttgatgc ttaaggaata    180

cacaaaggtg cccatcaagc gctcagaaat gctgagagat atcatccgtg aatacactga    240

tgtttatcca gaaatcattg aacgtgcatg ctttgtccta gagaagaaat ttgggattca    300

actgaaagaa attgacaaag aagaacacct gtatattctc atcagtaccc ccgagtccct    360

ggctggcata ctgggaacga ccaaagacac acccaagctc ggtctcttct tggtgattct    420

gggtgtcatc ttcatgaatg gcaaccgtgc cagtgaggct gtcttttggg aggcactacg    480

caagatggga ctgcgtcctg ggtgagaca tcccctccct tggagatcta aggaaacttc    540

tcacctatga gtttgtaaag cagaaatacc tggactacag acgagtgccc aacagcaacc    600

ccccggagta tgagttcctc tggggcctcc gtccctacca tgagactagc aagatgaaaa    660

tgctgagatt cattgcagag gttcagaaaa gagaccctcg tgactggact gcacagttca    720

tggaggctgc agatgaggac ctgcccgggc                                     750
```

<210> SEQ ID NO 59
<211> LENGTH: 505
<212> TYPE: DNA
<213> ORGANISM: Homo sapien

<400> SEQUENCE: 59

```
tggccgcccg ggcaggtcca gtctacaagc agagcactct catggggagc accagatgag     60

ttccagccgc agttctttta taagctttaa gtgcctcatg aagacgcgag gatctcttcc    120

aagtgcaacc tggtcacatc agggcacatt cagcagcaga agtctgtttc cagtatagtc    180

cttggtatgg ctaaattcca ctgtcccttt ctcagcagtc aataatccat gataaattct    240
```

-continued

```
gtacaacact gtagtcaata acagcagcac cagacagcat attaattctt ttaccataaa    300

tttgtgtgta attataatgt tctatgtgtg gtgttatcaa aagaatcact gtgtctctaa    360

atatcatata tgtatgtctg gataaataca ttgctgtaca acatctccaa catgcaggtc    420

atgctctaag acttggggat atagagtaat acatgtttcg tggacctcgg ccgcgaccac    480

gctaagggcg aattctgcag atatc                                          505
```

```
<210> SEQ ID NO 60
<211> LENGTH: 520
<212> TYPE: DNA
<213> ORGANISM: Homo sapien

<400> SEQUENCE: 60

cgtggtcgcg gccgaggtcc tcaggacaag gaaacaggta tcagcatgat ggtagcagaa     60

accttatcac caaggtgcag gagctgactt cttccaaaga gttgtggttc cgggcagcgg    120

tcattgcctg cccttgctgg agggctgatt ttagtgttgc ttattatgtt ggccctgagg    180

atgcttcgaa gtgaaaataa gaggctgcag gatcagcggc aacagatgct ctcccgtttg    240

cactacagct ttcacggaca ccattccaaa aaggggcagg ttgcaaagtt agacttggaa    300

tgcatggtgc cggtcagtgg gcacgagaac tgctgtctga cctgtgataa aatgagacaa    360

gcagacctca gcaacgataa gatcctctcg cttgttcact ggggcatgta cagtgggcac    420

gggaagctgg aattcgtatg acggagtctt atctgaacta cacttactga acagcttgaa    480

ggacctgccc gggcggccgc tcgaaagggg cgaattctgc                          520
```

```
<210> SEQ ID NO 61
<211> LENGTH: 447
<212> TYPE: DNA
<213> ORGANISM: Homo sapien

<400> SEQUENCE: 61

agagaggtgt ttttattctt tggggacaaa gccgggttct gtgggtgtag gattctccag     60

gttctccagg ctgtagggcc cagaggctta atcagaattt tcagacaaaa ctggaacctt    120

tctttttttcc cgttggttta tttgtagtcc ttgggcaaac caatgtcttt gttcgaaaga    180

gggaaaataa tccaaacgtt tttcttttaa cttttttttt aggttcaggg gcacatgtgt    240

aggcttgcta tataggtaaa ttgcatgtca ccagggtttg ttgtacagat tatttcatca    300

tccagataaa aagcatagta ccagataggt agttttttga tcctcaccct ccttccatgc    360

tccgacctca ggtaggcccc agtgtctgac ctgcccggcg gcccgctcga aagggccaat    420

tctgcagata tccatcacac tggccgg                                        447
```

```
<210> SEQ ID NO 62
<211> LENGTH: 83
<212> TYPE: PRT
<213> ORGANISM: Homo sapien

<400> SEQUENCE: 62

Lys Lys Val Leu Leu Leu Ile Thr Ala Ile Leu Ala Val Ala Val Gly
 1               5                  10                  15

Phe Pro Val Ser Gln Asp Gln Glu Arg Glu Lys Arg Ser Ile Ser Asp
            20                  25                  30

Ser Asp Glu Leu Ala Ser Gly Phe Phe Val Phe Pro Tyr Pro Tyr Pro
        35                  40                  45

Phe Arg Pro Leu Pro Pro Ile Pro Phe Pro Arg Phe Pro Trp Phe Arg
```

-continued

```
    50                  55                  60

Arg Asn Phe Pro Ile Pro Ile Pro Ser Ala Pro Thr Thr Pro Leu Pro
65                  70                  75                  80

Ser Glu Lys


<210> SEQ ID NO 63
<211> LENGTH: 683
<212> TYPE: DNA
<213> ORGANISM: Homo sapien

<400> SEQUENCE: 63

acaaagattg gtagctttta tattttttta aaaatgctat actaagagaa aaaacaaaag     60

accacaacaa tattccaaat tataggttga gagaatgtga ctatgaagaa agtattctaa    120

ccaactaaaa aaaatattga aaccactttt gattgaagca aaatgaataa tgctagattt    180

aaaaacagtg tgaaatcaca ctttggtctg taaacatatt tagctttgct tttcattcag    240

atgtatacat aaacttattt aaaatgtcat ttaagtgaac cattccaagg cataataaaa    300

aaagwggtag caaatgaaaa ttaaagcatt tattttggta gttcttcaat aatgatrcga    360

gaaactgaat tccatccagt agaagcatct ccttttgggt aatctgaaca agtrccaacc    420

cagatagcaa catccactaa tccagcacca attccttcac aaagtccttc cacagaagaa    480

gtgcgatgaa tattaattgt tgaattcatt tcagggcttc cttggtccaa ataaattata    540

gcttcaatgg gaagaggtcc tgaacattca gctccattga atgtgaaata ccaacgctga    600

cagcatgcat ttctgcattt tagccgaagt gagccactga acaaaactct tagagcacta    660

tttgaacgca tctttgtaaa tgt                                            683


<210> SEQ ID NO 64
<211> LENGTH: 749
<212> TYPE: DNA
<213> ORGANISM: Homo sapien
<220> FEATURE:
<221> NAME/KEY: misc_feature
<222> LOCATION: (1)...(749)
<223> OTHER INFORMATION: n = A,T,C or G

<400> SEQUENCE: 64

ctgttcattt gtccgccagc tcctggactg gatgtgtgaa aggcatcaca tttccatttt     60

cctccgtgta aatgttttat gtgttcgcct actgatccca ttcgttgctt ctattgtaaa    120

tatttgtcat ttgtatttat tatctctgtg ttttccccct aaggcataaa atggtttact    180

gtgttcattt gaacccattt actgatctct gttgtatatt tttcatgcca ctgctttgtt    240

ttctcctcag aagtcgggta gatagcattt ctatcccatc cctcacgtta ttggaagcat    300

gcaacagtat ttattgctca gggtcttctg cttaaaactg aggaaggtcc acattcctgc    360

aagcattgat tgagacattt gcacaatcta aaatgtaagc aaagtaagtc attaaaaata    420

caccctctac ttgggcttta tactgcatac aaatttactc atgagccttc ctttgaggaa    480

ggatgtggat ctccaaataa agatttagtg tttattttga gctctgcatc ttancaagat    540

gatctgaaca cctctccttt gtatcaataa atagccctgt tattctgaag tgagaggacc    600

aagtatagta aaatgctgac atctaaaact aaataaatag aaaacaccag gccagaacta    660

tagtcatact cacacaaagg gagaaattta aactcgaacc aagcaaaagg cttcacggaa    720

atagcatgga aaaacaatgc ttccagtgg                                      749

<210> SEQ ID NO 65
```

-continued

<211> LENGTH: 612
<212> TYPE: DNA
<213> ORGANISM: Homo sapien

<400> SEQUENCE: 65
acagcagcag tagatggctg caacaacctt cctcctaccc cagcccagaa aatatttctg 60
ccccacccca ggatccggga ccaaaataaa gagcaagcag gccccccttca ctgaggtgct 120 gggtagggct cagtgccaca ttactgtgct ttgagaaaga ggaaggggat ttgtttggca 180
ctttaaaaat agaggagtaa gcaggactgg agaggccaga gaagatacca aaattggcag 240
ggagagacca tttggcgcca gtcccctagg agatgggagg agggagatag gtatgagggt 300
aggcgctaag aagagtagga ggggtccact ccaagtggca gggtgctgaa atgggctagg 360
accaacagga cactgactct aggtttatga cctgtccata cccgttccac agcagctggg 420
tgggagaaat caccattttg tgacttctaa taaaataatg ggtctaggca acagttttca 480
atggatgcta aaacgattag gtgaaaagtt gatggagaat tttaattcag gggaattagg 540
ctgataccat ctgaaaccat ttggcatcat taaaaatgtg acaacctggt ggctgccagg 600
gaggaagggg ag 612

<210> SEQ ID NO 66
<211> LENGTH: 703
<212> TYPE: DNA
<213> ORGANISM: Homo sapien

<400> SEQUENCE: 66
tagcgtggtc gcggccgagg tacattgatg ggctggagag cagggttggc agcctgttct 60
gcacagaacc aagaattaca gaaaaaagtc caggagctgg agaggcacaa catctccttg 120
gtagctcagc tccgccagct gcagacgcta attgctcaaa cttccaacaa agctgcccag 180
accagcactt gtgttttgat tcttcttttt tccctggctc tcatcatcct gcccagcttc 240
agtccattcc agagtcgacc agaagctggg tctgaggatt accagcctca cggagtgact 300
tccagaaata tcctgaccca caaggacgta acagaaaatc tggagaccca agtggtagag 360
tccagactga gggagccacc tggagccaag gatgcaaatg gctcaacaag gacactgctt 420
gagaagatgg gagggaagcc aagacccagt gggcgcatcc ggtccgtgct gcatgcagat 480
gagatgtgag ctggaacaga ccttcctggc ccacttcctg atcacaagga atcctgggct 540
tccttatggc tttgcttccc actgggattc ctacttaggt gtctgccctc aggggtccaa 600
atcacttcag gacaccccaa gagatgtcct ttagtctctg cctgaggcct agtctgcatt 660
tgtttgcata tatgagaggg tacctgcccg ggcggccgct cga 703

<210> SEQ ID NO 67
<211> LENGTH: 1022
<212> TYPE: DNA
<213> ORGANISM: Homo sapien

<400> SEQUENCE: 67
cttgagaaag caggattgtt ttaagttcca agatttaaca aacttactgt tcagcatcat 60
attcaagcct aaaaggaaga taggattttc aagatatatt tccaacttct ttaacatggc 120
accatggatg aactgtttct cagcactgtg ctgcttcact tggaattaag gatgaattgg 180
gaggagacag tatgacatag gtgggtaggt tgggtggtga ggggaaccag ttctaatagt 240
cctcaactcc actccagctg ttcctgttcc acacggtcca ctgagctggc ccagtccctt 300
tcactcagtg tgtcaccaaa ggcagcttca aggctcaatg gcaagagacc acctataacc 360

-continued

```
tcttcacctt ctgctgcctc tttctgctgc cactgactgc catggccatc tgctatagcc    420

gcattgtcct cagtgtgtcc aggccccaga caaggaaggg gagccatggt gagactccaa    480

ttcccaggcc ttaatcctta accctagacc tgttgcctct agcatcattt atttatctac    540

ctacctaata gctatctacc agtcattaaa ccatggtgag attctaacca tgtctagcac    600

ctgatgctag agataatttt gttgaatccc ttcaattata aacagctgag ttagctggac    660

aaggactagg gaggcaatca gtattattta ttcttgaaca ccatcaagtc tagacttggt    720

ggcttcatat ttctatcata atccctgggg gtaagaaatc atatagcccc aggttgggaa    780

ggggaaaacg gtttgcaaca ttctcctcct tgtaggaggc gagctctgtc tcactagcta    840

tgcccctcca tcaattcacc ctatactcag atcagaagct gagtgtctga attacagtat    900

attttctaaa ttcctagccc ctgctggtga atttgccctc ccccgctcct ttgacaattg    960

tccccgtgtt cgtctccggg ccctgagact ggccctgctt atcttgctga ccttcatcct   1020

ct                                                                  1022
```

<210> SEQ ID NO 68
<211> LENGTH: 449
<212> TYPE: DNA
<213> ORGANISM: Homo sapien

<400> SEQUENCE: 68

```
ccagatccat tttcagtggt ctggatttct ttttattttc ttttcaactt gaaagaaact     60

ggacattagg ccactatgtg ttgttactgc cactagtgtt caagtgcctc ttgttttccc    120

agagatttcc tgggtctgcc agaggcccag acaggctcac tcaagctctt taactgaaaa    180

gcaacaagcc actccaggac aaggttcaaa atggttacaa cagcctctac ctgtcgcccc    240

agggagaaag gggtagtgat acaagtctca tagccagaga tggttttcca ctccttctag    300

atattcccaa aaagaggctg agacaggagg ttattttcaa ttttattttg gaattaaata    360

ctttttttccc tttattactg ttgtagtccc tcacttggat atacctctgt tttcacgata    420

gaaataaggg aggtctagag cttctattc                                     449
```

<210> SEQ ID NO 69
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 69

```
gcccttagcg tgggtcgcgg cncgangtct ggagcntatg tgatncctat ggtncncagg     60

cnnatactgc tantctcatt tattctcctg cnacctantc ctctnctctg gaatcacacc    120

attattgcct gttaacactg gactgtgagt accangcaat taatttgcac caanaaagtt    180

gagggtatta tcanatattg caatctgtac agagggaaga tgatttcaat ttgatttcaa    240

cttaaccttc atctttgtct gttaacacta atagagggtg tctaataaaa tggcaaattt    300

gngatctcat tnggtataac tacactcttt ttcacagatg tgatgactga atttccanca    360

acctgcccgg gcggncgntc naagggc                                        387
```

<210> SEQ ID NO 70
<211> LENGTH: 836
<212> TYPE: DNA

-continued

<213> ORGANISM: Homo sapien

<400> SEQUENCE: 70
tattccattt acaaaataaa ttcagccctg cactttcttt agatgccttg atttccagaa 60
tggagcttag tgctactgaa taccctggcc acagagccac ctcaggatat tcttttctcc 120
accctagttt atttatttat agatatctgt ttacaaagtc tgtagtaaat cctgatgctg 180
accatctgaa atgtactttt tttctgaatg ctgtttcaat ctaaaatagc agcttttgag 240
aaaacaatga tgtaaattcc ttatgataaa aggatgattc tatatattct ttaatgatat 300
taaatatgcc gaagccaagc acacagtctt tctaaagtgt gtgtatgttt gtgtgaatgt 360
gaatgatact gatcttatat ctgttaaaag ttgttttaaa aagctgtggc atcccattgt 420
tcatatttgc caagtcttct gtaaagatgt ctaggacgaa atattttatg tgctaatgca 480
tgtatttgta aaccagattt gtttaccact caaaattaac ttgttttctt catccaaaaa 540
agtttatttc ttccacgtac ttaaattttc tgtgtgggta taatatagct ttctaatttt 600
tttctttcac aaaggcaggt tcaaaattct gttgaaagaa aaatgctttc tgaaactgag 660
gtataacacc agagcttgct gtttaaagga ttatatgatg tacatcagtt ctataaatgt 720
gctcagcagt ttaacatgtg aatcctgttt taaagtgctc agatttcaac tgtgtaagcc 780
attgatataa cgctgtaatt aaaaatgttt atatgaaaaa aaaaaaaaaa aaaaaa 836

<210> SEQ ID NO 71
<211> LENGTH: 618
<212> TYPE: DNA
<213> ORGANISM: Homo sapien

<400> SEQUENCE: 71
gttgcagtga gctcaagtgt tgggtgtatc agctcaaaac accatgtgat gccaatcatc 60
tccacaggag caatttgttt accttttttt tctgatgctt tactaacttc atcttttaga 120
tttaaatcat tagtagatcc tagaggagcc agtttcagaa aatatagatt ctagttcagc 180
accacccgta gttgtgcatt gaaataatta tcattatgat tatgtatcag agcttctggt 240
tttctcattc tttattcatt tattcaacaa ccacgtgaca aacactggaa ttacaggatg 300
aagatgagat aatccgctcc ttggcagtgt tatactatta tataacctga aaaaacaaac 360
aggtaatttt cacacaaagt aatagatatc atgacacatt taaaataggg cactactgga 420
acacacagat aggacatcca ggttttgggt caatattgta gactttttgg tggatgagat 480
atgcaggttg atrccagaag gacaacaaaa acatatgtca gatagaaggg aggagcaaat 540
gccaagagct ggagctgagg aagatcactg tgaaattcta tgtagtctag ttggctggat 600
gctagagcaa agaggtgg 618

<210> SEQ ID NO 72
<211> LENGTH: 806
<212> TYPE: DNA
<213> ORGANISM: Homo sapien

<400> SEQUENCE: 72
tctacgatgg ccatttgctc attgtctttc ctctgtgtgt agtgagtgac cctggcagtg 60
tttgcctgct cagagtggcc cctcagaaca acagggctgg ccttggaaaa accccaaaac 120
aggactgtgg tgacaactct ggtcaggtgt gatttgacat gagggccgga ggcggttgct 180
gacggcagga ctggagaggc tgcgtgcccg gcactggcag cgaggctcgt gtgtccccca 240
ggcagatctg ggcactttcc caacccaggt ttatgccgtc tccagggaag cctcggtgcc 300

-continued

```
agagtggtgg gcagatctga ccatccccac agaccagaaa caaggaattt ctgggattac    360

ccagtccccc ttcaacccag ttgatgtaac cacctcattt tttacaaata cagaatctat    420

tctactcagg ctatgggcct cgtcctcact cagttattgc gagtgttgct gtccgcatgc    480

tccgggcccc acgtggctcc tgtgctctag atcatggtga ctcccccgcc ctgtggttgg    540

aatcgatgcc acggattgca ggccaaattt cagatcgtgt ttccaaacac ccttgctgtg    600

ccctttaatg ggattgaaag cacttttacc acatggagaa atatattttt aatttgtgat    660

gcttttctac aaggtccact atttctgagt ttaatgtgtt tccaacactt aaggagactc    720

taatgaaagc tgatgaattt tcttttctgt ccaaacaagt aaaataaaaa taaaagtcta    780

tttagatgtt gaaaaaaaaa aaaaaa                                          806
```

<210> SEQ ID NO 73
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 73

```
actctggtaa gcttgttgtt gtccaagtga agctccctca gatgaggcgt gttggccana     60

gagccattgt caacagcaga gatgctgttg aaactcaatc ccaacttagc caaattattc    120

agtcctttca ggctagctgc atcaactctg ctgattttgt tgccatcaag atgtaattcc    180

gtaagggaag gaggaagacc ttgaggaatg ctggygatat tggyatcagc aatgcggatg    240

tasgaagagc ttcttcmttc cctggaaagc cccattttca atyccttgag ctcttcakcg    300

g                                                                    301
```

<210> SEQ ID NO 74
<211> LENGTH: 401
<212> TYPE: DNA
<213> ORGANISM: Homo sapien

<400> SEQUENCE: 74

```
agtttacatg atccctgtaa cagccatggt ctcaaactca gatgcttcct ccatctgcca     60

agtgtgttct ggatacagag cacatcgtgg cttctggggt cacactcagc ttaggctgtg    120

ggtccacaga gcactcatct ggctgggcta tggtggtggt ggctctactc aagaagcaaa    180

gcagttacca gcacattcaa acagtgtatt gaacatcttt taaatatcaa agtgagaaac    240

aagaaggcaa cataataatg ttatcagaaa gatgttagga agtaaggaca gctgtgtaaa    300

gcttgaggct gaaaagtagc ttgccagctt catttctttg gtttcttggg tagtgggccg    360

ccggaacagc aagatgtgag gttctggttc atggatcata t                        401
```

<210> SEQ ID NO 75
<211> LENGTH: 612
<212> TYPE: DNA
<213> ORGANISM: Homo sapien

<400> SEQUENCE: 75

```
ttatttttca atttttattt tggttttctt acaaaggttg acattttcca taacaggtgt     60

aagagtgttg aaaaaaaaat tcaaattttt ggggagcgag ggaaggagtt aatgaaactg    120

tattgcacaa tgctctgatc aatccttctt tttctctttt gcccacaatt taagcaagta    180
```

-continued

```
gatgtgcaga agaaatggaa ggattcagct ttcagttaaa aaagaagaag aagaaatggc    240

aaagagaaag ttttttcaaa tttctttctt ttttaattta gattgagttc atttatttga    300

aacagactgg gccaatgtcc acaaagaatt cctggtcagc accaccgatg tccaaaggtg    360

caatatcaag gaagggcagg cgtgatggct tatttgtttt gtattcaatg attgtctttc    420

cccattcatt tgtcttttta gagcagccat ctacaagaac agtgtaagtg aacctgctgt    480

tgccctcagc aacaagttca acatcattag agccctgtag aatgacagcc tttttcaggt    540

tgccagtctc ctcatccatg tatgcaatgc tgttcttgca gtggtaggtg atgttctgag    600

aggcatagtt gg                                                        612
```

<210> SEQ ID NO 76
<211> LENGTH: 844
<212> TYPE: DNA
<213> ORGANISM: Homo sapien

<400> SEQUENCE: 76

```
ggctttcgag cggccgcccg ggcaggtctg atggttctcg taaaaacccc gctagaaact     60

gcagagacct gaaattctgc catcctgaac tcaagagtgg agaatactgg gttgacccta    120

accaaggatg caaattggat gctatcaagg tattctgtaa tatggaaact ggggaaacat    180

gcataagtgc caatcctttg aatgttccac ggaaacactg gtggacagat tctagtgctg    240

agaagaaaca cgtttggttt ggagagtcca tggatggtgg ttttcagttt agctacggca    300

atcctgaact tcctgaagat gtccttgatg tgcagcykgc attccttcga cttctctcca    360

gccgagcttc ccagaacatc acatatcact gcaaaaatag cattgcatac atggatcagg    420

ccagtggaaa tgtaaagaag gccctgaagc tgatggggtc aaatgaaggt gaattcaagg    480

ctgaaggaaa tagcaaattc acctacacag ttctggagga tggttgcacg aaacacactg    540

gggaatggag caaaacagtc tttgaatatc gaacacgcaa tgctgttcct tgacattgca    600

ccaccaatgt ccagaggtgc aatgtcaagg aacggcaggc gagatggctt atttgttttg    660

tattcaatga ttgtcttgcc ccattcattt gtctttttgg agcagccatc gactaggaca    720

gagtaggtga acctgctgtt gccctcagca acaagttcca catcgttgga accctgcaga    780

agcacagcct tgttcaarct gcccgtctcc tcatccagat acctcggccg cgaccacgct    840

aatc                                                                 844
```

<210> SEQ ID NO 77
<211> LENGTH: 314
<212> TYPE: DNA
<213> ORGANISM: Homo sapien

<400> SEQUENCE: 77

```
ccagtcctcc acttggcctg atgagagtgg ggagtggcaa gggacgtttc tcctgcaata     60

gacacttaga tttctctctt gtgggaagaa accacctgtc catccactga ctcttctaca    120

ttgatgtgga aattgctgct gctaccacca cctcctgaag aggcttccct gatgccaatg    180

ccagccatcc tggcatcctg gccctcgagc aggctgcggt aagtagcgat ctcctgctcc    240

agccgtgtct ttatgtcaag cagcatcttg tactcctggt tctgagcctc catctcgcat    300

cggagctcac tcag                                                      314
```

<210> SEQ ID NO 78
<211> LENGTH: 548
<212> TYPE: DNA
<213> ORGANISM: Homo sapien -continued

<400> SEQUENCE: 78
accaagagcc aagtgttaca caggatattt taaaaataaa atgtttttgg aatcctcacc 60
tcccatgcta tcttctaaga taactacaaa tattcttcaa agatttaact gagttctgcc 120
aaggacctcc caggactcta tccagaatga ttattgtaaa gctttacaaa tcccaccttg 180
gccctagcga taattaggaa atcacaggca aacctcctct ctcggagacc aatgaccagg 240
ccaatcagtc tgcacattgg ttttgttaga tactttgtgg agaaaaacaa aggctcgtga 300
tagtgcagct ctgtgcctac agagagcctc ccttttggtt ctgaaattgc tgatgtgaca 360
gagacaaagc tgctatgggt ctaaaacctt caataaagta actaatgaca ctcaaggtcc 420
tgggactctg agacagacgg tggtaaaacc cacagctgcg attcacattt ccaatttatt 480
ttgagctctt tctgaagctg ttgcttccta cctgagaatt cccatttaga gagctgcaca 540
gcacagtc 548

<210> SEQ ID NO 79
<211> LENGTH: 646
<212> TYPE: DNA
<213> ORGANISM: Homo sapien

<400> SEQUENCE: 79
accccgtcac tatgtgaata aaggcagcta gaaaatggac tcaattctgc aagccttcat 60
ggcaacagcc catattaaga cttctagaac aagttaaaaa aaatcttcca tttccatcca 120
tgcatgggaa aagggcttta gtatagttta ggatggatgt gtgtataata ataaaatgat 180
aagatatgca tagtggggga ataaagcctc agagtccttc cagtatgggg aatccattgt 240
atcttagaac cgagggattt gtttagattg ttgatctact aattttttc ttcacttata 300 tttgaatttt caatgatagg acttattgga aattggggat aattctgttg tggtattaaa 360
taatattcat tttttaaaaa ctcatcttgg tattgagtta gtgcattgac ttccaatgaa 420
ttgacataag cccatatttc attttaacca gaaacaaaaa ctagaaaatg ttactcccta 480
aataggcaac aatgtatttt ataagcactg cagagattta gtaaaaaaca tgtatagtta 540
ctttagaaac aacttctgac acttgagggt tacccaatgg tctccttccc attctttata 600
tgaggtaaat gcaaaccagg gagccaccga ataaacagcc ctgagt 646

<210> SEQ ID NO 80
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 80
gtctgaatga gcttcnctgc gagatgganc ancataaccc agaantccaa aancntanng 60
aacgnnaaaa cccgntngaa caagnaaacn gcaactnacg gccgcctgnt gnagggcgag 120
gacgcccacc tctcctcctc ccagttctcc tctggatcgc agncatccan agatgtgacc 180
tcttccagcc gccaaatccg caccaaggtc atggatgtgc acgatggcaa ggtgggtgtc 240
cacccacgaa caggtccttc gcaccaagaa ctgagg 276

<210> SEQ ID NO 81
<211> LENGTH: 647
<212> TYPE: DNA

-continued

<213> ORGANISM: Homo sapien

<400> SEQUENCE: 81
gtcctgcctt tcatcttttc tttaaaaaaa ataaatgttt acaaaacatt tccctcagat 60
tttaaaattc atggaagtaa taaacagtaa taaaatatgg atactatgaa aactgacaca 120
cagaaaaaca taaccataaa atattgttcc aggatacaga tattaattaa gagtgacttc 180
gttagcaaca cgtagacatt catacatatc cggtggaaga ctggtttctg agatgcgatt 240
gccatccaaa cgcaaatgct tgatcttgga gtaggrtaat ggccccagga tcttgcagaa 300
gctctttatg tcaaacttct caagttgatt gacctccagg taatagtttt caaggttttc 360
attgacagtt ggtatgtttt taagcttgtt ataggacaga tccagctcaa ccagggatga 420
cacattgaaa gaatttccag gtattccact atcagccagt tcgttgtgag ataaacgcag 480
atactgcaat gcattaaaac gcttgaaata ctcatcaggg atgttgctga tcttattgtt 540
gtctaagtag agagttagaa gagagacagg gagaccagaa ggcagtctgg ctatctgatt 600
gaagctcaag tcaaggtatt cgagtgattt aagaccttta aaagcag 647

<210> SEQ ID NO 82
<211> LENGTH: 878
<212> TYPE: DNA
<213> ORGANISM: Homo sapien

<400> SEQUENCE: 82
ccttctttcc ccactcaatt cttcctgccc tgttattaat taagatatct tcagcttgta 60
gtcagacaca atcagaatya cagaaaaatc ctgcctaagg caaagaaata taagacaaga 120
ctatgatatc aatgaatgtg ggttaagtaa tagatttcca gctaaattgg tctaaaaaag 180
aatattaagt gtggacagac ctatttcaaa ggagcttaat tgatctcact tgttttagtt 240
ctgatccagg gagatcaccc ctctaattat ttctgaactt ggttaataaa agtttataag 300
atttttatga agcagccact gtatgatatt ttaagcaaat atgttattta aaatattgat 360
ccttcccttg gaccaccttc atgttagttg ggtattataa ataagagata caaccatgaa 420
tatattatgt ttatacaaaa tcaatctgaa cacaattcat aaagatttct cttttatacc 480
ttcctcactg gccccctcca cctgcccata gtcaccaaat tctgttttaa atcaatgacc 540
taagatcaac aatgaagtat tttataaatg tatttatgct gctagactgt gggtcaaatg 600
tttccatttt caaattattt agaattctta tgagtttaaa atttgtaaat ttctaaatcc 660
aatcatgtaa aatgaaactg ttgctccatt ggagtagtct cccacctaaa tatcaagatg 720
gctatatgct aaaaagagaa aatatggtca agtctaaaat ggctaattgt cctatgatgc 780
tattatcata gactaatgac atttatcttc aaaacaccaa attgtcttta gaaaaattaa 840
tgtgattaca ggtagagaac ctcggccgcg accacgct 878

<210> SEQ ID NO 83
<211> LENGTH: 645
<212> TYPE: DNA
<213> ORGANISM: Homo sapien

<400> SEQUENCE: 83
acaaacattt tacaaaaaag aacattacca atatcagtgg cagtaagggc aagctgaaga 60
ataaatagac tgagtttccg ggcaatgtct gtcctcaaag acatccaaac tgcgttcagg 120
cagctgaaac aggcttcttt cccagtgaca agcatatgtg gtcagtaata caaacgatgg 180
taaatgaggc tactacatag gcccagttaa caaactcctc ttctcctcgg gtaggccatg 240

-continued

```
atacaagtgg aactcatcaa ataatttaaa cccaaggcga taacaacgct atttcccatc    300

taaactcatt taagccttca caatgtcgca atggattcag ttacttgcaa acgatcccgg    360

gttgtcatac agatacttgt ttttacacat aacgctgtgc catcccttcc ttcactgccc    420

cagtcaggtt tcctgttgtt ggaccgaaag gggatacatt ttagaaatgc ttccctcaag    480

acagaagtga gaaagaaagg agaccctgag gccaggatct attaaacctg gtgtgtgcgc    540

aaaagggagg gggaaggcag gaatttgaaa ggataaacgt ctcctttgcg ccgaggaatc    600

aggaagcgtg actcacttgg gtctgggacg ataccgaaat ccggt                    645


<210> SEQ ID NO 84
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 84

tctgatgtca atcacaactt gaaggatgcc aatgatgtac caatccaatg tgaaatctct     60

cctcttatct cctatgctgg agaaggatta gaaggttatg tggcagataa agaattccat    120

gcacctctaa tcatcgatga gaatggagtt catgggctgg tgaaaaatgg tatttgaacc    180

agataccaag ttttgtttgc cacgatagga atagctttta tttttgatag accaactgtg    240

aacctacaag acgtcttgga caactgaagn ttaaatatcc acanggggttt attttgcttg    300

g                                                                    301


<210> SEQ ID NO 85
<211> LENGTH: 296
<212> TYPE: DNA
<213> ORGANISM: Homo sapien
<220> FEATURE:
<221> NAME/KEY: misc_feature
<222> LOCATION: (1)...(296)
<223> OTHER INFORMATION: n = A,T,C or G

<400> SEQUENCE: 85

agcgtgggtc gcggcncgan gtagagaacc gactgaaacg tttgagatga agaaagttct     60

cctcctgatc acagccatct tggcagtggc tgttggtttc ccagtctctc aagaccagga    120

acgagaaaaa agaagtatca gtgacagcga tgaattagct tcagggtttt ttgtgttccc    180

ttacccatat ccatttcgcc cacttccacc aattccattt ccaagatttc catggtttan    240

acgtaatttt cctattccaa tacctgaatc tgcccctaca actccccttc ctagcg        296


<210> SEQ ID NO 86
<211> LENGTH: 806
<212> TYPE: DNA
<213> ORGANISM: Homo sapien

<400> SEQUENCE: 86

tctacgatgg ccatttgctc attgtctttc ctctgtgtgt agtgagtgac cctggcagtg     60

tttgcctgct cagagtggcc cctcagaaca acagggctgg ccttggaaaa accccaaaac    120

aggactgtgg tgacaactct ggtcaggtgt gatttgacat gagggccgga ggcggttgct    180

gacggcagga ctggagaggc tgcgtgcccg gcactggcag cgaggctcgt gtgtccccca    240

ggcagatctg ggcactttcc caacccaggt ttatgccgtc tccagggaag cctcggtgcc    300
```

-continued

```
agagtggtgg gcagatctga ccatccccac agaccagaaa caaggaattt ctgggattac    360

ccagtccccc ttcaacccag ttgatgtaac cacctcattt tttacaaata cagaatctat    420

tctactcagg ctatgggcct cgtcctcact cagttattgc gagtgttgct gtccgcatgc    480

tccgggcccc acgtggctcc tgtgctctag atcatggtga ctccccccgcc ctgtggttgg   540

aatcgatgcc acggattgca ggccaaattt cagatcgtgt ttccaaacac ccttgctgtg    600

ccctttaatg ggattgaaag cacttttacc acatggagaa atatattttt aatttgtgat    660

gcttttctac aaggtccact atttctgagt ttaatgtgtt tccaacactt aaggagactc    720

taatgaaagc tgatgaattt tcttttctgt ccaaacaagt aaaataaaaa taaaagtcta    780

tttagatgtt gaaaaaaaaa aaaaaa                                         806
```

<210> SEQ ID NO 87
<211> LENGTH: 620
<212> TYPE: DNA
<213> ORGANISM: Homo sapien

<400> SEQUENCE: 87

```
tttttgcatc agatctgaaa tgtctgagag taatagtttc tgttgaattt ttttttgttc     60

atttttctgc acagtccatt ctgtttttat tactatctag gcttgaaata tatagtttga    120

aattatgaca tccttcctct ttgttatttt cctcatgatt gctttggcta ttcaaagttt    180

attttagttt catgtaaatt tttgaattgt attttccatt attgtgaaaa tagtaccact    240

gcaattttaa taggaagttt attgaatcta tagattactt tggataatat ggcacttcaa    300

taatattcat gttttcaatt catagacaaa atattttaaa atttatttgt atcttttcta    360

atttttcctt tttttattgt aaagatttac ctccttggtt aatattttcc tcagaaattt    420

attatttaag gtatagtcaa taaaattttc ttcctctatt ttgtcagata gtttaagtgt    480

atgaaaccat agatatactt gtatgttaat tttatatttt gctaatttac tgagtgtatt    540

tattagttta gagaggtttt aatgtactgt ttatggtttt ttaaatataa gattacttat    600

tttttaaaaa aaaaaaaaaa                                                 620
```

<210> SEQ ID NO 88
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 88

```
tagctgtgnt cagcaggccg aggttttttt tttttttgag atggagtctc gccctgtcac     60

ccaggctgga gtgcagtggc ctgatctcag ctcactgcaa gctccacctc ctggattcac    120

gctattctcc tgcctcagcc tcccaagtag ctgggactac aggcgcccgc caccacgccc    180

agctaattnt ttgnattttt agtacnagat gcggtttcat cgtgttagcc agcatggnct    240

cgatctcctg acctcgtgaa ctgcccgcct cggcctccca aagacctgcc cgggcnggcc    300

gctcgaaa                                                              308
```

<210> SEQ ID NO 89
<211> LENGTH: 492
<212> TYPE: DNA
<213> ORGANISM: Homo sapien
<220> FEATURE:
<221> NAME/KEY: misc_feature -continued
<222> LOCATION: (1)...(492)
<223> OTHER INFORMATION: n = A,T,C or G

<400> SEQUENCE: 89
agcggccgcc cgggcaggtc tgttaagtaa catacatatc accttaataa aaatcaagat 60
gaaatgtttt agaaactatt ttatcaaaag tggctctgat acaaagactt gtacatgatt 120
gttcacagca gcactattaa tgccaaaaag tagacaaaac ctaaatgtcc attaactgat 180
aagcaaaatg tggtatatcc atacaatgga atattatgta gcccacaaca tggcatggag 240
tactacaaca tggatgagcc tcaaaaacgt tatgctaaat gaaaaaagtc agatatagga 300
aaccacatgt catatgatcc catttatatg aaatagccag aaaaggcaag tcatagaaac 360
aagatagatc ggaaaatggg ttggaggact acaaatggca ccagggatct ttgaagttga 420
tggaaatggt ctaaaatcag actgtggntg tggttgaaca agtctgtaaa tttaccaaaa 480
tgcgttaata ca 492

<210> SEQ ID NO 90
<211> LENGTH: 390
<212> TYPE: DNA
<213> ORGANISM: Homo sapien
<220> FEATURE:
<221> NAME/KEY: misc_feature
<222> LOCATION: (1)...(390)
<223> OTHER INFORMATION: n = A,T,C or G

<400> SEQUENCE: 90
tcgagcggcc gcccgggcag gtacaagctt tttttttttt tttttttttt ttttctaaca 60
gttctctgtt ttattgcaat acagcaaagt ctggttaata ttaagngata tcaacataaa 120
gtattggtga ggagtctttt gtgacatttt ttaccatccc accttaaata tttctgtgca 180
aaanaatcca catcattgtt tggtancana ggatctctta aaaagttccc taanacactg 240
agggcataaa accaaacaaa ataaaataag gagtgatagg ctaaagcagt atcttcccct 300
ccatccacat ttgncaagca ttatattcta accaaaaaat gatcacacca ggccatgcaa 360
aactgtccaa tattaccgag aaaaaaccct 390

<210> SEQ ID NO 91
<211> LENGTH: 192
<212> TYPE: DNA
<213> ORGANISM: Homo sapien

<400> SEQUENCE: 91
agcgtggtcg cggccgaggt ctgtcaatta atgctagtcc tcaggattta aaaaataatc 60
ttaactcaaa gtccaatgca aaaacattaa gttggtaatt actcttgatc ttgaattact 120
tccgttacga aagtccttca catttttcaa actaagctac tatatttaag gcctgcccgg 180
gcggccgctc ga 192

<210> SEQ ID NO 92
<211> LENGTH: 570
<212> TYPE: DNA
<213> ORGANISM: Homo sapien
<220> FEATURE:
<221> NAME/KEY: misc_feature
<222> LOCATION: (1)...(570)
<223> OTHER INFORMATION: n = A,T,C or G

<400> SEQUENCE: 92
agcgtggtcg cggccgaggt ctgacaacta acaaagaagc aaaaactggc atcttggaca 60

-continued

```
tcctagtatt acacttgcaa gcaattagaa cacaaggagg gccaaggaaa aagtttagct    120

ttgaatcact tccaaatcta ctgattttga ggttccgcag tagttctaac aaaacttttc    180

agacaatgtt aactttcgat taagaaagaa aaaaacccca aacatcttca ggaattccat    240

gccaggttca gtctcttcca gtgagcccgc ttgctaaaag tccacgtgca ccattaatta    300

gctgggctgg cagcaccatg taaaaagaag cctattcacc accaaccaca cagactagac    360

atgtaaagta ggatcaagta atggatgaca accatggtcg tggaatatgg tcaatgagag    420

tcagaaaagt acaggcacca gtacaagcag cagataacag aattgacggg ccaaaggata    480

aaaataggct tatttaaata ggatgctaca gaacacatnc acttctaatt ggaagctgct    540

ttacactggg tggcattgna ccatatgcat                                     570
```

<210> SEQ ID NO 93
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 93

```
tcgagcggcc gcccgggcag gtccaggttt ttatttagtt gtgtaatctt ggacaagtta     60

cctaactttt ttgagtctga atatatttaa tctgcaaaat gagaatcatg ataatacgtc    120

ataggcttaa ttaggaggat taaatgaaat aatttatagg tggtgccatg gttacataca    180

agtattagta gttaattctt ttcctttgtt tacttttata gtataggttg gatgaaggtt    240

ccagtatagg caaaaatact acttgggggt aaagtagagt gtgatacttt atttgaaatg    300

ttccctgaat ctgatcttta ctttttgnta ctgctgcact acccaaatcc aaattttcat    360

cccaacattc ttggatttgt gggacagcng tagcagcttt tccaatataa tctatactac    420

atcttttctt actttggtgc tttttg                                         446
```

<210> SEQ ID NO 94
<211> LENGTH: 409
<212> TYPE: DNA
<213> ORGANISM: Homo sapien

<400> SEQUENCE: 94

```
cgagcggccg cccgggcagg tccatcagct cttctgctta gaatacgagg cagacagtgg     60

agaggtcaca tcagttatcg tctatcaggg tgatgaccca agaaaggtga gtgagaaggt    120

gtcggcacac acgcctctgg atccacccat gcgagaagcc ctcaagttgc gtatccagga    180

ggagattgca aagcgccaga gccaacactg accatgttga aggcgttctc tccaggctgg    240

attcactgca ctcggaagaa ttctgcccag ggaatttagt gtgggggtac caggaccagt    300

ttgtcttgat cttgagaccc ccagagctgc tgcatccata gggtgttgca ggactacacc    360

tggcctgcct tgcagtcatt ctttcttata tgttgaccca tttgcccaa                409
```

<210> SEQ ID NO 95
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 95

-continued

```
tcgagcggcc gcccgggcag gtcctacttg tttgcagctt ccacacactg cacctaccta     60
ctacctctct tccatgctta actgggttta gaaaggtgag ctatgcgtag aagaactact    120
tgggatattc aagtgctgta tttgaacgat aagcctatag ataacagtct gaagctgcaa    180
gggagacttt gttagtacac tactataaac aggtaaacta cctgtttgta cttgatatag    240
tgcatatgaa atgactgatt taatacaaaa ctacagaaca tgcaaaattt tttctgagat    300
gttaagtatt acttcagtgg agaacaaaac ttacttaacc tttcgctaat gcatgtagta    360
ccagaaagca aacatggttt tagcttcctt tactcaaaat atgaacatta agtggttgtg    420
aattttgtct gccaagtggt tcagaaaata cattataaat aacctaagtt aaaaaaaaga    480
aactgngaac                                                           490
```

<210> SEQ ID NO 96
<211> LENGTH: 223
<212> TYPE: DNA
<213> ORGANISM: Homo sapien

<400> SEQUENCE: 96

```
agcgtggtcg cggccgaggt ctggaagccc accctaggac ttgaatggca ccttgtcctt     60
tctctgccag taatgcaatc caacacaata tgctacaggg aaaacagaat ttccacggtg    120
ccgccctctg gtacaaggga aacagcacgc aaagcaaaag gccacagagg gctccctgag    180
aatccagtac aactaagcga ggacctgccc gggcggccgc tcg                      223
```

<210> SEQ ID NO 97
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 97

```
tcgagcggcc gcccgggcag gtctgtgcag gagacactga agtgggtagt gtccataatc     60
tttttagcct gttgctgaaa ttccagttgt actccttcaa accaaaatgc ttacaggatc    120
atgggaaagc ctcggttgca gaaatcaaga caggcaagtg ggaagataac tcggctttga    180
ggttaaacag atctgggttc aaagcatagt ttcactctct gtcttgtgaa gtgtcctggg    240
tgaagtcatt tcctctcttg aatttcagag aggatgaaaa tataaaaagt ataataacta    300
tcttcataat ctttgtgagg attaaagaag acgaagtgtg tgaaaagcta agcacagagc    360
aggcattcta caataagtag ttattatttt tggaaccatc ccgnccctag ccccagccca    420
attaccttct cttagnctct tcatatcgaa ngccgtaatc ttgaccttct cttgcnactg    480
gattggtgct ggttgatgcc caaacttccc gagatgctgt ctgggaa                  527
```

<210> SEQ ID NO 98
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 98

```
tcgagcggcc gcccgggcag gtctggctcc catggccctt ggggtggcct gactctgtca     60
```

-continued

```
ctattcctaa aaccttctag gacatctgct ccaggaagaa ctttcaacac caaaattcat    120

ctcaatttta cagatgggaa aagtgattct gagaccagac cagggtcagg ccaaggtcat    180

ccagcatcag tggctgggct gagactgggc ccagggaacc ctgtctgctc ctctttttcc    240

cagagctgtg agttctctag ccaaggctgc actcttgagg gagagccagg aagcatagct    300

gaggccatga caacctcact cttcacctga aaatttaacc cgtggcagag gatccaggca    360

catataggct tcggagccaa acaggacctc ggccgcgacc acgctaagcc gaattccagc    420

acactggcgg ccgttactag tggatcccga gcttnggtac caagcttggc gtaatcatgg    480

gcatagctgg ttcctggggt gaaaatggta tccg                                514
```

<210> SEQ ID NO 99
<211> LENGTH: 530
<212> TYPE: DNA
<213> ORGANISM: Homo sapien
<220> FEATURE:
<221> NAME/KEY: misc_feature
<222> LOCATION: (1)...(530)
<223> OTHER INFORMATION: n = A,T,C or G

<400> SEQUENCE: 99

```
tcgagcggcc gcccgggcag gtctgaagaa acaggtataa atttggcagc cagtaatttt     60

gacagggaag ttacagcttg catgacttta aatatgtaaa tttgaaaata ctgaatttcg    120

agtaatcatt gtgctttgtg ttgatctgaa aaatataaca ctggctgtcg aagaagcatg    180

ttcaaaaata tttaattcac ttcaaaatgt catacaaatt atggtggttt ctatgcaccc    240

ctaaagcttc aagtcattta gctcaggtac atactaaagt aatatattaa ttcttccagt    300

acagtggtgt ttcataccat tgacatttgc ataccctaga ataatttaag aaagacatgt    360

gtaatattca caatgttcag aaaagcaagc aaaaggtcaa ggaacctgct ttggttcttc    420

tggagatggn ctcatatcag cttcataaac attcattcta caaaatagta agctaaccat    480

ttgaacccca atttccagat taagcatatt ttctcataaa tnatgaagcc               530
```

<210> SEQ ID NO 100
<211> LENGTH: 529
<212> TYPE: DNA
<213> ORGANISM: Homo sapien

<400> SEQUENCE: 100

```
agcgtggtcg cggccgaggt ccaggcacgg tggcttatgt gtgtaatccc agcacttggg     60

gaggctgagg gaggtggatc acttgagtcc aggagtttga gaccagtctg ggcaacatgg    120

cgaaacttca tcactaccaa agaagaaaaa aattagccag gtgtggtggt gtatgcctgt    180

agtcccagat actctggtgg ctgaggtgag aggatagctt gagcccagga aattgaggct    240

gcagtgaact atgattgcac tactgtgctc cagcttgggc aacagagtga gatcttgtct    300

ccaaaagtcc ttgaaggatt ttaggaagtt gttaaaagtc ttgaaacgat gtttgggggc    360

atgttagggt tcttgaatgt ttaattcctc taataactgc ttattcaaga gaagcatttc    420

tgactgggtg cggggcagtg gcttcatgcc ccataatccc agtactttgg gaggctgaag    480

caggaacatt gcttgagccc aggacttcaa gaacagcctg ggtaacata                529
```

<210> SEQ ID NO 101
<211> LENGTH: 277
<212> TYPE: DNA
<213> ORGANISM: Homo sapien -continued

<400> SEQUENCE: 101
tcgagcggcc gcccgggcag gtcgcaggaa gaggatggaa actgaggagt ccaggaagaa 60
gagggaacga gatcttgagc tggaaatggg agatgattat attttggatc ttcagaagta 120
ctgggattta atgaatttgt ctgaaaaaca tgataagata ccagaaatct gggaaggcca 180
taatatagct gattatattg atccagccat catgaagaaa ttggaagaat tagaaaaaga 240
agaagagctg agaacagacc tcggccgcga ccacgct 277

<210> SEQ ID NO 102
<211> LENGTH: 490
<212> TYPE: DNA
<213> ORGANISM: Homo sapien

<400> SEQUENCE: 102
gcgtggtcgc ggccgaggtc tgacggcttt gctgtcccag agccgcctaa acgcaagaaa 60
agtcgatggg acagttagag gggatgtgct aaagcgtgaa atcagttgtc cttaattttt 120
agaaagattt tggtaactag gtgtctcagg gctgggttgg ggtccaaagt gtaaggaccc 180
cctgccctta gtggagagct ggagcttgga gacattaccc cttcatcaga aggaattttc 240
ggatgttttc ttgggaagct gttttggtcc ttggaagcag tgagagctgg gaagcttctt 300
ttggctctag gtgagttgtc atgtgggtaa gttgaggtta tcttgggata aagggtcttc 360
tagggcacaa aactcactct aggtttatat tgtatgtagc ttatattttt tactaaggtg 420
tcaccttata agcatctata aattgacttc tttttcttag ttgtatgacc tgccccgggc 480
ggccgctcga 490

<210> SEQ ID NO 103
<211> LENGTH: 490
<212> TYPE: DNA
<213> ORGANISM: Homo sapien

<400> SEQUENCE: 103
gagcggccgc ccgggcaggt ccaaaccagc ttgctcataa gtcattaacc aaatccatta 60
taggtaattt gttcagttca atgtttacaa ttcttatgga aaaaattagc aacacacaca 120
tttaaaacgt gtgcatttac ctttgcgtga gtgcttaaaa tacatatttc tatttcaaga 180
tgacatttaa aaattattct aatatatcag cagcaaaaat ataatttgca attacaaaaa 240
actaaactag aatccttaag ttattctcat gtttacagtt gtgattcttt aataaatact 300
attatgcagc tctattgttt aagctttctg gatttggttt aaacacatgc atatatattg 360
tcaattgtgg gaagctttac aagttatatt ccatgcactt tttggacaga gttctaacag 420
agccagccag tccacaaaac aggcaagaca aaagttgaat taactggggc aaaataggac 480
tcttatgcaa 490

<210> SEQ ID NO 104
<211> LENGTH: 489
<212> TYPE: DNA
<213> ORGANISM: Homo sapien

<400> SEQUENCE: 104
cgtggtcgcg gccgaggtcc aggctggtct cgaactcctg accttgtgat ctgcccgcct 60
cggcctccca aagtgttggg attacaggca tgagccactg cgcccgaccg agttgaacat 120
ttaatgtcag actaggccag agtttctcaa tctttttatt ctcacttccc aaaggagccg 180
ttggagattt tcccctcaat ctctctcctt catgaaattt cataccacaa atatagtatg 240

-continued

```
ttttatttat gtactgtgac cctttgaagg atcacaaacc aatataatag tttttctttt    300

taacccgtca aggaccaagt ttttgcccct gttggaaatg cataaactgg actgatgaat    360

tggtatagat ggcttttatc atgaggatca gaaaaacttg aaattccttg gctacgacac    420

tccatattta tcaccgtata gggaggacct tggtatgggg aagtagaaac acttctacac    480

tttacagca                                                            489
```

<210> SEQ ID NO 105
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 105

```
gcgtggtcgc ggccgaggtc tgactggctt cagccccaga agttgagctg gcctttagac     60

aaaataattg cacctccctc tgctgcttat tcccttccgt tttcatttg agtgtgaaca    120

gttagataaa atctgtggct gnctcttcca ccttgctcta gtttccattg ctgtgagcag    180

gccctcctat gccccgcatt tagctacaat gctgtggact cacttgattc tttttctccg    240

agctttgtct agaaatatgt gaaggtgagg ttaagtgctt ctctgtgtag atccacttag    300

ccctgtctgc tgtctcgatg ggcgttgctt cgtctctcct ctcttccatc ctttccattt    360

gcttctcacc accttctggc ttcttttctt aatgcaataa aggcagtttc taacaaagaa    420

agaatgtggg ctttggagtt agacagacct ggntttaaat tctgcttctg gctctccaa     479
```

<210> SEQ ID NO 106
<211> LENGTH: 511
<212> TYPE: DNA
<213> ORGANISM: Homo sapien

<400> SEQUENCE: 106

```
tcgcggccga ggtccaaaac gtggattcca atgacctgcc ttgagcccgc ggttgccagg     60

agttggacct gcagtagtat gggaagctca cggcctaaat accgactgcc ctctgacccc    120

accgtccagc gattctagaa catttctagt aggaaagaca tagcaaggga ttttcatgat    180

tgggaaatac tgggagacaa gctgaagatt tgttaagggc tatgcttctg tcatctttta    240

ggtatttaag gctactcctt tagctagcta ctttgagctg tttaaagtga ctatctccct    300

acacagagtt acacaatgag catctctgaa agagaatatt accctggatt tccaaagatg    360

tactctaaca ggatgaccag gcaaaaggtg acccggggga ggagtctgtt ataacactcg    420

gacccacatg ttctcaaggc acttcagaac tttgggaaat cattttgtac cggatcctca    480

gaaagcattt atggaaatac acatccttta g                                   511
```

<210> SEQ ID NO 107
<211> LENGTH: 451
<212> TYPE: DNA
<213> ORGANISM: Homo sapien

<400> SEQUENCE: 107

```
ggccgcccgg gcaggtccag aatatcaaat caaaaggtca caaatgttca cttcctcctc     60

caccctctta catattggat cttcaattgc aatagggagt gtaagatggg cattttagag    120

acgtagttgc atcagcagaa gcaaacccat cttatacaaa tgggttttgg ggataggaaa    180
```

-continued

```
aggctgctaa aaattcacaa gtcaccattc cccagaagca atgaatagcc gtagaagacc    240

aaggaagatc aacaagtttc caaagtgcta aagccagaga tttggccctt ccaaaatacc    300

accaggacgc ctggacccgt gggctctccg catgtcacca ctgactgcca ggatgctgct    360

gcacctccct tccttgagac acaacagaga gacagtgaag tcacccaaga ctgggatcat    420

cagaggctcc tcatgcttgc tacagagaag c                                   451
```

<210> SEQ ID NO 108
<211> LENGTH: 461
<212> TYPE: DNA
<213> ORGANISM: Homo sapien

<400> SEQUENCE: 108

```
ccgcccgggc aggtcctgaa aacattcaga ctaatcaaaa tggtactact gtaacttctt     60

ataatacata atataaaagt ttttgaaaga tatagacaca attaacccct aaacaacaca    120

ctatctgatt ctcaaaagca atggctattt aacaagatgt aaaaggacaa taacatatca    180

aagaactttc acacacctaa agatagcatt tagcagcaag ttagtcagac aaaacaaaca    240

caaatatttt cacatttcct atgtttgttt ttaactttac ttcataaagc cactgataat    300

tgaggtttct ttcaagtata agatttctaa aattaaaaac tgtttttgac atatttttat    360

aaagaaataa aaagcaaaac gcaatccaac tatttatatg agtccctctt ctccaacagc    420

tttagatggt tttctgagta cttttttaca cagaatattt t                        461
```

<210> SEQ ID NO 109
<211> LENGTH: 441
<212> TYPE: DNA
<213> ORGANISM: Homo sapien

<400> SEQUENCE: 109

```
ggccgcccgg gcaggtctga ttataagaga aagaaatcca gtgacacgag ggcaggcagg     60

ccccgctctg ctctgatcga gaaaagcttc ctgatgtcag ggagatggaa ctgccaccat    120

cagaaccatg gcactttggg tgaaggtgtg tcagcgacca agggggcagg aaatgggcag    180

tgactaaggg ggcaggaaac aggcaggcac atggcaaggt tctcccagcc catcagccca    240

gtgatggcct cgattttgaa gctgcactac tgtctgaaaa gcacaattac tggtgactct    300

taacaaactt cagcatactg gggaaggaga ctgtcaagta actgaattgg aaagatgaaa    360

aagaaccatc tctaaaagtt gatgcttgtc agaagaataa cctcctttgt gcaagtcttg    420

caacatcttc attcaaccac a                                              441
```

<210> SEQ ID NO 110
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 110

```
ggtcgcggcc gaggtctggg gaaggggtga gaatccctgg gccttgccca gtcctgagct     60

ctgggtgtct gcagggaagc acagtggtga gttagtgtta aagaaagcat ccagagaggt    120

aagaggggct tgggtagcac cctttgcctc tgtcacttcc gcaaaaactt cttgttgagg    180

aggaagatga gaaggttgac attgactttg gccttgttga agagtttcat gacagccaca    240

ccctcatact ggagctgcan gagatcctga tagtgaagct tgaaatcgct ccatgtccac    300
```

-continued acccaggaac ttggcattta cttcaaactt tcctgcctca tctcccggcg tgatgtcaaa 360
natgacgttt cttgaagtga gaggcgggaa agatcttcaa tttccaccaa agacaccctt 420
tttccaggaa gcttgagcaa caagtgtaat g 451

<210> SEQ ID NO 111
<211> LENGTH: 407
<212> TYPE: DNA
<213> ORGANISM: Homo sapien
<220> FEATURE:
<221> NAME/KEY: misc_feature
<222> LOCATION: (1)...(407)
<223> OTHER INFORMATION: n = A,T,C or G

<400> SEQUENCE: 111
ggccgacgtt cgacctgact tctttngagc agntgncact acccgtcttg aggaatgccg 60
actgcagaca gtggcccang gcaaagagtg tgcgtcatcg atganattgg naagatggag 120
ctcttcagtc agnttttcat tcaagctgnt cgtcagacgc tgtctacccc agggactata 180
atcctnggca caatcccagt tcctanagga aagccactgn ctcttgtaga agaaatcana 240
cacanaaagg atgtgaacng tgtttaatgt caccaaggga aaacatgaaa ccaccttctg 300
ccagatatcg ggacgttgcg tgcagatcaa gcacgnaagt gaagacgcgt gcattccttg 360
ccttccgtga acgantgccc agntcaagaa gancctgatg gaaccct 407

<210> SEQ ID NO 112
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 112
tcgcggccga ggtcggccga ggtctgacat ctgttgtctg tgataaccac ttctgtattg 60
cgtcttaacc acttctgtat tgtgtggttt taactgccta aggcggcaat gggcagtggg 120
cccctttccc ttaggatggg tatcaattca acaatattta taaggcattt actgtgtgct 180
aagcatttgg aagacccagg ctacaaaata agacatagtt cctgccctcc aggccagcag 240
agggaggcac aaatacccag gaatctctga tgggtgtgaa gtgcggtcgt gggccacaga 300
aaatgaccgt catggagacc ctgctaaagg tcggaccctg agcccaaagg ggtattcaga 360
agnggagatg attttggccc cactcataga tgggtggcaa a 401

<210> SEQ ID NO 113
<211> LENGTH: 451
<212> TYPE: DNA
<213> ORGANISM: Homo sapien

<400> SEQUENCE: 113
gtcgcggccg aggtccatat taaaaagtcc atcataaaca aagactcctc ctcatggtat 60
gaatatgctc catatgccca taatggtgca taacggactt agaaattcca atgagtctta 120
gggttgaaat ttccaatgac ctgagcaagg cagctcccta tagcttctgg ataacatttt 180
acacccagag ttcaggctta aacagaccta tcaacacaat tattttcgga ttgtctgtct 240
agaaaacggc aatgctcaaa ggaatataaa taagggtggg gggacatatg cttccagcct 300
ggcctttctc catgtggtaa aaaacaatgg aatggctgtg ttaatttttt tttaatcttt 360

-continued tctgaccttt actatgtttg gtaatggaaa taagtcaggg aaaacaaaat gaacaggtct 420
catcacttaa ttaatactgg gttttcttct t 451

<210> SEQ ID NO 114
<211> LENGTH: 441
<212> TYPE: DNA
<213> ORGANISM: Homo sapien

<400> SEQUENCE: 114
ggccgcccgg gcaggtccat cctgtcagag atgggagaag tcacagacgg aatgatggat 60
acaaagatgg ttcactttct tacacactat gctgacaaga ttgaatctgt tcatttttca 120
gaccagttct ctggtccaaa aattatgcaa gaggaaggtc agcctttaaa gctacctgac 180
actaagagga cactgttgtt tacatttaat gtgcctggct caggtaacac ttacccaaag 240
gatatggagg cactgctacc cctgatgaac atggtgattt attctattga taaagccaaa 300
aagttccgac tcaacagaga aggcaaacaa aaagcagata agaaccgtgc ccgagtagaa 360
gagaacttct tgaaacttga cacatgtgca aagacaggaa gcagcacagt ctcggcggga 420
ggaagaaaaa aagaacagag a 441

<210> SEQ ID NO 115
<211> LENGTH: 431
<212> TYPE: DNA
<213> ORGANISM: Homo sapien
<220> FEATURE:
<221> NAME/KEY: misc_feature
<222> LOCATION: (1)...(431)
THER INFORMATION: n = A,T,C or G

SEQUENCE: 115 gccgcccggg caggtccatt ggcggtgaca aaaggaaaag aagcaaagag actcagtcca 60
taatgctgat tagttagaag aaagggctag gattgagaaa gtaccaggaa cttttaatta 120
tttaaaagag aatgctgact gttaatgttt taaatcttac tgttcaaatg tactaatatg 180
aatttttacc ctttgtgcat gaatattcta aacaactaga agacctccac aatttagcag 240
ttatgaaagt taaacttttt attataaaaa ttctaaacct tactgctcct ttaccaggaa 300
catgacacac tatttancat cagttgcata cctcgccaat agtataattc aactgtcttg 360
cccgaacaat catctccatc tggaagacgt aagcctttag aaacacattt ttctattaat 420
ttctctagaa c 431

<210> SEQ ID NO 116
<211> LENGTH: 421
<212> TYPE: DNA
<213> ORGANISM: Homo sapien

<400> SEQUENCE: 116
gtcgcggccg aggtccagaa atgaagaaga agtttgcaga tgtatttgca aagaagacga 60
aggcagagtg gtgtcaaatc tttgacggca cagatgcctg tgtgactccg gttctgactt 120
ttgaggaggt tgttcatcat gatcacaaca aggaaccggg gctcgtttat caccagtgag 180
gagcaggacg tgagcccccg ccctgcacct ctgctgttaa acaccccagc catcccttct 240
ttcaaaaggg atcctttcat aggagaacac actgaggaga tacttgaaga atttggattc 300
agcccgcgaa gagatttatc aagcttaact cagataaaat cattgaaagt aataaggtaa 360
aagctaagtc tctaacttcc aggcccacgg ctcaagtgaa tttcgaatac tgcatttaca 420
g 421

-continued

<210> SEQ ID NO 117
<211> LENGTH: 489
<212> TYPE: DNA
<213> ORGANISM: Homo sapien

<400> SEQUENCE: 117
agcgtggtcg cggccgaggt aaggctgcga ggttgtggtg tctgggaaac tccgaggaca 60
gagggctaaa tccatgaagt ttgtggatgg cctgatgatc cacagcggag accctgttaa 120
ctactacgtt gacactgctg tgcgccacgt gttgctcaga cagggtgtgc tgggcatcaa 180
ggtgaagatc atgctgccct gggacccaac tggtaagatt ggccctaaga agcccctgcc 240
tgaccacgtg agcattgtgg aacccaaaga tgagatactg cccaccaccc ccatctcaga 300
acagaagggt gggaagccag agccgcctgc catgccccag ccagtcccca cagcataaca 360
gggtctcctt ggcagacctg cccgggcggc cgctcgaaag cccgaattcc agcacactgg 420
cggccgttac tagtggatcc cagctcggta ccaagcttgg cgtaatcatg gtcatagctg 480
gtttcctgt 489

<210> SEQ ID NO 118
<211> LENGTH: 489
<212> TYPE: DNA
<213> ORGANISM: Homo sapien

<400> SEQUENCE: 118
tcgagcggcc gcccgggcag gtattgaata cagcaaaatt ctatatacaa agtgacctgg 60
acctgctgct tcaaaacatg atcctttctt actaatatct tgatagtcgg tccatagagc 120
attagaaagc aattgactct taaataaaca gaaaagtgcc taatgcacat taaatgaatg 180
gcctaactac tggaacttta gtagttctat aaggtgatta acataggtag gatccagttc 240
ctatgacagg ctgctgaaga acagatatga gcatcaagag gccattttgt gcactgccac 300
cgtgatgcca tcgtgtttct ggatcataat gttcccatta tctgattcta gacacaccac 360
aggaatatca gtggggtcag aggttagctt agctgcttgc tgggctagaa cagatatcac 420
tccagcatgc tcatctgaca gggtcccgcg gcaacccaga ttaagtcctt gtgaatctgt 480
gcacaggga 489

<210> SEQ ID NO 119
<211> LENGTH: 181
<212> TYPE: DNA
<213> ORGANISM: Homo sapien

<400> SEQUENCE: 119
taggttccag agacttttgg cccaggagga atatttactt ttagctctgg acatcattac 60
aaaaaggaat atttcccaaa cctcttcaga ccgagaatac atgggtaaaa ttattaaata 120
gttgtataat aaaaataatt ttttccttaa aaaaaaaaaa aacctcggcc gcgaccacgc 180
t 181

<210> SEQ ID NO 120
<211> LENGTH: 489
<212> TYPE: DNA
<213> ORGANISM: Homo sapien
<220> FEATURE:
<221> NAME/KEY: misc_feature
<222> LOCATION: (1)...(489)
<223> OTHER INFORMATION: n = A,T,C or G -continued

<400> SEQUENCE: 120
gcgtggtcgc ggccgaggtc catttaaaac aaagaaaaat actaaagcca ctagtaaaca 60
tctgatgtgc aaaatacaac atcctctagt tggctttatg ccattattac ataagctcca 120
aatagctcat cttaaattaa aaagaaaaag tggctgtccc atctctgctg cataaatcag 180
attttttttt aaaggtttag agtactttaa ggaagggaag ttcaaaactg ccagtgaaat 240
tcacagagaa tacaaattta gcaatttaat ttcccaaagc tctttgaaga agcaagagag 300
tctctcttct taatgcagtg ttctcccaag aggaactgta attttgcttg gtacttatgc 360
tgggagatat gcaaaatgtg tttttcaatg tttgctagaa tataatggtt cctcttcagt 420
gnctggttca tcctggaact catgggttaa gaaggacttc ttggagccga actgcccggg 480 cgggccntt 489

<210> SEQ ID NO 121
<211> LENGTH: 531
<212> TYPE: DNA
<213> ORGANISM: Homo sapien

<400> SEQUENCE: 121
cgagcggccg cccgggcagg tggccagcgc tggtcccgca gacgccgaga tggaggaaat 60
atttgatgat gcgtcacctg gaaagcaaaa ggaaatccaa gaaccagatc ctacctatga 120
agaaaaaatg caaactgacc gggcaaatag attcgagtat ttattaaagc agacagaact 180
ttttgcacat ttcattcaac ctgctgctca gaagactcca acttcacctt tgaagatgaa 240
accagggcgc ccacgaataa aaaaagatga gaagcagaac ttactatccg ttggcgatta 300
ccgacaccgt agaacagagc aagaggagga tgaagagcta ttaacagaaa gctccaaagc 360
aaccaatgtt tgcactcgat ttgaagactc tccatcgtat gtaaaatggg gtaaactgag 420
agattatcag gtcccgagga ttaaactggc tcatttcttt gtatgagaat ggcatcaatg 480
gtatccttgc agatgaaatg ggcctaggaa agactcttca acaatttctc t 531

<210> SEQ ID NO 122
<211> LENGTH: 174
<212> TYPE: DNA
<213> ORGANISM: Homo sapien

<400> SEQUENCE: 122
tcgagcggcc gcccgggcag gtctgccaac agcagaggcg gggcctccgg catcttcaaa 60
gcacctctga gcaggctcca gccctctggc tgcgggaggg gtctggggtc tcctctgagc 120
tcggcagcaa agcagatgtt atttctctcc cgcgacctcg gccgcgacca cgct 174

<210> SEQ ID NO 123
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 123
agcgtggtcg cggccgaggt cctcaaccaa gagggttgat ggcctccagt caagaaactg 60
tggctcatgc cagcagagct ctctcctcgt ccagcaggcg ccatgcaagg gcaggctaaa 120
agacctccag tgcatcaaca tccatctagc anagagaaaa ggggcactga agcagctatg 180
tctgccaggg gctaggggct cccttgcaga cagcaatgct acaataaagg acacagaaat 240

-continued

```
gggggaggtg ggggaagccc tatttttata acaaagtcaa acagatctgt gccgttcatt    300

cccccagaca cacaagtaga aaaaaaccaa tgcttgtggt ttctgccaag atggaatatt    360

cctccttcct aanttccaca catggccgtt tgcaatgctc gacagcattg cactgggctg    420

cttgtctctg tggtctgggc accagtagct tgggccccat atacacttct cagttcccac    480

anggcttatg gccnangggc angctccaat tttcaagcac cacgaaggaa g             531
```

<210> SEQ ID NO 124
<211> LENGTH: 416
<212> TYPE: DNA
<213> ORGANISM: Homo sapien

<400> SEQUENCE: 124

```
tcgagcggcc gcccgggcag gtccatctat actttctaga gcagtaaatc tcataaattc     60

acttaccaag cccaggaata atgactttta aagccttgaa tatcaactaa gacaaattat    120

gccaattctg atttctcaca tatacttaga ttacacaaag ataaagcttt agatgtgatc    180

attgtttaat gtagacttat ctttaaagtt tttaattaaa aactacagaa gggagtaaac    240

agcaagccaa atgatttaac caaatgattt aagagtaaaa ctcactcaga aagcattata    300

cgtaactaaa tatacatgag catgattata tacatacatg aaactgcaat tttatggcat    360

tctaagtaac tcatttaagt acatttttgg catttaaaca aagatcaaat caagct        416
```

<210> SEQ ID NO 125
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 125

```
agcgtggtcg cggccgaggt gctttttttt tttttttttt tttttttttt gctattctaa     60

aggggaaggc cccttttttat taaacttgta cattttactt tccttctttc anaatgctaa   120

taaaaaactt ttgtttatac ttaaaaaaac cataaatcan acaaacaaaa gaaacgattc    180

caacatcact tctgngatg                                                 199
```

<210> SEQ ID NO 126
<211> LENGTH: 490
<212> TYPE: DNA
<213> ORGANISM: Homo sapien

<400> SEQUENCE: 126

```
cgtggtcgcg gccgaggtcc agttgctcta agtggattgg atatggttgg agtggcacag     60

actggatctg ggaaaacatt gtcttatttg cttcctgcca ttgtccacat caatcatcag    120

ccattcctag agagaggcga tgggcctatt tgtttggtgc tggcaccaac tcgggaactg    180

gcccaacagg tgcagcaagt agctgctgaa tattgtagag catgtcgctt gaagtctact    240

tgtatctacg gtggtgctcc taagggacca caaatacgtg atttggagag aggtgtggaa    300

atctgtattg caacacctgg aagactgatt gactttttag agtgtggaaa aaccaatctg    360

agaagaacaa cctaccttgt ccttgatgaa gcagatagaa tgcttgatat gggctttgaa    420

ccccaaataa ggaagattgt ggatcaaata agacctgata ggcaaactct aatgtggagt    480

gcgacttggc                                                           490
```

-continued

<210> SEQ ID NO 127
<211> LENGTH: 490
<212> TYPE: DNA
<213> ORGANISM: Homo sapien

<400> SEQUENCE: 127

```
cgtggtcgcg gccgaggtcg gccgaggtct ggagatctga gaacgggcag actgcctcct     60

caagtgggtc cctgacccct gacccccgag cagcctaact gggaggcacc ccccagcagg    120

ggcacactga cacctcacac ggcagggtat tccaacagac ctgaagctga gggtcctgtc    180

tgttagaagg aaaactaaca agcagaaagg acagccacat caaaaaccca tctgtacatc    240

accatcatca aagaccaaaa gtaaataaaa ccacaaagat gggaaaaaaa cagaacagaa    300

aaactggaaa ctctaaaaag cagagcacct ctcctcttcc aaaggaacgc agttcctcac    360

cagcaatgga acaaagctgg atggagaatg actttgacga gctgagaaaa gaacgcttca    420

gacgatcaaa ttactctgag ctacgggagg acattcaaac caaaggcaaa gaagttgaaa    480

actttgaaaa                                                           490
```

<210> SEQ ID NO 128
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 128

```
cgtggtcgcg gccgaggtgc tttttttttt tttttttttt tttttttttt tgctgattta     60

tttttctnt ttattgttac atacaatgta taaacacata aaacanaaaa cagtagggat    120

cctctaggat ctctagggan acagtaaagt anaaagaggt ctcanaaaca tttttttaaa    180

gtacaagaca ttcagngctc ggcccaaagg cgtaaaaggt ttanagccag canatagctg    240

nactaaaggc tccgtctntn tccccanagc caggacaacc ccagggagct ntccattagc    300

agccagtcca cgcaggcagg atgctgcgga aaaagctcta tgctganaac attccccttg    360

atggaaagaa gggcaacaca aaaggggtaa ctaanagctc cttcctctcg tgagggcgac    420

aactgaggaa cagaaaagga gtgtcccatg tcacttttga ccccctccc                469
```

<210> SEQ ID NO 129
<211> LENGTH: 419
<212> TYPE: DNA
<213> ORGANISM: Homo sapien

<400> SEQUENCE: 129

```
gcgtggtcgc ggccgaggtc tgattttcat ttaaatattt cagagctata gcatttgcct     60

ccatgctcaa atccacacca ttggggctta agccgctcat gccaacatta gcaaatgaca    120

tgcagtttaa tccagagatc actgcttctg ggctgatgca tgccaacaca ctggcgtgat    180

ccacgttatg tgcatttttc ttcactttag tgggagaatc aatttttact ccaaggcttc    240

ttagttgctt aagagttgca ttaaggacac aatctttgtc caccagtctt gaatgatgtg    300

tttttttctt tgtatggtaa acgttttggg ttctggtgca ttcatgactg ataattactg    360

ctttggtaga cggctgctca agtttccttg gaggaactat ttaataggtg ggttacttg     419
```

<210> SEQ ID NO 130
<211> LENGTH: 354

-continued

<212> TYPE: DNA
<213> ORGANISM: Homo sapien

<400> SEQUENCE: 130
agcgtggtcg cggccgaggt ccatctgagg agataaccac atcactaaca aagtgggagt 60
gaccccgcag agcacgctgt ggaattccat agttggtctc atccctggtc agtttccaca 120
tgatgatggt cttatctcga gaggcggaga ggatcatgtc cgggaactgc ggggtagtag 180
cgatctgggt tacccagccg ttgtggccct tgagggtgcc acgaagggtc atctgctcag 240
tcatggcggc ggcgagagcg tgtgtcgctg cagcgacgag gatggcactg gatggcttag 300
agaaactagc accacaacct ctcctgccgc acctgcccgg gcggcccgct cgaa 354

<210> SEQ ID NO 131
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 131
cgagcggccg cccgggcagg tctggcagca gcttcctctg gaataattga cagctttgtg 60
ctgcctgact aaaatttgaa atgacaaccg ctgaatgtaa aatgatgtac ctacaatgag 120
agagatttag gaatactatc tgtcaatcca tagatgtaga aacaaaacaa actacagaat 180
gaaaacaaac ttattttaaa ccaaagaaac aaatgtatcc aaaatatagt ccatgatata 240
tttgattact agtataacca cagttgaaaa cttaaaaaaa aaaattgaca ttttttgtaa 300
tgggtactaa tggatttata aaaggtttct gtttccaaag atgttattgg ggtccacata 360
ttccttgaag acttcagcat cccaaagccc gacatcagag atactttcct ttagccattg 420
nttcccgtaa cttgcccact ccatggtgat gtgacaggct tcccttcatt agca 474

<210> SEQ ID NO 132
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 132
ggccgaggtg gggaattcat gtggaggtca gagtggaagc aggtgtgaga gggtccagca 60
gaaggaaaca tggctgccaa agtgtttgag tccattggca agtttggcct ggccttagct 120
gttgcaggag gcgtggtgaa ctctgcctta tataatgtgg atgctgggca cagagctgtc 180
atctttgacc gattccgtgg agtgcaggac attgtggtag gggaagggac tcattttctc 240
atcccgtggg tacagaaacc aattatcttt gactgccgtt ctcgaccacg taatgtgcca 300
gtcatcactg gtagcaaaga tttacagaat gtcaacatca cactgcgcat cctcttccgg 360
cctgtcgcca gccagcttcc tcgcatcttc accagcatcg ganaggacta tgatgaaccg 420
tgtgctgccg tccatcacaa ctgagatcct caagtcagtg gtggctcgct ttga 474

<210> SEQ ID NO 133
<211> LENGTH: 387
<212> TYPE: DNA
<213> ORGANISM: Homo sapien -continued

<400> SEQUENCE: 133
tgctcgagcg gccgccagtg tgatggatat ctgcagaatt cggcttagcg tggtcgcggc 60
cgaggtctgc gggcccctta gcctgccctg cttccaagcg acggccatcc cagtagggga 120
ctttcccaca ctgtgccttt acgatcagcg tgacagagta gaagctggag tgcctcacca 180
cacggcccgg aaacagcggg aagtaactgg aaagagcttt aggacagctt agatgccgag 240
tgggcgaatg ccagaccaat gatacccaga gctacctgcc gccaacttgt tgagatgtgt 300
gtttgactgt gagagagtgt gtgtttgtgt gtgtgttttg ccatgaactg tggccccagt 360
gtatagtgtt tcagtggggg agaactg 387

<210> SEQ ID NO 134
<211> LENGTH: 401
<212> TYPE: DNA
<213> ORGANISM: Homo sapien

<400> SEQUENCE: 134
ggccgcccgg gcaggtctga tgaagaacac gggtgtgatc cttgccaatg acgccaatgc 60
tgagcggctc aagagtgttg tgggcaactt gcatcggctg ggagtcacca acaccattat 120
cagccactat gatgggcgcc agttccccaa ggtggtgggg ggctttgacc gagtactgct 180
ggatgctccc tgcagtggca ctggggtcat ctccaaggat ccagccgtga agactaacaa 240
ggatgagaag gacatcctgc gcttgtgctc acctccagaa ggaagttgct cctgagtgct 300
attgactctt gtcaatgcga ccttcaagac aggaggctac ctggtttact gcacctgttc 360
tatcacagtg agacctctgc catggcagaa caggggaagc t 401

<210> SEQ ID NO 135
<211> LENGTH: 451
<212> TYPE: DNA
<213> ORGANISM: Homo sapien

<400> SEQUENCE: 135
ggtcgcggcc gaggtctgtt cctgagaaca gcctgcattg gaatctacag agaggacaac 60
taatgtgagt gaggaagtga ctgtatgtgg actgtggaga aagtaagtca cgtgggccct 120
tgaggacctg gactgggtta ggaacagttg tactttcaga ggtgaggtgt cgagaaggga 180
aagtgaatgt ggtctggagt gtgtccttgg ccttggctcc acagggtgtg ctttcctctg 240
gggccgtcag ggagctcatc ccttgtgttc tgccagggtg gggtaccggg gtttgacact 300
gaggagggta acctgctggc tggagcggca gaacagtggc cttgatttgt cttttggaag 360
attttaaaaa ccaaaaagca taaacattct ggtccttcac aatgctttct ctgaagaaat 420
acttaacgga aggacttctc cattcaccat t 451

<210> SEQ ID NO 136
<211> LENGTH: 411
<212> TYPE: DNA
<213> ORGANISM: Homo sapien

<400> SEQUENCE: 136
ggccgcccgg gcaggtctga atcacgtaga atttgaagat caagatgatg aagccagagt 60
tcagtatgag ggttttcgac ctgggatgta tgtccgcgtt gagattgaaa atgttccctg 120
tgaatttgtg cagaactttg accccccttta ccccattatc ctgggtggct tgggcaacag 180
tgagggaaat gttggacatg tgcaggtggg tccctttgct gcgtatttgg tgcctgaggc 240
tctgtggatt tcccctccat caatcatctt accctctcat ccccctcaga tgcgtctgaa 300

-continued gaaacatctc tggtataaga aaatcctcaa gtcccaagat ccaatcatat tttctgtagg 360
gtggaggaag tttcagacca tcctgctcta ttatatccga agaccacaat g 411

<210> SEQ ID NO 137
<211> LENGTH: 211
<212> TYPE: DNA
<213> ORGANISM: Homo sapien
<220> FEATURE:
<221> NAME/KEY: misc_feature
<222> LOCATION: (1)...(211)
<223> OTHER INFORMATION: n = A,T,C or G

<400> SEQUENCE: 137
cggccgcccg ggcaggtcgg ttggtgcggc ctccattgtt cgtgttttaa ggcgccatga 60
ggggtgacag aggccgtggt cgtggtgggc gctttggttc cagaggaggc ccaggaggag 120
ggttcaggcc ctttgcacca catatcccat ttgacttcta tttgtgtgaa atggcctttc 180
cccggntcaa gccagcacct cgatgaaact t 211

<210> SEQ ID NO 138
<211> LENGTH: 471
<212> TYPE: DNA
<213> ORGANISM: Homo sapien

<400> SEQUENCE: 138
gccgcccggg caggtctggg ctggcgactg gcatccaggc cgtaactgca aatctatgct 60
aggcggggtc tcccttctgt gtgttcaagt gttctcgact tggattctta actattttaa 120
aaaatgcact gagtttgggt taaaaaccaa ccaccaaaat ggatttcaac acagctctaa 180
agccaagggc gtggccggct ctcccaacac agcgactcct ggaggccagg tgcccatggg 240
cctacatccc ctctcagcac tgaacagtga gttgattttt ctttttacaa taaaaaaagc 300
tgagtaatat tgcataggag taccaagaaa ctgcctcatt ggaaacaaaa actatttaca 360
ttaaataaaa agcctggccg caggctgcgt ctgccacatt tacagcacgg tgcgatgcac 420
acggtgacca aaccacggag gcaagcttct ggcactcaca ccacgacccg c 471

<210> SEQ ID NO 139
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 139
gtcgcggccg aggtctgttc tttagctcag atttaaacct gctgtctctt ctttatttgc 60
agaatgaatt cccagttcct gagcagttca agaccctatg gaacgggcag aagttggtca 120
ccacagtgac agaaattgct ggataagcga agtgccactg ggttctttgc cctcccttca 180
caccatggga taaatctgta tcaagacggt tcttttctag atttcctcta cctttttgct 240
cttaaaactg cttctctgct ctgagaagca cagctacctg ccttcactga aatatacctc 300
aggctgaaat ttggggtggg atagcaggtc agttgatctt ctgcaggaag gtgcagcttt 360
tccatatcag ctcaaccacg ccgncagtcc attcttaagg aactgccgac taggactgat 420
gatgcatttt agcttttgag cttttggggg gtattctacc aaccaacagt ccatttggaa 480
a 481

-continued

<210> SEQ ID NO 140
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 140
gtcgcggccg aggtttccca tttaagaaaa atagatcttg agattctgat tcttttccaa 60
acagtcccct gctttcatgt acagcttttt ctttacctta cccaaaattc tggccttgaa 120
gcagttttcc tctatggctt tgcctttctg attttctcag aggctcgagt ctttaatata 180
accccaaatg aaagaaccaa ggggaggggt gggatggcac tttttttgt tggtcttgtt 240 ttgttttgtt ttttggttgg ttgggttccg ttatttttta agattagcca ttctctgctg 300
ctatttccct acataatgtc aatttttaac cataattttg acatgattga gatgtacttg 360
aggctttttt gntttaattg agaaaagact ttgcaatttt ttttttagga tgagcctctc 420
c 421

<210> SEQ ID NO 141
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 141
cgantngccc gcccgggcan gtctgtctaa ntttntcang gaccacgaac agaaactcgt 60
gcttcaccga anaacaatat cttaaacatc gaanaattta aatattatga aaaaaaacat 120
tgcaaaatat aaaataaata nnaaaaggaa aggaaacttt gaaccttatg taccgagcaa 180
atccaggtct agcaaacagt gctagtccta nattacttga tntacaacaa cacatgaata 240
ca 242

<210> SEQ ID NO 142
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 142
agcgtggtcg cggcncgang tccacagggc anatattctt ttagtgtctg gaattaaaat 60
gtttgaggtt tangtttgcc attgtctttc caaaaggcca aataattcan atgtaaccac 120
accaagtgca aacctgtgct ttctatttca cgtactgttg tccatacagt tctaaataca 180
tgtgcagggg attgtagcta atgcattaca cagtcgttca gtcttctctg cagacacact 240
aagtgatcat accaacgtgt tatacactca actagaanat aataagcttt aatctgaggg 300
caagtacagt cctgacaaaa gggcaagttt gcataataga tcttcgatca attctctctc 360
caaggggccc gcaactaggc tattattcat aaaacacaac tgaanagggg attggtttta 420
ctggtaaatc atgtgntgct aaatcatttt ctgaacagtg gggtctaaat cantcattga 480
tttagtggca gccacctgcc cggcggccgn tcgaagccca attctgcaga tatccatcac 540

-continued actggcggcc g 551

<210> SEQ ID NO 143
<211> LENGTH: 515
<212> TYPE: DNA
<213> ORGANISM: Homo sapien
<220> FEATURE:
<221> NAME/KEY: misc_feature
<222> LOCATION: (1)...(515)
<223> OTHER INFORMATION: n = A,T,C or G

<400> SEQUENCE: 143
cgagnggccc gcccgggcag gtatcttcac aaactcaaca aaggcactac atgagacttc 60
acattcccct agtccaatag ctgacaaatt tttgcaacgt tctgcaatgc gaattaactc 120
ttcatcaagt ggccgtaatc catttgcaca cactactagt tcaaccagtc tagggcatgt 180
cattcccaca cggccaagca catctttgct tactgatctc ccaaagtaca gatgggtggc 240
aggtatttca tagcgaaaga aggggtcaaa ttcttcttca tataanaaaa aatacatcac 300
taagttcact ttgggtgaat gtctgatgaa agcatcccag ctactcttct gaatagtatg 360
gaagtgtgtc tgtccaggat tctcactgac tacatcaatg cgcaaatgtt ctaatcgaac 420
atgtttttca gaagacaatg caagtaacaa ctcatcactc aataagtggt aagttcaggg 480
ctagttctct taagccgnga cactgatcag cacac 515

<210> SEQ ID NO 144
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 144
tgcattctct ntggatgcan acctgcccgt tggtagggac tntgctcaca cggaacatgg 60
acggttacac ctgtgccgtg ggtgacgtcc accagcttct ggatcatctc ggcgngggtg 120
ttgtggaagg gcagactatc cacctccatg cncacgatgc ccganacgcc actccggact 180
ntgtgctgca ccaanatgcc cagcattnta tcttcaagca nagcacttat cagggtcctt 240
ggcacac 247

<210> SEQ ID NO 145
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 145
cgtgggtcgc ggcccgangt ctgctgtaac aaaacaccat agtctgggca gctcatagac 60
aatggaattt tatttctcac gcttctggag gctggattcc aagatcaagg ttccaggaga 120
ctcagtgtct ggcaaggtct cggtttctgc ctcanagatg gtgccatctg gctgtgtcct 180
cacaagtagg aaggtgcaag aagctcccct caggctctgt ctgtaagaca ctgatcccat 240
tcatganggg gaaacgtaat gacctaatca gcccccagag accccacttc taacaccatc 300
accttgggg 309

-continued

<210> SEQ ID NO 146
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 146
agcgtgggtc gcggcncgac gtcctgtcca tatttcacag cccgagaact aatacaagat 60
gctgacatca tattttgtcc ctacaactat cttctanatg cacaaataag ggaaagtatg 120
gatttaaatc tgaaagaaca ggttgtcatt ttanatgaag ctcataacat cgaggactgt 180
gctcgggaat cagcaagtta cagtgtaaca gaagttcagc ttcggtttgc tcgggatgaa 240
ctanatagta tggtcaacaa taatataagg aaganagatc atgaacccct acgagctgtg 300
tgctgtagcc tcattaattg gntagaagca aacgctgaat atcttgnana angagantat 360
gaatcagctt gtaaaatatg gagtggaaat gaaatgctct taactttaca caaaatgggt 420
atcaccactg ctacttttcc cattttgcng gtaagatatn ttttctacct gngaaacgta 480
tttaag 486

<210> SEQ ID NO 147
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 147
gccgcccggg cangttcgac attacntnga gttccatgat gtacaattct ttcacgaaaa 60
acaatgaatg caagaatttg aggatctcct tactcctccc ttttacagat ggtctctcaa 120
tcccttcttc ttcctcttca tcttcatctt cttctgaacg cgctgccggg taccacggct 180
ttctttgtct ttatcgtgag atgaaggtga tgcttctgtt tcttctacca taactgaaga 240
aatttcgctg caagtctctt gactggctgt ttctccgact tcgcctttnt gtcaaacgng 300
agtcttttta cctcatgccc ctcagcttca cagcatcttc atctggatgt tnatttctca 360
aagggctcac tgaggaaact tctgattcan atgtcgaana gcactgtgaa gttttctctt 420
cattttgctg 430

<210> SEQ ID NO 148
<211> LENGTH: 483
<212> TYPE: DNA
<213> ORGANISM: Homo sapien
<220> FEATURE:
<221> NAME/KEY: misc_feature
<222> LOCATION: (1)...(483)
<223> OTHER INFORMATION: n = A,T,C or G

<400> SEQUENCE: 148
cccgggcagg tctgtgttgn tttncaaccg gtgtcctccc cagcgtccag aanangsaaa 60
tgtggagcgg gtgatgatga cccctcgctg tcctgtcacc tcctgcacag cttcgtatgt 120
gggtctggtc tgggaccacc cgtacaggtt gtgcacgttg tagtgctcca cgggggagct 180
gtccggcagg atctgctgac tctccatgca cagagtcttg ctgctcaggc ccttgtccct 240
agattccaaa tatggcatat agggtggggt tatttagcat ttcattgctg cagcccctga 300

-continued

```
cagatccatc cacaaaattt gatggctcat tcatatcaat ccacaatcca tcaaacttca    360

agctcttctc tggntctcga nggtttgcat agaactcttc tatctctttc ttccaccacg    420

canacctcgg ncgcgaccac gctaagccga attctgcana tatccatcac actggcggcc    480

gct                                                                  483


<210> SEQ ID NO 149
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 149

ctttcacgaa nacaatgaat gcaagaattt gaggatctcc ttactcctcc cttttacaga     60

tggtctctca atcccttctt cttcctcttc atcttcatct tcttctgaac gcgctgccgg    120

gtaccacggc tttctttgtc tttatcgtga gatgaaggtg atgcttctgt ttcttctacc    180

ataactgaag aaatttcgct gcaagtctct tgactggctg tttctccgac ttcgcctttt    240

tgcaaacgtg agtcttttta cctcatgccc ctcagcttcc acagcatctt catctggatg    300

ttcatttctc aaagggctca ctgaggaaac ttctgactca catgtcgaag aagcactgng    360

agtttctctt catttgctgc aaanttgctc tttgctggct gngctctcag accacccatt    420

tggctgcatg ggggctgac                                                 439


<210> SEQ ID NO 150
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 150

ggcncgcccg ggcangtcca ctccactttt gagctctgag ggaatacctt caggagggac     60

agggtcaggg agtcctggca gctccgcagc agagattcac attcattcag agacttgttg    120

tccagtgcaa tgccattgat cgcaacgatc ctgtctccca cagcaaggga cccttcttta    180

gcggcagggc ttccaggcag cacagcggca gcatacactc cattctccag actgatgcca    240

ctgtctttct gtccactgan gttgatgtgc agcggcgtga ccaccttccc acccagggac    300

ttcctccgcc gcacgaccat gttgatgggc cccctnccca ttgaggagcg ccttgatggc    360

ctgcttcttg nccttggtga tgaagtccac atcggtgatt ctcacagcca gtcattgacc    420

cttaagcggn catcagcaat gcttcctttg gccactttag ngacaaatat gccacagtcc    480

ccgggaaaca agggtcattc acaccttctg gcatatcaaa cacctcggcc gggancacta    540

agccgaattc tgcagatatc catcacactg gngggccg                            578


<210> SEQ ID NO 151
<211> LENGTH: 503
<212> TYPE: DNA
<213> ORGANISM: Homo sapien
<220> FEATURE:
<221> NAME/KEY: misc_feature
<222> LOCATION: (1)...(503)
<223> OTHER INFORMATION: n = A,T,C or G
```

-continued

<400> SEQUENCE: 151

```
cgagcggccc gcccgggcag gtctgggaga tcagcgactg ctgccacgtg cccagaaatg     60
gctcgtcctt tcactacagc ggaatgcaat gagggtgggt gagaagatga tgggtcggtt    120
atttcattcc ttttcttttt acaacttcac tttcagagac ttcagcgttc catgtctgct    180
gtgctgtgga acccagagtg ctcttgcctg gatggctgag aatcccttgg accctggaag    240
cacctactcc atgatggccc ggtatagtgc aggctcaata taatcttccc ggtatcttga    300
gttgataact cgttgccgtt tcttttcttg cttaacctct ttctctgtga aaatctcatt    360
gaagcgcatg tctgaagcta ctgacagtct anatttgact ctcttgggaa gctcttcatc    420
cagtgtgtat acatcatctc tcttaaccac aagttggagc catncttaaa cttcacctgg    480
tacatttgga tagggtggga ggc                                            503
```

<210> SEQ ID NO 152
<211> LENGTH: 553
<212> TYPE: DNA
<213> ORGANISM: Homo sapien
<220> FEATURE:
<221> NAME/KEY: misc_feature
<222> LOCATION: (1)...(553)
<223> OTHER INFORMATION: n = A,T,C or G

<400> SEQUENCE: 152

```
agcgtggtcg cggcccgagg tccactgagc tccgccttcc ccgggctccc tgaggaagca     60
gagtcctgac ttccaggaag gacaggacac agaggcaaga actcagcctg tgaggctctg    120
ggtggctcct gaggccagag gacgccttcc gcgatccatg gctcagcatc gtccttctgg    180
cttcccagcc ccgggccgaa cgttcgggtt aataagcaga gcagttattc ggctcctggc    240
aggagctccc ccgttagttt ccacgttgtg agcacattca tacttaagac tgnttctctt    300
tgtgttttaa gcgtctgtct ctgtagtaaa ctgaaatgtt aacagaaatg cagacctgcc    360
cgggcggccg ctcgaaagcc gaattctgca gatatccatc acactggcgg ccgctcgagc    420
atgcatctag anggcccaat tcgccctata gtgagtcgna ttacaattca ctgggccgcg    480
ntttacaacg tcgtgactgg gaaaaccctg cggtacccac ttaatcgcct tgcagnacat    540
ccccctttcg cca                                                       553
```

<210> SEQ ID NO 153
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 153

```
tcgagcggct cgcccgggca ggtccaccta gcatggctcc tctaaacacg caactcagcg     60
aggggacccc cttcacctct ggcaagagag ctgggtagat cagaaacttg gtgacacctg    120
gctagcacag agcaggctca cttgtcttgg tcccactacc cagattcctg cagacattgc    180
aaaccaaatg aaggttgntg aatgacccct gtccccagcc acttgttttg gtatcatctg    240
ctctgcagtg gaatgcctgt gtgtttgagt tcactctgca tctgtatatt tgagtataga    300
aaccgantca agtgatctgt gcatncagac acactggggc acctgancac agaacaaatc    360
accttaacga tctggaatga aactgnganc antgcccgcc tgggtgggtc tgganaaact    420
gccgncttct tgttggacct tggccgcacc acct                                454
```

-continued

<210> SEQ ID NO 154
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 154
agcgtggtcg cggcccgang gcggcctcct gantganggg aagggacgtg ggggcggcca 60
cggcaggatt aacctccatt tcagctaatc atgggagaga ttaaagtctc tcctgattat 120
aactggttta naggtacagt tccccttaaa aagattattg tggatgatga tgacagtaag 180
atatggtcgc tctatgacgc gggcccccga agtatcaggt gtcctctcat attcctgccc 240
cctgtcagtg gaactgcaga tgtctttttc cggcagattt tggctctgac tggatggggt 300
taccgggtta tcgctttgca gtatccagtt tattgggacc atctcgagtt cttgtgatgg 360
attcacaaaa cttttanacc atttacaatt ggataaagtt catctttttg gcgcttcttt 420
gggangcttt ttggcccana aatttgctga atacactcac aaatctccta gaagccattc 480
cctaatcctc tgcaattcct tcagngacac ctctatcttc aaccaacttg gactggaaac 540
agctttggct gatgcctgca tttatgctca aaaaatagtt cttggaaatt ttcatc 596

<210> SEQ ID NO 155
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 155
ctcganttgg cncgcccggg cangtctgcc tggtttttga ccgngcgagc tatttagnct 60
ctggctctgt ttccggagct caaggnaaaa atcttgaana actcgagcag cttctgtgga 120
tagccttggg tacacatact gccgagcata gccaatgtac tttctcaata gctggtgggg 180
aatgggatct attgtttctc caggaaccac ctttagtctt tctgataatg gcttctcaga 240
aactacttca agtacggaag tatttgaatc ttgactatnc atacgagcta ctgtggcact 300
gctaatgggn tctctgctnt ccagctctta ttgcaatcac atg 343

<210> SEQ ID NO 156
<211> LENGTH: 556
<212> TYPE: DNA
<213> ORGANISM: Homo sapien
<220> FEATURE:
<221> NAME/KEY: misc_feature
<222> LOCATION: (1)...(556)
<223> OTHER INFORMATION: n = A,T,C or G

<400> SEQUENCE: 156
tcgagcggcc cgcccgggca ggtctggcac cacncagatc gattaactgg ctcatctgat 60
ctcgtggccc ccaccctgga actgacttag cacaaaagga cacctcaatt ccttatgatt 120
tcatctccga cccaaccaat caacaccctt gactcactgg ccttccccct cccaccaaat 180
tatccttaaa aactctgatc cccgaatgct cagggagatc gatttgagta ctaataagac 240
tccagtctcc tgcacaagca gctctgtgta ctcttcctct attgcaattc ctgtcttgat 300

-continued

```
aaatcggctc tgtgtaggcg gcggaagaag tgaacctgtt gggcggttac cacctctgtc    360

gtgtgtgaca gttgntttga atctctaatt gctcagtaca gatccacatg caggttaagt    420

aagaagcttt tgaagaaaat ggaaagtctt aagtgatggc ttccaagaaa tcaaacctac    480

attaattagg gaacaacgga ctttacgtat cacaaatgaa gagactgacn aagtaaatca    540

acttggcctt ttctta                                                    556
```

```
<210> SEQ ID NO 157
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 157

ggtccacaaa aatatatnaa ataagctgga tatataaaan caaacactta acatngncan     60

cattccttca gttattcaaa ctcactgata nctaacnggg agnagttggn attctggaag    120

acttcctaag ctaaaagtat atttacatat ttacaacaca ngtaaatata acngaagaac    180

tacttcaaat aangnngaaa ttccagaatt ctanagattt atagctatag ntnacaanta    240

tcaccaattg gtttgcaatc aanngnccag cactacttat gannaangtt taactannaa    300

accaaaaggg gagaaaacct ggnagggaaa nat                                 333
```

```
<210> SEQ ID NO 158
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 158

tcgagcggcc gcccgggcag gtctggtaca tttgtgcgag gtccggcact ctgttctcat     60

ccagtaagtg gtcgagccct ttctgcagaa ttgctgttaa atgttctcct aatagctgtt    120

tctccacaca agcaatcagt ggtttctgtg tgctgtggtc caagtaagtg attactctgt    180

ctccctcttc ttctaagcgt ttacttacat ggttaagata ttctggaacc tctctttcct    240

gcattaacct ttggccttcg gcagcatata agcaattagt ctcttccaaa aatttcagtt    300

caaatgaatc tttatacacc tgcaggtcag acagcatgcc caggnaggct ccgcaacagg    360

ctccggtcca cggcctcgcc gctcctctcg cgctcgatca gcagtaggat tccatcaatg    420

gttttactct gaaccatttt atcactaata atatgggttc taaacagttc taatcccata    480

tcccagatgg agggcagcgt ggagttctgc agcacatagg tgcggtccaa gaacaggaag    540

atgcttctga tcatgaatca tttgnctggc aatggtcctg ccagcacgtg gtaatctttc    600

ttttaaaaat aaacccttat ctaaacgtc                                      629
```

```
<210> SEQ ID NO 159
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 159
```

-continued tcgagcggcc gcccgggcag gttctagagg ganaatctgg ctgatttggg aataaaatat 60
aatcgaatat tcaacaccat gaagataaat cttattttgg aaatctactg accttaatac 120
cccaagcttg ccctgaatac tttgattgga attggaatat atcaaaaaag gttagtattt 180
ttgttgtagt taggatacta aaaggatatt agttacccaa gagatccaat ttgtttttct 240
gatgaatagt gttcagtaaa atgaagcagt cttaagagtg actaataatt tcaaagtgat 300
ttttcgtcta ttcttaatat tttttaatta tttattttta agagttttat accttgagca 360
gatacaatga tccgctttag tgagaggaca atttctgatt gattgttttc tcttcaggcc 420
atctcacctc ttcattctct tgttacattt gaagcagttg atataatggg tttatacttt 480
aaaagataga catggtgcca tgaagtttgg ggaagttggg tgaattatcc cattctagtt 540
acagangagc tttccttaaa tgccctttac ttctangttt ggtcaagaag tcattttctg 600
agtaaaagtt attttcatat atgttgggg 629

<210> SEQ ID NO 160
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 160
tcgagcggcg cgcccgggca ggtctgctgg gattaatgcc aagttnttca gccataaggt 60
agcgaaatct agcagaatcc agattacatc cacttccaat cacgcggtgt ttgggtaatc 120
cacttagttt ccagataaca tacgtaagaa tgtccactgg gttggaaacc acaattatga 180
tgcaatcagg actgtacttg acgatctgag gaataatgaa tttgaagaca ttaacatttc 240
tctgcaccag attgagccga ctctcccctt cttgctgacg gactcctgca gttaccacta 300
caatcttana attgggcggg tcacagaata atctttatct gccacaattt taggtgctga 360
agaaataagc tcccatgctg cagatccatc atttctnctt taagcttatc ttccaaaaca 420
tccacaagan caangttcat cagccagaga ctttcccaga atgctgatag nacacgccat 480
accaacttgt ccaacancca ctacagcgat cttattggt 519

<210> SEQ ID NO 161
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 161
cgagnggccc gcccgggcag gtccagtaag cntttnacga tgatgggaaa ggttatgcaa 60
ggtcccagcg gtacaacgag ctgtttctac atcatttgta ttctgcatgg tacgtacaat 120
agcagacacc atctgaggag aacgcatgat agcgtgtctg gaagcttcct ttttagaaag 180
ctgatggacc ataactgcag ccttattaac caccacctgg tcctcgtcat ttagcagttt 240
tgtcagttca gggattgcac gtgtggcang ttctgcatca tcttgatagt taatcaagtt 300
tacaactggc atgtttcagc atctgcgatg ggctcagcaa acgctggaca ttantgggat 360
gagcagcatc aaactgtgta natgggatct gcatgccctc atctaatgtc tcagggaaca 420

-continued

```
tagcagctcg taccctctga gctcga                                          446


<210> SEQ ID NO 162
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 162

agcgtngtcg cggcccgang tcctgggaag cctttnttgc tgagcctcac agcctctgtc     60

aggcggctgc ggatccagcg gtccaccagg ctctcatggc ctccgggctg ggaggngggt    120

gagggcacaa aacccttccc aaggccacga anggcaaact tggtggcatt ccanagcttg    180

ttgcanaagt ggcggnaacc cagtatccgg ttcacatcca ggntgatgtc acgaccctgg    240

gacatgtang cacataatcc aaaccggaga gcatcggtgc cacattcacg aatccccgct    300

gggaagtcag ctttctgccc ttctttggcc ttctccacct cgctgggatc cagg          354


<210> SEQ ID NO 163
<211> LENGTH: 258
<212> TYPE: DNA
<213> ORGANISM: Homo sapien
<220> FEATURE:
<221> NAME/KEY: misc_feature
<222> LOCATION: (1)...(258)
<223> OTHER INFORMATION: n = A,T,C or G

<400> SEQUENCE: 163

tttttcncca agtcctcttg ccgngggatc tngactgcaa tttaagacac ttctaattag     60

ttatacccag gccctgcaaa attgctgggt ttatataata tattcttgct gcacgaagat    120

ttattattct gttggatgat tctattttaa ttntatttat tctggccaaa aaagaacctt    180

ctccgctcgt caagagangc caatntgtct tgaaggacaa gagaaagatg ctaacacaca    240

ctttcttctt cttgagga                                                   258


<210> SEQ ID NO 164
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 164

ggaacatatt acttttaaat tacttgggtc aatgaaacat ttaataaaaa catttgcttc     60

tctatataat acgtatgtat aaaataagcc ttttcanaaa ctctggttct cataatcctc    120

tataaatcan atgatctgac ttctaagagg aacaaattac agnaaggggt atacattnat    180

gaatactggt agtactagag ganngacgct aaaccactct actaccactt gcggaactct    240

cacagggtaa atgacaaagc caatgactga ctctaaaaac aa                        282


<210> SEQ ID NO 165
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G
```

-continued

<400> SEQUENCE: 165
gcccgggcan gtcctgtaat cccagctact cangangctg agtcatgana atcgcctgaa 60
tccgggaggt agaggccgca gcgagcaaag attaagccac tgcactccag tctgggtgac 120
agagtgagaa tctgtctgtt gctcctctgg cattggtctg aaatgggttt gtagaacatg 180
ccacagaagg accagcanca gcaacaaatg gatttgtgga angcgtagct ccaaatggag 240
cangcacact tgatgaagca cgctgtgtct gtgcagangc aaccactggc actgttccaa 300
aaacattgct gctagcatta cttgtggaag tatacgcatt actggaggtg gctgcanaac 360
tgaaaacgct gtctagttct gccanagctg catacttgnc tgaanatgca cttgactgac 420
tgggaactga accacanaac caacaggacc tttacctgtg ga 462

<210> SEQ ID NO 166
<211> LENGTH: 365
<212> TYPE: DNA
<213> ORGANISM: Homo sapien
<220> FEATURE:
<221> NAME/KEY: misc_feature
<222> LOCATION: (1)...(365)
<223> OTHER INFORMATION: n = A,T,C or G

<400> SEQUENCE: 166
cgtgggtcgc ggcncgangt ctgaaaccaa tccagaacta aacatcagca cacaaaaaat 60
accaggatag atggaatcaa aagactctga agccaaaagg aggctaggga gagcaactga 120
acttagcaag ctgaggactt cagtgtccat catccgatcc tgccctgtaa caacaggtct 180
atatgataga gatattccat ctgagctgga ggccattatc cttagcaaac taacacagaa 240
cagaaaacca aatacatgtt ctcatttaga agtaggagct aaatgatgag aactcaagga 300
cacaaagaaa ggaacaacag acactggggc ctacttgagg gtggagggtg ggaggaggga 360
gaaga 365

<210> SEQ ID NO 167
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 167
agcgtggtcg cggcgcgang tccagcccta gcttgcctgt gactccgcct tcactgggtg 60
ctctctctaa aagttgctga ctctttactg tatctcccaa ttcccactcc attggttcca 120
taaggggagg ggtgtctcac tcaacatggt gttcctggta ccaagaactg gctgacgaag 180
ctgggtgccg tggctcatgc ctgtaatccc agcacttttg ggaggccaag aagggcggat 240
cacctgaggt ctggagttca agatcagcct gaccaacatg atgaaaccaa gtctccacta 300
aaaatataaa acaattagcc aggcatggtg gtgggtgcct gnaatcccag ctactgggga 360 ngct 364

<210> SEQ ID NO 168
<211> LENGTH: 447
<212> TYPE: DNA
<213> ORGANISM: Homo sapien
<220> FEATURE:
<221> NAME/KEY: misc_feature
<222> LOCATION: (1)...(447)

-continued

<223> OTHER INFORMATION: n = A,T,C or G

<400> SEQUENCE: 168
cccgggcagg tcaaaaccca aaacctttca ttttagccca aaccagctca tgattaggta 60
tacaaggata acagaaccag ttgtcaggac gagcatttga caagtaaaag caattcttgc 120
aaagctgcag ttcatccagc tcatggcatg tgtctttata tagcatcctc gcaatgtcag 180
cttgctcact gtctgctcca tagaaaatca cggtattgtg gagaagcaat tgggcatcag 240
ctttgaactc ttcataactt cggtatttcc cttcattcac tttctcttga atggtgggaa 300
cgtccacaga cctcggccgc gaccacgcta agcccgaatt ctgcagatat ccatcacact 360
ggcggccgtt cgagcatggc atctagaagg cccaattcgc ctatagngag tcgnattacc 420
aattcactgg ccgtcgnttt acaacgc 447

<210> SEQ ID NO 169
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 169
cgantngcgc gcccgggcag gtctgagcag cctttctgnn tgctggacta ttgggattgg 60
gttcatccaa cagagactgt atggatgtta gaatggaaga cacatcatag gttggactcc 120
aacggttctg aagtatgtcc agacatatac taccatctgc atagactaag aacaaagaag 180
taggtacatt aaacgtaaca agaccactaa ggttttaaca ttatagacaa aacanaaata 240
gtcaaganta ctttgctttt gaagtttaaa gattcctatg ttgcttccca gttaactgcc 300
taaaaagata agncataacc accactagtg aaataatcan gatgatcaga gaatgtcana 360
tgtgatcagt ataaaactgg angatattna gtgtcatcct ttggaaaagg ctgccctatn 420
atccaggaaa tcanaaacat tnttgaacag ggnccctagc tatccacaga catgtgggaa 480
attcattccc caaatngtag gctggatccc ctatctgaaa taac 524

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170
tcgancggcn cgcccgggca ggtgacaaac ctgttattga agatgttggt tctgatgagg 60
aanaanatca gaagggatgg tgacaagaan aanaanaaga agattaagga aaagtacatc 120
gatcaagaag agctcaacaa aacaaagccc atctggacca gaaatcccga cgatattact 180
aatgangagt acggagaatt ctataanagc ttgaccaatg actgggaaga tcacttggca 240
gtgaagcatt tttcagttga nggacagttg gaattcagag cccttctatn tgtcccacga 300
cgtgctcctt ttgatctgtt tganancaga aa 332

<210> SEQ ID NO 171
<211> LENGTH: 334
<212> TYPE: DNA
<213> ORGANISM: Homo sapien -continued
<220> FEATURE:
<221> NAME/KEY: misc_feature
<222> LOCATION: (1)...(334)
<223> OTHER INFORMATION: n = A,T,C or G

<400> SEQUENCE: 171

```
cgagnggcnc gcccgggcag gtctgttgat agcgacttaa cagaaaagtc tagacaaaca     60

taagcataaa aaattacagt ctttctaccc ttgggaatgg ggagaaaaag gaatctctac    120

cccaagacca gaaataataa gtcctgtttc tggtcctgaa catccagaat tatggaggct    180

ttggcctgac accacattan aatttggtct ggaaatcaaa ctttaganac angagatcgt    240

aagccatttt atactatcga cctaaattcc agtctaacgg ttcctttaca aagttgcgga    300

aagccctctt atatgctagc tgtaggaaat atag                                334
```

<210> SEQ ID NO 172
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 172

```
agcgtggtcg cggcccgang tctgcctata aaactagact tctgacgctg ggctccagct     60

tcattctcac aggtcatcat cctcatccgg gagagcagtt gtctgagcaa cctctaagtc    120

gtgctcatac tgtgctgcca aagctgggtc catgacaact tctggtgggg cgagagcagg    180

catggcaaca aattccaagt tagggtctcc aatgagcttc ctagcaagcc agaggaaggg    240

cttttcaaag ttgtagttac ttttggcaga aatgtcgtag tactgaagat tcttctttcg    300

gtggaagaca atggatttcg ccttcacttt ctgccttaat atccactttg gtgccacaca    360

acacaatggg gatgntttca cacacttngn accanatctc tatgccagnt aggccatttt    420

ggaagnactt cganggtac                                                 439
```

<210> SEQ ID NO 173
<211> LENGTH: 599
<212> TYPE: DNA
<213> ORGANISM: Homo sapien
<220> FEATURE:
<221> NAME/KEY: misc_feature
<222> LOCATION: (1)...(599)
<223> OTHER INFORMATION: n = A,T,C or G

<400> SEQUENCE: 173

```
cgatnggccg cccgggcagg tcctgtaaaa naggaaattc agacatcgta cgactcgtaa     60

ttgaatgtgg agctgactgc aatattttgt caaagcacca gaatagtgcc ctgcactttg    120

cgaagcagtc taacaatgtg cttgtgtacg acttgctgaa gaaccattta gagacacttt    180

caagagtagc agaagagaca ataaaggatt actttgaagc tcgccttgct ctgctagaac    240

cagtttttcc aatcgcatgt catcgactct gtgagggtcc agatttttca acagatttca    300

attaccaacc cccacagaac ataccagaag gctctggcat cctgctgttt atcttccatg    360

caaacttttt gggtaaagaa gttattgctc ggctctgtgg accgtgtagt gtacaagctg    420

tagttctgaa tgataaattt cagcttcctg tttttctggg tctcgctctg ttgtccaggc    480

tggagtgcag tggcgcggat tacagctcac tggagtcttg acttcccagg cacaagcaat    540

cctcccacct cagcctccta actacctggg actaaaaatg caccgccacc acattccgg     599
```

-continued

<210> SEQ ID NO 174
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 174

```
tcgatttggc cgcccgggca ggtccatgcn gnttntgccc attcccatgg ngcccgacaa     60

ncccatcccc gaggccgaca tccccatgtt catgttcatg cccaccatgc cctggctcat    120

ccctgcgctg ttccccagag gggccattcc catggtgccc gtcattacac cgggcatgtt    180

cataggcatg ggtcccccca ggagagggtt agnttgaggc cggacaggaa gcatgtttga    240

tggagaactg aggttcacag nctccaaaac tttgagtcat cacattcata ggctgctgca    300

tattctgtct gctgaatcca ttgtatncag tgatggcctg ctggggnttt ggaaggctng    360

cataccaggt agtaagntcg tctaggctga tgtttacacc tggggtcaga ccaagtanga    420

gggcaaggtt ttgctgactg attttctgga cccatatc                            458
```

<210> SEQ ID NO 175
<211> LENGTH: 1206
<212> TYPE: DNA
<213> ORGANISM: Homo sapien

<400> SEQUENCE: 175

```
ggcacgagga agttttgtgt actgaaaaag aaactgtcag aagcaaaaga aataaaatca     60

cagttagaga accaaaaagt taaatgggaa caagagctct gcagtgtgag gtttctcaca    120

ctcatgaaaa tgaaaattat ctcttacatg aaaattgcat gttgaaaaag gaaattgcca    180

tgctaaaact ggaaatagcc acactgaaac accaatacca ggaaaaggaa aataaatact    240

ttgaggacat taagatttta aaagaaaaga atgctgaact tcagatgacc ctaaaactga    300

aagaggaatc attaactaaa agggcatctc aatatagtgg gcagcttaaa gttctgatag    360

ctgagaacac aatgctcact tctaaattga aggaaaaaca agacaaagaa atactagagg    420

cagaaattga atcacaccat cctagactgg cttctgctgt acaagaccat gatcaaattg    480

tgacatcaag aaaaagtcaa gaacctgctt tccacattgc aggagatgct tgtttgcaaa    540

gaaaaatgaa tgttgatgtg agtagtacga tatataacaa tgaggtgctc catcaaccac    600

tttctgaagc tcaaaggaaa tccaaaagcc taaaaattaa tctcaattat gccggagatg    660

ctctaagaga aaatacattg gtttcagaac atgcacaaag agaccaacgt gaaacacagt    720

gtcaaatgaa ggaagctgaa cacatgtatc aaaacgaaca agataatgtg aacaaacaca    780

ctgaacagca ggagtctcta gatcagaaat tatttcaact acaaagcaaa aatatgtggc    840

ttcaacagca attagttcat gcacataaga aagctgacaa caaaagcaag ataacaattg    900

atattcattt tcttgagagg aaaatgcaac atcatctcct aaaagagaaa aatgaggaga    960

tatttaatta caataaccat ttaaaaaacc gtatatatca atatgaaaaa gagaaagcag   1020

aaacagaagt tatataatag tataacactg ccaaggagcg gattatctca tcttcatcct   1080

gtaattccag tgtttgtcac gtggttgttg aataaatgaa taaagaatga gaaaaccaga   1140

agctctgata cataatcata atgataatta tttcaatgca caactacggg tggtgctgct   1200

cgtgcc                                                              1206
```

-continued

<210> SEQ ID NO 176
<211> LENGTH: 317
<212> TYPE: PRT
<213> ORGANISM: Homo sapien

<400> SEQUENCE: 176

```
Met Gly Thr Arg Ala Leu Gln Cys Glu Val Ser His Thr His Glu Asn
 1               5                  10                  15

Glu Asn Tyr Leu Leu His Glu Asn Cys Met Leu Lys Lys Glu Ile Ala
            20                  25                  30

Met Leu Lys Leu Glu Ile Ala Thr Leu Lys His Gln Tyr Gln Glu Lys
        35                  40                  45

Glu Asn Lys Tyr Phe Glu Asp Ile Lys Ile Leu Lys Glu Lys Asn Ala
    50                  55                  60

Glu Leu Gln Met Thr Leu Lys Leu Lys Glu Glu Ser Leu Thr Lys Arg
65                  70                  75                  80

Ala Ser Gln Tyr Ser Gly Gln Leu Lys Val Leu Ile Ala Glu Asn Thr
                85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
    130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
    210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
        275                 280                 285

Lys Asn Glu Glu Ile Phe Asn Tyr Asn Asn His Leu Lys Asn Arg Ile
    290                 295                 300

Tyr Gln Tyr Glu Lys Glu Lys Ala Glu Thr Glu Val Ile
305                 310                 315
```

<210> SEQ ID NO 177
<211> LENGTH: 20
<212> TYPE: DNA
<213> ORGANISM: Artificial Sequence
<220> FEATURE:
<223> OTHER INFORMATION: Made in the Lab

<400> SEQUENCE: 177

```
ccaatcatct ccacaggagc                                                20
```

-continued

<210> SEQ ID NO 178
<211> LENGTH: 1665
<212> TYPE: DNA
<213> ORGANISM: Homo sapien

<400> SEQUENCE: 178

```
gcaaactttc aagcagagcc tcccgagaag ccatctgcct tcgagcctgc cattgaaatg     60
caaaagtctg ttccaaataa agccttggaa ttgaagaatg aacaaacatt gagagcagat    120
cagatgttcc cttcagaatc aaaacaaaag aaggttgaag aaaattcttg ggattctgag    180
agtctccgtg agactgtttc acagaaggat gtgtgtgtac ccaaggctac acatcaaaaa    240
gaaatggata aaataagtgg aaaattagaa gattcaacta gcctatcaaa aatcttggat    300
acagttcatt cttgtgaaag agcaagggaa cttcaaaaag atcactgtga acaacgtaca    360
ggaaaaatgg aacaaatgaa aaagaagttt tgtgtactga aaaagaaact gtcagaagca    420
aaagaaataa aatcacagtt agagaaccaa aaagttaaat gggaacaaga gctctgcagt    480
gtgaggtttc tcacactcat gaaaatgaaa attatctctt acatgaaaat tgcatgttga    540
aaaaggaaat tgccatgcta aaactggaaa tagccacact gaaacaccaa taccaggaaa    600
aggaaaataa atactttgag gacattaaga ttttaaaaga aaagaatgct gaacttcaga    660
tgaccctaaa actgaaagag gaatcattaa ctaaaagggc atctcaatat agtgggcagc    720
ttaaagttct gatagctgag aacacaatgc tcacttctaa attgaaggaa aaacaagaca    780
aagaaatact agaggcagaa attgaatcac accatcctag actggcttct gctgtacaag    840
accatgatca aattgtgaca tcaagaaaaa gtcaagaacc tgctttccac attgcaggag    900
atgcttgttt gcaaagaaaa atgaatgttg atgtgagtag tacgatatat aacaatgagg    960
tgctccatca accactttct gaagctcaaa ggaaatccaa aagcctaaaa attaatctca   1020
attatgccgg agatgctcta agagaaaata cattggtttc agaacatgca caaagagacc   1080
aacgtgaaac acagtgtcaa atgaaggaag ctgaacacat gtatcaaaac gaacaagata   1140
atgtgaacaa acacactgaa cagcaggagt ctctagatca gaaattattt caactacaaa   1200
gcaaaaatat gtggcttcaa cagcaattag ttcatgcaca taagaaagct gacaacaaaa   1260
gcaagataac aattgatatt cattttcttg agaggaaaat gcaacatcat ctcctaaaag   1320
agaaaaatga ggagatattt aattacaata accatttaaa aaaccgtata tatcaatatg   1380
aaaaagagaa agcagaaaca gaaaactcat gagagacaag cagtaagaaa cttcttttgg   1440
agaaacaaca gaccagatct ttactcacaa ctcatgctag gaggccagtc ctagcattac   1500
cttatgttga aaatcttacc aatagtctgt gtcaacagaa tacttatttt agaagaaaaa   1560
ttcatgattt cttcctgaag cctgggcgac agagcgagac tctgtctcaa aaaaaaaaaa   1620
aaaaaaagaa agaaagaaat gcctgtgctt acttcgcttc ccagg                   1665
```

<210> SEQ ID NO 179
<211> LENGTH: 179
<212> TYPE: PRT
<213> ORGANISM: Homo sapien

<400> SEQUENCE: 179

```
Ala Asn Phe Gln Ala Glu Pro Pro Glu Lys Pro Ser Ala Phe Glu Pro
 1               5                  10                  15

Ala Ile Glu Met Gln Lys Ser Val Pro Asn Lys Ala Leu Glu Leu Lys
            20                  25                  30

Asn Glu Gln Thr Leu Arg Ala Asp Gln Met Phe Pro Ser Glu Ser Lys
```

-continued

```
        35                  40                  45

Gln Lys Lys Val Glu Glu Asn Ser Trp Asp Ser Glu Ser Leu Arg Glu
    50                  55                  60

Thr Val Ser Gln Lys Asp Val Cys Val Pro Lys Ala Thr His Gln Lys
65                  70                  75                  80

Glu Met Asp Lys Ile Ser Gly Lys Leu Glu Asp Ser Thr Ser Leu Ser
                85                  90                  95

Lys Ile Leu Asp Thr Val His Ser Cys Glu Arg Ala Arg Glu Leu Gln
            100                 105                 110

Lys Asp His Cys Glu Gln Arg Thr Gly Lys Met Glu Gln Met Lys Lys
        115                 120                 125

Lys Phe Cys Val Leu Lys Lys Lys Leu Ser Glu Ala Lys Glu Ile Lys
    130                 135                 140

Ser Gln Leu Glu Asn Gln Lys Val Lys Trp Glu Gln Glu Leu Cys Ser
145                 150                 155                 160

Val Arg Phe Leu Thr Leu Met Lys Met Lys Ile Ile Ser Tyr Met Lys
                165                 170                 175

Ile Ala Cys
```

<210> SEQ ID NO 180
<211> LENGTH: 1681
<212> TYPE: DNA
<213> ORGANISM: Homo sapien

<400> SEQUENCE: 180

```
gatacagtca ttcttgtgaa agagcaaggg aacttcaaaa agatcactgt gaacaacgta     60

caggaaaaat ggaacaaatg aaaaagaagt tttgtgtact gaaaaagaaa ctgtcagaag    120

caaaagaaat aaaatcacag ttagagaacc aaaaagttaa atgggaacaa gagctctgca    180

gtgtgagatt gactttaaac caagaagaag agaagagaag aaatgccgat atattaaatg    240

aaaaaattag ggaagaatta ggaagaatcg aagagcagca taggaaagag ttagaagtga    300

aacaacaact tgaacaggct ctcagaatac aagatataga attgaagagt gtagaaagta    360

atttgaatca ggtttctcac actcatgaaa atgaaaatta tctcttacat gaaaattgca    420

tgttgaaaaa ggaaattgcc atgctaaaac tggaaatagc cacactgaaa caccaatacc    480

aggaaaagga aaataaatac tttgaggaca ttaagatttt aaaagaaaag aatgctgaac    540

ttcagatgac cctaaaactg aaagaggaat cattaactaa aagggcatct caatatagtg    600

ggcagcttaa agttctgata gctgagaaca caatgctcac ttctaaattg aaggaaaaac    660

aagacaaaga aatactagag gcagaaattg aatcacacca tcctagactg gcttctgctg    720

tacaagacca tgatcaaatt gtgacatcaa gaaaaagtca agaacctgct ttccacattg    780

caggagatgc ttgtttgcaa agaaaaatga atgttgatgt gagtagtacg atatataaca    840

atgaggtgct ccatcaacca ctttctgaag ctcaaaggaa atccaaaagc ctaaaaatta    900

atctcaatta tgccggagat gctctaagag aaaatacatt ggtttcagaa catgcacaaa    960

gagaccaacg tgaaacacag tgtcaaatga aggaagctga acacatgtat caaaacgaac   1020

aagataatgt gaacaaacac actgaacagc aggagtctct agatcagaaa ttatttcaac   1080

tacaaagcaa aaatatgtgg cttcaacagc aattagttca tgcacataag aaagctgaca   1140

acaaaagcaa gataacaatt gatattcatt ttcttgagag gaaaatgcaa catcatctcc   1200

taaaagagaa aaatgaggag atatttaatt acaataacca tttaaaaaac cgtatatatc   1260

aatatgaaaa agagaaagca gaaacagaaa actcatgaga gacaagcagt aagaaacttc   1320
```

-continued

```
ttttggagaa acaacagacc agatctttac tcacaactca tgctaggagg ccagtcctag   1380

cattacctta tgttgaaaaa tcttaccaat agtctgtgtc aacagaatac ttattttaga   1440

agaaaaattc atgatttctt cctgaagcct acagacataa aataacagtg tgaagaatta   1500

cttgttcacg aattgcataa aagctgccca ggatttccat ctaccctgga tgatgccgga   1560

gacatcattc aatccaacca gaatctcgct ctgtcactca ggctggagtg cagtgggcgc   1620

aatctcggct cactgcaact ctgcctccca ggttcacgcc attctctggc acagcctccc   1680

g                                                                   1681
```

```
<210> SEQ ID NO 181
<211> LENGTH: 432
<212> TYPE: PRT
<213> ORGANISM: Homo sapien

<400> SEQUENCE: 181

Asp Thr Val His Ser Cys Glu Arg Ala Arg Glu Leu Gln Lys Asp His
 1               5                  10                  15

Cys Glu Gln Arg Thr Gly Lys Met Glu Gln Met Lys Lys Lys Phe Cys
            20                  25                  30

Val Leu Lys Lys Lys Leu Ser Glu Ala Lys Glu Ile Lys Ser Gln Leu
        35                  40                  45

Glu Asn Gln Lys Val Lys Trp Glu Gln Glu Leu Cys Ser Val Arg Leu
    50                  55                  60

Thr Leu Asn Gln Glu Glu Glu Lys Arg Arg Asn Ala Asp Ile Leu Asn
65                  70                  75                  80

Glu Lys Ile Arg Glu Glu Leu Gly Arg Ile Glu Glu Gln His Arg Lys
                85                  90                  95

Glu Leu Glu Val Lys Gln Gln Leu Glu Gln Ala Leu Arg Ile Gln Asp
            100                 105                 110

Ile Glu Leu Lys Ser Val Glu Ser Asn Leu Asn Gln Val Ser His Thr
        115                 120                 125

His Glu Asn Glu Asn Tyr Leu Leu His Glu Asn Cys Met Leu Lys Lys
    130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220

Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Lys Ser Leu Lys Ile Asn Leu Asn Tyr
    290                 295                 300
```

-continued

```
Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
                325                 330                 335

Tyr Gln Asn Glu Gln Asp Asn Val Asn Lys His Thr Glu Gln Gln Glu
            340                 345                 350

Ser Leu Asp Gln Lys Leu Phe Gln Leu Gln Ser Lys Asn Met Trp Leu
        355                 360                 365

Gln Gln Gln Leu Val His Ala His Lys Lys Ala Asp Asn Lys Ser Lys
    370                 375                 380

Ile Thr Ile Asp Ile His Phe Leu Glu Arg Lys Met Gln His His Leu
385                 390                 395                 400

Leu Lys Glu Lys Asn Glu Glu Ile Phe Asn Tyr Asn Asn His Leu Lys
                405                 410                 415

Asn Arg Ile Tyr Gln Tyr Glu Lys Glu Lys Ala Glu Thr Glu Asn Ser
            420                 425                 430


<210> SEQ ID NO 182
<211> LENGTH: 511
<212> TYPE: DNA
<213> ORGANISM: Homo sapiens

<400> SEQUENCE: 182

gaagtttcat gaggtttagc ttttctgggc tggggagtgg agagaaagaa gttgcagggc     60

ttacaggaaa tcccagagcc tgaggttttc tcccagattt gagaactcta gattctgcat    120

cattatcttt gagtctatat tctcttgggc tgtaagaaga tgaggaatgt aataggtctg    180

ccccaagcct ttcatgcctt ctgtaccaag cttgtttcct tgtgcatcct tcccaggctc    240

tggctgcccc ttattggaga atgtgatttc caagacaatc aatccacaag tgtctaagac    300

tgaatacaaa gaacttcttc aagagttcat agacgacaat gccactacaa atgccataga    360

tgaattgaag gaatgttttc ttaaccaaac ggatgaaact ctgagcaatg ttgaggtgtt    420

tatgcaatta atatatgaca gcagtctttg tgatttattt taactttctg caagaccttt    480

ggctcacaga actgcagggt atggtgagaa a                                    511


<210> SEQ ID NO 183
<211> LENGTH: 260
<212> TYPE: DNA
<213> ORGANISM: Homo sapiens

<400> SEQUENCE: 183

cacctcgcgg ttcagctcct ctgtcttggt gaagaaccat tcctcggcat ccttgcggtt     60

cttctctgcc atcttctcat actggtcacg catctcgttc agaatgcggc tcaggtccac    120

gccaggtgca gcgtccatct ccacattgac atctccaccc acctggcctc tcagggcatt    180

catctcctcc tcgtggttct tcttcaggta ggccagctcc tccttcaggc tctcaatctg    240

catctccagg tcagctctgg                                                 260


<210> SEQ ID NO 184
<211> LENGTH: 461
<212> TYPE: DNA
<213> ORGANISM: Homo sapiens

<400> SEQUENCE: 184

gtctgatggg agaccaaaga atttgcaagt ggatggtttg gtatcactgt aaataaaaag     60
```

-continued

```
agggcctttt ctagctgtat gactgttact tgaccttctt tgaaaagcat tcccaaaatg    120

ctctatttta gatagattaa cattaaccaa cataattttt tttagatcga gtcagcataa    180

atttctaagt cagcctctag tcgtggttca tctctttcac ctgcatttta tttggtgttt    240

gtctgaagaa aggaaagagg aaagcaaata cgaattgtac tatttgtacc aaatctttgg    300

gattcattgg caaataattt cagtgtggtg tattattaaa tagaaaaaaa aaattttgtt    360

tcctaggttg aaggtctaat tgataccgtt tgacttatga tgaccattta tgcactttca    420

aatgaatttg ctttcaaaat aaatgaagag cagacctcgg c                        461
```

<210> SEQ ID NO 185
<211> LENGTH: 531
<212> TYPE: DNA
<213> ORGANISM: Homo sapiens

<400> SEQUENCE: 185

```
tctgatttta tttccttctc aaaaaaagtt atttacagaa ggtatatatc aacaatctga     60

caggcagtga acttgacatg attagctggc atgatttttt cttttttttc ccccaaacat    120

tgtttttgtg gccttgaatt ttaagacaaa tattctacac ggcatattgc acaggatgga    180

tggcaaaaaa aagtttaaaa acaaaaaccc ttaacggaac tgccttaaaa aggcagacgt    240

cctagtgcct gtcatgttat attaaacata catacacaca atctttttgc ttattataat    300

acagacttaa atgtacaaag atgttttcca ctttttttcaa tttttaaaca caacagctat    360

aaacctgaac acatatgcta tcatcatgcc ataagactaa aacaattata tttagcgaca    420

agtagaaagg attaaatagt caaatacaag aatgaaaaac gcagtacata gtgtcgcgaa    480

ctcaaatcgg catttagata gatccagtgg tttaaacggc acgtttttgc t             531
```

<210> SEQ ID NO 186
<211> LENGTH: 441
<212> TYPE: DNA
<213> ORGANISM: Homo sapiens

<400> SEQUENCE: 186

```
cattcctttc ctcgcgttgg ggtttctctg tgtcagcgag cctcggtaca ctgatttccg     60

atcaaaagaa tcatcatctt taccttgact tttcagggaa ttactgaact ttcttctcag    120

aagatagggc acagccattg ccttggcctc acttgaaggg tctgcatttg ggtcctctgg    180

tctcttgcca agtttcccaa ccactcgagg gagaaatatc gggaggtttg acttcctccg    240

gggctttccc gagggcttca ccgtgagccc tgcggccctc agggctgcaa tcctggattc    300

aatgtctgaa acctcgctct ctgcctgctg gacttctgag gccgtcactg ccactctgtc    360

ctccagctct gacagctcct catctgtggt cctgttgtac tggacggggt ccccagggtc    420

ctgggggctt ttttcctgtc t                                              441
```

<210> SEQ ID NO 187
<211> LENGTH: 371
<212> TYPE: DNA
<213> ORGANISM: Homo sapiens

<400> SEQUENCE: 187

```
aaaagtgaat gagtaactat tatattgttg gcaataataa gttgcaaaat catcaggctg     60

caggctgctg atggtgagag tgaactctgt cccagatcca ctgccgctga accttgatgg    120

gaccccagat tctaaactag acgccttatg gatcaggagc tttggggctt tccctggttt    180

ctgttgatac caggccaacc aactactaac actctgactg gcccggcaag tgatggtgac    240
```

-continued

```
tctgtctcct acagttgcag acagggtgga aggagactgg gtcatctgga tgtcacattt    300

ggcacctggg agccagagca gcaggagccc caggagctga gcggggaccc tcatgtccat    360

gctgagtcct g                                                         371
```

<210> SEQ ID NO 188
<211> LENGTH: 226
<212> TYPE: DNA
<213> ORGANISM: Homo sapiens

<400> SEQUENCE: 188

```
ggtatataaa ttgagatgcc cccccaggcc agcaaatgtt cctttttgtt caaagtctat     60

ttttattcct tgatattttt cttttttttt tttttgtgga tggggacttg tgaatttttc    120

taaaggtgct atttaacatg ggaggagagc gtgtgcggct ccagcccagc ccgctgctca    180

ctttccaccc tctctccacc tgcctctggc ttctcaggac ctgccc                   226
```

<210> SEQ ID NO 189
<211> LENGTH: 391
<212> TYPE: DNA
<213> ORGANISM: Homo sapiens
<220> FEATURE:
<221> NAME/KEY: misc_feature
<222> LOCATION: (1)...(391)
<223> OTHER INFORMATION: n=A,T,C or G

<400> SEQUENCE: 189

```
tgggtgaagt ttattctgtt ttcacatcta ggttgttggg ganagtgata gacaaagttc     60

tggattctgg gcatcgtcgg cgcatgcttg taatcctact tggggaggttg anacaggaga    120

cctcggccgc naccacgcta agggcgaatt ctgcanatat ccatcacact ggcggccgct    180

cgagcatgca tctanagggc ccaattcncc ctatagtgag ncgtattaca attcactggc    240

cgtcgtttta caacgtcgtg actgggaaaa ccctggcgtt acccaactta atcgccttgc    300

agcacatccc cctttcncca gctggcttaa tancgaagag gcccgcaccg atcgcccttc    360

ccaacanttg cgcagcctga atggcgaatg g                                   391
```

<210> SEQ ID NO 190
<211> LENGTH: 501
<212> TYPE: DNA
<213> ORGANISM: Homo sapiens

<400> SEQUENCE: 190

```
catcttggcc tttttgagct gtttccgctt cttctcatcc cggtcactgt caccctcatt     60

actggaggag ctggcagagg cgttgctgtc aaactcctct gccacatctt cctcctcttc    120

acctgggttg aatgactcat cggtttcttc tcctgagtca tcgctgctgt cattggcatt    180

ctcctcccgg atcttgcctt cctccttcat cctctccaag taggcatcat gctggtcctc    240

atcagagtca gcatattcat cgtagcttgg gttcatgccc tctttcaatc ctcggttttt    300

gatgttgagc tttttcgcgt tgacaaaatc aaacagtttc ccgtactcct ccctctcaat    360

gctgctgaag gtatactgag tgccctgctt ggtctcaatt tcaaagtcaa aggaacgagt    420

agtagtggta ccacgagcaa agttgacaaa ggagatctca tcgaagcgga tgtgcacagg    480

tggcttgtgg acgtagatga a                                              501
```

<210> SEQ ID NO 191
<211> LENGTH: 241
<212> TYPE: DNA

-continued

<213> ORGANISM: Homo sapiens
<220> FEATURE:
<221> NAME/KEY: misc_feature
<222> LOCATION: (49)
<223> OTHER INFORMATION: n=A,T,C or G

<400> SEQUENCE: 191
ggaaaaactg tgaaaaatat atctgaattt attaagtaca gtataaaana gggttgtggc 60
aacagaaagt aaaaactaac atggattgct ataaatatgc tgaagcctag ttgttcaaat 120
gatacaattc tctcatgcta ctctaaagtt tataaagaaa aaggatttac actttacaca 180
ctgtacacaa aaggaatacc ttctgagagc cagggagtgg ggaaagggga aggagacttg 240
a 241

<210> SEQ ID NO 192
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n=A,T,C or G

<400> SEQUENCE: 192
tggtcntgga ttcacanata aantanatcg actaaaactg gcagaaattg tgaagcaggt 60
gatagaagan caaaccacgt cccacgaatc ccaataatga cagcttcaga ctttgctttt 120
ttaacaattt gaaaaattat tctttaatgt ataaagtaat tttatgtaaa ttaataaatc 180
ataatttcat ttccacattg attaaagctg ctgtatagat ttagggngca ggacttaata 240
atagnggaaa tgaaattatg atttattaat c 271

<210> SEQ ID NO 193
<211> LENGTH: 351
<212> TYPE: DNA
<213> ORGANISM: Homo sapiens

<400> SEQUENCE: 193
agtcgaggcg ctgatcccta aaatggcgaa catgtgtttt catcatttca gccaaagtcc 60
taacttcctg tgcctttcct atcacctcga gaagtaatta tcagttggtt tggatttttg 120
gaccaccgtt cagtcatttt gggttgccgt gctcccaaaa cattttaaat gaaagtattg 180
gcattcaaaa agacagcaga caaaatgaaa gaaaatgaga gcagaaagta agcatttcca 240
gcctatctaa tttctttagt tttctatttg cctccagtgc agtccatttc ctaatgtata 300
ccagcctact gtactattta aaatgctcaa tttcagcacc gatggacctg c 351

<210> SEQ ID NO 194
<211> LENGTH: 311
<212> TYPE: DNA
<213> ORGANISM: Homo sapiens

<400> SEQUENCE: 194
ctgagacaca gaggcccact gcgagggggga cagtggcggt gggactgacc tgctgacagt 60
caccctccct ctgctgggat gaggtccagg agccaactaa aacaatggca gaggagacat 120
ctctggtgtt cccaccaccc tagatgaaaa tccacagcac agacctctac cgtgtttctc 180
ttccatccct aaaccacttc cttaaaatgt ttggatttgc aaagccaatt tggggcctgt 240
ggagcctggg gttggatagg gccatggctg gtcccccacc atacctcccc tccacatcac 300
tgacacagac c 311

-continued

<210> SEQ ID NO 195
<211> LENGTH: 381
<212> TYPE: DNA
<213> ORGANISM: Homo sapiens

<400> SEQUENCE: 195
tgtcagagtg gcactggtag aagttccagg aaccctgaac tgtaagggtt cttcatcagt 60
gccaacagga tgacatgaaa tgatgtactc agaagtgtcc tggaatgggg cccatgagat 120
ggttgtctga gagagagctt cttgtcctgt ctttttcctt ccaatcaggg gctcgctctt 180
ctgattattc ttcagggcaa tgacataaat tgtatattcg gttcccggtt ccaggccagt 240
aatagtagcc tctgtgacac cagggcgggg ccgagggacc acttctctgg gaggagaccc 300
aggcttctca tacttgatga tgtagccggt aatcctggca cgtggcggct gccatgatac 360
cagcagggaa ttgggtgtgg t 381

<210> SEQ ID NO 196
<211> LENGTH: 401
<212> TYPE: DNA
<213> ORGANISM: Homo sapiens

<400> SEQUENCE: 196
cacaaacaag aggagcacca gacctcctct tggcttcgag atggcttcgc cacaccaaga 60
gcccaaacct ggagacctga ttgagatttt ccgccttggc tatgagcact gggccctgta 120
tataggagat ggctacgtga tccatctggc tcctccaagt gagtaccccg gggctggctc 180
ctccagtgtc ttctcagtcc tgagcaacag tgcagaggtg aaacgggagc gcctggaaga 240
tgtggtggga ggctgttgct atcgggtcaa caacagcttg gaccatgagt accaaccacg 300
gcccgtggag gtgatcacca gttctgcgaa ggagatggtt ggtcagaaga tgaagtacag 360
tattgtgagc aggaactgtg agcactttgt cacccagacc t 401

<210> SEQ ID NO 197
<211> LENGTH: 471
<212> TYPE: DNA
<213> ORGANISM: Homo sapiens

<400> SEQUENCE: 197
ctgtaatgat gtgagcaggg agccttcctc cctgggccac ctgcagagag ctttcccacc 60
aactttgtac cttgattgcc ttacaaagtt atttgtttac aaacagcgac catataaaag 120
cctcctgccc caaagcttgt gggcacatgg gcacatacag actcacatac agacacacac 180
atatatgtac agacatgtac tctcacacac acaggcacca gcatacacac gtttttctag 240
gtacagctcc caggaacagc taggtgggaa agtcccatca ctgagggagc ctaaccatgt 300
ccctgaacaa aaattgggca ctcatctatt cctttctct tgtgtcccta ctcattgaaa 360
ccaaactctg gaaaggaccc aatgtaccag tatttatacc tctagtgaag cacagagaga 420
ggaagagagc tgcttaaact cacacaacaa tgaactgcag acacagacct g 471

<210> SEQ ID NO 198
<211> LENGTH: 201
<212> TYPE: DNA
<213> ORGANISM: Homo sapiens

<400> SEQUENCE: 198
ggtccattga ggctctgtcg gccatgccca cagttcgaag ctttgccaac gaggagggcg 60

-continued

```
aagcccagaa gtttagggaa aagctgcaag aaataaagac actcaaccag aaggaggctg    120

tggcctatgc agtcaactcc tggaccacta gtatttcagg tatgctgctg aaagtgggaa    180

tcctctacat tggtgggcag a                                              201


<210> SEQ ID NO 199
<211> LENGTH: 551
<212> TYPE: DNA
<213> ORGANISM: Homo sapiens

<400> SEQUENCE: 199

tctggcacag atcttcaccc acacggcggt ccacgtgctg atcatcttcc gggtctcacc     60

gggcctggaa cacaccatct tccccatgag cccggtgccc agtctggtga cttccatctt    120

ggcccctggc cttatgtccc agttatgacc cctgacttca actctggctc ttaccctgta    180

actccagtcc atctctgaca tttttaacac ccggccttgt gaccgtggac atagctcctg    240

acctcgattc ccatcttgag cccagtgtta gtccatgaga tcatgacctg actcctggtc    300

tccaaccttg tgatcctaat tctgggacct caatcctagc ctctgaactt gggaccctgg    360

agctcctgac cttagtcctg accgctaccc ttgattctga cctttgatcc tgtaacttag    420

gggtggcccc tgaccttatt actgtcattt agctccttga ccttgccact tcaatcctgg    480

ctttatgacc tcctactctc aattttaact ttaaccaaat gaccaaattt gtgacactaa    540

atgaccacaa t                                                         551


<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: (1)...(211)
<223> OTHER INFORMATION: n=A,T,C or G

<400> SEQUENCE: 200

cagctcancg ggcgacatgc ccctacaagt tggcanaagn ggctgccact gctgggtttg     60

tgtaagagag gctgctgnca ccattacctg cagaaacctt ctcatagggg ctacgatcgg    120

tactgctagg gggcacatag cgcccatggg tgtggtaggt ggggnactcn ntnataggat    180

ggtaggtatc ccgggctgga aanatgnnca g                                   211


<210> SEQ ID NO 201
<211> LENGTH: 111
<212> TYPE: DNA
<213> ORGANISM: Homo sapiens

<400> SEQUENCE: 201

ccagtgaaag gaaacaaaac tggcagtttg tccatttgaa tatcagacct agtttcttct     60

taatttccac actatttctc ccatattcct taaacttctt ggcatccacc t             111


<210> SEQ ID NO 202
<211> LENGTH: 331
<212> TYPE: DNA
<213> ORGANISM: Homo sapiens

<400> SEQUENCE: 202

tgaaaataca gaataccagg tggtcccaaa tgtttgaagt tctttgaaca gaaagagaga     60

ggagagagag agagaggaaa attccctaac ccttggttta aagacaatat tcatttattg    120

ctcaaatgat gcttttaagg gaggacagtg gaataaaata aactttttt ttctccctac     180
```

-continued

```
aatacataga agggttatca aaccactcaa gtttcaaaat ctttccaggg tccaatatca    240
cttttttttct ttcggttcaa tgaaaagcta aatgtaataa tactaattat agataaaatt    300
ttattttact ttttaaaaat ttgtccagac c                                    331
```

<210> SEQ ID NO 203
<211> LENGTH: 491
<212> TYPE: DNA
<213> ORGANISM: Homo sapiens

<400> SEQUENCE: 203

```
agtcacccag tctacttagt acctggttgc tgcctctgac cttttcagct tgataccctg     60
ggctttagtg taaccaataa atctgtagtg accttacctg tattccctgt gctatcctgt    120
gggaaggtag gaatgggcta agtatgatga atgtataggt tagggatctt ttggttttaa    180
atcacagaaa acctaattca aactggctta aaataaaaag gatttattgg ttcatgtaac    240
tagaaagtcc ataggtagtg ctggctccag gtgaagactt gacccagtag ttcagtatgt    300
ctctaaatac cggactgact tttttctcac tgttgcatct tctgtaggac catttaagtc    360
tgggccactt aatggctgcc agcattccta agattacact tttccccatt tatgtccaat    420
cagaaaaaga aggcatcttt gtaccagaaa tctcagcaaa agccctaata ttcacactga    480
ttaggacctg c                                                          491
```

<210> SEQ ID NO 204
<211> LENGTH: 361
<212> TYPE: DNA
<213> ORGANISM: Homo sapiens

<400> SEQUENCE: 204

```
tcccttcctc ccccatgtga taaatgggtc cagggctgat caaagaactc tgactgcaga     60
actgccgctc tcagtggaca gggcatctgt tatcctgaga cctgtggcag acacgtcttg    120
ttttcatttg atttttgtta agagtgcagt attgcagagt ctagaggaat ttttgtttcc    180
ttgattaaca tgattttcct ggttgttaca tccagggcat ggcagtggcc tcagccttaa    240
acttttgttc ctactcccac cctcagcgaa ctgggcagca cggggagggt ttggctaccc    300
ctgcccatcc ctgagccagg taccaccatt gtaaggaaac actttcagaa attcagacct    360
c                                                                     361
```

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G
<221> NAME/KEY: misc_feature
<222> LOCATION: (3)
<223> OTHER INFORMATION: n=A,T,C or G

<400> SEQUENCE: 205

```
cnngtacagt tcttcctgga tggccgacac agatcctggg gaaaggcaat cctggcactg     60
ctctgaaacc agagctcctc ctccctcccc gggcagggtg gagctgagaa gggctgctct    120
agcgttggga ctccacctcc atacacctga tattttgata gggcaggtcc ctgctatggg    180
ccactgttct gggcagtata gtatgcttga cagcatcctt ggcatctatc caccagatcc    240
cagagcaccc gctactagct gtgacaacat cctccaaaca ttgcaaaatt tcccctggga    300
```

-continued

```
ggcaagattg cctcagatgg gagaatcacg ctctagggaa atctgctggt atgagaaccc    360

caactcccca ctccactgag cctccagatg gcgagcaggc tgcagctcca gcacagacac    420

gaagctccct ccagccactg acggtccatg gctggggtta cccaggacct c             471


<210> SEQ ID NO 206
<211> LENGTH: 261
<212> TYPE: DNA
<213> ORGANISM: Homo sapiens

<400> SEQUENCE: 206

tagagtattt agagtcctga gataacaagg aatccaggca tcctttagac agtcttctgt     60

tgtcctttct tcccaatcag agatttgtgg atgtgtggaa tgacaccacc accagcaatt    120

gtagccttga tgagagaatc caattcttca tctccacgaa tagcaagttg caagtgacga    180

ggggtaatac gctttacctt taagtctttt gatgcatttc ctgccagttc aagtacctct    240

gcggtgaggt actccaggat g                                              261


<210> SEQ ID NO 207
<211> LENGTH: 361
<212> TYPE: DNA
<213> ORGANISM: Homo sapiens

<400> SEQUENCE: 207

gctctccggg agcttgaaga agaaactggc tacaaagggg acattgccga atgttctcca     60

gcggtctgta tggacccagg cttgtcaaac tgtactatac acatcgtgac agtcaccatt    120

aacggagatg atgccgaaaa cgcaaggccg aagccaaagc caggggatgg agagtttgtg    180

gaagtcattt ctttacccaa gaatgacctg ctgcagagac ttgatgctct ggtagctgaa    240

gaacatctca cagtggacgc cagggtctat tcctacgctc tagcactgaa acatgcaaat    300

gcaaagccat ttgaagtgcc cttcttgaaa ttttaagccc aaatatgaca ctggacctgc    360

c                                                                    361


<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 208

agaggagatn tttgccatgc ctgaatnctt tcctatncca ccctancact taacatatta     60

cttagtctgc tttgntaaaa gcaagtatta ccttnaactt gnctcttact ctttgccctt    120

tagctaacta ataaagnttg atntaggcat tattatataa ttctgagtca ttcatggtat    180

ctctcatgtt tgatgtattt tncaaactaa gatctatgat agttttttt ccanagttcc    240

attaaatcat ttatttcctt tactttctca cctctgtnga aacatttaga aactggattt    300

gggaacccan ttttggaaaa ccagattcat agtcatgaaa atggaaactt ncatattctg    360

tttttgaaaa gatgtggacc t                                              381


<210> SEQ ID NO 209
<211> LENGTH: 231
<212> TYPE: DNA
<213> ORGANISM: Homo sapiens
<220> FEATURE:
```

-continued

<221> NAME/KEY: misc_feature
<222> LOCATION: (83)
<223> OTHER INFORMATION: n=A,T,C or G

<400> SEQUENCE: 209
gtggagagca agtgatttat taaagcaaga cgttgaaacc tttacattct gcagtgaaga 60
tcagggtgtc attgaaagac agnggaaacc aggatgaaag tttttacatg tcacacacta 120
catttcttca atattttcac caggacttcc gcaatgaggc ttcgtttctg aagggacatc 180
tgatccgtgc atctcttcac tcctaacttg gctgcaacag cttccacctg c 231

<210> SEQ ID NO 210
<211> LENGTH: 371
<212> TYPE: DNA
<213> ORGANISM: Homo sapiens

<400> SEQUENCE: 210
tccatcctgg ttttgcagag atcaggttgt tgacagttcc tggttgaccc acagctaccc 60
atgtcagtta tctccactaa catatccaag aatctttgta ggacaatttc tccacctgca 120
aggtttttta ggtagaactc ttcttttaag gcaattagcc cattgccaaa aggttttact 180
gtcttaaagc tgtctttctg agatctaatt ccaaggactt ctccacagct aagtgagatg 240
cctcacacca ttaggtgatg ctttggacag aacagagtat tttcatcttg tgtttaaagc 300
aattccttgg cttcggctcc tcaccacttt ctatgccagt ctcccattta tgtccctagt 360
aatgcctatg c 371

<210> SEQ ID NO 211
<211> LENGTH: 471
<212> TYPE: DNA
<213> ORGANISM: Homo sapiens

<400> SEQUENCE: 211
tttattttaa aagaaaaaaa ttaaaataga gccaacaaat gcaattaaga aaaaaaaagt 60
attgagacac aaggggacct acatgttctg gtctaagaag catgcaagta ttacaaagca 120
ttccagatac agtatgacag aggaacagtg aacaagcatt ggaacgatgc tctttctttc 180
agaaacggga agtctaacag ttatgttttc acaatggtag tgattaaacc atctttattt 240
ttaaggaatt ttataggaag aattttagca ccatcattaa aggaaaaata ataatacctt 300
tttagccctg cctatctcca gtcttggaat aataacagaa gcatagcacc tttcagtatc 360
taaaatataa acaagaatag taagtccatc ccagcttcta gagatgaggt agctcatgct 420
aagaaatgtt gggtcatttt tcctatgaaa gttcaaaggc caaatggtca c 471

<210> SEQ ID NO 212
<211> LENGTH: 401
<212> TYPE: DNA
<213> ORGANISM: Homo sapiens

<400> SEQUENCE: 212
tggcctgtct ccttcacata gtccatatca ccacaaatca cacaacaaaa gggagaggat 60
atattttggg ttcaaaaaaa gtaaaaagat aatgtagctg catttctttg gttattttgg 120
gccccaaata tttcctcatc tttttgttgt tgtcatggat ggtggtgaca tggacttgtt 180
tatagaggac aggtcagctc tctggctcgg tgatctacat tctgaagttg tctgaaaatg 240
tcttcatgat taaattcagc ctaaacgttt tgccgggaac actgcagaga caatgctgtg 300
agtttccaac ctcagcccat ctgcgggcag agaaggtcta gtttgtccat caccattatg 360

-continued atatcaggac tggttacttg gttaaggagg ggtctacctc g 401

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: (1)...(461)
<223> OTHER INFORMATION: n=A,T,C or G

<400> SEQUENCE: 213
tgtgaagcat acataaataa atgaagtaag ccatactgat ttaatttatt ggatgttatt 60
ttccctaaga cctgaaaatg aacatagtat gctagttatt tttcagtgtt agccttttac 120
tttcctcaca caatttggaa tcatataata taggtacttt gtccctgatt aaataatgtg 180
acggatagaa tgcatcaagt gtttattatg aaaagagtgg aaaagtatat agcttttanc 240
aaaaggtgtt tgcccattct aagaaatgag cgaatatata gaaatagtgn gggcatttct 300
tcctgttagg tggagtgtat gtgttgacat ttctccccat ctcttcccac tctgtttnnt 360
ccccattatt tgaataaagt gactgctgaa nangactttg aatccttatc cacttaattt 420
aatgtttaaa gaaaaaccta taatggaaag tgagactcct t 461

<210> SEQ ID NO 214
<211> LENGTH: 181
<212> TYPE: DNA
<213> ORGANISM: Homo sapiens

<400> SEQUENCE: 214
cctgagcttc tactcctttc ccttaagatt cctccaaagc accagctcca taaaatcctt 60
cagctcccca gacccacacc aagaacccca catgttaatt ggatcagcca aatctacaag 120
cagataagtc ctaaggagaa tgccgaagcg tttttcttct tcctcaagcc tagcatgaga 180
c 181

<210> SEQ ID NO 215
<211> LENGTH: 581
<212> TYPE: DNA
<213> ORGANISM: Homo sapiens

<400> SEQUENCE: 215
ctgctttaag aatggttttc caccttttcc ccctaatctc taccaatcag acacatttta 60
ttatttaaat ctgcacctct ctctatttta tttgccaggg gcacgatgtg acatatctgc 120
agtcccagca cagtgggaca aaaagaattt agaccccaaa agtgtcctcg gcatggatct 180
tgaacagaac cagtatctgt catggaactg aacattcatc gatggtctcc atgtattcat 240
ttattcactt gttcattcaa gtatttattg aatacctgcc tcaagctaga gagaaaagag 300
agtgcgcttt ggaaatttat tccagttttc agcctacagc agattatcag ctcggtgact 360
tttctttctg ccaccattta ggtgatggtg tttgattcag agatggctga atttctattc 420
ttagcttatt gtgactgttt cagatctagt ttgggaacag attagaggcc attgtcctct 480
gtcctgatca ggtggcctgg ctgtttcttt ggatccctct gtcccagagc cacccagaac 540
cctgactctt gagaatcaag aaaacaccca gaaaggacct c 581

<210> SEQ ID NO 216
<211> LENGTH: 281
<212> TYPE: DNA

-continued

<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 216
ccgatgtcct gcttctgtgg accaggggct cctctgnngg tggcctcaac cacggctgag 60
atccctagaa gtccaggagc tgtggggaag agaagcactt agggccagcc agccgggcac 120
ccccacttgc gccccgaccc acgctcacgc accagacctg cccnggcggt cgctcnaaag 180
ggcgaattct gcagatatcc atcacactgg cggacgctcg agcatgcatc tagagggccc 240
aattcaccct atantgagtc gtattacaat tcactggccg t 281

<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: (1)...(356)
<223> OTHER INFORMATION: n=A,T,C or G

<400> SEQUENCE: 217
atagcaggtt tcaacaattg tcttgtagtt tgnagtaaaa agacataaga aagagaaggt 60
gtggtttgca gcaatccgta gttggtttct caccataccc tgcagttctg tgagccaaag 120
gtcttgcaga aagttaaaat aaatcacaaa gactgctgtc atatattaat tgcataaaca 180
cctcaacatt gctcagagtt tcatccgttt ggttaagaaa acattccttc aattcatcta 240
tggcatttgt agtggcattg tcgtctatga actcttgaag aagttctttg tattcagtct 300
tagacacttg tggattgatt gncttggaaa tcacattctc caataaggga cctcgg 356

<210> SEQ ID NO 218
<211> LENGTH: 321
<212> TYPE: DNA
<213> ORGANISM: Homo sapiens

<400> SEQUENCE: 218
ttgtccatcg ggagaaaggt gtttgtcagt tgtttcataa accagattga ggaggacaaa 60
ctgctctgcc aatttctgga tttctttatt ttcagcaaac actttcttta aagcttgact 120
gtgtgggcac tcatccaagt gatgaataat catcaagggt ttgttgcttg tcttggattt 180
atatagagct tcttcatatg tctgagtcca gatgagttgg tcaccccaac ctctggagag 240
ggtctggggc agtttgggtc gagagtcctt tgtgtccttt ttggctccag gtttgactgt 300
ggtatctctg gacctgcctg g 321

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: (41)
<223> OTHER INFORMATION: n=A,T,C or G

<400> SEQUENCE: 219
ccggttaggt ccacgcgggg gcagtggagg cacaggctca nggtggccgg gctacctggc 60
accctatggc ttacaaagta gagttggccc agtttccttc cacctgaggg gagcactctg 120
actcctaaca gtcttccttg ccctgccatc atctggggtg gctggctgtc aagaaaggcc 180

-continued

```
gggcatgctt tctaaacaca gccacaggag gcttgtaggg catcttccag gtggggaaac    240

agtcttagat aagtaaggtg acttgtctaa g                                   271


<210> SEQ ID NO 220
<211> LENGTH: 351
<212> TYPE: DNA
<213> ORGANISM: Homo sapiens
<220> FEATURE:
<221> NAME/KEY: misc_feature
<222> LOCATION: (1)...(351)
<223> OTHER INFORMATION: n=A,T,C or G

<400> SEQUENCE: 220

gtcctacgac gaggaccagc ttttcttctt cnacttttcc canaacactc gggtgcctcg     60

cctgcccgaa tttgctgact gggctcagga acagggagat gctcctgcca ttttatttga    120

caaagagttc tgcgagtgga tgatccagca aatagggcca aaacttgatg ggaaaatccc    180

ggtgtccaga gggtttccta tcgctgaagt gttcacgctg aagcccctgg agtttggcaa    240

gcccaacact ttggtctgtt ttgtcagtaa tctcttccca cccatgctga cagtgaactg    300

gtagcatcat tccgtccctg tggaaggatt tgggcctact tttgtctcag a             351


<210> SEQ ID NO 221
<211> LENGTH: 371
<212> TYPE: DNA
<213> ORGANISM: Homo sapiens

<400> SEQUENCE: 221

gtctgcagaa gcgtgtctga ggtgtccggt ggaggtggca gccgagctct gggactaatc     60

accgtgctgg ggacggcacc gcgtcaggat gcaggcagat ccctgcagaa gtgtctaaaa    120

ttcacactcc tcttctggag ggacgtcgat ggtattagga tagaagcacc aggggacccc    180

acgaacggtg tcgtcgaaac agcagccctt atttgcacac tgggagggcg tgacaccagg    240

aaaaccacaa ttctgtcttt cacggggggc cactgtacac gtctctgtct gggcctcggc    300

cagggtgccg agggccagca tggacaccag gaccagggcg cagatcacct tgttctccat    360

ggtggacctc g                                                         371


<210> SEQ ID NO 222
<211> LENGTH: 471
<212> TYPE: DNA
<213> ORGANISM: Homo sapiens

<400> SEQUENCE: 222

gtccatgttc catcattaat gttccaacat caccagggac acaaagctgc aaaaatgaga     60

agggaaataa ggttagagaa aggatccggg caatcttaag gactgaggaa gacatgttcc    120

ccaacccttg aactcacaaa ccctgaagct caaggattgc atccttcctc caaatctcac    180

tcaacataat aagtgcagaa caacatgcca aagcactgta tgaagcacta gggacaaaga    240

caaggtcaaa atccttgtaa ccaaatttaa tggtattgta atgcagtgtt aacacaggac    300

agtaacagaa cacccaagaa ccaaacagaa gagggtaggg ataagcataa atgaagtaac    360

atgaaataaa cttccaaatg gaaaacttgt ccataccccc agggcaagtc aactacagtc    420

tcccaaagga cataaattcc acttagggca cactagacag aaaacaatat t             471


<210> SEQ ID NO 223
<211> LENGTH: 411
<212> TYPE: DNA
```

-continued

<213> ORGANISM: Homo sapiens

<400> SEQUENCE: 223
agttgctcta caatgacaca caaatcccgt taaataaatt ataaacaagg gtcaattcaa 60
atttgaagta atgttttagt aaggagagat tagaagacaa caggcatagc aaatgacata 120
agctaccgat taactaatcg gaacatgtaa aacagttaca aaaataaacg aactctcctc 180
ttgtcctaca atgaaagccc tcatgtgcag tagagatgca gtttcatcaa agaacaaaca 240
tccttgcaaa tgggtgtgac gcggttccag atgtggattt ggcaaaacct catttaagta 300
aaaggttagc agagcaaagt gcggtgcttt agctgctgct tgtgccgctg tggcgtcggg 360
gaggctcctg cctgagcttc cttccccagc tttgctgcct gagaggaacc a 411

<210> SEQ ID NO 224
<211> LENGTH: 321
<212> TYPE: DNA
<213> ORGANISM: Homo sapiens
<220> FEATURE:
<221> NAME/KEY: misc_feature
<222> LOCATION: (31)
<223> OTHER INFORMATION: n=A,T,C or G

<400> SEQUENCE: 224
ggtctgaagt ttgataacaa agaaatatat ntaagacaaa aatagacaag agttaacaat 60
aaaaacacaa ctatctgttg acataacata tggaaacttt ttgtcagaaa gctacatctt 120
cttaatctga ttgtccaaat cattaaaata tggatgattc agtgccattt tgccagaaat 180
tcgtttggct ggatcataga ttaacatttt cgagagcaaa tccaagccat tttcatccaa 240
gtttttgaca tgggatgcta ggcttcctgg tttccatttg ggaaatgtat tcttatagtc 300
ctgtaaagat tccacttctg g 321

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: (34)
<223> OTHER INFORMATION: n=A,T,C or G

<400> SEQUENCE: 225
atgtctgggg aaagagttca ttggcaaaag tgtnctccca agaatggttt acaccaagca 60
gagaggacat gtcactgaat ggggaaaggg aacccccgta tccacagtca ctgtaagcat 120
ccagtaggca ggaagatggc tttgggcagt ggctggatga aagcagattt gagataccca 180
gctccggaac gaggtcatct tctacaggtt cttccttcac tgagacaatg aattcagggt 240
gatcattctc t 251

<210> SEQ ID NO 226
<211> LENGTH: 331
<212> TYPE: DNA
<213> ORGANISM: Homo sapiens
<220> FEATURE:
<221> NAME/KEY: unsure
<222> LOCATION: (1)...(331)
<223> OTHER INFORMATION: n=A,T,C or G

<400> SEQUENCE: 226
gttaggtccc aggccccccg ccaagnggtt accnnnntna ccactcctga cccaaaaatc 60
aggcatggca ttaaaacgtt gcaaattcct ttactgttat cccccccacc accaggacca 120

-continued tgtagggtgc agtctttact ccctaacccg tttcccgaaa aaggtgctac ctcctttcca 180
gacagatgag agagggcagg acttcaggct ggatccacca ctgggctctc cctcccccag 240
cctggagcac gggaggggag gtgacggctg gtgactgatg gatgggtagt gggctgagaa 300
gaggggacta ggaagggcta ttccaggctc a 331

<210> SEQ ID NO 227
<211> LENGTH: 391
<212> TYPE: DNA
<213> ORGANISM: Homo sapiens

<400> SEQUENCE: 227
aggtctgccc ttgaagtata ggaaggaatc atagttggag gacttctgca ttatttgttg 60
gctgaagcta gaagtgcaac cccctcctga tttctgcagc aagatgaact gccttatccc 120
cagcccgcag gaatgttcat atctgagcaa tcaatgggca ctgtgttcaa ccacgccatt 180
ttcaagattg gctccttaaa ccacccacaa ggcaccagct ctgggagaag ctgcagggag 240
aagagaacaa agccctcgct gtgatcagga tgggtgtctc atacctttc tctggggtca 300 ttccaggtat gagacagagt tgaacctgcg catgagcgtg gaggccgaca tcaacggcct 360
gcgcagggtg ctggatgagc tgaccctgga c 391

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: (35)
<223> OTHER INFORMATION: n=A,T,C or G

<400> SEQUENCE: 228
gttgtccata gccacctcct gggatagaag ctttntagtt catagttcga ttagtgtgtc 60
cttaggacat aggtccagcc ctacagatta gctgggtgaa gaaggcaagt gtctcgacag 120
ggcttagtct ccaccctcag gcatggaacc attcagggtg aagcctggga tgtgggcaca 180
ggagactcag gctgatataa aaataacaaa atcagtaata aaaaaattat aaaacctgtt 240
gcttgtctga atagatttga gcaacagtct tgcttttgtt aaaatcctgg agccgttaag 300
tcctgaatat tcttctggac atcattgctg gctggagaaa ggagccccag gcccggctcg 360
gctgacatct gtcaggtttg gaagtctcat c 391

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: (202)
<223> OTHER INFORMATION: n=A,T,C or G

<400> SEQUENCE: 229
gtccatggct tctcacccag acagtctttc tgggcaactt ggggaagccc ctgttctgct 60
caagtctcac cccatggaag aggtggggga agggggcctt ggtttttcag gaagacgggt 120
tggagagcac gagtcactac aaagcagtaa aagtgaatgg tgtctccagg ggctgggtcc 180
agaacaccgc ggagagcccc anccataaag gtgtgttccg cctctggcct gcaggaatct 240
ctttgaatct ctttgattgg tggctccaag agcaatggga agtcaacagc caggaggctg 300

-continued gactgggttc cctgggaccc cgaggtccca gaggctgctg g 341

<210> SEQ ID NO 230
<211> LENGTH: 511
<212> TYPE: DNA
<213> ORGANISM: Homo sapiens

<400> SEQUENCE: 230
gtccaagcca aggaaaccat tcccttacag gagacctccc tgtacacaca ggaccgcctg 60
gggctaaagg aaatggacaa tgcaggacag ctagtgtttc tggctacaga aggggaccat 120
cttcagttgt ctgaagaatg gttttatgcc cacatcatac cattccttgg atgaaacccg 180
tatagttcac aatagagctc agggagcccc taactcttcc aaaccacatg ggagacagtt 240
tccttcatgc ccaagcctga gctcagatcc agcttgcaac taatccttct atcatctaac 300
atgccctact tggaaagatc taagatctga atcttatcct ttgccatctt ctgttaccat 360
atggtgttga atgcaagttt aattaccatg gagattgttt tacaaacttt tgatgtggtc 420
aagttcagtt ttagaaaagg gagtctgttc cagatcagtg ccagaactgt gcccaggccc 480
aaaggagaca actaactaaa gtagtgagat a 511

<210> SEQ ID NO 231
<211> LENGTH: 311
<212> TYPE: DNA
<213> ORGANISM: Homo sapiens

<400> SEQUENCE: 231
ggtccaagta agctgtgggc aggcaagccc ttcggtcacc tgttggctac acagacccct 60
cccctcgtgt cagctcaggc agctcgaggc ccccgaccaa cacttgcagg ggtccctgct 120
agttagcgcc ccaccgccgt ggagttcgta ccgcttcctt agaacttcta cagaagccaa 180
gctccctgga gccctgttgg cagctctagc tttgcagtcg tgtaattggc ccaagtcatt 240
gtttttctcg cctcactttc caccaagtgt ctagagtcat gtgagcctcg tgtcatctcc 300
ggggtggacc t 311

<210> SEQ ID NO 232
<211> LENGTH: 351
<212> TYPE: DNA
<213> ORGANISM: Homo sapiens

<400> SEQUENCE: 232
tcgtttagct aataatccct tccttgatga tacactccaa cttcttgttt ttctttattt 60
ctaaaaagcg gttctgtaac tctcaatcca gagatgttaa aaatgtttct aggcacggta 120
ttagtaaatc aagtaaattt catgtcctct taaaggacaa acttccagag atttgaatat 180
aaatttttat atgtgttatt gattgtcgtg taacaaatgg cccccacaaa ttagtagctt 240
aaaatagcat ttatgatgtc actgttttct ttgccttttc attaatgttc tgtacagacc 300
tatgtaaaca acttttgtat atgcatatag gatagctttt ttgagggtat a 351

<210> SEQ ID NO 233
<211> LENGTH: 511
<212> TYPE: DNA
<213> ORGANISM: Homo sapiens

<400> SEQUENCE: 233
aggtctggat gtaaggatgg atgctctcta tacatgctgg gttggggatg ctgggactgc 60

-continued

```
acagccaccc ccagtatgcc gctccaggac tctgggacta gggcgccaaa gtgtgcaaat    120

gaaaatacag gatacccagg gaactttgaa tttcagattg tgaaaagaaa acaaatcttg    180

agactccaca atcaccaagc taaaggaaaa agtcaagctg ggaactgctt agggcaaagc    240

tgcctcccat tctattcaca gtcatccccc tgaggctcac ctgcatagct gattgcttcc    300

tttcccctat cgcttctgta aaaatgcaga ctcactgagc cagactaaat tgtgtgttca    360

gtggaaggct gatcaagaac tcaaaagaat gcaacctttt gtctcttatc tactacaacc    420

aggaagcccc cacttaaggg ttgtcccacc ttactggact gaaccaaggt acatcttaca    480

cctactgatt gatgtctcat gtccccctaa g                                   511


<210> SEQ ID NO 234
<211> LENGTH: 221
<212> TYPE: DNA
<213> ORGANISM: Homo sapiens

<400> SEQUENCE: 234

caggtccagc gaaggggctt cataggctac accaagcatg tccacataac cgaggaagct     60

ctctccatca gcatagcctc cgatgaccat ggtgttccac aaagggttca tcttcgagcg    120

ccggctgtac atggccctgg tcagccatga atgaatagct ctaggactat agctgtgtcc    180

atctcccaga agctcctcat caatcaccat ctggccgaga c                        221


<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: (33)
<223> OTHER INFORMATION: n=A,T,C or G

<400> SEQUENCE: 235

ggtccaagaa agggacatct atgtgaaagt ganactgaga cagtgctggt cacaggtcat     60

gctgcagaat aatacattcc caggcactgt cacgtggggg acccaagagg ccccaggagt    120

gacctataac ctctccagaa agaccactct gtgtggcatc acagtccaca cagtttaagg    180

aaatatttag acttaacaat cagacaccag ctcttactca cacttacact cacagcccac    240

acacaagtgt gcaaacatac acacacatat atatttcctg atacattcat ggaatatcag    300

agccctgccc tgaagtcgtt agtgtctctg ctccccaaac cgctgctccc acattggcta    360

agctccctca agagacctca g                                              381


<210> SEQ ID NO 236
<211> LENGTH: 441
<212> TYPE: DNA
<213> ORGANISM: Homo sapiens

<400> SEQUENCE: 236

aggtcctgtt gccccttct tttgcccaac ttcgccattt gggaattgga atatttaccc      60

aacacctgta ctgcattgaa tattggaagc aaataacttg gctttgatct tataggctca    120

cagatggagg aacgtacctt gaagttcaga tgagatttcg gacttttgag ttgatgctga    180

aacagcttga gatttttggg gactactgag agatgataat tgtattgtgc aatatgagaa    240

ggacatgaga tttggtgggc ataggtgtga aatgacattg tttggatgtg tttaccctcc    300

aaatctcttg ttgaatgtga tcttaaacgt tggtggtggg cctagtggaa ggtgttgaat    360

catgggggtg gactcttcat aatttgctta gctccatccc cttggtgatg agcaagtcct    420
```

-continued

```
tgctctgttg tgtcacatga g                                              441


<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 237

tcctaaaaaa ttagctgacc ttgttaaaaa tgttggcgtg agcagtatat tattacctat     60

ctttttttat tgtgtgtgtg ngtgtgtgtn ttaaactaat tggctgaaat atctgcctgt    120

ttccctcttt acatttttct tgtttctttc cttatttatc tttgtccatc ttgagatcta    180

ctgtaaagtg aatnttttaa tgaaaacann nccaagttnt actctcactg ggnttgggac    240

atcagatgta attgagaggc caacaggtaa gtcttcatgt c                        281


<210> SEQ ID NO 238
<211> LENGTH: 141
<212> TYPE: DNA
<213> ORGANISM: Homo sapiens
<220> FEATURE:
<221> NAME/KEY: misc_feature
<222> LOCATION: (1)...(141)
<223> OTHER INFORMATION: n=A,T,C or G

<400> SEQUENCE: 238

gtctgcctcc tcctactgtt tccctctatn aaaaagcctc cttggcgcag gttccctgag     60

ctgtgggatt ctgcactggt gcttnggatt ccctgatatg ttccttcaaa tccactgaga    120

attaaataaa catcgctaaa g                                              141


<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: (1)...(501)
<223> OTHER INFORMATION: n=A,T,C or G

<400> SEQUENCE: 239

aacaatctaa acaaatccct cggttctann atacaatgga ttccccatat tggaaggact     60

ctgangcttt attcccccac tatgcntatc ttatcatttt attattatac acacatccat    120

cctaaactat actaaagccc ttttcccatg catggatgga aatggaagat ttttttttaa    180

cttgttctag aagtcttaat atgggctgtt gccatgaagg cttgcagaat tgagtccatt    240

ttctagctgc ctttattcac atagtgatgg ggtactaaaa gtactgggtt gactcagaga    300

gtcgctgtca ttctgtcatt gctgctactc taacactgag caacactctc ccagtggcag    360

atcccctgta tcattccaag aggagcattc atccctttgc tctaatgatc aggaatgatg    420

cttattagaa aacaaactgc ttgacccagg aacaagtggc ttagcttaag naaacttggc    480

tttgctcana tccctgatcc t                                              501


<210> SEQ ID NO 240
<211> LENGTH: 451
<212> TYPE: DNA
<213> ORGANISM: Homo sapiens
```

-continued

<400> SEQUENCE: 240
tgtcctgaaa ggccattact aatagaaaca cagcctttcc aatcctctgg aacatattct 60
gtctgggttt ttaatgtctg tggaaaaaaa ctaaacaagt ctctgtctca gttaagagaa 120
atctattggt ctgaaggttt ctgaacctct ttctggttct cagcagaagt aactgaagta 180
gatcaggaag gggctgcctc aggaaaattc ctagatccta ggaattcagt gagaccctgg 240
gaaggaccag catgctaatc agtgtcagtg aatccacagt ctttacttcc tgcctcataa 300
agggccaggt ctccccagta ccaagtcctt tcctcatgaa gttgtgttgc ctcaggctgt 360
ttagggacca ttgcctgtct tggtcacatg agtctgtctc cttactttag tccctgggca 420
atccttgctt aatgcttttg ttgactcaac g 451

<210> SEQ ID NO 241
<211> LENGTH: 411
<212> TYPE: DNA
<213> ORGANISM: Homo sapiens
<220> FEATURE:
<221> NAME/KEY: misc_feature
<222> LOCATION: (1)...(411)
<223> OTHER INFORMATION: n=A,T,C or G

<400> SEQUENCE: 241
aatctccagt gtgatggtat cggggttaga gcttcaatct ccagtgtgat ggtactgcag 60
cnagagcttc aatctccagt gngatggtat tagggttaga tcttcaatct ccagtgtgat 120
ggtatcaggg ttagagcttc agcctccagt gtgatggtat cagggttaga gcttcagcct 180
ccagtgtgat ggtatcgggg ttagatcttc aatccccagt ggtggtggtt agagcttcaa 240
tctccagtgt gatggtattg ggttagagc ttcaatctcc agtctgatgg tgtttcggga 300
tggggctttt aagatgtaat tagggtttaa gatcataagg gacctggtct gatggggatt 360
agtncgcttn tatgaagaga cacangaggg cttgctctat ctctgactct c 411

<210> SEQ ID NO 242
<211> LENGTH: 351
<212> TYPE: DNA
<213> ORGANISM: Homo sapiens

<400> SEQUENCE: 242
ttccccttca caacagtaga gacctacaca gtgaactttg gggacttctg agatcagcgt 60
cctaccaaga ccccagccca actcaagcta cagcagcagc acttcccaag cctgctgacc 120
acagtcacat cacccatcag cacatggaag gcccctggta tggacactga aaggaagggc 180
tggtcctgcc cctttgaggg ggtgcaaaca tgactgggac ctaagagcca gaggctgtgt 240
agaggctcct gctccacctg ccagtctcgt aagaaatggg gttgctgcag tgttggagta 300
ggggcagagg gagggagcca aggtcactcc aataaaacaa gctcatggca c 351

<210> SEQ ID NO 243
<211> LENGTH: 241
<212> TYPE: DNA
<213> ORGANISM: Homo sapiens

<400> SEQUENCE: 243
gtctgtgctt tatcaggaaa agcacaagaa tatgtttttc tacctaaaac cctcttctac 60
tttaaaaatg gtttgctgaa tttttctatg tttttaaaat gtttttatgc tttttttaa 120 acacgtaaag gatggaacct aatcctctcc cgagacgcct cctttgtgtt aatgcctatt 180
cttacaacag agaaacaagt acattaatat aaaaacgagt tgattattgg ggtataaaat 240

-continued

```
a                                                                     241


<210> SEQ ID NO 244
<211> LENGTH: 301
<212> TYPE: DNA
<213> ORGANISM: Homo sapiens

<400> SEQUENCE: 244

ggtccagagc aatagcgtct gtggtgaagc gcctgcactc ctcgggagac atgcctggct     60

tatatgctgc atccacataa ccatagataa aggtgctgcc ggagccacca atggcaaaag    120

gctgtcgagt cagcattcct cccagggttc catatacctg acctccttca cgttggtccc    180

agccagctac catgagatgt gcagacaagt cctctcgata tttatagctg atatttctca    240

ccacatttgc agcagccaaa acaagtggag gttcctccag ttctatccca tggagctcca    300

g                                                                     301


<210> SEQ ID NO 245
<211> LENGTH: 391
<212> TYPE: DNA
<213> ORGANISM: Homo sapiens

<400> SEQUENCE: 245

ctgacactgc tgatgtgggc cggggggcgc cgaggcacaa ctggtggccg gaccattgag     60

gcacctggag ggtaggcagc ttgtggtgca gacaccacag agagagaaaa gttggatgga    120

gtggtgggaa taatcagggt ggcacactgt gcctagaagc ttccagggcc accaagagaa    180

tgggaaggga aactacaaca ttcacaacag aaataggagt caattcactt agacccagaa    240

ctccagaaag ggggagtgta ggaatctaca atttcaaagc cagctcgtgt ctacctagag    300

ccccaaactg cataagcacc aggattgtac accttagtcc ctcaagatag tttcaagtga    360

gcgtgcaatt cactcttaca gaggagggcc t                                   391


<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: (1)...(291)
<223> OTHER INFORMATION: n=A,T,C or G

<400> SEQUENCE: 246

tcctccacag gggaagcagg aagttngacc agcttcaggc tggaacgtgc ccagggcaca     60

gagctggcaa ggtgcaaagn cntctgcaga atattcacca ggttgacaca gacctccaca    120

ttcagacata ttccaagctt ctggggtctt cagggcccca gaatttcctg gtcttgggca    180

tggtncacaa gtcatttgtc cttcctcatt ttggaaggtt ccatttggac ataaaatgca    240

agcgttctcg tgctncatna taataggtcc cagcctgcac tgacacattt g             291


<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 247
```

-continued

```
cactgagtga atgagtatat aatttatgaa aacagaaaag tgctttggaa aaaaaaaaag     60

acaacaggag tacatacagn gaaccaaaaa gagtgtacca ggaggagcan accctgaaca    120

gttanaacta tggaaatcgc tatgctttgt gttgtcacag gagttaaaat aggaataccc    180

tgcatacaat aaatatttat tggataaata actaagcctg ataccctttt caatgcgtta    240

tacanactnt atcatcacac cactaatcta agttctcana agttaaacat tacaagactt    300

cagaacaaca taggcgtntt tggctccatt taacanaana aggaccatag tgatcattta    360

atctctatga gtctgtctta tcttctggaa aaggggccta acaccatttc cttttgcaaa    420

aaggtagctg ccttgcttcc agttctacca tcctntagca acccatcttt n             471
```

<210> SEQ ID NO 248
<211> LENGTH: 551
<212> TYPE: DNA
<213> ORGANISM: Homo sapiens

<400> SEQUENCE: 248

```
ccatgggatc aggaatgggg tcaggtcagt tgacctgagc atacccatta aacatgttca     60

aatgtcccca tcccacccac tcacatgaca tggctcccga gccctgagat ctgtatccca    120

agaacctcag ttgagaaata tttatggcag cttcactgtt gctcaagagc ctgggtattg    180

tagcagcctg gggcaggtt gtccctaatg ttctccaagt tcttcacatc agccagaatc     240

ccatctatgc ttgtctccag caaatggagg tggcccctct gctgacgtgc cctctcttcc    300

agctctgaca tcatgggccg cagttggctg ttgatctggg tcttggctcg ggaaagcttc    360

tgctccagta agaccagccc ctcttcatct acactgagag gctggtccat cagatgcagg    420

aggccgtcta atgtgttgag tgtgtcttgg attgtaaccc cagcgttctt ggctctggta    480

tcaaccttct gggcttctgt aatcaccatc tgtactgcat ccatattcgt gtcgaactcc    540

agctccttcc t                                                          551
```

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: (1)...(181)
<223> OTHER INFORMATION: n=A,T,C or G

<400> SEQUENCE: 249

```
atntccagag ggaccgtaag actggtacaa gtttacacca taagaggcga cgtggtcagc     60

cacaatgtct tcacctccac aggggctcat cacggngqtc agggcaaggg cccccagcat    120

cagagctttg tttaggatca tcctcttccc aaggcagcct tagcagttgc tgacctgccc    180

g                                                                     181
```

<210> SEQ ID NO 250
<211> LENGTH: 551
<212> TYPE: DNA
<213> ORGANISM: Homo sapiens

<400> SEQUENCE: 250

```
tctgtagcta ggatgagctg gctctcaagc aaaagtttgt cttcctgggt ccatttgtgg     60

ttatcacttg ttattgaatg tacatcacaa attaaagtct gcattgttgg acgtaagaga    120

atgtgccgac tttggtaacc aggagatttc atgttactgg actgcctgta gtcacgtatt    180

tctgctatga cacatccgca atgaaaaata ttaacctgag atttttctag gagatcaacc    240
```

-continued aaaataggag gtaattcttc tgcatccaaa tattcaagca actctccttc ttcatagggc 300
agtcgaatgg tctcggaatc tgatccgttt tttcccctga gcatcagaga atatccctca 360
tttcctgggt atagattgac cactaaacat gacaaagtct cttgcataac aagcttctct 420
aacaagttca catttcttct taatttctta acttcaggtt ctttttcaca ttcttcaata 480
tacaagtcat aaagtttttg aaatacagat tttcttccac ttgataggta tttcctttta 540
ggaggtctct g 551

<210> SEQ ID NO 251
<211> LENGTH: 441
<212> TYPE: DNA
<213> ORGANISM: Homo sapiens

<400> SEQUENCE: 251
tgtctgctct cccatcctgg ttactatgag tcgctcttgg cagaaaggac cacagatgga 60
gagcttggca ctcgctccaa ctttgccgaa aagaggacaa ccaccaaagt agtaggtaaa 120
aacacaattt tagcagcagt gaaataaaaa gaggaagtga ggatggggcc aggccgcaac 180
tataattaaa ctgtctgttt aggagaagct gaatccagaa gaaacacaag ctgtaaagtg 240
agagaggaca gggagcaggg cctttggaga gcaggagagg acaggctgtc accaagcgct 300
gctcggactc tgccctgaaa gatttgaatt ggacactgtc cagtcacgtg tgtggcaaac 360
cgtactccaa gcacttttct cacggcagag gaaggagctg ccatggctgt acccctgaac 420
gtttgtgggg ccagcgatgt g 441

<210> SEQ ID NO 252
<211> LENGTH: 406
<212> TYPE: DNA
<213> ORGANISM: Homo sapiens

<400> SEQUENCE: 252
tttttttttg aacaagtaaa aatttcttta tttgctgaca ataagataac ctacagggaa 60
aacctgatga aatctattaa aaagttacta aaactaataa aagaatttag gaaggttata 120
gaatgtaaga ccaagacaca aaaatcaatt acatttctat ataatagcaa tgaacagata 180
ctgaaatttt aaaaactaaa tcattttaca aaagtatcac aatatgaaac actccgggat 240
aaattggata aaagatgtgc aagactgtac aaaagctaca aaacatttat gaaggaaatt 300
ggaagataga aacaagatag aaaatgaaaa tattgtcaag agtttcagat agaaaatgaa 360
aaacaagcta agacaagtat tggagaagta tagaagatag aaaaat 406

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: (224)
<223> OTHER INFORMATION: n=A,T,C or G

<400> SEQUENCE: 253
gaaggagttc agtagcaaag tcacacctgt ccaattccct gagctttgct cactcagcta 60
atgggatggc aaaggtggtg gtgctttcat cttcaggcag aagcctctgc ccatccccct 120
caagggctgc aggcccagtt ctcatgctgc ccttgggtgg gcatctgtta acagaggaga 180
acgtctgggt ggcggcagca gctttgctct gagtgcctac aaanctaatg cttggtgcta 240

-continued

```
gaaacatcat cattattaaa cttcagaaaa gcagcagcca tgttcagtca ggctcatgct    300

gcctcactgc ttaagtgcct gcaggagccg cctgccaagc tcccctcct acacctggca    360

cactggggtc tgcacaaggc tttgtcaacc aaagacagct tcccccttt gattgcctgt    420

agactttgga gccaagaaac actctgtgtg actctacaca cacttcaggt ggtttgtgct    480

tcaaagtcat tgatgcaact tgaaaggaaa cagtttaatg gtggaaatga actaccattt    540

ataa                                                                 544


<210> SEQ ID NO 254
<211> LENGTH: 339
<212> TYPE: DNA
<213> ORGANISM: Homo sapiens

<400> SEQUENCE: 254

tggcattcag ggcagtgtct tctgcatctc ctaggaacct cgggagcggc agctccggcg     60

cctggtagcg agaggcgggt tccggagatc ccggcctcac ttcgtcccac tgtggttagg    120

ggtgagtcct gcaaatgtta agtgatttgc tcaaggtgcc catttcgcag gaattggagc    180

ccaggccagt tctctgagcc tatcattagg gctaaaggag tgcgtgatca gaatggtgtc    240

tggacggttc tacttgtcct gcctgctgct ggggtccctg ggctctatgt gcatcctctt    300

cactatctac tggatgcagt actggcgtgg tggctttgc                           339


<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: (1)...(405)
<223> OTHER INFORMATION: n=A,T,C or G

<400> SEQUENCE: 255

gaggtttttt nttttttttt tttttttttt caattaaana tttgatttat tcaagtatgt     60

gaaaacattn tacaatggaa acttttntta aatgctgcat gtnctgtgct atggaccacn    120

cacatacagc catgctgttt caaaaaactt gaaatgccat tgatagttta aaaactntac    180

ncccgatgga aaatcgagga aaacaattta atgtttcatn tgaatccana ggngcatcaa    240

attaaatgac agctccactt ggcaaataat agctgttact tgatggtatc caaaaaaaaa    300

tggttgggga tggataaatt caaaaatgct tccccaaagg ngggngggtt ttaaaaagtt    360

tcaggncaca acccttgcan aaaacactga tgcccaacac antga                    405


<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: (6)
<223> OTHER INFORMATION: n=A,T,C or G

<400> SEQUENCE: 256

gggcangtct ggtcctctcc ccacatgtca cactctcctc agcctctccc ccaaccctgc     60

tctccctcct cccctgccct agcccaggga cagagtctag gaggagcctg ggcagagct    120

ggaggcagga agagagcact ggacagacag ctatggtttg gattggggaa gaggttagga    180

agtaggttct taaagaccct tttttagta                                      209
```

-continued

<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: (1)...(343)
<223> OTHER INFORMATION: n=A,T,C or G

<400> SEQUENCE: 257
tctggacacc ataatccctt ttaagtggct ggatggtcac acctctccca ttgacaagct 60
gggttaagtc aataggttga ctaggatcaa cacgacccaa atcaataaga tactgcagtc 120
tattgagact caaaggctta tactggcgtc tgaaactatg tccttcgtta aacccgtatt 180
ttgggattcg gatgtaaaat ggagtctggc ctccctcaaa gcccaagcgg ggccgggttc 240
ctctttgcct ttctccttta tggcctctgc cacattttct acctcttctc cgacctcttg 300
gtcttntctc nggtttcttg gagccgggat tcggctttaa gtn 343

<210> SEQ ID NO 258
<211> LENGTH: 519
<212> TYPE: DNA
<213> ORGANISM: Homo sapiens

<400> SEQUENCE: 258
gcggcttctg acttctagaa gactaaggct ggtctgtgtt tgcttgtttg cccacctttg 60
gctgataccc agagaacctg ggcacttgct gcctgatgcc cacccctgcc agtcattcct 120
ccattcaccc agcgggaggt gggatgtgag acagcccaca ttggaaaatc cagaaaaccg 180
ggaacaggga tttgcccttc acaattctac tccccagatc ctctcccctg gacacaggag 240
acccacaggg caggacccta agatctgggg aaaggaggtc ctgagaacct tgaggtaccc 300
ttagatcctt ttctacccac tttcctatgg aggattccaa gtcaccactt ctctcaccgg 360
cttctaccag ggtccaggac taaggcgttt tctccatagc ctcaacattt tgggaatctt 420
cccttaatca cccttgctcc tcctgggtgc ctggaagatg gactggcaga gacctctttg 480
ttgcgttttg tgctttgatg ccaggaatgc cgcctagtt 519

<210> SEQ ID NO 259
<211> LENGTH: 371
<212> TYPE: DNA
<213> ORGANISM: Homo sapiens

<400> SEQUENCE: 259
attgtcaact atatacacag tagtgaggaa taaaatgcac acaaaacaat ggatagaata 60
tgaaaatgtc ttctaaatat gaccagtcta gcatagaacc ttcttctctt ccttctcagg 120
tcttccagct ccatgtcatc taacccactt aacaaacgtg gacgtatcgc ttccagaggc 180
cgtcttaaca actccatttc caaaagtcat ctccagaaga catgtatttt ctatgatttc 240
ttttaaacaa atgagaattt acaagatgtg taactttcta actctatttt atcatacgtc 300
ggcaacctct ttccatctag aagggctaga tgtgacaaat gttttctatt aaaaggttgg 360
ggtggagttg a 371

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: (1)...(430)

-continued

<223> OTHER INFORMATION: n=A,T,C or G

<400> SEQUENCE: 260

```
ttggattttt tgacttgcga tttcagtttt tttacttttt tttttttttt ttttganaaa     60
tactatattt attgtcaaag agtggtacat aggtgagtgt tcatcttccc tctcatgccg    120
gtatactctg cttcgctgtt tcagtaaaag ttttccgtag ttctgaacgt cccttgacca    180
caccataana caagcgcaag tcactcanaa ttgccactgg aaaactggct caactatcat    240
ttgaggaaag actganaaag cctatcccaa agtaatggac atgcaccaac atcgcggtac    300
ctacatgttc ccgtttttct gccaatctac ctgtgtttcc aagataaatt accacccagg    360
gagtcacttc ctgctatgtg aacaaaaacc cggtttcttt ctggaggtgc ttgactactc    420
tctcgngagc                                                           430
```

<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: (178)
<223> OTHER INFORMATION: n=A,T,C or G

<400> SEQUENCE: 261

```
tcctgacgat agccatggct gtaccactta actatgattc tattccaact gttcagaatc     60
atatcacaaa atgacttgta cacagtagtt tacaacgact cccaagagag gaaaaaaaaa    120
aaaaaagacg cctcaaaatt cactcaactt ttgagacagc aatggcaata ggcagcanag    180
aagctatgct gcaactgagg gcacatatca ttgaagatgt cacaggagtt taagagacag    240
gctggaaaaa atctcatact aagcaaacag tagtatctca taccaagcaa aaccaagtag    300
tatctgctca gcctgccgct aacagatctc acaatcacca actgtgcttt aggactgtca    360
ccaaa                                                                365
```

<210> SEQ ID NO 262
<211> LENGTH: 500
<212> TYPE: DNA
<213> ORGANISM: Homo sapiens

<400> SEQUENCE: 262

```
cctagatgtc atttgggacc cttcacaacc attttgaagc cctgtttgag tccctgggat     60
atgtgagctg tttctatgca taatggatat tcggggttaa caacagtccc ctgcttggct    120
tctattctga atccttttct ttcaccatgg ggtgcctgaa gggtggctga tgcatatggt    180
acaatggcac ccagtgtaaa gcagctacaa ttaggagtgg atgtgttctg tagcatccta    240
tttaaataag cctattttat cctttggccc gtcaactctg ttatctgctg cttgtactgg    300
tgcctgtact tttctgactc tcattgacca tattccacga ccatggttgt catccattac    360
ttgatcctac tttacatgtc tagtctgtgt ggttggtggt gaataggctt ctttttacat    420
ggtgctgcca gcccagctaa ttaatggtgc acgtggactt ttagcaagcg ggctcactgg    480
aagagactga acctggcatg                                                500
```

<210> SEQ ID NO 263
<211> LENGTH: 413
<212> TYPE: DNA
<213> ORGANISM: Homo sapiens

<400> SEQUENCE: 263

-continued

```
ctcagagagg ttgaaagatt tgcctacgaa agggacagtg atgaagctaa gctctagatc     60

caggatgtct gacttcaaat tgaaactccc aaagtaatga gtttggaagg gtggggtgtg    120

gcctttccag gatgggggtc ttttctgctc ccagcggata gtgaaacccc tgtctgcacc    180

tggttgggcg tgttgctttc ccaaaggttt tttttttagg tccgtcgctg tcttgtggat    240

taggcattat tatctttact ttgtctccaa ataacctgga gaatggagag agtagtgacc    300

agctcagggc cacagtgcga tgaggaccat cttctcacct ctctaaatgc aggaagaaac    360

gcagagtaac gtggaagtgg tccacaccta ccgccagcac attgtgaatg aca           413


<210> SEQ ID NO 264
<211> LENGTH: 524
<212> TYPE: DNA
<213> ORGANISM: Homo sapiens

<400> SEQUENCE: 264

tccaatgggg ccctgagagc tgtgacagga actcacactc tggcactggc agcaaaacac     60

cattccaccc cactcatcgt ctgtgcacct atgttcaaac tttctccaca gttccccaat    120

gaagaagact catttcataa gtttgtggct cctgaagaag tcctgccatt cacagaaggg    180

gacattctgg agaaggtcag cgtgcattgc cctgtgtttg actacgttcc cccagagctc    240

attaccctct ttatctccaa cattggtggg aatgcacctt cctacatcta ccgcctgatg    300

agtgaactct accatcctga tgatcatgtt ttatgaccga ccacacgtgt cctaagcaga    360

ttgcttaggc agatacagaa tgaagaggag acttgagtgt tgctgctgaa gcacatcctt    420

gcaatgtggg agtgcacagg agtccaccta aaaaaaaaaa tccttgatac tgttgcctgc    480

ctttttagtc accccgtaac aagggcacac atccaggact gtgt                     524


<210> SEQ ID NO 265
<211> LENGTH: 344
<212> TYPE: DNA
<213> ORGANISM: Homo sapiens

<400> SEQUENCE: 265

tcctttcttc tacttcagga gatgattcaa agttacttgt ggacatttct ttaagttctg     60

aagacaaatg agacaggatt tggcctgcgg gttcttcaga cttctctacc acctccatta    120

actcttcatc ttggcttgac gtaggcaatg cactattttg ctcttttgtt tctggagatg    180

acccagcacc acttctttct cttggcgggg ttctaagtgt gtctttgaat accagtgaag    240

actcaggcct atcctgtact ggaaagggac taaatttgtc tttctgtcta ggaggtgatg    300

cagtagcatc ctcctgaggg ggtaaggcca ttttctcttt ttga                     344


<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: (78)
<223> OTHER INFORMATION: n=A,T,C or G

<400> SEQUENCE: 266

ccacaatgtc cataacttga gcaggctttg gcatcccacc accccttca gaccaataca      60

cactatgttg gaggaacnac tttaaaatgt aaaatgagaa atgggcactg aacactccat    120

cctcactccc aacagcccac ccacacacct cttcaactgc tatccaaaca tggaggagct    180
```

-continued

```
cttgtggaag agaggctcaa caccaaataa                                   210


SEQ ID NO 267
<211> LENGTH: 238
<212> TYPE: DNA
<213> ORGANISM: Homo sapiens
<220> FEATURE:
<221> NAME/KEY: misc_feature
<222> LOCATION: (1)...(238)
<223> OTHER INFORMATION: n=A,T,C or G

<400> SEQUENCE: 267

tcggncctcc caccctctna ctgaaattct ntgaaattct cccctttggg atgaggatgg    60

caaccccagg catgtaccct cccaacctgg gacccgacct aataccctaa catcctgctg   120

acagtggctg ttctcgctgg gcaggcgtcc caaagcacat cgagccagat tcaggcagag   180

tggaactggc ccctcagcca tcagtggagg tggcctggga ggctctaccc tgaacggg     238


SEQ ID NO 268
<211> LENGTH: 461
<212> TYPE: DNA
<213> ORGANISM: Homo sapiens
<220> FEATURE:
<221> NAME/KEY: misc_feature
<222> LOCATION: (459)
<223> OTHER INFORMATION: n=A,T,C or G

<400> SEQUENCE: 268

tcctcaagga catgcccctt gatagaaact cagttcctgt ctccagttcc ctcctggacc    60

tgatccccca aatgcagggc ctgggactat atccagttcc ttattttcag aggcccatgc   120

acaagatgca cagcaaataa gtgctgaata aagacccagc tactgctagc ttaccctgct   180

ccaaacattc accaagtcct cagcaaagag ggccatccat tcacctcttc taaaaacaca   240

ctgagctccc cagtctatac cccaagatat gcttggctcc caactatccc tcctctctca   300

tctccaagcc agtttcccct ttctaagtat actgatatta ccaaagacac tgacaatctt   360

cttttcctac ctctccccag tgactaggtt tgcagcagga gctctataag tcctagtata   420

cagcagaagc tccataaatg tgtgctgacc taacattang c                      461


<210> SEQ ID NO 269
<211> LENGTH: 434
<212> TYPE: DNA
<213> ORGANISM: Homo sapiens

<400> SEQUENCE: 269

ctgtgttggt gagcaccgat tcccactcaa tatggcgtgg cttacagtct tcattaggtt    60

cccgctccca accagaatga ggaatgatca cttcatctgt caaggcatgc agtgcatggt   120

ccacaatctc cattttgatt gagtcatggg atgaaagatt ccacagggtt ccggtaataa   180

cttcagtaag gtccatatca cgagcctttc gaagcaatcg cacaagggca ggcacaccat   240

cacagttttt tatggcaatc ttgttatcct ggtcacgtcc aaaagagata ttcttgagag   300

ctccacaggc tccaaggtgc acttcctttt tgggatggtc taacaatccc accagtactg   360

ggatgccctt gagcttccgc acgtcagtct tcaccttgtc attgcggtag cataagtgtt   420

gcaggtatgc aaga                                                    434


<210> SEQ ID NO 270
<211> LENGTH: 156
<212> TYPE: DNA
<213> ORGANISM: Homo sapiens
```

-continued

<400> SEQUENCE: 270
ctgcaccagc gattaccagt ggcattcaaa tactgtgtga ctaaggattt tgtatgctcc 60
ccagtagaac cagaatcaga caggtatgag ctagtcaaca gcaagtcttt gttggattcg 120
agtaggctca ggatctgctg aaggtcggag gagtta 156

<210> SEQ ID NO 271
<211> LENGTH: 533
<212> TYPE: DNA
<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 271
ccactgtcac ggtctgtctg acacttactg ccaaacgcat ggcaaggaaa aactgcttag 60
tgaagaactt agaagctgtg gagaccttgg ggtccacgtn caccatctgc tctgataaaa 120
ctggaactct gactcanaac cggatgacag tggcccacat gtggtttgac aatcaaatcc 180
atgaagctga tacgacagag aatcagagtg gtgtctcttt tgacaagact tcagctacct 240
ggcttgctct gtccagaatt gcaggtcttt gtaacagggc agtgtttcag gctaaccagg 300
aaaacctacc tattcttaag cgggcagttg caggagatgc ctctgagtca gcactcttaa 360
agtgcataga gctgtgctgt ggntncgtga aggagatgag agaaagatac nccaaaatcg 420
tcgagatacc cttcaactcc accaacaagt accagttgtc tattcataag aaccccaaca 480
catcggagcc ccaacacctg ttggtgatga agggcgcccc agaaaggatc cta 533

<210> SEQ ID NO 272
<211> LENGTH: 630
<212> TYPE: DNA
<213> ORGANISM: Homo sapiens

<400> SEQUENCE: 272
tggtattttt ctttttcttt tggatgtttt atactttttt ttctttttttc ttctctattc 60 ttttcttcgc cttcccgtac ttctgtcttc cagttttcca cttcaaactt ctatcttctc 120
caaattgttt catcctacca ctcccaatta atctttccat tttcgtctgc gtttagtaaa 180
tgcgttaact aggctttaaa tgacgcaatt ctccctgcgt catggatttc aaggtctttt 240
aatcaccttc ggtttaatct ctttttaaaa gatcgccttc aaattatttt aatcacctac 300
aacttttaaa ctaaacttta agctgtttaa gtcaccttca ttttaatcta aaagcattgc 360
ccttctattg gtattaattc ggggctctgt agtcctttct ctcaattttc ttttaaatac 420
attttttact ccatgaagaa gcttcatctc aacctccgtc atgttttaga aaccttttat 480
cttttccttc ctcatgctac tcttctaagt cttcatattt tctcttaaaa tcttaagcta 540
ttaaaattac gttaaaaact taacgctaag caatatctta gtaacctatt gactatattt 600
tttaagtagt tgtattaatc tctatctttc 630

<210> SEQ ID NO 273
<211> LENGTH: 400
<212> TYPE: DNA
<213> ORGANISM: Homo sapiens

<400> SEQUENCE: 273
tctggtttgc cctccagttc attctgaatc tagacttgct cagcctaatc aagttcctgt 60

-continued

```
acaaccagaa gcgacacagg ttcctttggt atcatccaca agtgaggggt acacagcatc    120

tcaacccttg taccagcctt ctcatgctac agagcaacga ccacagaagg aaccaattga    180

tcagattcag gcaacaatct ctttaaatac agaccagact acagcatcat catcccttcc    240

tgctgcgtct cagcctcaag tatttcaggc tgggacaagc aaacctttac atagcagtgg    300

aatcaatgta aatgcagctc cattccaatc catgcaaacg gtgttcaata tgaatgcccc    360

agttcctcct gttaatgaac cagaaacttt aaaacagcaa                          400
```

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G

<400> SEQUENCE: 274

```
tntgagtatg tcccagagaa ggtgaagaaa gcggaaaaga aattagaaga gaatccatat     60

gaccttgatg cttggagcat tctcattcga gaggcacaga atcaacctat agacaaagca    120

cggaagactt atgaacgcct tgttgcccag ttccccagtt ctggcagatt ctggaaactg    180

tacattgaag cagaggttac tattttattt tattttttct tatatcagta ttgcagcatt    240

cactgtagtg atagaaaaca agttaggaac atagccaatt aggacaagga ggatttaaat    300

gtgtcttacc tttattttgt aaaataggta taaaggagta attaaaatga a             351
```

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 275

```
gcgnggtcgc nnncgaggtc tgagaagccc ataccactat ttgttgagaa atgtgtggaa     60

tttattgaag atacagggtt atgtaccgaa ggactctacc gtgtcagcgg gaataaaact    120

gaccaagaca atattcaaaa gcagtttgat caagatcata atatcaatct agtgtcaatg    180

gaagtaacag taaatgctgt agctggagcc cttaaagctt tctttgcaga tctgccagat    240

cctttaattc catattctct tcatccagaa ctattggaag cagcaaaaat cccggataaa    300

acagaacgtc ttcatgcctt gaaagaaatt gttaagaaat ttcatcctgt aaactatgat    360

gtattcagat acgtgataac a                                              381
```

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: (5)
<223> OTHER INFORMATION: n=A,T,C or G

<400> SEQUENCE: 276

```
gctcngactc cggcgggacc tgctcggagg aatggcgccg ccgggttcaa gcactgtctt     60

cctgttggcc ctgacaatca tagccagcac ctgggctctg acgcccactc actacctcac    120

caagcatgac gtggagagac taaaagcctc gctggatcgc cctttcacaa atttggaatc    180
```

-continued

```
tgccttctac tccatcgtgg gactcagcag ccttggtgct caggtgccag atgcaaagaa    240

agcatgtacc tacatcagat ctaaccttga tcccagcaat gtggattccc tcttctacgc    300

tgcccaggcc agccaggccc tctcaggatg tgagatctct atttcaaatg agaccaaaga    360

tctgcttctg gcagacctcg gccgcgacca                                     390


<210> SEQ ID NO 277
<211> LENGTH: 378
<212> TYPE: DNA
<213> ORGANISM: Homo sapiens

<400> SEQUENCE: 277

tgggaacttc tggggtagga cgttgtctgc tatctccagt tccacagacc caaccagtta     60

cgatggtttt ggaccattta tgccgggatt cgacatcatt ccctataatg atctgcccgc    120

actggagcgt gctcttcagg atccaaatgt ggctgcgttc atggtagaac caattcaggg    180

tgaagcaggc gttgttgttc cggatccagg ttacctaatg ggagtgcgag agctctgcac    240

caggcaccag gttctcttta ttgctgatga aatacagaca ggattggcca gaactggtag    300

atggctggct gttgattatg aaaatgtcag acctgatata gtcctccttg gaaaggccct    360

ttctgggggc ttataccc                                                  378


<210> SEQ ID NO 278
<211> LENGTH: 366
<212> TYPE: DNA
<213> ORGANISM: Homo sapiens

<400> SEQUENCE: 278

ggagggcaca ttccttttca cctcagagtc ggtcggggaa ggccacccag ataagatttg     60

tgaccaaacc agtgatgctg tccttgatgc ccaccttcag caggatcctg atgccaaagt    120

agcttgtgaa actgttgcta aaactggaat gatccttctt gctggggaaa ttacatccag    180

agctgctgtt gactaccaga aagtggttcg tgaagctgtt aaacacattg gatatgatga    240

ttcttccaaa ggttttgact acaagacttg taacgtgctg gtagccttgg agcaacagtc    300

accagatatt gctcaaggtg ttcatcttga cagaaatgaa gaagacattg gtgctggaga    360

ccaggg                                                               366


<210> SEQ ID NO 279
<211> LENGTH: 435
<212> TYPE: DNA
<213> ORGANISM: Homo sapiens

<400> SEQUENCE: 279

cctaagaact gagacttgtg acacaaggcc aacgacctaa gattagccca gggttgtagc     60

tggaagacct acaacccaag gatggaaggc ccctgtcaca aagcctacct agatggatag    120

aggacccaag cgaaaaagat atctcaagac taacggccgg aatctggagg cccatgaccc    180

agaacccagg aaggatagaa gcttgaagac ctggggaaat cccaagatga gaaccctaaa    240

ccctacctct tttctattgt ttacacttct tactcttaga tatttccagt tctcctgttt    300

atctttaagc ctgattcttt tgagatgtac tttttgatgt tgccggttac ctttagattg    360

acaagtatta tgcctggcca gtcttgagcc agctttaaat cacagctttt acctatttgt    420

taggctatag tgttt                                                     435


<210> SEQ ID NO 280
```

-continued

<211> LENGTH: 435
<212> TYPE: DNA
<213> ORGANISM: Homo sapiens

<400> SEQUENCE: 280
tctggatgag ctgctaactg agcacaggat gacctgggac ccagcccagc caccccgaga 60
cctgactgag gccttcctgg caaagaagga gaaggccaag gggagccctg agagcagctt 120
caatgatgag aacctgcgca tagtggtggg taacctgttc cttgccggga tggtgaccac 180
ctcgaccacg ctggcctggg gcctcctgct catgatccta cacctggatg tgcagcgtga 240
gcccagacct gtccgggcgg ccgctcgaaa ttccagcaca ctggcggccg ttactagtgg 300
atccgagctc ggtaccaagc ttggcgtaat catggtcata gctgtttcct gtgtgaaatt 360
gttatccgct cacaattcca cacaacatac gagccggaag cataaagtgt aaagcctggg 420
gtgcctaatg agtga 435

<210> SEQ ID NO 281
<211> LENGTH: 440
<212> TYPE: DNA
<213> ORGANISM: Homo sapiens

<400> SEQUENCE: 281
catctgatct ataaatgcgg tggcatcgac aaaagaacca ttgaaaaatt tgagaaggag 60
gctgctgaga tgggaaaggg ctccttcaag tatgcctggg tcttggataa actgaaagct 120
gagcgtgaac gtggtatcac cattgatatc tccttgtgga aatttgagac cagcaagtac 180
tatgtgacta tcattgatgc cccaggacac agagacttta tcaaaaacat gattacaggg 240
acatctcagg ctgactgtgc tgtcctgatt gttgctgctg gtgttggtga atttgaagct 300
ggtatctcca agaatgggca gacccgagag catgcccttc tggcttacac actgggtgtg 360
aaacaactaa ttgtcggtgt taacaaaatg gattccactg agccccctac agccagaaga 420
gatatgagga aattgttaag 440

<210> SEQ ID NO 282
<211> LENGTH: 502
<212> TYPE: DNA
<213> ORGANISM: Homo sapiens

<400> SEQUENCE: 282
tctgtggcgc aggagccccc tcccccggca gctctgacgt ctccaccgca gggactggtg 60
cttctcggag ctcccactcc tcagactccg gtggaagtga cgtggacctg gatcccactg 120
atggcaagct cttccccagc gatggttttc gtgactgcaa gaagggggat cccaagcacg 180
ggaagcggaa acgaggccgg ccccgaaagc tgagcaaaga gtactgggac tgtctcgagg 240
gcaagaagag caagcacgcg cccagaggca cccacctgtg ggagttcatc cgggacatcc 300
tcatccaccc ggagctcaac gagggcctca tgaagtggga gaatcggcat gaaggcgtct 360
tcaagttcct gcgctccgag gctgtggccc aactatgggg ccaaaagaaa aagaacagca 420
acatgaccta cgagaagctg agccgggcca tgaggtacta ctacaaacgg gagatcctgg 480
aacgggtgga tggccggcga ct 502

<210> SEQ ID NO 283
<211> LENGTH: 433
<212> TYPE: DNA
<213> ORGANISM: Homo sapiens
<220> FEATURE:
<221> NAME/KEY: misc_feature -continued
<222> LOCATION: (1)...(433)
<223> OTHER INFORMATION: n=A,T,C or G

<400> SEQUENCE: 283

```
ccatattaga ttactggaac atctaagcat cagtgtgtga ccatgcgaac aaaagacttc     60

ggggagtgtc tatttttaaa aaggtttatg tgtgtcgagg cagttgtaaa agatttactg    120

cagaatcaan cccactttta ggcttangac caggttctaa ctatctaaaa atattgactg    180

ataacaaaaa gtgttctaaa tgtggctatt ctgatcccata nttgnttttt aaagaaaaaa    240

antgtntata cagaaagagt ntaaaagttc tgtgaattna atgcaaatta gncnccantc    300

ttgacttccc aaanacttga ttnatacctt tnactcctnt cnnttcctgn ncttcnttaa    360

nntcaatnat tnggnagtnn anggccntcn gnanaacacc nttncncgnt ccncgcaatc    420

canccgcctt nan                                                       433
```

<210> SEQ ID NO 284
<211> LENGTH: 479
<212> TYPE: DNA
<213> ORGANISM: Homo sapiens

<400> SEQUENCE: 284

```
tctggaagga tcagggatct gagcaaagcc aagtttactt aagctaagcc acttgttcct     60

gggtcaagca gtttgttttc taataagcat cattcctgat cattagagca aagggatgaa    120

tgctcctctt ggaatgatac aggggatctg ccactgggag agtgttgctc agtgttagag    180

tagcagcaat gacagaatga cagcgactct ctgagtcaac ccagtacttt tagtaccccg    240

tcactatgtg aataaaggca gctagaaaat ggactcaatt ctgcaagcct tcatggcaac    300

agcccatatt aagacttcta gaacaagtta aaaaaaaatc ttccatttcc atccatgcat    360

gggaaaaggg ctttagtata gtttaggatg gatgtgtgta taataataaa atgataagat    420

atgcatagtg ggggaataaa gcctcagagt ccttccagta tggggaatcc attgtatct     479
```

<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n=A,T,C or G

<400> SEQUENCE: 285

```
tttttttttt tttttttttt tcaatanaaa tgccataatt tattccattg tataaaaaag     60

tcatccttat gtaacaaaat gtnttcttan aanaanaaat atattatttc aggtcataaa    120

taatcagcaa acatacaact gttggcaact aaaaaaaaac ccaacactgg tattttccat    180

cagngctgaa aacaaacctg cttaaanata tatttacagg gatagtncag tnctcaaaaa    240

caaaaattga ggtattttgg ttcttctagg agtagacaat gacattttgg gangggcaga    300

cccctnnccc aaaaaataaa ataagggnat nttcttcant atngaanann gggggcgccc    360

cggggaaaan naaaccttgg gnngggggtt tggcccaagc ccttgaaaaa aaantttntt    420

tcccaaaaaa aacng                                                     435
```

<210> SEQ ID NO 286
<211> LENGTH: 301
<212> TYPE: DNA
<213> ORGANISM: Homo sapiens -continued

<400> SEQUENCE: 286
cctggtttct ggtggcctct atgaatccca tgtagggtgc agaccgtact ccatccctcc 60
ctgtgagcac cacgtcaacg gctcccggcc cccatgcacg ggggagggag ataccccaa 120
gtgtagcaag atctgtgagc ctggctacag cccgacctac aaacaggaca agcactacgg 180
atacaattcc tacagcgtct ccaatagcga gaaggacatc atggccgaga tctacaaaaa 240
cggccccgtg gagggagctt tctctgtgta ttcggacttc ctgctctaca agtcaggagt 300
g 301

<210> SEQ ID NO 287
<211> LENGTH: 432
<212> TYPE: DNA
<213> ORGANISM: Homo sapiens

<400> SEQUENCE: 287
tccagcttgt tgccagcatg agaaccgcca ttgatgacat tgaacgccgg gactggcagg 60
atgacttcag agttgccagc caagtcagcg atgtggcggt acagggggac cccttctca 120
acggcaccag ctttgcagac ggcaagggac acccccagaa tggcgttcgc accaaactta 180
gatttatttt ctgttccatc catctcgatc atcagtttgt caatcttctc ttgttctgtg 240
acgttcagtt tcttgctaac cagggcaggc gcaatagttt tattgatgtg ctcaacagcc 300
tttgagacac ccttccccat atagcgagtc ttatcattgt cccggagctc tagggcctca 360
tagataccag ttgaagcacc actgggcaca gcagctctga agagaccttt tgaggtgaag 420
agatcaacct ca 432

<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: (254)
<223> OTHER INFORMATION: n=A,T,C or G

<400> SEQUENCE: 288
tctggctcaa gtcaaagtcc tggtcctctt ctccgcctcc ttcttcatca tagtaataaa 60
cgttgtcccg ggtgtcatcc tctgggggca gtaagggctc tttgaccacc gctctcctcc 120
gaagaaacag caagagcagc agaatcagaa ttagcaaagc aagaattcct ccaagaatcc 180
ccagaatggc aggaatttgc aatcctgctt cgacaggctg tgccttccta cagacgccgg 240
cggccccttc acantcacac acgctgacct ctaaggtggt cacttggtct ttattctggt 300
tatccatgag cttgagattg attttg 326

<210> SEQ ID NO 289
<211> LENGTH: 451
<212> TYPE: DNA
<213> ORGANISM: Homo sapiens

<400> SEQUENCE: 289
gtcccggtgt ggctgtgccg ttggtcctgt gcggtcactt agccaagatg cctgaggaaa 60
cccagaccca agaccaaccg atggaggagg aggaggttga gacgttcgcc tttcaggcag 120
aaattgccca gttgatgtca ttgatcatca atactttcta ctcgaacaaa gagatctttc 180
tgagagagct catttcaaat tcatcagatg cattggacaa aatccggtat gaaagcttga 240
cagatcccag taaattagac tctgggaaag agctgcatat taaccttata ccgaacaaac 300

-continued

```
aagatcgaac tctcactatt gtggatactg gaattggaat gaccaaggct gacttgatca    360

ataaccttgg tactatcgcc aagtctggga ccaaagcgtt catggaagct ttgcaggctg    420

gtgcagatat ctctatgatt ggacctcggc c                                   451
```

<210> SEQ ID NO 290
<211> LENGTH: 494
<212> TYPE: DNA
<213> ORGANISM: Homo sapiens
<220> FEATURE:
<221> NAME/KEY: misc_feature
<222> LOCATION: (421)
<223> OTHER INFORMATION: n=A,T,C or G

<400> SEQUENCE: 290

```
ttttttttt tcaaaacagt atattttatt ttacaatagc aaccaactcc ccagtttgtt      60

tcaattgtga catctagatg gcttaagatt actttctggt ggtcacccat gctgaacaat    120

atttttcaat cttccaaaca gcaaagactc aaaagagatt ctgcatttca catcagttca    180

caagttcaag agtcttccat ttatcttagc ttttggaata aattatcttt gaggtagaag    240

gacaatgacg aagccactta attccttgtg tctgcataaa agcagattta ttcatcacaa    300

cttcatttat gtgaataaag cagatgatga taaaatgttc tcttattctt gtttaatcag    360

tagtggtagt gatgccagaa acttgtaaat gcacttcaaa ccaattgtgg ctcaagtgta    420

ngtggttccc caaggctggt accaatgaga ctggggtttg ggaattagtt ggtcatcatc    480

cctcctgctg ccca                                                      494
```

<210> SEQ ID NO 291
<211> LENGTH: 535
<212> TYPE: DNA
<213> ORGANISM: Homo sapiens

<400> SEQUENCE: 291

```
tcgcgtgctt aacatgaaaa caaactttgt gctgtttggt tcattgtatg cattgatgga     60

gtcttgtctc tcatcatggg gtgtctgacc atccaacctg cagtactcat aatttctcca    120

catgcaataa tcttccaaaa tgtccaatac ccttgtcatt tgactgaaga ttagtactcg    180

tgaaccttgt tcttttaact tagggagcag cttgtctaaa accaccattt tgccactgtt    240

ggttactaga tgcatatctg ttgtataagg tggaccaggt tctgctccat caaagagata    300

tggatgatta caacattttc tcaactgcat taggatgttc aataacctca ttttgtccat    360

cttgcctgct gagttgagta tatctatatc cttcattaat atccgagtat accattccct    420

ttgcattttg ctgaggccca catagatttt tacttccttc tttggaggca aactcttttc    480

aacatcagcc ttaattcgac gaaggaggaa tggacgcaaa accatatgaa gcctc         535
```

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: (1)...(376)
<223> OTHER INFORMATION: n=A,T,C or G

<400> SEQUENCE: 292

```
tacnagcccg tgctgatcga gatcctggtg gaggtgatgg atccttcctt cgtgtgcttg     60

aaaattggag cctgcccctc ggcccataag cccttgttgg gaactgagaa gtgtatatgg    120
```

-continued ggcccaagct actggtgcca gaacacagag acagcagccc agtgcaatgc tgtcgagcat 180
tgcaaacgcc atgtgtggaa ctaggaggag gaatattcca tcttggcaga aaccacagca 240
ttggtttttt tctacttgtg tgtctggggg aatgaacgca cagatctgtt tgactttgtt 300
ataaaaatag ggctccccca cctcccccat ttttgtgtcc tttattgnag cattgctgtc 360
tgcaagggag ccccta 376

<210> SEQ ID NO 293
<211> LENGTH: 320
<212> TYPE: DNA
<213> ORGANISM: Homo sapiens

<400> SEQUENCE: 293
tcggctgctt cctggtctgg cggggatggg tttgctttgg aaatcctcta ggaggctcct 60
cctcgcatgg cctgcagtct ggcagcagcc ccgagttgtt tcctcgctga tcgatttctt 120
tcctccaggt agagttttct ttgcttatgt tgaattccat tgcctctttt ctcatcacag 180
aagtgatgtt ggaatcgttt cttttgtttg tctgatttat ggttttttta agtataaaca 240
aaagtttttt attagcattc tgaaagaagg aaagtaaaat gtacaagttt aataaaaagg 300
ggccttcccc tttagaatag 320

<210> SEQ ID NO 294
<211> LENGTH: 359
<212> TYPE: DNA
<213> ORGANISM: Homo sapiens

<400> SEQUENCE: 294
ctgtcataaa ctggtctgga gtttctgacg actccttgtt caccaaatgc accatttcct 60
gagacttgct ggcctctccg ttgagtccac ttggctttct gtcctccaca gctccattgc 120
cactgttgat cactagcttt ttcttctgcc cacaccttct tcgactgttg actgcaatgc 180
aaactgcaag aatcaaagcc aaggccaaga gggatgccaa gatgatcagc cattctggaa 240
tttggggtgt ccttatagga ccagaggttg tgtttgctcc accttcttga ctcccatgtg 300
agtgtccatc tgattcagat ccatgagtgg tatgggaccc cccactgggg tggaatgtg 359

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: (558)
<223> OTHER INFORMATION: n=A,T,C or G

<400> SEQUENCE: 295
cctgagttgg gctgactgcc agagacagac ccctctgggt ctcggtgaac cagccaggca 60
tttacctcag tggttggcac ctggaacctg tccagggccc tcacctgact gaggagccgc 120
cgggcagtga agtaattgtc caggtctatg ctcttggggt ggataccata gccatccaag 180
gtattcctca ggttgtggaa ctgggtctga gtataggcag aactgggccc caggatgatc 240
tcccggagtg ggggaagctg tgaggtcagg taagtatcca cgtccacccg taccccaatc 300
aaactcagca gaatggtgaa ctggagaagt ccttccgtta agtatttctt cagagaaagc 360
attgctgaag gaccagaatg tttatgcttt ttggttttta aaatcttcca aaagacaaat 420
caaggccact gctctgccgc tccagccagc aggttaccct cctcagtgtc aaaccccgta 480
ccccaccctg gcagaacaca agggatgagc tccctgacgg ccccagagga aagcacaccc 540

-continued

```
tgtggagcca aggccaanga cacactccag accacattca cttt                584


<210> SEQ ID NO 296
<211> LENGTH: 287
<212> TYPE: DNA
<213> ORGANISM: Homo sapiens

<400> SEQUENCE: 296

ccttatcatt cattcttagc tcttaattgt tcattttgag ctgaaatgct gcattttaat     60

tttaaccaaa acatgtctcc tatcctggtt tttgtagcct tcctccacat cctttctaaa    120

caagatttta aagacatgta ggtgtttgtt catctgtaac tctaaaagat ccttttttaaa    180

ttcagtccta agaaagagga gtgcttgtcc cctaagagtg tttaatggca aggcagccct    240

gtctgaagga cacttcctgc ctaagggaga gtggtatttg cagacta                 287


SEQ ID NO 297
<211> LENGTH: 457
<212> TYPE: DNA
<213> ORGANISM: Homo sapiens

<400> SEQUENCE: 297

ccaattgaaa caaacagttc tgagaccgtt cttccaccac tgattaagag tggggtggca     60

ggtattaggg ataatattca tttagccttc tgagctttct gggcagactt ggtgaccttg    120

ccagctccag cagccttctt gtccactgct ttgatgacac ccaccgcaac tgtctgtctc    180

atatcacgaa cagcaaagcg acccaaaggt ggatagtctg agaagctctc aacacacatg    240

ggcttgccag gaaccatatc aacaatggca gcatcaccag acttcaagaa tttagggcca    300

tcttccagct tttaccagaa acggcgatca atcttttcct tcagctcagc aaacttgcat    360

gcaatgtgag ccgtgtggca atccaataca ggggcatagc cggcgcttat ttggcctgga    420

tggttcagga taatcacctg agcagtgaag ccagacc                            457


<210> SEQ ID NO 298
<211> LENGTH: 469
<212> TYPE: DNA
<213> ORGANISM: Homo sapiens

<400> SEQUENCE: 298

tctttgactt tccttgtcta cctcctctgg agatctcaaa ttctccaggt tccatgctcc     60

cagagatctc aatgattcct gattctcctc ttccaggagt ctgaatgtct cttggttcac    120

ttccacagac tccagtggtt cttgaatttc cttttctaga ggattcattg ccccctgatt    180

tatttcttct ggagtccaca gtggtgcttg agtttctgga gatttcagtg tttccaggtt    240

ctcttgtccc gcagacttca gtgattctag gatctctgtt tctaaagatt ttactgcctc    300

tatgctctct tctttgagtg actttaagaa ctcttgattc tcattttcaa gaggtctagc    360

tatctcctgg tcaagagact tcagtggttc tagatccact tttctgggg gtcttaatgt    420

catctgatcc tgttccccta gagacctccg tcgctgttga gtctctttt               469


<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: (1)...(165)
<223> OTHER INFORMATION: n=A,T,C or G
```

-continued

<400> SEQUENCE: 299
tctgtggaga ggatgaggtt gagggaggtg gggtatntcg ctgctctgac cttaggtaga 60
gtcctccaca gaagcatcaa antggactgg cacatatgga ctcccttcac aggccacaat 120
gatgtgtctc tccttcgggc tggnccggta tgcacagttg gggta 165

SEQ ID NO 300
LENGTH: 506
TYPE: DNA
<213> ORGANISM: Homo sapiens

<400> SEQUENCE: 300
tctgaggaaa gtttgggctt attagtattt gctccagcga acctccaagt tttctccatt 60
gcggacaacg taactaccag ctccttggct cagtggttcg cctccactca gaagttccca 120
gtaggttctg tcattattgt tggcacatag gccctgaata caggtgatat agggccccca 180
tgagcgctcc tccattgtga aaccaaatat agtatcattc attttctggg ctttctccat 240
cacactgagg aagacagaac catttagcac agtgacattg gtgaaatatg tttcattgat 300
tctcacagag taattgacgg agatatatga ttgtgagtca ggaggtgtca cagttatagg 360
ctcatcagcg gagatgttga agttacctga agcagagacg caagaagagt ctttgttaat 420
atccaagaag gtctttccca tcagggcagg taagacctgg gctgcagcgt ttggattgct 480
gaatgctcct tgagaaattt ccgtga 506

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: n=A,T,C or G

<400> SEQUENCE: 301
tcctaaggca gagcccccat cacctcaggc ttctcagttc ccttagccgt cttactcaac 60
tgcccctttc ctctccctca gaatttgtgt ttgctgcctc tatcttgttt tttgtttttt 120
cttctggggg gggtctagaa cagtgcctgg cacatagtag gcgctcaata aatacttgtt 180
tgttgaatgt ctcctctctc tttccactct gggaaaccta ngnttctgcc attctgggtg 240
accctgtatt tntttctggt gcccattcca tttgnccagn taatacttcc tcttaaaaat 300
ctcc 304

<210> SEQ ID NO 302
<211> LENGTH: 492
<212> TYPE: DNA
<213> ORGANISM: Homo sapiens

<400> SEQUENCE: 302
ttttcagtaa gcaacttttc catgctctta atgtattcct ttttagtagg aatccggaag 60
tattagattg aatggaaaag cacttgccat ctctgtctag gggtcacaaa ttgaaatggc 120
tcctgtatca catacggagg tcttgtgtat ctgtggcaac agggagtttc cttattcact 180
ctttatttgc tgctgtttaa gttgccaacc tcccctccca ataaaaattc acttacacct 240
cctgcctttg tagttctggt attcacttta ctatgtgata gaagtagcat gttgctgcca 300
gaatacaagc attgcttttg gcaaattaaa gtgcatgtca tttcttaata cactagaaag 360
gggaaataaa ttaaagtaca caagtccaag tctaaaactt tagtactttt ccatgcagat 420

-continued ttgtgcacat gtgagagggt gtccagtttg tctagtgatt gttatttaga gagttggacc 480
actattgtgt gt 492

<210> SEQ ID NO 303
<211> LENGTH: 470
<212> TYPE: DNA
<213> ORGANISM: Homo sapiens

<400> SEQUENCE: 303
tctggggcag caggtactcc ctacggcact agtctacagg gggaaggacg ctctgtgctg 60
gcagcggtgg ctcacatggc ctgtctgcac tgtaaccaca ggctgggatg tagccaggac 120
ttggtctcct tggaagacag gtctgatgtt tggccaatcc agtccttcag accctgcctg 180
aaacttgtat cttacgtgaa cttaaagaat aaaatgcatt tctaccccga tctcgccccc 240
aggactggca cgacaggccc acggcagatt agatcttttc ccagtactga tcggtgcgtg 300
gaattccagc caccacttct gattcgattc cacagtgatc ctgtcctctg agtattttaa 360
agaagccatt gtcaccccag tcagtgttcc aggagttggc aaccagccag tagggtgtgc 420
cattctccac tccccagccc aggatgcgga tggcatggac ctcggccgcg 470

<210> SEQ ID NO 304
<211> LENGTH: 79
<212> TYPE: DNA
<213> ORGANISM: Homo sapiens

<400> SEQUENCE: 304
tgtcccattg ttaactcagc ctcaaatctc aactgtcagg ccctacaaag aaaatggaga 60
gcctcttctg gtggatgcg 79

<210> SEQ ID NO 305
<211> LENGTH: 476
<212> TYPE: DNA
<213> ORGANISM: Homo sapiens

<400> SEQUENCE: 305
tcactgagcc accctacagc cagaagagat atgaggaaat tgttaaggaa gtcagcactt 60
acattaagaa aattggctac aaccccgaca cagtagcatt tgtgccaatt tctggttgga 120
atggtgacaa catgctggag ccaagtgcta acgtaagtgg ctttcaagac cattgttaaa 180
aagctctggg aatggcgatt tcatgcttac acaaattggc atgcttgtgt ttcagatgcc 240
ttggttcaag ggatggaaag tcacccgtaa ggatggcaat gccagtggaa ccacgctgct 300
tgaggctctg gactgcatcc taccaccaac tcgtccaact gacaagccct tgcgcctgcc 360
tctccaggat gtctacaaaa ttggtggtaa gttggctgta aacaaagttg aatttgagtt 420
gatagagtac tgtctgcctt cataggtatt tagtatgctg taaatatttt taggta 476

<210> SEQ ID NO 306
<211> LENGTH: 404
<212> TYPE: DNA
<213> ORGANISM: Homo sapiens

<400> SEQUENCE: 306
tctgtctcgg agctcagggc gcagccagca cacacaggag cccacaggac agccacgtct 60
tcacagaaac tacagaagtc aggacccagg cgaggacctc aggaacaagt gccccctgca 120
gacagagaga cgcagtagca acagcttctg aacaactaca taataatgcg gggagaatcc 180

-continued

```
tgaagaccac tgcatcccac aagcactgac aaccacttca ggattttatt tcctccactc    240

taacccccag atccatttat gagaagtgag tgaggatggc aggggcatgg agggtgaagg    300

gacagcaagg atggtctgag ggcctggaaa caatagaaaa tcttcgtcct ttagcatatc    360

ctggactaga aaacaagagt tggagaagag gggggttgat acta                     404


<210> SEQ ID NO 307
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n=A,T,C or G

<400> SEQUENCE: 307

tcctgcctan acatctgtga gggcctcaag ggctgctgcc tcgactttct ccctagctaa     60

gtccacccgt ccagggacac agccagggca ctgctctgtg ctgacttcca ctgcagccaa    120

gggtcaaaat gaagcatctg cggaggccag gactccttgg catcggacac agtcagggga    180

aaagccaccc tgactctgca ggacagaggg tctagggtca tttggcagga gaacactggt    240

gtgccaaggg aagcnancat                                                260


SEQ ID NO 308
<211> LENGTH: 449
<212> TYPE: DNA
<213> ORGANISM: Homo sapiens

<400> SEQUENCE: 308

tctgtgctcc cgactcctcc atctcaggta ccaccgactg cactgggcgg ggccctctgg     60

ggggaaaggc tccacggggc agggatacat ctcgaggcca gtcatcctct ggaggcagcc    120

caatcaggtc aaagattttg cccaactggt cggcttcaga gtttccacag aagagaggct    180

ttcgacgaaa catctctgca aagatacagc caacactcca catgtccaca ggtgttgcat    240

atgtggactg cagaagaact tcgggagctc ggtaccagag tgtaacaacc ttgatcgttt    300

cggctggcaa gcctggtggg ggtgccttgt ccagatatgt ccttaggtcc tggtctacat    360

gctcaaacac cagggttacc ttgatctccc ggtcagttcg ggatgtggca cagacgtcca    420

tcagccggac aacattggga tgctcaaaa                                      449


<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: (384)
<223> OTHER INFORMATION: n=A,T,C or G

<400> SEQUENCE: 309

ctgtggaaac ctggggtgcc gggtaaatgg agaactccag cttggatttc ttgccataat     60

caactgagag acgttccatg agcagggagg tgaacccaga accagttccc ccaccaaagc    120

tgtggaaaac caagaagccc tgaagaccgg tgcactggtc agccagcttg cgaattcggt    180

ccaacacaag gtcaatgatc tccttgccaa tggtgtagtg ccctcgggca tagttattgg    240

cagcatcttc cttgcctgtg atgagctgct cagggtggaa gagctggcgg taggtgccag    300

tgcgaacttc atcaatgact gtgggttcca agtctacaaa cacagcccgg ggcacgtgct    360

tgccagcgcc cgtctcactt gaanaagggt gtttgaagga agtcatctcc t             411
```

<210> SEQ ID NO 310
<211> LENGTH: 320
<212> TYPE: DNA
<213> ORGANISM: Homo sapiens
<220> FEATURE:
<221> NAME/KEY: misc_feature
<222> LOCATION: (250)
<223> OTHER INFORMATION: n=A,T,C or G

<400> SEQUENCE: 310
tcctcgtcca gcttgactcg attagtcctc ataaggtaag caaggcagat ggtggctgac 60
cgggaaatgc ctgcctggca gtggacaaac acccttcctc cagcattctt gatggagtct 120
atgaagtcaa tggcctcgtt gaaccaggag ctgatgtctg ccttgtggtt gtcctccaca 180
gggatgctct tgtactggta gtgaccctca aaatggttgg gacaattggc tgagacgttg 240
atcaaggcan ttatgcccaa ggcatccagc atgtccttgc gggaagcgtg atacgcactg 300
cccaggtaca gaaagggcag 320

<210> SEQ ID NO 311
<211> LENGTH: 539
<212> TYPE: DNA
<213> ORGANISM: Homo sapiens

<400> SEQUENCE: 311
tctggcccat gaagctgaag ttgggagaga tgatgcttcg cctctgcttc acaaactcaa 60
aggcctcgtc cagcttgact cgattagtcc tcataaggta agcaaggcag atggtggctg 120
accgggaaat gcctgcctgg cagtggacaa acacccttcc tccagcattc ttgatggagt 180
ctatgaagtc aatggcctcg ttgaaccagg agctgatgtc tgccttgtgg ttgtcctcca 240
cagggatgct cttgtactgg tagtgaccct caaaatggtt gggacaattg gctgagacgt 300
tgatcaaggc agttatgccc aaggcatcca gcatgtcctt gcgggaagcg tgatacgcac 360
tgcccaggta cagaaagggc aggatttcca ccgggccacc ctgaaatcca gaaatatcca 420
acattcatca agcttgctca aagccaaggc cagtgcccat acccacaaaa actttctgct 480
ggaaaagtca atttcagata ccgagtgaac tcagttctgt tgctggagga taaataaat 539

<210> SEQ ID NO 312
<211> LENGTH: 475
<212> TYPE: DNA
<213> ORGANISM: Homo sapiens

<400> SEQUENCE: 312
tcaaggatct tcctaaagcc accatgtgag aggattcgga cgagagtctg agctgtatgg 60
cagaccatgt cctgctgttc tagggtcatg actgtgtgta ctctaaagtt gccactctca 120
caggggtcag tgatacccac tgaacctggc aggaacagtc ctgcagccag aatctgcaag 180
cagcgcctgt atgcaacgtt tagggccaaa ggctgtctgg tggggttgtt catcacagca 240
taatggccta gtaggtcaag gatccagggt gtgaggggct caaagccagg aaaacgaatc 300
ctcaagtcct tcagtagtct gatgagaact ttaactgtgg actgagaagc attttcctcg 360
aaccagcggg catgtcggat ggctgctaag gcactctgca atactttgat atccaaatgg 420
agttctggat ccagttttcg aagattgggt ggcactgttg taatgagaat cttca 475

<210> SEQ ID NO 313
<211> LENGTH: 456
<212> TYPE: DNA

-continued

<213> ORGANISM: Homo sapiens

<400> SEQUENCE: 313
tccacttaaa gggtgcctct gccaactggt ggaatcatcg ccacttccag caccacgcca 60
agcctaacat cttccacaag gatcccgatg tgaacatgct gcacgtgttt gttctgggcg 120
aatggcagcc catcgagtac ggcaagaaga agctgaaata cctgccctac aatcaccagc 180
acgaatactt cttcctgatt gggccgccgc tgctcatccc catgtatttc cagtaccaga 240
tcatcatgac catgatcgtc cataagaact gggtggacct ggcctgggcc gtcagctact 300
acatccggtt cttcatcacc tacatccctt tctacggcat cctgggagcc ctcctttcc 360 tcaacttcat caggttcctg gagagccact ggtttgtgtg ggtcacacag atgaatcaca 420
tcgtcatgga gattgaccag gaggacctcg gcccgc 456

<210> SEQ ID NO 314
<211> LENGTH: 477
<212> TYPE: DNA
<213> ORGANISM: Homo sapiens

<400> SEQUENCE: 314
tgcgtgggct tctggaagcc tggatctgga atcattcacc agattattct ggaaaactat 60
gcgtaccctg gtgttcttct gattggcact gactcccaca cccccaatgg tggcggcctt 120
gggggcatct gcattggagt tgggggtgcc gatgctgtgg atgtcatggc tgggatcccc 180
tgggagctga agtgccccaa ggtgattggc gtgaagctga cgggctctct ctccggttgg 240
tcctcaccca aagatgtgat cctgaaggtg gcaggcatcc tcacggtgaa aggtggcaca 300
ggtgcaatcg tggaatacca cgggcctggt gtagactcca tctcctgcac tggcatggcg 360
acaatctgca acatgggtgc agaaattggg gccaccactt ccgtgttccc ttacaaccac 420
aggatgaaga agtatctgag caagaccggc cgggaagaca ttgccaatct agctgat 477

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 315
caggtactgg atgtcaggtc tgcgaaactt cttanatttt gacctcagtc cataaaccac 60
actatcacct cggccatcat atgtgtctac tgtggggaca actggagtga aaacttcggt 120
tgctgcaggt ccgtgggaaa atcagtgacc agttcatcag attcatcaga atggtgagac 180
tcatcagact ggtgagaatc atcagtgtca tctacatcat cagagtcgtt cgagtcaatg 240
g 241

SEQ ID NO 316
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 316
nttntgtgat agtgtggttt atggactgag gncaaaatnt aagaagtttc gcagacctga 60

-continued

```
catccaancc tgcccgngcg gncgctcgaa aggncgaatt ctgcagatat ccatcacact    120

ggcggccgct cgagcatgca tctagagggc ccaattcgcc ctatantgag tnatattaca    180

attcactggc cgtcnnttta caacgtcgtg actgggaaaa ccctggcgtt acccaactta    240

a                                                                      241


SEQ ID NO 317
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 317

aggtaccctg ctcancagcc tgggngcctg ggttgtctcc ttgtccatcc actggtccat     60

tctgctctgc attttttttgt tcctcttttg gaggttccac tttgggtttg ggctttgaaa    120

ttatagggct acaantacct cggccgaaac cacnctaagg gcgaattctg cagatatcca    180

tcacactggc ggncgctcga gcatgcatct agagggccca attcgcccta tagtgagtcg    240

t                                                                      241


SEQ ID NO 318
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 318

cgngnacaan ntacattgat gganggtntg nggntctgan tntttantta cantggagca     60

ttaatatttt cttnaacgtn cctcaccttc ctgaantaaa nactctgggt tgtagcgctc    120

tgtgctnana accacntnaa ctttacatcc ctcttttgga ttaatccact gcgcggccac    180

ctctgccgcg accacgctaa gggcnaattc tgcagatatc catcacactg gcggccgctc    240

n                                                                      241


<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 319

caggtactga tcggtgcgtg gaantccagc caccanttnt gattcgattc cacagtgatc     60

ctgtcctctg agtattttaa agaagccatt gtcaccccag tcagtgttcc aggagttggc    120

aaccagccag tagggtgtgc cattctccac tccccagccc aggatgcgga tggcatggcc    180

acccatcatc tctccggtga cgtgttggta cctcggccgc gaccacgcta agggcgaatt    240

c                                                                      241


<210> SEQ ID NO 320
<211> LENGTH: 241
<212> TYPE: DNA
```

-continued

<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 320
ggcaggtacc aacagagctt agtaatntct aaaaagaaaa aatgatcttt ttccgacttc 60
taaacaagtg actatactag cataaatcat tctagtaaaa cagctaaggt atagacattc 120
taataatttg ggaaaaccta tgattacaag tgaaaactca gaaatgcaaa gatgttggtt 180
ttttgtttct cagtctgctt tagcttttaa ctctnnnaan cncatgcaca cttgnaactc 240
t 241

<210> SEQ ID NO 321
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 321
angtaccaac agagcttagt aattnntaaa aagaaaaaat gatctttttc cgacttctaa 60
acaagtgact atactagcat aaatcattct agtaaaacag ctaaggtata gacattctaa 120
taatttggga aaacctatga ttacaagtga aaactcagaa atgcaaagat gttggttttt 180
tgtttctcag tctgctttag cttttaactc tggaagcgca tgcacacntg aactctgctc 240
a 241

<210> SEQ ID NO 322
<211> LENGTH: 241
<212> TYPE: DNA
<213> ORGANISM: Homo sapiens

<400> SEQUENCE: 322
ggtaccaaca gagcttagta atttctaaaa agaaaaaatg atctttttcc gacttctaaa 60
caagtgacta tactagcata aatcattctt ctagtaaaac agctaaggta tagacattct 120
aataatttgg gaaaacctat gattacaagt aaaaactcag aaatgcaaag atgttggttt 180
tttgtttctc agtctgcttt agcttttaac tctggaagcg catgcacact gaactctgct 240
c 241

SEQ ID NO 323

LENGTH: 241
<212> TYPE: DNA
<213> ORGANISM: Homo sapiens

<400> SEQUENCE: 323
cgaggtactg tcgtatcctc agccttgttc tatttcttta ttttagcttt acagagatta 60
ggtctcaagt tatgagaatc tccatggctt tcaggggcta aacttttctg ccattctttt 120
gctcttaccg ggctcagaag gacatgtcag gtgggatacg tgtttctctt tcagagctga 180
agaaagggtc tgagctgcgg aatcagtaga gaaagccttg gtctcagtga ctccttggct 240
t 241

<210> SEQ ID NO 324

-continued

<211> LENGTH: 241
<212> TYPE: DNA
<213> ORGANISM: Homo sapiens

<400> SEQUENCE: 324
aggtactgtc gtatcctcag ccttgttcta tttctttatt ttagctttac agagattagg 60
tctcaagtta tgagaatctc catggctttc aggggctaaa cttttctgcc attcttttgc 120
tcttaccggg ctcagaagga catgtcaggt gggatacgtg tttctctttc agagctgaag 180
aaagggtctg agctgcggaa tcagtagaga aagccttggt ctcagtgact ccttggcttt 240
c 241

<210> SEQ ID NO 325
<211> LENGTH: 241
<212> TYPE: DNA
<213> ORGANISM: Homo sapiens

<400> SEQUENCE: 325
ggcaggtaca tttgttttgc ccagccatca ctcttttttg tgaggagcct aaatacattc 60
ttcctggggt ccagagtccc cattcaaggc agtcaagtta agacactaac ttggcccttt 120
cctgatggaa atatttcctc catagcagaa gttgtgttct gacaagactg agagagttac 180
atgttgggaa aaaaaaagaa gcattaactt agtagaactg aaccaggagc attaagttct 240
g 241

<210> SEQ ID NO 326
<211> LENGTH: 241
<212> TYPE: DNA
<213> ORGANISM: Homo sapiens

<400> SEQUENCE: 326
gcaggtacat ttgttttgcc cagccatcac tcttttttgt gaggagccta aatacattct 60
tcctggggtc cagagtcccc attcaaggca gtcaagttaa gacactaact tggccctttc 120
ctgatggaaa tatttcctcc atagcagaag ttgtgttctg acaagactga gagagttaca 180
tgttgggaaa aaaaagaagc attaacttag tagaactgat ccaggagcat taagttctga 240
a 241

<210> SEQ ID NO 327
<211> LENGTH: 241
<212> TYPE: DNA
<213> ORGANISM: Homo sapiens

<400> SEQUENCE: 327
ggtaccagac caagtgaatg cgacagggaa ttatttcctg tgttgataat tcatgaagta 60
gaacagtata atcaaaatca attgtatcat cattagtttt ccactgcctc acactagtga 120
gctgtgccaa gtagtagtgt gacacctgtg ttgtcatttc ccacatcacg taagagcttc 180
caaggaaagc caaatcccag atgagtctca gagagggatc aatatgtcca tgattatcag 240
g 241

<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G -continued

<400> SEQUENCE: 328
ggtacnagac caaatgaang ccacagggaa ttatttcctg tgttgataat tcatgaagta 60
gaacantata atcaaaatca attgtatcat cattagtttt ccactgcctc acactagtga 120
gctgtgccaa gtagtagtgt gacacctgtg ttgtcatttc ccacatcacg taagagcttc 180
caaggaaagc caaatcccag atgagtctca gagagggatc aatatgtcca tnatcatcan 240
g 241

<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 329
ttcaggtcga gttggctgca gatttgtggt gcnttctgag ccgtctgtcc tgcgccaaaa 60
ngcttcaaag tattattaaa aacatatgga tccccatgaa gccctactac accaaagttt 120
accaggagat ttggatagga atggggctga tgggcttcat cgtttataaa atccgggctg 180
ctgataagaa gtaaggcttt gaaagcttca gcgcctgctn ctggtcanna ctaaccatan 240 n 241

<210> SEQ ID NO 330
<211> LENGTH: 241
<212> TYPE: DNA
<213> ORGANISM: Homo sapiens

<400> SEQUENCE: 330
ttttgtgcag atttgtggtg cgttctgagc cgtctgtcct gcgccaagat gcttcaaagt 60
attattaaaa acatatggat ccccatgaag ccctactaca ccaaagttta ccaggagatt 120
tggataggaa tggggctgat gggcttcatc gtttataaaa tccgggctgc tgataaaaga 180
agtaaggctt tgaaagcttc agcgcctgct cctggtcatc actaaccaga tttacttgga 240
g 241

<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 331
nttttaggna ctttgggctc cagacttcac tggtcttagg nattgaaacc atcacctggn 60
ntgcattcct catgactgag gttaacttaa aacaaaaatg gtaggaaagc tttcctatnc 120
ttcnggtaag anacaaatnt nctttaaaaa aangtggaag gcatgacnta cgtgagaact 180
gcacaaactg gccactgaca aaaatgaccc ccatttgtgt gacttcattg agacacatta 240
c 241

<210> SEQ ID NO 332
<211> LENGTH: 241
<212> TYPE: DNA

-continued

<213> ORGANISM: Homo sapiens

<400> SEQUENCE: 332
tgtgaggaga gggaacatgc tgagaaactg atgaagctgc agaaccaacg aggtggccga 60
atcttccttc aggatatcaa gaaaccagac tgtgatgact gggagagcgg gctgaatgca 120
atggagtgtg cattacattt ggaaaaaaat gtgaatcagt cactactgga actgcacaaa 180
ctggccactg acaaaaatga cccccatttg tgtgacttca ttgagacaca ttacctgaat 240
g 241

<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 333
caggtacaag cttttttttt tttttttttt tttttttttt ttgnaaatac tntttattgn 60
aaatattcta tcctaaattc catatagcca attaattntt acanaatntt ttgttaattt 120
ttgngngtat aaattttaca aaaataaagg gtatgtttgt tgcacacaac ttacaaataa 180
taataaactn tttattgnaa atattnttta ttgnaaatat tctttatcct aaattccata 240
t 241

<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 334
tacctgctgn aggggntgaa gncntctctg ctgccccagg catctgcanc ccctgctgct 60
ggttctgccc ctgctgcagc agaggagaag aaagatgaga agaaggagga gtctgaagag 120
tcagatgatg acatgggatt tggccttttt gattaaannc ctgctcccct gcaaataaag 180 ccttttttaca caaaaaaaaa aaaaaaaaaa aaaaaaaaaa aagcttgtac ctgcccnggc 240
g 241

<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 335
ctatgtgctg ggatgactat ggagacccaa atgtctcana atgtatgtcc cagaaacctg 60
tggctgcttc aaccattgac agttttgctg ctgctggctt ctgcagacag tcaagctgca 120
gctcccccaa aggctgtgct gaaacttgag cccccgtgga tcaacgtgct ccaggaggac 180
tctgtgactc tgacatgcca gggggctcgc agccctgaga gcgactccat tcagtggttc 240
c 241

<210> SEQ ID NO 336
<211> LENGTH: 241
<212> TYPE: DNA
<213> ORGANISM: Homo sapiens

<400> SEQUENCE: 336
taccaaccta tgcagccaag caacctcagc agttcccatc aaggccacct ccaccacaac 60
cgaaagtatc atctcaggga aacttaattc ctgcccgtcc tgctcctgca cctcctttat 120
atagttccct cacttgattt ttttaacctt ctttttgcaa atgtcttcag ggaactgagc 180
taatactttt ttttttcttg atgttttctt gaaaagcctt tctgttgcaa ctatgaatga 240
a 241

<210> SEQ ID NO 337
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 337
ggtactgtat gtagctgcac tacaacagat tcttaccgtc tccacanagg tcatanattg 60
taaatggtna atactgactt tttttttatt cccttgactc aagacagcta acttcatttt 120
cagaactgtt ttaaaccttt gtgtgctggt ttataaaata atgtgtgtaa tccttgttgc 180
tttcctgata ccagactgtt tcccgtggtt ggttagaata tattttgntt tgatgcttat 240
a 241

<210> SEQ ID NO 338
<211> LENGTH: 241
<212> TYPE: DNA
<213> ORGANISM: Homo sapiens

<400> SEQUENCE: 338
aggtacaggt gtgcgctgag ccgagtttac acggaaagga taaagcccat ttagtttctt 60
ctcaaatgga gttttccact ttcctttgaa gtagacagca ttcaccagga tcatcctggt 120
atccccatct acagaacctt caggtaacaa gtttgggatt ttgcctttgg tttgagtctt 180
gacccaggaa ttaatctttt ttctagcttc ttctgcacat tctaggaagt ctactgcctg 240
g 241

<210> SEQ ID NO 339
<211> LENGTH: 241
<212> TYPE: DNA
<213> ORGANISM: Homo sapiens

<400> SEQUENCE: 339
taccgacggc tcctggaggg agagagtgaa gggacacggg aagaatcaaa gtcgagcatg 60
aaagtgtctg caactccaaa gatcaaggcc ataacccagg agaccatcaa cggaagatta 120
gttctttgtc aagtgaatga aatccaaaag cacgcatgag accaatgaaa gtttccgcct 180
gttgtaaaat ctattttccc ccaaggaaag tccttgcaca gacaccagtg agtgagttct 240
a 241

<210> SEQ ID NO 340

-continued

<211> LENGTH: 241
<212> TYPE: DNA
<213> ORGANISM: Homo sapiens

<400> SEQUENCE: 340
gtagccctca cacacacatg cccgtaacag gatttatcac aagacacgcc tgcatgtaga 60
ccagacacag ggcgtatgga aagcacgtcc tcaagactgt agtattccag atgagctgca 120
gatgcttacc taccacggcc gtctccacca gaaaaccatc gccaactcct gcgatcagct 180
tgtgacttac aaaccttgtt taaaagctgc ttacatggac ttctgtcctt taaaagcttc 240
c 241

SEQ ID NO 341
LENGTH: 241
<212> TYPE: DNA
<213> ORGANISM: Homo sapiens

<400> SEQUENCE: 341
gtaccgccta ctttcgtctc atgtctccga acttcttgct gatggccgtt ccaacgttgc 60
tgaaagctgc agttgccttt tgccctgcgt gactcagggt ttcatgtgtt ttcttgtagg 120
cagtggtagt ctgcatgtca tgccagcttt tgctgaagtt ctgttttaat tcattcatca 180
ggttcatgcc gagttttgtt ttatctcaac tagatgcctt tctttcgctg acaaaacttg 240
t 241

<210> SEQ ID NO 342
<211> LENGTH: 241
<212> TYPE: DNA
<213> ORGANISM: Homo sapiens

<400> SEQUENCE: 342
gtacattggt gctataaata taaatgctac ttatgaagca tgaaattaag cttcttttt 60 cttcaagttt tttctcttgt ctagcaatct gttaggcttc tgaaccaaga ccaaatgttt 120
acgttcctct gctgcatacc aacgttactc caaacaataa aaatctatca tttctgctct 180
gtgctgagga atggaaaatg aaaccccccac cccctgaccc ctaggactat acagtggaaa 240
c 241

<210> SEQ ID NO 343
<211> LENGTH: 241
<212> TYPE: DNA
<213> ORGANISM: Homo sapiens

<400> SEQUENCE: 343
gtacatgtgg tagcagtaat ttttttgaag caactgcact gacattcatt tgagttttct 60
ctcattatca gattctgttc caaacaagta ttctgtagat ccaaatggat taccagtgtg 120
ctacagactt cttattatag aacagcattc tattctacat caaaaatagt ttgtgtaagt 180
tagttttggt taccatctaa aatattttta aatgttcttt acataaaaat ttatgttgtg 240
t 241

<210> SEQ ID NO 344
<211> LENGTH: 241
<212> TYPE: DNA
<213> ORGANISM: Homo sapiens

<400> SEQUENCE: 344
ggtacaaaat tgttggaatt tagctaatag aaaaacatag taaatattta caaaaacgtt 60

-continued

```
gataacatta ctcaagtcac acacatataa caatgtagac aggtcttaac aaagtttaca    120

aattgaaatt atggagattt cccaaaatga atctaatagc tcattgctga gcatggttat    180

caatataaca tttaagatct tggatcaaat gttgtccccg agtcttctgc aatccagtcc    240

t                                                                    241


<210> SEQ ID NO 345
<211> LENGTH: 241
<212> TYPE: DNA
<213> ORGANISM: Homo sapiens

<400> SEQUENCE: 345

ggtacgaagc tgagcgcacg ggggttgccc cagcgtggag cctggacctc aaacttcacg     60

gaaaatgctc tctctctttg acaggcttcc agctgtctcc taatttcctg gatgaactct    120

ccccggcgat ttaactgatc ctgaaaagtg gtgagaggac tgaggaagac aaccaggtca    180

gcgttagatc ggcctctgag ggtggtgccc ttgcctgagg agccaccctt taccaccttg    240

g                                                                    241


<210> SEQ ID NO 346
<211> LENGTH: 241
<212> TYPE: DNA
<213> ORGANISM: Homo sapiens

<400> SEQUENCE: 346

caggtaccac tgagcctgag atggggatga gggcagagag aggggagccc cctcttccac     60

tcagttgttc ctactcagac tgttgcactc taaacctagg gaggttgaag aatgagaccc    120

ttaggtttta acacgaatcc tgacaccacc atctataggg tcccaacttg gttattgtag    180

gcaaccttcc ctctctcctt ggtgaagaac atcccaagcc agaaagaagt taactacagt    240

g                                                                    241


<210> SEQ ID NO 347
<211> LENGTH: 241
<212> TYPE: DNA
<213> ORGANISM: Homo sapiens

<400> SEQUENCE: 347

aggtacatct aaaggcatga agcactcaat tgggcaatta acattagtgt ttgttctctg     60

atggtatctc tgagaatact ggttgtagga ctggccagta gtgccttcgg gactgggttc    120

acccccaggt ctgcggcagt tgtcacagcg ccagccccgc tggcctccaa agcatgtgca    180

ggagcaaatg gcaccgagat attccttctg ccactgttct cctacgtggt atgtcttccc    240

a                                                                    241


<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 348

angtacttgg caagattnga tgctcttgng ctcantgaca tcattcataa cttgtnngtg     60

tgancagagg aggagnncat catcntgtcc tcattcgtca gnnncctctc ctctctgaat    120
```

-continued

```
ctcaaacaag ttgataatgg agaaaaattt gaattctcag gattgaggct ggactggttc    180

cgcctacang catacactag cgtggctaag gcccctctgc accctgcatg anaaccctga    240

c                                                                     241
```

<210> SEQ ID NO 349
<211> LENGTH: 241
<212> TYPE: DNA
<213> ORGANISM: Homo sapiens

<400> SEQUENCE: 349

```
gcaggtacca tttgtctgac ctctgtaaaa aatgtgatcc tacagaagtg gagctggata     60

atcagatagt tactgctacc cagagcaata tctgtgatga agacagtgct acagagacct    120

gctacactta tgacagaaac aagtgctaca cagctgtggt cccactcgta tatggtggtg    180

agaccaaaat ggtggaaaca gccttaaccc cagatgcctg ctatcctgac taatttaagt    240

c                                                                     241
```

<210> SEQ ID NO 350
<211> LENGTH: 241
<212> TYPE: DNA
<213> ORGANISM: Homo sapiens

<400> SEQUENCE: 350

```
aggtactgtg gatatttaaa atatcacagt aacaagatca tgcttgttcc tacagtattg     60

cgggccagac acttaagtga aagcagaagt gtttgggtga ctttcctact taaaattttg    120

gtcatatcat ttcaaaacat ttgcatcttg gttggctgca tatgctttcc tattgatccc    180

aaaccaaatc ttagaatcac ttcatttaaa atactgagcg gtattgaata cttcgaagca    240

g                                                                     241
```

<210> SEQ ID NO 351
<211> LENGTH: 241
<212> TYPE: DNA
<213> ORGANISM: Homo sapiens

<400> SEQUENCE: 351

```
tacagaaatc atttggagcc gttttgagac agaagtagag gctctgtcaa gtcaatactg     60

cattgcagct tggtccactg aagaagccac gcctgagata caaaagatgc actacacttg    120

acccgcttta tgttcgcttc ctctcccctt ctctctcatc aactttatta ggttaaaaca    180

ccacatacag gctttctcca aatgactccc tatgtctggg gtttggttag aattttatgc    240

c                                                                     241
```

<210> SEQ ID NO 352
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 352

```
gtaccctgtn gagctgcacc aagattannt ggggccatca tgactgcanc cacnacgang     60

acgcaggcgt gnagtgcatc gtctgacccg gaaacccttt cacttctctg ctcccgaggt    120

gtcctcnggc tcatatgtgg gaaggcanan gatctctgan gagttncctg gggacaactg    180

ancagcctct ggagaggggc cattaataaa gctcaacatc attggcaaaa aaaaaaaaaa    240
```

-continued

```
a                                                                  241


<210> SEQ ID NO 353
<211> LENGTH: 241
<212> TYPE: DNA
<213> ORGANISM: Homo sapiens

<400> SEQUENCE: 353

aggtaccagt gcattaattt gggcaaggaa agtgtcataa tttgatactg tatctgtttt     60

ccttcaaagt atagagcttt tggggaagga aagtattgaa ctgggggttg gtctggccta    120

ctgggctgac attaactaca attatgggaa atgcaaaagt tgtttggata tggtagtgtg    180

tggttctctt ttggaatttt tttcaggtga tttaataata atttaaaact actataaaaa    240

c                                                                  241


<210> SEQ ID NO 354
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 354

ngcaggtccg ggcaggtacc aagattcatt ctcatcaaaa actagaaaca gaagggcaaa     60

ttccagtttc cttctgggat tgaatacttt caagtaaggt cttcgacaaa caatcagggg    120

gccaattaat ccactgtaga ggtccttaac ttgatccaca gttgaataat aagcccatgg    180

aatacaagca gaatcctctg ttccagctcc agatctttct gggattttcc atacgtaagt    240

g                                                                  241


<210> SEQ ID NO 355
<211> LENGTH: 241
<212> TYPE: DNA
<213> ORGANISM: Homo sapiens

<400> SEQUENCE: 355

ggtacccacc ctaaatttga actcttatca agaggctgat gaatctgacc atcaaatagg     60

ataggatgga cctttttttg agttcattgt ataaacaaat tttctgattt ggacttaatt    120

cccaaaggat taggtctact cctgctcatt cactctttca aagctctgtc cactctaact    180

tttctccagt gtcatagata gggaattgct cactgcgtgc ctagtctttc ttcacttacc    240

t                                                                  241


<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 356

aggtactgta attgagcatc cggaatntgg agaagtaatt tagctacagg gtgaccaacg     60

caagaacata tgccagttcc tcgtagagat tggactggct aaggacgatc agctgaaggt    120

tcatgggttt taagtgcttg tggctcactg aagcttaagt gaggatttcc ttgcaatgag    180
```

-continued

```
tagaatttcc cttctctccc ttgtcacagg tttaaaaacc tcacagcttg tataatgtaa    240

c                                                                    241


<210> SEQ ID NO 357
<211> LENGTH: 241
<212> TYPE: DNA
<213> ORGANISM: Homo sapiens

<400> SEQUENCE: 357

ttttgtacca ccgatatgat caaggaaaat tctgcccatt tttatggctg aagttctaaa     60

aacctaattc aaagttcttc catgatccta cactgcctcc aagatggtcc aggctggcat    120

aaggcctgag cggcggtgag atccgcggct gccagcagct tgtcgctctt cagctggtat    180

gaagcccctc ggccacccga gtctccagga cctgcccggg cgccgctcga aagggcgaat    240

t                                                                    241


<210> SEQ ID NO 358
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 358

aggtacgggg agtgggggtg aagcntgttc tctacatagg caacacagcc gcctaantca     60

caaagtcagt ggtcggccgc ttcgaccaac atgtggtgag cattccacgg gcgcatgaag    120

tctgggtgct gtgctcgagt ctctgaatat tttgatagga agcgacaaga aaattcaaac    180

tgctctttgc tgactactgg aaagtgaaaa gatgctcaag tttaccattc aaagaaacca    240

t                                                                    241


<210> SEQ ID NO 359
<211> LENGTH: 241
<212> TYPE: DNA
<213> ORGANISM: Homo sapiens

<400> SEQUENCE: 359

gaggtacaca aaaggaatac cttctgagag ccagggagtg aggaaagggg aaggagactt     60

gacgtcaagg gtgcttttga ggaacatgac gggccagcca gcctgcccca actttgaggc    120

cctgctgggc tcttgtgact ataaatatac tgtctatttc taatgcaatc cgtctttcct    180

gaaagatctt gttatctttt actattgaga catgctttca tttttgtggt cctgtttcca    240

a                                                                    241


<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 360

ngtactctat actaattctg ccttttttata cttaattcta aatttctccc ctctaattta     60

caacaaattt tgtgattttt ataagaatct atgcctcccc aattctcaga ttcttctctt    120

ttctccttta tttctttgct taaattcagt ataagctttc ttggtatttt aggcttcatg    180
```

-continued cacattctta ttcctaaaca ccagcagttc ttcagagacc taaaatccag tataggaata 240
a 241

<210> SEQ ID NO 361
<211> LENGTH: 241
<212> TYPE: DNA
<213> ORGANISM: Homo sapiens

<400> SEQUENCE: 361
aggtactctc cgtgccccga cactgaacat tatccagcca gatctgccca gtgccagctc 60
ccactttgta cttttcttac tatcctgtct agaatcatgt cttatgattt taacagatat 120
agaaccactc ctagaaaatg ttctttcact ttctcgtttc ctttttaatc tatcatcctg 180
actactgaac ttaaaatctt tttcttccct tttttgtttc tcttttcttt tatcctgttc 240
a 241

<210> SEQ ID NO 362
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 362
aggtactttt atacctngct tangtcagtg acagatttac caatgacaac acaattttaa 60
aattccaaca catatattac tttgtcctat gaagggcaaa aagtcaatat attttaaatt 120
ttaaaaacag aatggatata atgacctttt tacacatcag tgatatttaa aagacttaaa 180
gagacaatac tatggttgag acactggctt cctattccag ccctaattaa agaaaaaata 240
g 241

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 363
ttangtacta aaaacaaaat cctaattctg ttttaaagag ctgggagatg ttaatcatat 60
gctcagtttt tccacgttat aatttcctaa atgcaaactt ttcaatcagg gcagttcaaa 120
ttcattacat cacagtaaat aacagtagcc aactttgatt ttatgcttat aggaaaaaaa 180
atcctgtaga tataaaaaca gcaaattttg acaaataaaa ctcaaaccat tcatccctaa 240
a 241

<210> SEQ ID NO 364
<211> LENGTH: 241
<212> TYPE: DNA
<213> ORGANISM: Homo sapiens

<400> SEQUENCE: 364
ggtacaagca gttagtcctg aaggcccctg ataagaatgt catcttctcc ccactgagca 60
tctccaccgc cttggccttc ctgtctctgg gggcccataa taccaccctg acagagattc 120

-continued

```
tcaaaggcct caagttcaac ctcacggaga cttctgaggc agaaattcac cagagcttcc    180

agcacctcct gcgcaccctc aatcagtcca gcgatgagct gcagctgagt atgggaaatg    240

c                                                                    241
```

<210> SEQ ID NO 365
<211> LENGTH: 241
<212> TYPE: DNA
<213> ORGANISM: Homo sapiens

<400> SEQUENCE: 365

```
cgaggtactg agattacagg catgagccac cacgcccggc caaaaacatt taaaaaatga     60

ctgtccctgc tcaaatactg cagtaggaaa tgtaatttga catatatcac ttccagaaaa    120

aaactttaaa tctttctata aaatgaattt gatacatcat cagcatgaag tgaagttaaa    180

atctcttaca aagtaaattc aggtatatca acaatgagat ccaaaagtat cggttcaaga    240

t                                                                    241
```

<210> SEQ ID NO 366
<211> LENGTH: 241
<212> TYPE: DNA
<213> ORGANISM: Homo sapiens

<400> SEQUENCE: 366

```
ggcaggtaca catcaaacac ttcattgcct aaatgcaggg acatgcttcc atctgaccac     60

ttgactatcc gagcattgct ttctttaatt tcatttcctt cttcatctcg gcgtatcctc    120

catcttatag tattttctac ctttaatttt aacctggttc taccttcttc atccagcatt    180

tcttcatctt caaattcatc ttcataatac tgggctctac acttgagaaa gttgggcagt    240

t                                                                    241
```

<210> SEQ ID NO 367
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 367

```
gcaggtacaa ataattcctg ttgtnacatt tagtggacgc gattatctgt atacctcaaa     60

ttttaattta agaaagtatc acttaaagag catctcattt tctatagatt gaggcttaat    120

tactgaaaag tgactcaacc aaaaagcaca taacctttta aaggagctac acctaccgca    180

gaaagtcaga tgccctgtaa ataactttgg tctttcaaaa tagtggcaat gcttaagata    240

c                                                                    241
```

<210> SEQ ID NO 368
<211> LENGTH: 241
<212> TYPE: DNA
<213> ORGANISM: Homo sapiens

<400> SEQUENCE: 368

```
tttgtacatt gttaatagtg accctcggag gaaatggatt tctcttctat taaaaactct     60

atggtatata agcattacat aataatgcta cttaaccacc ttttgtctca agaattatca    120

ccaaagtttt ctggaaataa gtccacataa gaattaaata tttaaaaggt gaaatgttcc    180

ttattttaac tttagcaaga tcttttcttt ttcattaaga aacactttaa taattttaaa    240
```

-continued g 241

<210> SEQ ID NO 369
<211> LENGTH: 241
<212> TYPE: DNA
<213> ORGANISM: Homo sapiens

<400> SEQUENCE: 369
gcaggtactt tattcttatt tcttatccta tattctgtgt tacagaaaaa ctactaccat 60
aaacaaaaca ccaaccagcc acagcagttg tgtcaagcat gacaattggt ctagtcttca 120
cattttatta gtaagtctat caagtaagag atgaagggtc tagaaaacta gacacaaagc 180
aaccagggtc caaatcacca aggtagatct gtgcttagct aaagggaaac acccgaagat 240
t 241

<210> SEQ ID NO 370
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 370
ngttcacagt gcccctccgg cctcgccatg aggctcttcc tgtcgctccc ggtcctggtg 60
gtggttctgt cgatcgtctt ggaaggccca gccccagccc aggggacccc agacgtctcc 120
agtgccttgg ataagctgaa ggagtttgga aacacactgg aggacaaggc tcgggaactc 180
atcagccgca tcaaacagag tgaactttct gccaagatgc gggagtggtt ttcagaagac 240
a 241

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 371
ggcaggtcat cttgagcctt gcacatgata ctcagattcc tcacccttgc ttaggagtaa 60
aacaatatac tttacagggt gataataatc tccatagtta tttgaagtgg cttgaaaaag 120
gcaagattga cttttatgac attggataaa atctacaaat cagccctcga gttattcaat 180
gataactgac aaactaaatt atttccctag aaaggaagat gaaaggnagt ggagtgtggt 240
t 241

<210> SEQ ID NO 372
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 372
aggtacagca aagcgaccct tggtgnnata gatcagacgg aaattctctc ccgtcttgnc 60

-continued

```
aatgctgatg acatccatga atccagcagg gtaggttata tcagttcgga ccttgccatc    120

gattttaatg aaccgctgca tgcaaatctt ctttacttca tctcctgtca gggcatactt    180

aagtctgttc ctcaggaaaa tgatgagggg gagacactct ctcaacttgt ggggaccggt    240

g                                                                   241


<210> SEQ ID NO 373
<211> LENGTH: 241
<212> TYPE: DNA
<213> ORGANISM: Homo sapiens

<400> SEQUENCE: 373

tactgaaaca gaaaaaatgt attcccacaa aagctgttac acagcggttt cccgtcccca     60

gaagcagtag aaaatcttag cattccaatg gaaggcatgt atttgtaaaa tattctaaaa    120

tcagctctat agtttccttg tcctctttga taagggatca gacagagggt gtgtcccccct   180

tcagcagcta cccttcttga caaactggtc tccaataata cctttcagaa acttacaaga    240

c                                                                   241


<210> SEQ ID NO 374
<211> LENGTH: 241
<212> TYPE: DNA
<213> ORGANISM: Homo sapiens

<400> SEQUENCE: 374

caggtactaa aacttacaat aaatatcaga gaagccgtta gtttttacag catcgtctgc     60

ttaaaagcta agttgaccag gtgcataatt tcccatcagt ctgtccttgt agtaggcagg    120

gcaatttctg ttttcatgat cggaatactc aaatatatcc aaacatcttt ttaaaacttt    180

gatttatagc tcctagaaag ttatgttttt taatagtcac tctactctaa tcaggcctag    240

c                                                                   241


<210> SEQ ID NO 375
<211> LENGTH: 241
<212> TYPE: DNA
<213> ORGANISM: Homo sapiens

<400> SEQUENCE: 375

aggtacaaag gaccagtatc cctacctgaa gtctgtgtgt gagatggcag agaacggtgt     60

gaagaccatc acctccgtgg ccatgaccag tgctctgccc atcatccaga agctagagcc    120

gcaaattgca gttgccaata cctatgcctg taaggggcta gacaggattg aggagagact    180

gcctattctg aatcagccat caactcagat tgttgccaat gccaaaggcg ctgtgactgg    240

g                                                                   241


<210> SEQ ID NO 376
<211> LENGTH: 241
<212> TYPE: DNA
<213> ORGANISM: Homo sapiens

<400> SEQUENCE: 376

ggtacatttt actttccttc tttcagaatg ctaataaaaa acttttgttt atacttaaaa     60

aaaccataaa tcagacaaac aaaagaaacg attccaacat cacttctgtg atgagaaaag    120

aggcaatgga attcaacata agcaaagaaa actctacctg gaggaaagaa atcgatcagc    180

gaagaaacaa ctcggggctg ctgccagact gcaggccatg cgaggaggag cctcctagag    240

g                                                                   241
```

-continued

<210> SEQ ID NO 377
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 377
tcctttctgt ccaggtgatt cacagactag acctttctta tcctcctcct agagttttga 60
cttgggactc tagtgttaag atgatgagcc cgtgcatcag gtccttctgc actttggtgg 120
aagtctccca gggtaggttt cctatttgaa acagtggaat catgtttcca gtgataaagt 180
ttaatgacct catccttttt tttttttttc tcatctgcca tttgtgtgtc ttanatgggt 240
t 241

<210> SEQ ID NO 378
<211> LENGTH: 241
<212> TYPE: DNA
<213> ORGANISM: Homo sapiens

<400> SEQUENCE: 378
aggtcagcga tcaggtcctt tatgggcagc tgctgggcag ccccacaagc ccagggccag 60
ggcactatct ccgctgcgac tccactcagc ccctcttggc gggcctcacc cccagcccca 120
agtcctatga gaacctctgg ttccaggcca gccccttggg gaccctggta accccagccc 180
caagccagga ggacgactgt gtctttgggc cactgctcaa cttccccctc ctgcagggga 240
t 241

<210> SEQ ID NO 379
<211> LENGTH: 241
<212> TYPE: DNA
<213> ORGANISM: Homo sapiens

<400> SEQUENCE: 379
tacggagcaa tcgaagaggc atatccacac ttggggtggc tatagggctg gaaaatgctg 60
aagatgactg ctttcactga ggtcaaggat tgtaatattg ccagctttgt aaagccatta 120
aagcagaagt ttcttcagtg atcttctctc taagaaacac catcacctcc atgtgcctta 180
cagaggcccc ctgcgttctg ctgcattgct tttgcgcaat cccttgatga tgaagatggt 240
c 241

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 380
acgtacacgc agaccgacat gggnnnttca ggcntnagat caaactcaaa acctgnaatg 60
atatccactc tctttttctt aagctcaggg aaatattcca agtagaagtc canaaagtca 120
tcggctaana tgcttcngaa tttgaattca tgcacatagg ccttgaaaaa actgtcaaac 180
tgannctgat cacccaccaa gtgggccntn tatgacacaa agcagaaacc tttctcntan 240

-continued g 241

<210> SEQ ID NO 381
<211> LENGTH: 241
<212> TYPE: DNA
<213> ORGANISM: Homo sapiens

<400> SEQUENCE: 381
aggtacaact taatggatta gcttttgggt ttaactgaat atatgaagaa attgggtctg 60
tctaaagaga gggtatttca tatggctttt agttcacttg tttgtatttc atcttgattt 120
ttttctttgg aaaataaagc attctatttg gttcagattt ctcagatttg aaaaaggctc 180
tatctcagat gtagtaaatt atttcctttc agtttgtgaa agcaggattt gactctgaaa 240
g 241

<210> SEQ ID NO 382
<211> LENGTH: 241
<212> TYPE: DNA
<213> ORGANISM: Homo sapiens

<400> SEQUENCE: 382
gtactgctat aatcaatacg tctgatagac aggtttatcc actatattga ccctacctct 60
aaaaggattg tcataattta tatgctttat gtttacacct atgatacagt tgccttggaa 120
cacaaaattt ttcattgtaa ttaaaaaaag aagagttgtg cagacagaag aaatcaaatc 180
taagaaaatc acaggagtag ataaatactc tagaattcat atacccttgg aagatgggtt 240
t 241

<210> SEQ ID NO 383
<211> LENGTH: 241
<212> TYPE: DNA
<213> ORGANISM: Homo sapiens

<400> SEQUENCE: 383
ggcaggtaca aagtcttctc tttgcttttt ataattttaa agcaaataac acatttaact 60
gtatttaagt ctgtgcaaat aatccttcag aagaaatatc caagattctg tttgcagagg 120
tcattttgtc tctcaaagat gattaaatga gtttgtcttc agataaagtg ctcctgtcca 180
gcagaactca aaaggccttc aagctgttca gtaagtgtag ttcagataag actccgtcat 240
a 241

<210> SEQ ID NO 384
<211> LENGTH: 241
<212> TYPE: DNA
<213> ORGANISM: Homo sapiens

<400> SEQUENCE: 384
ggtacacaaa atacacttgc aagcttgctt acagagacct gttaaacaaa gaacagacag 60
attctataaa atcagttata tcaacatata aaggagtgtg attttcagtt tgttttttta 120
agtaaatatg accaaactga ctaaataaga aggcaaaaca aaaaattatg cttccttgac 180
aaggcctttg gagtaaacaa aatgctttaa ggctcctggt gaatggggtt gcaaggatga 240
a 241

<210> SEQ ID NO 385
<211> LENGTH: 241
<212> TYPE: DNA
<213> ORGANISM: Homo sapiens -continued

<400> SEQUENCE: 385
ggcaggtcta caatggctct gtcccttctg tggaatcgtt acaccaagag gtctcagtcc 60
tggtccctga ccccacagtg agctgtttag atgatccttc acatcttcct gatcaactgg 120
aagacactcc aatcctcagt gaagactctc tggagccctt caactctctg gcaccaggta 180
ggtttggagg ctatgtccct ttaacttatc catgcagagt agccaaactt tacctgaaag 240
a 241

<210> SEQ ID NO 386
<211> LENGTH: 241
<212> TYPE: DNA
<213> ORGANISM: Homo sapiens

<400> SEQUENCE: 386
aggtaccttt ttcctctcca aaggaacagt ttctaaagtt ttctgggggg aaaaaaaact 60
tacatcaaat ttaaaccata tgttaaactg catattagtt gtgttacacc aaaaaattgc 120
ctcagctgat ctacacaagt ttcaaagtca ttaatgcttg atataaattt actcaacatt 180
aaattatctt aaattattaa ttaaaaaaaa aactttctaa gggaaaaata aacaaatgta 240
g 241

<210> SEQ ID NO 387
<211> LENGTH: 241
<212> TYPE: DNA
<213> ORGANISM: Homo sapiens

<400> SEQUENCE: 387
accccactgg ccgctgtgga gtatctccac tctcccctcg tgagggccgc tcccaccgac 60
cagtcgaact ttcgtaaatg gagttaatgt gtttccactc cccttttccc ctttctggcc 120
ttttggtcca gaatttcctg gccttccggc atatcctggg agtcctcgac ttccaggaaa 180
gccaattgct ccccgatcac ctttaagacc cggaggacct attggacctg gaaatcctcg 240
t 241

<210> SEQ ID NO 388
<211> LENGTH: 241
<212> TYPE: DNA
<213> ORGANISM: Homo sapiens

<400> SEQUENCE: 388
tttgtactct tgtccacagc agagacattg agtataccat tggcatcaat gtcaaaagtg 60
acttcaatct gaggaacacc tcggggtgca ggaggtatgc ctgtgagttc aaacttgcca 120
agcaggttgt tatcctttgt catggcacgc tcgccttcat aaacctgaat aagtacacca 180
ggctggttgt cagaataggt agtgaaggtc tgtgtctgct tggtaggaat ggtggtatta 240
c 241

<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 389

-continued

```
tacctntgtt agtgagcacc ttgtcttntg tgcttatntc ttnaagataa atacatggaa     60

ggatgtgaaa atcggaacac caactatgtg tctcactgca tctaagtgaa gcagccacag    120

ctgtgagagt tttcaaagca gaaagatgct gatgtgacct ctggaattca gacatactga    180

gctatgggtc agaagtgttt tacttaaaaa gcaaacaatc cccaggaaat actgaatagg    240

a                                                                    241


<210> SEQ ID NO 390
<211> LENGTH: 241
<212> TYPE: DNA
<213> ORGANISM: Homo sapiens

<400> SEQUENCE: 390

gcaggtacat ccacatgttc ctccaaatga cgtttggggt cctgcttgcc aacattcttt     60

attgccagct gttcaggtgt catcttatct tcttcttcta cagccttatt gtaattcttg    120

gctaattcca acatctcttt taccactgat tcattgcgtt tacaatgttc actgtagtcc    180

tgaagtgtca aaccttccat ccaactcttc ttatgcaaat ttagcaacat cttctgttcc    240

a                                                                    241


<210> SEQ ID NO 391
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 391

cnggcacaan cttntgtttt tnntnttttt tttttttttn tctttatttn tttttantnt     60

taaanaaaaa nnntannnaa annngggttt aaatnctntn nncagancat taaaactgaa    120

ggggaaaaaa aaaccaaaaa cgagcttntt anttnacntg ggnttgggnn gntgctgatn    180

tnaagaagca anntttanan cnngcnnnat ganngagngn tcannttgaa atttnnaccc    240

t                                                                    241


<210> SEQ ID NO 392
<211> LENGTH: 241
<212> TYPE: DNA
<213> ORGANISM: Homo sapiens

<400> SEQUENCE: 392

gaggtactaa atggtatcct tagattaaaa ttttgtgctt gataacagct gttttttcta     60

cattagaaat aagatgccac acaaggaact acattccaga tttaaagaaa tgaaaggata    120

ccattagtgt gtataacaga ttattgttca tacttgtaaa gcatcttatg tcattgagaa    180

tataaagaac agtgccttag aagacagtga aaggtaagct ctagcttaat gtctatgatt    240

t                                                                    241


<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 393
```

-continued

```
ggcaggtaca taagcataat cagttatgga cagcttcttg tataaattgc tattcancaa     60

tacataaact gcctnaaaga tttatgctta caggtagaca ttcaatttac caataaaaca    120

gcatgttctg aaaatatggg cacattttaa aacatattaa gacagttctg ttaaccataa    180

tagtcccaca gtatgactga gtaataagaa tctacttcaa aagnaaaaaa aaaattaatc    240

a                                                                    241
```

<210> SEQ ID NO 394
<211> LENGTH: 241
<212> TYPE: DNA
<213> ORGANISM: Homo sapiens

<400> SEQUENCE: 394

```
aggtacagca gcagtagatg gctgcaacaa ccttcctcct accccagccc agaaaatatt     60

tctgccccac cccaggatcc gggaccaaaa taaagagcaa gcaggccccc ttcactgagg    120

tgctgggtag ggctcagtgc cacattactg tgctttgaga aagaggaagg ggatttgttt    180

ggcactttaa aaatagagga gtaagcagga ctggagaggc cagagaagat accaaaattg    240

g                                                                    241
```

<210> SEQ ID NO 395
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 395

```
nggcnggnnc caanatatga aatntnanta tnatacatga tnaaaagctt tatntatttt     60

agtgagtaat taagtttaca ctgtgaataa ggattaattc ccagatgacc atctacagtt    120

actaccacat agagggtata cacggatgga tcgattacaa gaatataaaa cttattttcc    180

ttcctgtatc cacatttctt tgcaatgtga atttgcaggc cctctcaaga agtggagtct    240

a                                                                    241
```

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 396

```
gaggtacacc ttgaatgaca atgctnggag ccccccctgtg gtcatcgacg cctccactgc     60

cattgatgca ccatccaacc tgcgtttcct ggccaccaca cccaattcct tgctggtatc    120

atggcagccg ccacgtgcca ggattaccgg ctacatcatc aagtatgaga agcctgggtc    180

tcctcccaga gaagtggtcc ctcggccccg ccctggtgtc acagaggcta ctattactgg    240

c                                                                    241
```

<210> SEQ ID NO 397
<211> LENGTH: 241
<212> TYPE: DNA
<213> ORGANISM: Homo sapiens
<220> FEATURE:

-continued

<221> NAME/KEY: misc_feature
<222> LOCATION: (1)...(241)
<223> OTHER INFORMATION: n = A,T,C or G

<400> SEQUENCE: 397
ggcaggtacc agcaggggga tgtgtttctg gggaattgtg gctctggaag cttcacggtt 60
tcccagaatg tggaaaatat atctgtgcan gatagaaatc ctgcccagag gctgtttctg 120
tctcatttga gctctccttc atgtggcaga gctgactgtg gcggtttagg agcctacatt 180
ttagaaaagc ttacctcaaa gttctgcatt gagcctgagc actggaaagg agataaaata 240
a 241

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 398
gangtgacca ngacatcacc tnacacntgg aaagcganga nttgaatggt gcntacaang 60
ccntacccnt tgcccannac ctgaacgcgc cttntgattg ggacagccgt gggaaggaca 120
gttatgaaac nantcanctg gatgaccana gtgntgaaac cnacanncac angcnntcna 180
cattatataa ncggaaagct aatgatgaga gcaatgatca ttccgatgtn attgatagtc 240
a 241

<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 399
cagagtgaga tgggagtggg agggccaatc tgatacagaa gggggtgaag ggtagggccc 60
ctgagcagcc caccccttac cctgacgaag gcaatcctcc tctggaatgt ctcttccctc 120
ttcagtctgg gttctgcctc agccacgaac tgggaaggag tgaggaacat cccaacggca 180
atgagagtat cccagtgact ccaaacagga angaatcagt gttcanaaag tcagggccct 240
t 241

<210> SEQ ID NO 400
<211> LENGTH: 241
<212> TYPE: DNA
<213> ORGANISM: Homo sapiens

<400> SEQUENCE: 400
ggtactcttg ctcttttagc tagagtgtat gtgaaaataa agaaatacat cattgtattc 60
acaaccatgt gtcttcattt ataacttttt gtttaaaaaa tttttagttc aagtttagtt 120
cattgatatt atcctctgaa tgcagttaag gctgggcaga aattctactc atgtgacatc 180
tgccacaggt ctattttgaa gcttttcttc taatgggcaa tgtttgtcct taccaggatt 240
t 241

-continued

<210> SEQ ID NO 401
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 401
nncaggtact ttgtagagca gagagaggct ttggttcctc ctttcttcaa tcacgtggag 60
atgtgtcatc acctgggatt tcatctgggc cgccttttct gggtcaacag ccaacacatg 120
ctggtaatga cggatggtat gtaagcgatc tttgttctca gcacggacat aacgccgtaa 180
ggcctggaga atgcgatgag gccgtggcgg gtcagactgc aaggcagcca ggtagttctc 240
c 241

<210> SEQ ID NO 402
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 402
ggcaggtcca aaaaaaacct aaaaanngtt tcaggaatgt agagaaatat ccaacttaaa 60
tagcgaaaaa gtgcaccata attactgctg cactgcagtc atttctgcaa ttcccatgtt 120
tcttaaataa ctatcttgtc agataacaca caatataaag agcaattatg aaaaacagac 180
atttacatat acttctaaag tcttattggg aatatcctgt ttggccattg ggataaccaa 240
t 241

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 403
aggtgttaac tacccgctcc gagacgggat tgatgacgag tcctatgang ccattttcaa 60
gccggtcatg tccaaagtaa tggagatgtt ccagcctagt gcggtggtct tacagtgtgg 120
ctcagactcc ctatctgggg atcggttagg ttgcttcaat ctaactatca aaggacacgc 180
caagtgtgtg gaatttgtca agagctttaa cctgcctatg ctgatgctgg gaggcggtgg 240
t 241

<210> SEQ ID NO 404
<211> LENGTH: 241
<212> TYPE: DNA
<213> ORGANISM: Homo sapiens

<400> SEQUENCE: 404
caggtactgc aacccataaa atactgtttc ctcatatttc accttcctta atttggagtt 60
ttctgtcttc ttttcacggc attcaaagta ggaataaact ttgcttgtgt tgggtggata 120
ttgtttatag tgagtaacct tgtaggagtc ggtggccagg aggatgttga actcggcttc 180

-continued tgccgcagga ttcatctcgg gccggaggac aaggggcccg cgcgccgcga gctccctgac 240
c 241

<210> SEQ ID NO 405
<211> LENGTH: 266
<212> TYPE: DNA
<213> ORGANISM: Homo sapiens

<400> SEQUENCE: 405
ttctgggctg gggagtggag agaaagaagt tgcagggctt acaggaaatc ccagagcctg 60
aggttttctc ccagatttga gaactctaga ttctgcatca ttatctttga gtctatattc 120
tcttgggctg taagaagatg aggaatgtaa taggtctgcc ccaagccttt catgccttct 180
gtaccaagct tgtttccttg tgcatccttc ccaggctctg gctgcccctt attggagaat 240
gtgatttcca agacaatcaa tccaca 266

<210> SEQ ID NO 406
<211> LENGTH: 231
<212> TYPE: DNA
<213> ORGANISM: Homo sapiens

<400> SEQUENCE: 406
ttggtgaaga accattcctc ggcatccttg cggttcttct ctgccatctt ctcatactgg 60
tcacgcatct cgttcagaat gcggctcagg tccacgccag gtgcagcgtc catctccaca 120
ttgacatctc cacccacctg gcctctcagg gcattcatct cctcctcgtg gttcttcttc 180
aggtaggcca gctcctcctt caggctctca atctgcatct ccaggtcagc t 231

<210> SEQ ID NO 407
<211> LENGTH: 266
<212> TYPE: DNA
<213> ORGANISM: Homo sapiens

<400> SEQUENCE: 407
cagcatcatt gtttataatc agaaactctg gtccttctgt ctggtggcac ttagagtctt 60
ttgtgccata atgcagcagt atggagggag gattttatgg agaaatgggg atagtcttca 120
tgaccacaaa taaataaagg aaaactaagc tgcattgtgg gttttgaaaa ggttattata 180
cttcttaaca attctttttt tcagggactt ttctagctgt atgactgtta cttgaccttc 240
tttgaaaagc attcccaaaa tgctct 266

<210> SEQ ID NO 408
<211> LENGTH: 261
<212> TYPE: DNA
<213> ORGANISM: Homo sapiens

<400> SEQUENCE: 408
ctgtgtcagc gagcctcggt acactgattt ccgatcaaaa gaatcatcat ctttaccttg 60
acttttcagg gaattactga actttcttct cagaagatag ggcacagcca ttgccttggc 120
ctcacttgaa gggtctgcat ttgggtcctc tggtctcttg ccaagtttcc cagccactcg 180
agggagtaat atctggaggg caaagaagag acttatgtta ttgttgaacc tccagccaca 240
gggaggagca tgggcatggg t 261

<210> SEQ ID NO 409
<211> LENGTH: 266
<212> TYPE: DNA

-continued

<213> ORGANISM: Homo sapiens

<400> SEQUENCE: 409
gctgacagta atacactgcc acatcttcag cctgcaggct gctgatggtg agagtgaaat 60
ctgtcccaga cccgctgcca ctgaatcggt cagggatccc ggattcccgg gtagatgccc 120
agtaaatgag cagtttagga ggctgtcctg gtttctgctg gtaccaagct aagtagttct 180
tattgttgga gctgtctaaa acactctggc tggtcttgca gttgatggtg gccctctcgc 240
ccagagacac agccagggag tgtgga 266

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 410
caaaaggtnc tttttgntca aaancnattt ttattccttg atatttttct tttttttttt 60
tttgnggatg gggacttgtg aatttttcta aaggggnnnn ttnannnngg aagaaaaccn 120
ngntccggtt ccagccaaac cngtngctna ctttccacct tntttccacc tccctcnggt 180
t 181

<210> SEQ ID NO 411
<211> LENGTH: 261
<212> TYPE: DNA
<213> ORGANISM: Homo sapiens

<400> SEQUENCE: 411
gcccctgcag tacttggccg atgtggacac ctctgatgag gaaagcatcc gggctcacgt 60
gatggcctcc caccattcca agcggagagg ccgggcgtct tctgagagtc agggtctagg 120
tgctggagtg cgcacggagg ccgatgtaga ggaggaggcc ctgaggagga agctggagga 180
gctggccagc aacgtcagtg accaggagac ctcgtccgag gaggaggaag ccaaggacga 240
aaaggcagag cccaacaggg a 261

<210> SEQ ID NO 412
<211> LENGTH: 171
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 412
nttttntctt tacaattcag tcttcaacaa cttgagagct ttcttcatgt tgncaagcaa 60
cagagctgta tctgcaggnt cgtaagcata nagacngttt gaatatcttc cagngatatc 120
ggctctaact gncagagatg ggtcaacaaa cataatcctg gggacatact g 171

<210> SEQ ID NO 413
<211> LENGTH: 266
<212> TYPE: DNA
<213> ORGANISM: Homo sapiens

<400> SEQUENCE: 413
ttaggaccaa agatagcatc aactgtattt gaaggaactg tagtttgcgc attttatgac 60

-continued

```
atttttataa agtactgtaa ttctttcatt gaggggctat gtgatggaga cagactaact    120

cattttgtta tttgcattaa aattattttg ggtctctgtt caaatgagtt tggagaatgc    180

ttgacttgtt ggtctgtgta aatgtgtata tatatatacc tgaatacagg aacatcggag    240

acctattcac tcccacacac tctgct                                          266


<210> SEQ ID NO 414
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 414

tttgccataa ttgagtgaaa agtggcagat ggcattaact ctgctccgct tcaagctggc     60

tccatgacca ctcaaggcct ccccancctg ttcgtcaagt tgtcctcaag tccaagcaat    120

ggaatccatg tgtttgcaaa aaaagtgtgc tanttttaag gnctttcgta taagaatnaa    180

tganacaatt ttcctaccaa aggangaaca aaaggataaa tataatacaa aatatatgta    240

tatggttgtt tgacaaatta tataac                                          266


<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 415

cctccatcca gtctattaat tgttgccggg aagctanagt aagtagttcg ccagttaata     60

gtttgcgcaa cgttgttgcc attgctacag gcatcgtggt gtnacgctcg tcgattggta    120

tggcttcatt cagctccggt tcccaacgat caaggcgagt tacatgatcc cccatgttgt    180

gcaaaaaagc ggttagctcc ttcggtcctc cgatcgttgt canaagtaag ttggccgcag    240

tgttatcact catggttatg gcagca                                          266


<210> SEQ ID NO 416
<211> LENGTH: 878
<212> TYPE: DNA
<213> ORGANISM: Homo sapiens

<400> SEQUENCE: 416

cctgacgata gccatggctg taccacttaa ctatgattct attccaactg ttcagaatca     60

tatcacaaaa tgacttgtac acagtagttt acaacgactc ccaagagagg aaaaaaaaaa    120

aaaaagacgc ctcaaaattc actcaacttt tgagacagca atggcaatag gcagcagaga    180

agctatgctg caactgaggg cacatatcat tgaagatgtc acaggagttt aagagacagg    240

ctggaaaaaa tctcatacta agcaaacagt agtatctcat accaagcaaa accaagtagt    300

atctgctcag cctgccgcta acagatctca caatcaccaa ctgtgcttta ggactgtcac    360

caaagtcaga ttcggtgcta accaggtggc atctatgatc aacgtcgccc ctcttattta    420

acaaagggct ctgaaggagg tgttctccaa gcaacaagga gactgcttca gtacaagact    480

ttgcaccttg aattcaattg catcaagtgt ggatagcaaa ataagtatct taccattgaa    540
```

-continued

```
atatgtgttc agcctaagat tttacccacc agcagaacaa aagtgagggt gagagggatg    600

ggccagtgag gggatggggg agaaaaaaaa atcacaggat taccaccaaa gccttgtttt    660

aaaagggctc ccttcactat tcaggaaggg aagtggaagg agaaattaac caattcctgc    720

cacagcagcc ctttttggct gcttccacaa tagatacttt atggagtggc acagccaacc    780

ctatctgtga cctgccctgc ggataaacac agccaagcag gtttaattag atcaaagaca    840

caaagggcta ttccctcctt tcataacaac gcagacct                            878
```

<210> SEQ ID NO 417
<211> LENGTH: 514
<212> TYPE: DNA
<213> ORGANISM: Homo sapiens

<400> SEQUENCE: 417

```
ttctgacttc tagaagacta aggctggtct gtgtttgctt gtttgcccac ctttggctga     60

tacccagaga acctgggcac ttgctgcctg atgcccaccc ctgccagtca ttcctccatt    120

cacccagcgg gaggtgggat gtgagacagc ccacattgga aaatccagaa aaccgggaac    180

agggatttgc ccttcacaat tctactcccc agatcctctc ccctggacac aggagaccca    240

cagggcagga ccctaagatc tggggaaagg aggtcctgag aaccttgagg taccettaga    300

tccttttcta cccactttcc tatggaggat tccaagtcac cacttctctc accggcttct    360

accagggtcc aggactaagg cgttttctcc atagcctcaa cattttggga atcttccctt    420

aatcaccctt gctcctcctg ggtgcctgga agatggactg gcagagacct ctttgttgcg    480

ttttgtgctt tgatgccagg aatgccgcct agtt                                514
```

<210> SEQ ID NO 418
<211> LENGTH: 352
<212> TYPE: DNA
<213> ORGANISM: Homo sapiens

<400> SEQUENCE: 418

```
ctgcaccagc gattaccagt ggcattcaaa tactgtgtga ctaaggattt tgtatgctcc     60

ccagtagaac cagaatcaga caggtatgag ctagtcaaca gcaagtcttt gttggattcg    120

agtaggctca ggatctgctg aaggtcggag gagttagtcc ccgcaatcaa gagcctgtct    180

tcctgaagcc cttggtgata ttttgccact cagccaagaa tgaggatgca tccttcagat    240

tctctatgtc ccgaacctgg aacccatcca cgccagcttg cagccaaaac tccagagcat    300

ccttcacctt ggtggaaaaa aaaaaaaaaa aaaaaaaaaa aaaaaaaaaa aa            352
```

<210> SEQ ID NO 419
<211> LENGTH: 344
<212> TYPE: DNA
<213> ORGANISM: Homo sapiens

<400> SEQUENCE: 419

```
ctggacacca taatcccttt taagtggctg gatggtcaca cctctcccat tgacaagctg     60

ggttaagtca ataggttgac taggatcaac acgacccaaa tcaataagat actgcagtct    120

attgagactc aaaggcttat actggcgtct gaaactatgt ccttcgttaa acccgtattt    180

tgggattcgg atgtaaaatg gagtctggcc tccctcaaag cccaagcggg gccgggttcc    240

tctttgcctt tctcctttat ggcctctgcc acattttcta cctcttctcc gacctcttgg    300

tcttctctcc ggtttcttgg agccgggatt cggctttaag ttgg                     344
```

-continued

<210> SEQ ID NO 420
<211> LENGTH: 935
<212> TYPE: DNA
<213> ORGANISM: Homo sapiens

<400> SEQUENCE: 420
cgaaagtcaa cgttaagggg ctcaggtgaa ccatgatgat gaccttctgt tgactttgaa 60
atattggctc ttgtgggtga caaaagccag acaagctgtg gctgtggtcc gattttaaga 120
cgaggttctc aaagatccaa aggagggaaa gggtattgga aacactgtgt atcatctgag 180
acacacgtgt cctcatgatc ttaaatgcct actttaaagc cacctaatac tgcccttcat 240
tgtggtcaga agagatttct acaaaagcac tcagaattct ggaggcagtt gtgattttgc 300
catgtggcag ttggtttgtg gagttgggca ggtgtgaaag ggtaaaactc cacttctgaa 360
tgctgcttct gccccctggg acccagcaca ttgttagacc atcttcttga ctgaaaattc 420
tctcctgatg ctgagccctg caccaccacc ttccttttcc taactatgaa ttgatggcaa 480
agtccactca aaacaaccag ttaagtgctc acgagagagt agtcaagcac ctccagaaag 540
aaaccgggtt tttgttcaca tagcaggaag tgactccctg ggtggtaatt tatcttggaa 600
acacaggtag attggcagaa aaacgggaac atgtaggtac cgcgatgttg gtgcatgtcc 660
attactttgg gataggcttt ctcagtcttt cctcaaatga tagttgagcc agttttccag 720
tggcaattct gagtgacttg cgcttgtctt atggtgtggt caagggacgt tcagaactac 780
ggaaaacttt tactgaaaca gcgaagcaga gtataccggc atgagaggga agatgaacac 840
tcacctatgt accactcttt gacaataaat atagtatttc tcaaaaaaaa aaaaaaaaaa 900
agtaaaaaaa ctgaaatcgc aagtcaaaaa atcca 935

<210> SEQ ID NO 421
<211> LENGTH: 745
<212> TYPE: DNA
<213> ORGANISM: Homo sapiens

<400> SEQUENCE: 421
ggcttcgagc ggccgcccgg gcaggtccta gatgtcattt gggacccttc acaaccattt 60
tgaagccctg tttgagtccc tgggatatgt gagctgtttc tatgcataat ggatattcgg 120
ggttaacaac agtcccctgc ttggcttcta ttctgaatcc ttttctttca ccatggggtg 180
cctgaagggt ggctgatgca tatggtacaa tggcacccag tgtaaagcag ctacaattag 240
gagtggatgt gttctgtagc atcctattta aataagccta ttttatcctt tggcccgtca 300
actctgttat ctgctgcttg tactggtgcc tgtacttttc tgactctcat tgaccatatt 360
ccacgaccat ggttgtcatc cattacttga tcctacttta catgtctagt ctgtgtggtt 420
ggtggtgaat aggcttcttt ttacatggtg ctgccagccc agctaattaa tggtgcacgt 480
ggacttttag caagcgggct cactggaaga gactgaacct ggcatggaat tcctgaagat 540
gtttggggtt tttttctttc ttaatcgaaa gttaacattg tctgaaaagt tttgttagaa 600
ctactgcgga acctcaaaat cagtagattt ggaagtgatt caaagctaaa ctttttcctt 660
ggccctcctt gtgttctaat tgcttgcaag tgtaatacta ggatgtccaa gatgccagtt 720
tttgcttctt tgttagttgt cagac 745

<210> SEQ ID NO 422
<211> LENGTH: 764
<212> TYPE: DNA
<213> ORGANISM: Homo sapiens -continued

<400> SEQUENCE: 422

```
gagttcagta gcaaagtcac acctgtccaa ttccctgagc tttgctcact cagctaatgg     60
gatggcaaag gtggtggtgc tttcatcttc aggcagaagc ctctgcccat ccccctcaag    120
ggctgcaggc ccagttctca tgctgccctt gggtgggcat ctgttaacag aggagaacgt    180
ctgggtggcg gcagcagctt tgctctgagt gcctacaaag ctaatgcttg gtgctagaaa    240
catcatcatt attaaacttc agaaaagcag cagccatgtt cagtcaggct catgctgcct    300
cactgcttaa gtgcctgcag gagccgcctg ccaagctccc cttcctacac ctggcacact    360
ggggtctgca caaggctttg tcaaccaaag acagcttccc ccttttgatt gcctgtagac    420
tttggagcca agaaacactc tgtgtgactc tacacacact tcaggtggtt tgtgcttcaa    480
agtcattgat gcaacttgaa aggaaacagt ttaatggtgg aaatgaacta ccatttataa    540
cttctgtttt tttattgaga aaatgattca cgaattccaa atcagattgc caggaagaaa    600
taggacgtga cggtactggg ccctgtgatt ctcccagccc ttgcagtccg ctaggtgaga    660
ggaaaagctc tttacttccg cccctggcag ggacttctgg gttatgggag aaaccagaga    720
tgggaatgag gaaaatatga actacagcag aagcccctgg gcag                     764
```

<210> SEQ ID NO 423
<211> LENGTH: 1041
<212> TYPE: DNA
<213> ORGANISM: Homo sapiens

<400> SEQUENCE: 423

```
ctcagagagg ttgaaagatt tgcctacgaa agggacagtg atgaagctaa gctctagatc     60
caggatgtct gacttcaaat tgaaactccc aaagtaatga gtttggaagg gtggggtgtg    120
gcctttccag gatgggggtc ttttctgctc ccagcggata gtgaaacccc tgtctgcacc    180
tggttgggcg tgttgctttc ccaaaggttt ttttttagg tccgtcgctg tcttgtggat     240
taggcattat tatctttact ttgtctccaa ataacctgga gaatggagag agtagtgacc    300
agctcagggc cacagtgcga tgaggaccat cttctcacct ctctaaatgc aggaagaaac    360
gcagagtaac gtggaagtgg tccacaccta ccgccagcac attgtgaatg acatgaaccc    420
cggcaacctg cacctgttca tcaatgccta caacaggtat tgggatgtag ttcagccaca    480
tcattgctat ttatgaggtg tcttctgtag atccgaaatg tgggacagat gagagggaga    540
gtataaaatg agcggaagag gcaggctctg agtttgagca aatagattaa taggacaggt    600
gtccccagga aggacacctg gcctgtaagc tggttcctgg cattcagctc gccttgcagg    660
gatctgaaca aacactccag accactgggg gtgcagacgt gagagggacg cagtcgcaca    720
ctcagagggt tgagagtaaa tatgtgtgcc cgctgctgac cttcacgaaa ggccaaatgt    780
aagaagagct aagtgagaga gcagcaaagc actcctggag gccggggata atccaggcag    840
gcttctggga gtttgtcatt ccaaggataa ggaggacctg aacatggcct ttgcctaagg    900
cgtggccctc tcaaccagca ctaggtgctt atctggagct cagctagggg aggagacagc    960
tcagggccat tggtgtcagc cagagactct gtaatcttcc agggagctcg ctcaacctgc   1020
tgagctcgct ctgccacgca c                                             1041
```

<210> SEQ ID NO 424
<211> LENGTH: 1288
<212> TYPE: DNA
<213> ORGANISM: Homo sapiens

<400> SEQUENCE: 424

-continued

```
ctaagaactg agacttgtga cacaaggcca acgacctaag attagcccag ggttgtagct      60
ggaagaccta caacccaagg atggaaggcc cctgtcacaa agcctaccta gatggataga     120
ggacccaagc gaaaaaggta tctcaagact aacggccgga atctggaggc ccatgaccca     180
gaacccagga aggatagaag cttgaagacc tggggaaatc ccaagatgag aaccctaaac     240
cctacctctt ttctattgtt tacacttctt actcttagat atttccagtt ctcctgttta     300
tctttaagcc tgattctttt gagatgtact ttttgatgtt gccggttacc tttagattga     360
cagtattatg cctgggccag tcttgagcca gctttaaatc acagctttta cctatttgtt     420
aggctatagt gttttgtaaa cttctgtttc tattcacatc ttctccactt gagagagaca     480
ccaaaatcca gtcagtatct aatctggctt ttgttaactt ccctcaggag cagacattca     540
tataggtgat actgtatttc agtcctttct tttgacccca gaagccctag actgagaaga     600
taaaatggtc aggttgttgg ggaaaaaaaa gtgccaggct ctctagagaa aaatgtgaag     660
agatgctcca ggccaatgag aagaattaga caagaaatac acagatgtgc cagacttctg     720
agaagcacct gccagcaaca gcttccttct ttgagcttag tccatccctc atgaaaaatg     780
actgaccact gctgggcagc aggagggatg atgaccaact aattcccaaa ccccagtctc     840
attggtacca gccttgggga accacctaca cttgagccac aattggtttt gaagtgcatt     900
tacaagtttc tggcatcact accactactg attaaacaag aataagagaa cattttatca     960
tcatctgctt tattcacata aatgaagttg tgatgaataa atctgctttt atgcagacac    1020
aaggaattaa gtggcttcgt cattgtcctt ctacctcaaa gataatttat tccaaaagct    1080
aagataaatg gaagactctt gaacttgtga actgatgtga aatgcagaat ctcttttgag    1140
tctttgctgt ttggaagatt gaaaaatatt gttcagcatg ggtgaccacc agaaagtaat    1200
cttaagccat ctagatgtca caattgaaac aaactgggga gttggttgct attgtaaaat    1260
aaaatatact gttttgaaaa aaaaaaac                                       1288
```

<210> SEQ ID NO 425
<211> LENGTH: 446
<212> TYPE: DNA
<213> ORGANISM: Homo sapiens

<400> SEQUENCE: 425

```
ccacttaaag ggtgcctctg ccaactggtg gaatcatcgc cacttccagc accacgccaa      60
gcctaacatc ttccacaagg atcccgatgt gaacatgctg cacgtgtttg ttctgggcga     120
atggcagccc atcgagtacg gcaagaagaa gctgaaatac ctgccctaca atcaccagca     180
cgaatacttc ttcctgattg ggccgccgct gctcatcccc atgtatttcc agtaccagat     240
catcatgacc atgatcgtcc ataagaactg ggtggacctg gcctgggccg tcagctacta     300
catccggttc ttcatcacct acatcccttt ctacggcatc ctgggagccc tccttttcct     360
caacttcatc aggttcctgg agagccactg gtttgtgtgg gtcacacaga tgaatcacat     420
cgtcatggag attgaccagg aggacc                                          446
```

<210> SEQ ID NO 426
<211> LENGTH: 874
<212> TYPE: DNA
<213> ORGANISM: Homo sapiens

<400> SEQUENCE: 426

```
tttttttttt tttttttttt ttttttcaat taaagatttg atttattcaa gtatgtgaaa      60
```

-continued

```
acattctaca atggaaactt ttattaaatg ctgcatgtac tgtgctatgg accacgcaca    120

tacagccatg ctgtttcaga agacttgaaa tgccattgat agtttaaaaa ctctacaccc    180

gatggagaat cgaggaagac aatttaatgt ttcatctgaa tccagaggtg catcaaatta    240

aatgacagct ccacttggca aataatagct gttacttgat ggtatccaag aagaaatggt    300

tggtgatgga taaattcaga aatgcttccc caaaggtggg tggtttttaa aaagttttca    360

ggtcacaacc cttgcagaaa acactgatgc ccaacacact gattcgcggt ccaggaaaca    420

cgggtcttcc aagttccaag gggctggggt tccccaacga tcaagttcct gtgctgtaat    480

caagagggtc ctttggactg gatagggagc acttgggagc tgtacaccat cagtcataat    540

ggatggcagt gtaaaagatg atccaaatga cctgagatgc tcctgaggag tggtgcacca    600

gacccaggag tgccactgta gggctgcttc tttgctttag tcatcacaca cacacacagc    660

tccagagcag caatggcctt tcctgtaaca ggaaaaaagc ctcctgctat tcccaagaac    720

cctcgtaatg gcaaaactcc ccaaatgaca cccaggacca cagcaatgat ctgtcggaac    780

cagtagatca catctaaaaa ttcatcctta tcctcccagg ccgcgtcgct ccgcagcacc    840

ttactccaga cggagacttt gagggccccg ttgg                                874
```

<210> SEQ ID NO 427
<211> LENGTH: 638
<212> TYPE: DNA
<213> ORGANISM: Homo sapiens

<400> SEQUENCE: 427

```
acttgtaatt agcacttggt gaaagctgga aggaagataa ataacactaa actatgctat     60

ttgatttttc ttcttgaaag agtaaggttt acctgttaca ttttcaagtt aattcatgta    120

aaaaatgata gtgattttga tgtaatttat ctcttgtttg aatctgtcat tcaaaggcca    180

ataatttaag ttgctatcag ctgatattag tagctttgca accctgatag agtaaataaa    240

ttttatgggc gggtgccaaa tactgctgtg aatctatttg tatagtatcc atgaatgaat    300

ttatggaaat agatatttgt gcagctcaat ttatgcagag attaaatgac atcataatac    360

tggatgaaaa cttgcataga attctgatta aatagtgggt ctgtttcaca tgtgcagttt    420

gaagtattta aataaccact cctttcacag tttattttct tctcaagcgt tttcaagatc    480

tagcatgtgg attttaaaag atttgccctc attaacaaga ataacattta aaggagattg    540

tttcaaaata tttttgcaaa ttgagataag gacagaaaga ttgagaaaca ttgtatattt    600

tgcaaaaaca agatgtttgt agctgtttca gagagagt                            638
```

<210> SEQ ID NO 428
<211> LENGTH: 535
<212> TYPE: DNA
<213> ORGANISM: Homo sapiens

<400> SEQUENCE: 428

```
acaagatgat tcttcctcct caatttgaca gatcaaagaa gtatcccttg ctaattcaag     60

tgtatggtgg tccctgcagt cagagtgtaa ggtctgtatt tgctgttaat tggatatctt    120

atcttgcaag taaggaaggg atggtcattg ccttggtgga tggtcgagga acagctttcc    180

aaggtgacaa actcctctat gcagtgtatc gaaagctggg tgtttatgaa gttgaagacc    240

agattacagc tgtcagaaaa ttcatagaaa tgggtttcat tgatgaaaaa agaatagcca    300

tatggggctg gtcctatgga ggatacgttt catcactggc ccttgcatct ggaactggtc    360

ttttcaaatg tggtatagca gtggctccag tctccagctg ggaatattac gcgtctgtct    420
```

-continued acacagagag attcatgggt ctcccaacaa aggatgataa tcttgagcac tataagaatt 480
caactgtgat ggcaagagca gaatatttca gaaatgtaga ctatcttctc atcca 535

<210> SEQ ID NO 429
<211> LENGTH: 675
<212> TYPE: DNA
<213> ORGANISM: Homo sapiens

<400> SEQUENCE: 429
actattttca accctgagca ttaacactgc ataccaaggg ggggtgggtc aagaagctgg 60
ttagatcgaa gcacaagcac aagccactga tattctctat gtgatcaggt ttttacaaaa 120
aaatacatag ttttcaataa ataatgctta attttacaac tttgatacag caatgtcata 180
caccgtttca acacactaca ctctgcatgc tagatagtct acgagaagac gaaactttgc 240
catgcatttt ctttcccccc tagtgctatc aaacacttca tcctccagcg cactgcctca 300
ggtagcttta ccttctctct gtttcacagc aataggccgt gcgctggcat gcaaactcta 360
aaaaaggtcc cccccacaaa ccactcagac ttctacacaa aagggttttt cagcttttct 420
gctcccaaac ctggagtggc taagaaagta agtttcatgt ggccttggaa aatacacact 480
tgttaacagt gtcatgctga aaactgctct aaaacatcag gtggttctgt cctggtggcc 540
gtcacgaagc attatgggat gccataacca ctaggagtcc caaaccggaa aaaataggcc 600
tccgttttaa aacagtcaat tcaaaaaagg tgtcacagaa caaatgcaaa agactcttaa 660
acccacaaca tatgt 675

<210> SEQ ID NO 430
<211> LENGTH: 434
<212> TYPE: DNA
<213> ORGANISM: Homo sapiens

<400> SEQUENCE: 430
acctctgcca gaagtccagc gagaggacct cacagtagag cacaggccac tccgggagtg 60
catcagaaga ttcatcctca tggaggaaga aggcttcaaa cgtgaatggg taggagaagt 120
gagccacctt gtccattgcc agggacttgg tggtgcaggt ctgtgttact cctgagagct 180
gctggaatgc tgggcttgac cagtgagcag ttggcaattc tacaaagaag tggacgtaga 240
gattgtcata ctcatagcct tgggctgaaa cgacctctcc atttacaaag agccggaggg 300
cacctgggac agtcatctca aagtcggtgc ctacgaggct gctgagatac tccttgtgcc 360
ggccataaag atccttgaac actcgccgtt cccgctcctc ctcctccggc tgtgcgtggg 420
gggaaacatt gtcg 434

<210> SEQ ID NO 431
<211> LENGTH: 581
<212> TYPE: DNA
<213> ORGANISM: Homo sapiens

<400> SEQUENCE: 431
acacaagcct ccagcccgac ccagcggcct aatgaaactc tggcaaccta tcctgggcgt 60
ggccacgagt atccagctcc aagcccaagt gaggcgggga gtcaacttcc ccatgattgc 120
caagtgacca agaccagaag cagggacgat taggctagtt ctgcggcaag gtgaactgga 180
gaccctgtct ctgccctcct tccctggcct gtcccacaga catcccgttg tttaacccac 240
tgcctttgca aggacctgct ctgtccactc caaatcaaag gatacttgca tccttcttac 300

-continued

```
acagactccc atctctctgc tcatagtggt cccaggctgc ccgagaaaaa gaaacttggg    360

tcagtagaag gctcattagt gtgaaggagt gagaggccag gccttcctgt gacataatgc    420

ttctatgctt gtttcctaaa cacttggtcc acacacaata cctgggcagg aagagagaac    480

caagcaccac tggatggctc tggagccagg ggacttctat gcacatacaa ccaacatcac    540

cccactctgc tcatctgtgc ctccaccctg aacagcagag t                        581
```

```
<210> SEQ ID NO 432
<211> LENGTH: 532
<212> TYPE: DNA
<213> ORGANISM: Homo sapiens

<400> SEQUENCE: 432

actccaactc aagtttacaa gttacacctt tgccacagcc ttggctaaat cttgaactag     60

tgcagaattc agctgtggta gagtgctgat cttagcatgc ttcgatgtgg catacttgtt    120

cttgacagtc atgtgctttg taagtccttg atttaccatg actacattct tagccaggtg    180

ctgcataact ggaagaagag attcttcagt atatgacagg taatgttgta gagttggtgt    240

ccattcacca ttatccagaa ttttcagtgc taagcaaaaa gctcctgctg caatttgaga    300

aggaggaaag tgcaccatgt catagtccaa catagttagt tccatcaggt atttggccaa    360

agtatgttgc tcgacatcaa cctctccaat cttagatgct ctccgaagga agtgcaaagg    420

tagaggccga cccagaccaa agtttaaagc tcttagaatc ttcatttcca tctgtctgat    480

ttggtgctta gtataagtgt tgtcagtcac aaaagcaaag tcaccaattt ct            532
```

```
<210> SEQ ID NO 433
<211> LENGTH: 531
<212> TYPE: DNA
<213> ORGANISM: Homo sapiens

<400> SEQUENCE: 433

acttggtttt acagctcctt tgaaaactct gtgtttggaa tatctctaaa aacatagaaa     60

acactacagt ggtttagaaa ttactaattt tacttctaag tcattcataa accttgtcta    120

tgaaatgact tcttaaatat ttagttgata gactgctaca ggtaataggg acttagcaag    180

ctcttttata tgctaaagga gcatctatca gattaagtta gaacatttgc tgtcagccac    240

atattgagat gacactaggt gcaatagcag ggatagattt tgttggtgag tagtctcatg    300

ccttgagatc tgtggtggtc ttcaaaatgg tggccagcca gatcaaggat gtagtatctc    360

atagttccca ggtgatattt ttcttattag aaaaatatta taactcattt gttgtttgac    420

acttatagat tgaaatttcc taatttattc taaattttaa gtggttcttt ggttccagtg    480

ctttatgttg ttgttgtttt tggatggtgt tacatattat atgttctaga a             531
```

```
<210> SEQ ID NO 434
<211> LENGTH: 530
<212> TYPE: DNA
<213> ORGANISM: Homo sapiens

<400> SEQUENCE: 434

acaagagaaa acccctaaaa aaaggatggc tttagatgac aagctctacc agagagactt     60

agaagttgca ctagctttat cagtgaagga acttccaaca gtcaccacta atgtgcagaa    120

ctctcaagat aaaagcattg aaaaacatgg cagtagtaaa atagaaacaa tgaataagtc    180

tcctcatatc tctaattgca gtgtagccag tgattattta gatttggata agattactgt    240

ggaagatgat gttggtggtg ttcaagggaa aagaaaagca gcatctaaag ctgcagcaca    300
```

-continued

```
gcagaggaag attcttctgg aaggcagtga tggtgatagt gctaatgaca ctgaaccaga    360
ctttgcacct ggtgaagatt ctgaggatga ttctgatttt tgtgagagtg aggataatga    420
cgaagacttc tctatgagaa aaagtaaagt taaagaaatt aaaaagaaag aagtgaaggt    480
aaaatcccca gtagaaaaga aagagaagaa atctaaatcc aaatgtaatg               530
```

<210> SEQ ID NO 435
<211> LENGTH: 677
<212> TYPE: DNA
<213> ORGANISM: Homo sapiens

<400> SEQUENCE: 435

```
accttatgat ctaattaata gatattagaa acagtagaaa gacaagttac acgtcaatgc     60
ccaatgacta gagtcaacat taaagagttg taatttaagt aatccaaact gacatctaat    120
tccaaaatca tttataaaat gtatttggct ttggaatcca caggacttca aacaagcaaa    180
gtttcactgc agatagtcac aaagatgcag atacactgaa atacttaaga gccttattaa    240
tgatttttgt tattttggat cttctgtttt tttcttatta tggtccgaag cctccttaat    300
accaatttat cagacagaag catgtcatct tgttgttcaa gataatccag taaattttca    360
gtccattcaa gtgccgcttt atggctaata cgcttctctg gattcagttc tgtttttcta    420
ctcttactgg aaggcttttg ctcagcagcc ttggtctggt cctcagcact ttcactgtca    480
gtcagcacct gacagcttga gtcactgctc cgagagtcga accactgatc aatattctca    540
atgtcaacat gttcacattc ttctgtgttc tgtaaaactg ttgctaaatt agctgctaaa    600
atggctcctt catcaatgtt catacctgaa ttctcttcat tgccagggaa aagtttttc     660
catgctttgg ttatggt                                                   677
```

<210> SEQ ID NO 436
<211> LENGTH: 573
<212> TYPE: DNA
<213> ORGANISM: Homo sapiens

<400> SEQUENCE: 436

```
acctcttagg gtgggagaaa tggtgaagag ttgttcctac aacttgctaa cctagtggac     60
agggtagtag attagcatca tccggataga tgtgaagagg acggctgttt ggataataat    120
taaggataaa atttggccag ttgacagatt ctgtttccag cagtttttac agcaacagtg    180
gagtgcttca gtattgtgtt cctgtaaatt taattttgat ccgcaatcat ttggtataca    240
atgctgtttg aagttttgtc ctattggaaa agtcttgtgt tgcaggggtg cagttaagat    300
ctttgtgatg aggaatggga tgggctaatt ttttgccgtt ttcttggaat tgggggcatg    360
gcaaatacag tagggtagtt tagttcttta cacagaacat gataaactac acctgttgat    420
gtcaccgtct gtcaatgaat attatagaag gtatgaaggt gtaattacca taataacaaa    480
acaccctgtc tttagggctg acctttcgtc ctttgacctc ctcagcctcc attcccatct    540
tcgctcagac tgcaagtatg tttgtattaa tgt                                 573
```

<210> SEQ ID NO 437
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G -continued

<400> SEQUENCE: 437
acaattggta tccatatctt gttgaaattg taatgggaaa acaatatatt tcaatctcta 60
tgtagatagt gggtttttgt tttcataata tattctttta gtttactgta tgagttttgc 120
aggactgcat aatagatcac cacaatcata acatcttagg accacagaca tttatgagat 180
catggcttct gtgggttaga agtatgctca tgtcttaact gggtcctctg ctcagtctta 240
tctggctgca atcaaggtgt cagctgggct gaattttcat ttggaatctt gactgggaaa 300
gagtctgctt ccaaggtcat gaagtttgct ggcaaaatgt atgtttttat gacagtatga 360
ctgaaatccc aagctatctc ctgactttta gctgggtaat ctcaggccct aaatgttgcc 420
tacagttcct agaggctggt cacagttctt agccatgtgg atttcctcaa catggctgct 480
tgcttcatca agtcagcaag aatagcctgt catatcagtg tatatcaggc tcactcagga 540
taatttccct actgatgagc caaacactaa ctgattttag agcttaacta catctgcaaa 600
attcngttca ccagaggcaa gtcatattca gggaaggaga agtgt 645

<210> SEQ ID NO 438
<211> LENGTH: 485
<212> TYPE: DNA
<213> ORGANISM: Homo sapiens

<400> SEQUENCE: 438
acagaattga gagacaagat tgcttgtaat ggagatgctt ctagctctca gataatacat 60
atttctgatg aaaatgaagg aaaagaaatg tgtgttctgc gaatgactcg agctagacgt 120
tcccaggtag aacagcagca gctcatcact gttgaaaagg ctttggcaat tctttctcag 180
cctacaccct cacttgttgt ggatcatgag cgattaaaaa atcttttgaa gactgttgtt 240
aaaaaaagtc aaaactacaa catatttcag ttggaaaatt tgtatgcagt aatcagccaa 300
tgtatttatc ggcatcgcaa ggaccatgat aaaacatcac ttattcagaa aatggagcaa 360
gaggtagaaa acttcagttg ttccagatga tgatgtcatg gtatcgagta ttctttatat 420
tcagttccta tttaagtcat ttttgtcatg tccgcctaat tgatgtagta tgaaaccctg 480
catct 485

<210> SEQ ID NO 439
<211> LENGTH: 533
<212> TYPE: DNA
<213> ORGANISM: Homo sapiens

<400> SEQUENCE: 439
acagcagttt cctcatccct gcagctgtgt ttgaacaggt catttaccat actgtcctcc 60
aggttcaaca gtatggctcc aaatgatgaa atttcattct gattttctgg ctgaagacta 120
ttctgtttgt gtatgtccac cacagttact ttatcccttc atctgtggat gggcagaatg 180
aaacatatat ggaaatgttc tgtgcaataa aaacagcagt ggtaacacag atgtaggctc 240
tgagtgtctc actggagact gaagtccaca gatatgcaac aaagcctttg tctccctgat 300
gtttttgcct cctgctggtc atgtgctttc acacatcaag agaggacatt taacatttga 360
gccacagtgt catttgctgt tgtctgatgg ttggttggca gagaatttga actggagatg 420
aactttatta tccaggacgc tgagagtata acatgcatga cagagctttt agagcactgt 480
gatgtaacat gtcaagcaga aatagggagc atgtttacag ccattctatg aaa 533

<210> SEQ ID NO 440

-continued

<211> LENGTH: 341
<212> TYPE: DNA
<213> ORGANISM: Homo sapiens

<400> SEQUENCE: 440
catggggtag gggggtcggg gattcattga attgtggttg gcaggagcaa gccctgctca 60
cactctcaca ctcgcaccca gaattgtcaa agatacagat tgtaaaaatc tacgatccct 120
cagtctcact cacaaaaaat aaaatctcat gtccccaacg aacccagagt cagacgacag 180
ctggagcatt ggcagggaca gtcagaaagg agacaagtga aaacggtcag atggacacag 240
gcggaggaga aaagacagag ggagagagac catcgggaac aatcagaggg gccgagacga 300
tcagaaaagg gtcagcccga gacaggctga gccagagttt c 341

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 441
aagtttgggg ataatttatt atgcagcaag agataataca caggacttct canagcactt 60
aatatgttaa tataaatctc caanaaaaaa gatatacaat gaaacattcc tcttagttat 120
ctggccaagg anactttntt tttttganaa tattcttcaa aaagctgatc taatgatatg 180
gctctggtcc tacaattcca tgtaacttct aaccttgatt ttatctcatg agcaaatcat 240
ttatccttcc agaacctcaa cttttccctt ttacaaagta gaaataaacc atctgccttt 300
acataaatca ttaatacagc cctggatggg cagattctga gctatttttg gctgggggt 360 gggaaatagc ctgtggaggt cctaaaaaga tctacggggc tcgagatggt tctctgcaag 420
gtagcaggtg ggctcagggc ccatttcagt ctttgttccc caggccattt ccacaaaatg 480
gtgagaaata gtgtcttctt ttagcttgct cataactcaa agatgggggg catggacctg 540
ggcctttcta ggctagggca tgaacctcct cc 572

<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: (1)...(379)
<223> OTHER INFORMATION: n = A,T,C or G

<400> SEQUENCE: 442
tcccagctgc actgcttaca cgtcttcctt cgtnttcacc taccccgagg ctgactcctt 60
ccccagntgt gcagctgccc accgcaaggg cagcagcagc aatgagcctt cctctgactc 120
gctcagctca cccacgctgc tggccctgtg agggggcagg gaaggggagg cagccggcac 180
ccacaagtgc cactgcccga gctggtgcat tacagagagg agaaacacat cttccctaga 240
gggttcctgt agacctaggg aggaccttat ctgtgcgtga aacacaccag gctgtgggcc 300
tcaaggactt gaaagcatcc atgtgtggac tcaagtcctt acctcttccg gagatgtagc 360
aaaacgcatg gagtgtgta 379

<210> SEQ ID NO 443
<211> LENGTH: 511

-continued

<212> TYPE: DNA
<213> ORGANISM: Homo sapiens
<220> FEATURE:
<221> NAME/KEY: misc_feature
<222> LOCATION: (1)...(511)
<223> OTHER INFORMATION: n = A,T,C or G

<400> SEQUENCE: 443
acatgccccc aaaggctcgc ttcattgcta cgattctcta cttaaatcca cattcacagc 60
tattgcctca gaccctctgg aggaggggcc aggggttagc tggctttgaa tagcatgtag 120
agcacaggca gtgtggccac aaatgtcaca caggtgacca gggtgctata gatggtgttc 180
ctgttgactt gggcttctag tctctgctcc gtgtctgaca gtgccaagat catgctcccc 240
tgctccagca agaagctggg catagccccg tctgctggtt ccaccaggcc tgggtgtgct 300
gcagacttta caagctgaac caccccagcc atttggctac aagtcttttc taggccatca 360
agctgctctc gtaagccttc tagacatgaa tggacttgcc tggaatgact aagctgctct 420
ttcaaggcag ctgaaaggac atcnacatct ctgtctctgg tcgggggact acctgcctgt 480
gacccagagt cctgccctgg cccagcagca t 511

<210> SEQ ID NO 444
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 444
acaggaagaa ttctacagtt aatctatcac agtgttccag caaagcatat gttgaaaact 60
acagttttca atctaacatc taaattttaa aaagtagcat ttcagcaaca aacaagctca 120
gagaggctca tggcaaaagt gaaataacag aactattgct cagatgtctg caaagtcaag 180
ctgctgccct cagctccgcc cacttgaagg cttaggcaga cacgtaaggt ggcggtggct 240
ccttggcagc accattcaca gtggcatcat catacggagg tagcagcacc gtagtgtcat 300
tgctggtaac ataaaccagg acatcagagg agttcctacc attgatgtat cggtagcagt 360
tccaaacaca gctaatcaag taacccttaa aagtcaagat aatgctaata aacagaagaa 420
taataaggac caaacaggta ggattcactg acatgacatc atctctgtag ggaaaattag 480
gaggcagttg ccgtatgtat tcctgaatgg agtttggata aataagcaca gtgattgcaa 540
ccaacanctt cagggcaaag tcaaagatct ggtaacagaa gaatgggatg atccaggctg 600
cgcgttgctt gt 612

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: (1)...(708)
<223> OTHER INFORMATION: n = A,T,C or G

<400> SEQUENCE: 445
accatcctgt tccaacagag ccattgccta ttcctaaatt gaatctgact gggtgtgccc 60
ctcctcggaa cacaacagta gaccttaata gtggaaacat cgatgtgcct cccaacatga 120
caagctgggc cagctttcat aatggtgtgg ctgctggcct gaagatagct cctgcctccc 180

-continued

```
agatcgactc agcttggatt gtttacaata agcccaagca tgctgagttg gccaatgagt    240

atgctggctt tctcatggct ctgggtttga atgggcacct taccaagctg gcgactctca    300

atatccatga ctacttgacc aagggccatg aaatgacaag cattggactg ctacttggtg    360

tttctgctgc aaaactaggc accatggata tgtctattac tcggcttgtt agcattcgca    420

ttcctgctct cttacccccca acgtccacag agttggatgt tcctcacaat gtccaagtgg    480

ctgcagtggt tggcattggc cttgtatatc aagggacagc tcacagacat actgcagaag    540

tcctgttggc tgagatagga cggcctcctg gtcctgaaat ggaatactgc actgacagag    600

agtcatactc cttagctgct ggcttggccc tgggcatggt ctncttgggg catggcagca    660

atttgatagg tatgtntgat ctcaatgtgc ctgagcagct ctatcagt                 708
```

```
<210> SEQ ID NO 446
<211> LENGTH: 612
<212> TYPE: DNA
<213> ORGANISM: Homo sapiens

<400> SEQUENCE: 446

acaagcaacg cgcagcctgg atcatcccat tcttctgtta ccagatcttt gactttgccc     60

tgaacatgtt ggttgcaatc actgtgctta tttatccaaa ctccattcag gaatacatac    120

ggcaactgcc tcctaatttt ccctacagag atgatgtcat gtcagtgaat cctacctgtt    180

tggtccttat tattcttctg tttattagca ttatcttgac ttttaagggt tacttgatta    240

gctgtgtttg gaactgctac cgatacatca atggtaggaa ctcctctgat gtcctggttt    300

atgttaccag caatgacact acggtgctgc tacccccgta tgatgatgcc actgtgaatg    360

gtgctgccaa ggagccaccg ccaccttacg tgtctgccta agccttcaag tgggcggagc    420

tgagggcagc agcttgactt tgcagacatc tgagcaatag ttctgttatt tcacttttgc    480

catgagcctc tctgagcttg tttgttgctg aaatgctact tttaaaattt tagatgttag    540

attgaaaact gtagttttca acatatgctt tgctggaaca ctgtgataga ttaactgtag    600

aattcttcct gt                                                        612
```

```
<210> SEQ ID NO 447
<211> LENGTH: 642
<212> TYPE: DNA
<213> ORGANISM: Homo sapiens

<400> SEQUENCE: 447

actgaaagaa ttaaagtcag aagtcttccc aaaacaaaaa gaactgccca cagagaaaat     60

cctttctgat acttttcatt gctaaaataa aacaggcggg aaatgtggaa aagaaattca    120

acaaaataat gtagcaccag aagaacaagt cctagatgat tcaagttcaa aaggtaagct    180

ccagcaatgt ggaagaggta aagaccaatg tagacaagct gacgaggaat atcttctttt    240

ttggttttct ggaagtagag ttcaggaaaa gcatgaagcc agtaagccag ctgtgatatg    300

tagaaaaact tcatttgaaa tgtcatcagg ttatggggat aagccctcca taagatagtt    360

gggtctgaga tgtagttttc agagatgaga atgaatgtgc cccaaacaca ggcaaaaagg    420

tagaacgcac taagctgacc agattcatta aacttgctgt gttttgtttt ggagaagtgc    480

attcgcctgt taattttatc caacatatac tcttgaatta cggcatgaat aattatcgcc    540

actagcatgt agaagaaaac agtagccaaa tctttgatgc catagtaata aagggacact    600

gattcagtag cttgttcttc tgttgctggg agggtgacat tg                       642
```

-continued

<210> SEQ ID NO 448
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 448
accagaagac cttagaaaaa ggaggaaagg aggagaggca gataatttgg atgaattcct 60
caaagngttt gaaaatccag aggttcctag agaggaccag caacagcagc atcagcagcg 120
tgatgttatc gatgagccca ttattgaaga gccaagccgc ctccaggagt cagtgatgga 180
ggccagcaga acaaacatag atgagtcagc tatgcctcca ccaccacctc agggagttaa 240
gcgaaaagct ggacaaattg acccagagcc tgtgatgcct cctcagcagg tagagcagat 300
ggaaatacca cctgtagagc ttcccccaga agaacctcca aatatctgtc agctaatacc 360
agagttagaa cttctgccag aaaaagagaa ggag 394

<210> SEQ ID NO 449
<211> LENGTH: 494
<212> TYPE: DNA
<213> ORGANISM: Homo sapiens
<220> FEATURE:
<221> NAME/KEY: misc_feature
<222> LOCATION: (1)...(494)
<223> OTHER INFORMATION: n = A,T,C or G

<400> SEQUENCE: 449
acaaaaaaca caaggaatac aacccaatag aaaatagtcc tgggaatgtg gtcagaagca 60
aaggcntgag tgtctttctc aaccgtgcaa aagccgtgtt cttcccggga aaccaggaaa 120
aggatccgct actcaaaaac caagaattta aaggagtttc ttaaatttcg accttgtttc 180
tgaagctcac ttttcagtgc cattgatgtg agatgtgctg gagtggctat taaccttttt 240
ttcctaaaga ttattgttaa atagatattg tggtttgggg aagttgaatt ttttataggt 300
taaatgtcat tttagagatg gggagaggga ttatactgca ggcagcttca gccatgttgt 360
gaaactgata aaagcaactt agcaaggctt cttttcatta ttttttatgt ttcacttata 420
aagtcttagg taactagtag gatagaaaca ctgtgtcccg agagtaagga gagaagctac 480
tattgattag agcc 494

<210> SEQ ID NO 450
<211> LENGTH: 547
<212> TYPE: DNA
<213> ORGANISM: Homo sapiens

<400> SEQUENCE: 450
actttgggct ccagacttca ctgtccttag gcattgaaac catcacctgg tttgcattct 60
tcatgactga ggttaactta aaacaaaaat ggtaggaaag ctttcctatg cttcgggtaa 120
gagacaaatt tgcttttgta gaattggtgg ctgagaaagg cagacagggc ctgattaaag 180
aagacatttg tcaccactag ccaccaagtt aagttgtgga acccaaaggt gacggccatg 240
gaaacgtaga tcatcagctc tgctaagtag ttaggggaag aaacatattc aaaccagtct 300
ccaaatggga tcctgtggtt acagtgaatg gccactcctg ctttattttt cctgagattg 360
ccgagaataa catggcactt atactgatgg gcagatgacc agatgaacat catcatccca 420
agaatatgga accaccgtgc ttgcatcaat agatttttcc ctgttatgta ggcattcctg 480

-continued ccatccattg gcacttggct cagcacagtt aggccaacaa ggacataata gacaagtcca 540
aaacagt 547

<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: (1)...(384)
<223> OTHER INFORMATION: n = A,T,C or G

<400> SEQUENCE: 451
actacttnnt ggttaaaang ccactggtag agtcatctga ntgtaaacaa tgtccctgca 60
ctgctggaaa aatccactgg ctcccaagaa aagaaaatgg tctgaagcct ctgttgtggc 120
tctcacaact catctttccc taagtcatca agctccacat cactgaggtc aatgtcatcc 180
tccacgggaa gctcgccatc cctgccgtcc caaggctctc tctcaacgat ggtagggaaa 240
gccccgcctc ctacaggtgc cgtggagcca cgcccaaaag agagctccct gagaaactcg 300
ttgatgcctt gctcactgaa ggagcctttt agcagagcaa atttcatctt gcgtgcattg 360
atggcggcca tggcggggta ccca 384

<210> SEQ ID NO 452
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n = A,T,C or G

<400> SEQUENCE: 452
actctaaagt tgccactctc acaggggtca gtgataccca ctgaacctgg caggaacagt 60
cctgcagcca gaatctgcaa gcagcgcctg tatgcaacgt ttagggccaa aggctgtctg 120
gtggggttgt tcatcacagc ataatggcct agtaggtcaa ggatccaggg tgtgaggggc 180
tcaaagccag gaaaacgaat cctcaagtcc ttcagtagtc tgatgagaac tttaactgtg 240
gactgagaag cattttcctc gaaccagcgg gcatgtcgga tggctgctaa ngcactctgc 300
aatactttga tatccaaatg gagttctgga tccagttttc naagattggg tggcactgtt 360
gtaatganaa tcttcactgt a 381

<210> SEQ ID NO 453
<211> LENGTH: 455
<212> TYPE: DNA
<213> ORGANISM: Homo sapiens

<400> SEQUENCE: 453
actgtgctaa acagcctata gccaagtttt aaagagttac aggaacaact gctacacat 60 caaagaacag gcattcactg cagcctcctg atttgacctg atgggaggga caggagaatg 120
agtcactctg ccaccacttt tcctgccttg gatttgtaga ggatttgttt tgctctaatt 180
tgtttttcct atatctgccc tactaaggta cacagtctgg gcactttgaa aatgttaaag 240
tttttaacgt ttgactgaca gaagcagcac ttaaaggctt catgaatcta ttttccaaaa 300
aaagtatgct ttcagtaaaa cattttacca ttttatctaa ctatgcactg acatttttgt 360
tcttcctgaa aaggggattt atgctaacac tgtattttta atgtaaaaat atacgtgtag 420
agatatttta acttcctgag tgacttatac ctcaa 455

-continued

<210> SEQ ID NO 454
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 454
acagagcanc tttacaagtt gtcacatttc tttataaatt tttttaaagc tacagtttaa 60
tacaaaatga attgcggttt tattacatta ataacctttc acctcagggt tttatgaaga 120
ggaaagggtt ttatgcaaaa gaaagtgcta caattcctaa tcattttaga cactttagga 180
gggggtgaag ttgtatgata aagcagatat tttaattatt tgttatcttt ttgtattgca 240
agaaatttct tgctagtgaa tcaagaaaac atccagattg acagtctaaa atggctactg 300
gtattttagt taattcaaaa atgaaacttt tcagtgattc actttactaa cattctattt 360
gagaaggctt attggtaaag ttt 383

<210> SEQ ID NO 455
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 455
actcctttan gacaaggaaa caggtatcag catgatggta gcagaaacct tatcaccaag 60
gtgcaggagc tgacttcttc caaagagttg tggttccggg cagcggtcat tgccgtgccc 120
attgctggag ggctgatttt agtgttgctt attatgttgg ccctgaggat gcttcgaagt 180
gaaaataaga ggctgcagga tcagcggcaa cagatgctct cccgtttgca ctacagcttt 240
cacggacacc attccaaaaa ggggcaggtt gcaaagttag acttggaatg catggtgccg 300
gtcagtgggc acgagaactg ctgtctgacc tgtgataaaa tgagacaagc agacctcagc 360
aacgataaga tcctctcgct tgt 383

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: (1)...(543)
<223> OTHER INFORMATION: n = A,T,C or G

<400> SEQUENCE: 456
acaaacattt tacaaaaaag aacattacca atatcagtgg cagtaagggc aagctgaaga 60
atangtagac tgagtttccg ggcaatgtct gtcctcaaag acatccaaac tgcgttcagg 120
cagctgaaac aggcttcttt cccagtgaca agcatatgtg gtcagtaata caaacgatgg 180
taaatgaggc tactacatag gcccagttaa caaactcctc ttctcctcgg gtaggccatg 240
atacaagtgg aactcatcaa ataatttaaa cccaaggcga taacaacact atttcccatc 300
taaactcatt taagccttca caatgtcgca atggattcag ttacttgcaa acgatcccgg 360
gttgtcatac agatacttgt tttttacaca taacgctgtg ccatcccttc cttcactgcc 420

-continued

```
ccagtcaggt ttcctgttgt tggaccgaaa ggggatacat tttagaaatg cttccctcaa    480

gacagaagtg agaaagaaag gagaccctga ggccaggatc tattaaacct ggtgtgtgcg    540

caa                                                                  543
```

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: (1)...(544)
<223> OTHER INFORMATION: n = A,T,C or G

<400> SEQUENCE: 457

```
actggtgcca atattgncat ggtgagctcc tctctaatgt cttccagggc accaatatct     60

gcccatgtca cattagggac agtgacaaag ccttcccttt tggcagaggg ttggactgag    120

gatagagcaa caatgaaatc attcagttca atgcacagtc cttgcatctg ctcctctgag    180

aggggatctt ggtctcttag caaccccagc agcctttgta attcatcctg tgtttcagaa    240

gtgggctcag ttcccagcct ttcctcctgg actcctttag atggcaaatc ttccatttca    300

ggatttttct tctgctgttc ctgtagcttc attaagactc tattgactgc acacattgct    360

gcctctcggc acagtgccat gagatcagca ccaacaaagc ctggagttag gtgtgctaag    420

tgacagaaat caaaagcttg aggaagcctc agttttctgc acaatgtttg aagtattctt    480

tccctggatg cttcatctgg gatacctagg catatttctc ggtcgaacct tcccgcacgt    540

ctca                                                                 544
```

<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: (1)...(382)
<223> OTHER INFORMATION: n = A,T,C or G

<400> SEQUENCE: 458

```
acctntaggc tcaacggcag aancttcacc acaaaagcga aatgggcaca ccacagggag     60

aaaactggtt gtcctggatg tttgaaaagt tggtcgttgt catggtgtgt tacttcatcc    120

tatctatcat taactccatg gcacaaagtt atgccaaacg aatccagcag cggttgaact    180

cagaggagaa aactaaataa gtagagaaag ttttaaactg cagaaattgg agtggatggg    240

ttctgcctta aattgggagg actccaagcc gggaaggaaa attccctttt ccaacctgta    300

tcaattttta caactttttt cctgaaagca gtttagtcca tactttgcac tgacatactt    360

tttccttctg tgctaaggta ag                                             382
```

<210> SEQ ID NO 459
<211> LENGTH: 168
<212> TYPE: DNA
<213> ORGANISM: Homo sapiens

<400> SEQUENCE: 459

```
ctcgtactct agccaggcac gaaaccatga agtagcctga tccttcttag ccatcctggc     60

cgccttagcg gtagtaactt tgtgttatga atcacatgaa agcatggaat cttatgaact    120

taatcccttc attaacagga gaaatgcaaa taccttcata tcccctca                 168
```

<210> SEQ ID NO 460
<211> LENGTH: 190

-continued

<212> TYPE: DNA
<213> ORGANISM: Homo sapiens
<220> FEATURE:
<221> NAME/KEY: misc_feature
<222> LOCATION: (1)...(190)
<223> OTHER INFORMATION: n = A,T,C or G

<400> SEQUENCE: 460
acanctgcta ccagggagcc gagagctgac tatcccagcc tcggctaatg tattctacgc 60
catggatgga gcttcacacg atttcctcct gcggcagcgg cgaaggtcct ctactgctac 120
acctggcgtc accagtggcc cgtctgcctc aggaactcct ccgagtgagg gaggaggggg 180
ctcctttccc 190

<210> SEQ ID NO 461
<211> LENGTH: 495
<212> TYPE: DNA
<213> ORGANISM: Homo sapiens

<400> SEQUENCE: 461
acagacaggc ttctctgcta tcctccaggc agtgtaatag tcaaggaaaa gggcaacagt 60
attggatcat tccttagaca ctaatcagct ggggaaagag ttcattggca aaagtgtcct 120
cccaagaatg gtttacacca agcagagagg acatgtcact gaatggggaa agggaacccc 180
cgtatccaca gtcactgtaa gcatccagta ggcaggaaga tggctttggg cagtggctgg 240
atgaaagcag atttgagata cccagctccg gaacgaggtc atcttctaca ggttcttcct 300
tcactgagac aatgaattca gggtgatcat tctctgaggg gctgagaggt gcttcctcga 360
ttttcactac cacattagct tggctctctg tctcagaggg tatctctaag actaggggct 420
tggtatatat gtggtcaaaa cgaattagtt cattaatggc ttccagcttg gctgatgacg 480
tccccactga cagag 495

<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: (1)...(493)
<223> OTHER INFORMATION: n = A,T,C or G

<400> SEQUENCE: 462
acactgaaac ataaatccgc aagtcaccac acatacaaca cccggcagga aaaaaacaaa 60
aacagggngt ttacatgatc cctgtaacag ccatggtctc aaactcagat gcttcctcca 120
tctgccaagt gtgttttgga tacagagcac atcgtggctt ctggggtcac actcagctta 180
ggctgtgggt ccacagagca ctcatctggc tgggctatgg tggtggtggc tctactcaag 240
aagcaaagca gttaccagca cattcaaaca gtgtattgaa catcttttaa atatcaaagt 300
gagaaacaag aaggcaacat aataatgtta tcagaaagat gttaggaagt aaggacagct 360
gtgtaaagct tgaggctgaa aagtagcttg ccagcttcat ttctttggtt tcttgggtag 420
tgggcgccgg aacagcaaga tgtgaggttc tggttcatgg atcatataat ggacccatcc 480
ctgactctgc tga 493

<210> SEQ ID NO 463
<211> LENGTH: 3681
<212> TYPE: DNA
<213> ORGANISM: Homo sapiens

<400> SEQUENCE: 463
tccgagctga ttacagacac caaggaagat gctgtaaaga gtcagcagcc acagccctgg 60

-continued

```
ctagctggcc ctgtgggcat ttattagtaa agttttaatg acaaaagctt tgagtcaaca    120
cacccgtggg taattaacct ggtcatcccc accctggaga gccatcctgc ccatgggtga    180
tcaaagaagg aacatctgca ggaacacctg atgaggctgc acccttggcg gaaagaacac    240
ctgacacagc tgaaagcttg gtggaaaaaa cacctgatga ggctgcaccc ttggtggaaa    300
gaacacctga cacggctgaa agcttggtgg aaaaaacacc tgatgaggct gcatccttgg    360
tggagggaac atctgacaaa attcaatgtt tggagaaagc gacatctgga aagttcgaac    420
agtcagcaga agaaacacct agggaaatta cgagtcctgc aaaagaaaca tctgagaaat    480
ttacgtggcc agcaaaagga agacctagga agatcgcatg ggagaaaaaa gaagacacac    540
ctagggaaat tatgagtccc gcaaaagaaa catctgagaa atttacgtgg gcagcaaaag    600
gaagacctag gaagatcgca tgggagaaaa aagaaacacc tgtaaagact ggatgcgtgg    660
caagagtaac atctaataaa actaaagttt tggaaaaagg aagatctaag atgattgcat    720
gtcctacaaa agaatcatct acaaaagcaa gtgccaatga tcagaggttc ccatcagaat    780
ccaaacaaga ggaagatgaa gaatattctt gtgattctcg gagtctcttt gagagttctg    840
caaagattca agtgtgtata cctgagtcta tatatcaaaa agtaatggag ataaatagag    900
aagtagaaga gcctcctaag aagccatctg ccttcaagcc tgccattgaa atgcaaaact    960
ctgttccaaa taaagccttt gaattgaaga atgaacaaac attgagagca gatccgatgt   1020
tcccaccaga atccaaacaa aaggactatg aagaaaattc ttgggattct gagagtctct   1080
gtgagactgt ttcacagaag gatgtgtgtt tacccaaggc tacacatcaa aaagaaatag   1140
ataaaataaa tggaaaatta gaagagtctc ctaataaaga tggtcttctg aaggctacct   1200
gcggaatgaa agtttctatt ccaactaaag ccttagaatt gaaggacatg caaactttca   1260
aagcagagcc tccggggaag ccatctgcct tcgagcctgc cactgaaatg caaaagtctg   1320
tcccaaataa agccttggaa ttgaaaaatg aacaaacatt gagagcagat gagatactcc   1380
catcagaatc caaacaaaag gactatgaag aaagttcttg ggattctgag agtctctgtg   1440
agactgtttc acagaaggat gtgtgtttac ccaaggctrc rcatcaaaaa gaaatagata   1500
aaataaatgg aaaattagaa gggtctcctg ttaaagatgg tcttctgaag gctaactgcg   1560
gaatgaaagt ttctattcca actaaagcct tagaattgat ggacatgcaa actttcaaag   1620
cagagcctcc cgagaagcca tctgccttcg agcctgccat tgaaatgcaa aagtctgttc   1680
caaataaagc cttggaattg aagaatgaac aaacattgag agcagatgag atactcccat   1740
cagaatccaa acaaaaggac tatgaagaaa gttcttggga ttctgagagt ctctgtgaga   1800
ctgtttcaca gaaggatgtg tgtttaccca aggctrcrca tcaaaaagaa atagataaaa   1860
taaatggaaa attagaagag tctcctgata atgatggttt tctgaaggct ccctgcagaa   1920
tgaaagtttc tattccaact aaagccttag aattgatgga catgcaaact ttcaaagcag   1980
agcctcccga gaagccatct gccttcgagc ctgccattga aatgcaaaag tctgttccaa   2040
ataaagcctt ggaattgaag aatgaacaaa cattgagagc agatcagatg ttcccttcag   2100
aatcaaaaca aaagaasgtt gaagaaaatt cttgggattc tgagagtctc cgtgagactg   2160
tttcacagaa ggatgtgtgt gtacccaagg ctacacatca aaaagaaatg gataaaataa   2220
gtggaaaatt agaagattca actagcctat caaaaatctt ggatacagtt cattcttgtg   2280
aaagagcaag ggaacttcaa aaagatcact gtgaacaacg tacaggaaaa atggaacaaa   2340
tgaaaaagaa gttttgtgta ctgaaaaaga aactgtcaga agcaaaagaa ataaaatcac   2400
```

-continued

```
agttagagaa ccaaaaagtt aaatgggaac aagagctctg cagtgtgagg tttctcacac   2460

tcatgaaaat gaaaattatc tcttacatga aaattgcatg ttgaaaaagg aaattgccat   2520

gctaaaactg gaaatagcca cactgaaaca ccaataccag gaaaaggaaa ataaatactt   2580

tgaggacatt aagattttaa aagaaaagaa tgctgaactt cagatgaccc taaaactgaa   2640

agaggaatca ttaactaaaa gggcatctca atatagtggg cagcttaaag ttctgatagc   2700

tgagaacaca atgctcactt ctaaattgaa ggaaaaacaa gacaaagaaa tactagaggc   2760

agaaattgaa tcacaccatc ctagactggc ttctgctgta caagaccatg atcaaattgt   2820

gacatcaaga aaaagtcaag aacctgcttt ccacattgca ggagatgctt gtttgcaaag   2880

aaaaatgaat gttgatgtga gtagtacgat atataacaat gaggtgctcc atcaaccact   2940

ttctgaagct caaaggaaat ccaaaagcct aaaaattaat ctcaattatg cmggagatgc   3000

tctaagagaa aatacattgg tttcagaaca tgcacaaaga gaccaacgtg aaacacagtg   3060

tcaaatgaag gaagctgaac acatgtatca aaacgaacaa gataatgtga acaaacacac   3120

tgaacagcag gagtctctag atcagaaatt atttcaacta caaagcaaaa atatgtggct   3180

tcaacagcaa ttagttcatg cacataagaa agctgacaac aaaagcaaga taacaattga   3240

tattcatttt cttgagagga aaatgcaaca tcatctccta aaagagaaaa atgaggagat   3300

atttaattac aataaccatt taaaaaaccg tatatatcaa tatgaaaaag agaaagcaga   3360

aacagaaaac tcatgagaga caagcagtaa gaaacttctt ttggagaaac aacagaccag   3420

atctttactc acaactcatg ctaggaggcc agtcctagca tcaccttatg ttgaaaatct   3480

taccaatagt ctgtgtcaac agaatactta ttttagaaga aaaattcatg atttcttcct   3540

gaagcctaca gacataaaat aacagtgtga agaattactt gttcacgaat tgcataaagc   3600

tgcacaggat tcccatctac cctgatgatg cagcagacat cattcaatcc aaccagaatc   3660

tcgctctgtc actcaggctg g                                              3681
```

<210> SEQ ID NO 464
<211> LENGTH: 1424
<212> TYPE: DNA
<213> ORGANISM: Homo sapiens

<400> SEQUENCE: 464

```
tccgagctga ttacagacac caaggaagat gctgtaaaga gtcagcagcc acagccctgg     60

ctagctggcc ctgtgggcat ttattagtaa agttttaatg acaaaagctt tgagtcaaca    120

cacccgtggg taattaacct ggtcatcccc accctggaga gccatcctgc ccatgggtga    180

tcaaagaagg aacatctgca ggaacacctg atgaggctgc acccttggcg gaaagaacac    240

ctgacacagc tgaaagcttg gtggaaaaaa cacctgatga ggctgcaccc ttggtggaaa    300

gaacacctga cacggctgaa agcttggtgg aaaaaacacc tgatgaggct gcatccttgg    360

tggagggaac atctgacaaa attcaatgtt tggagaaagc gacatctgga aagttcgaac    420

agtcagcaga agaaacacct agggaaatta cgagtcctgc aaaagaaaca tctgagaaat    480

ttacgtggcc agcaaaagga agacctagga agatcgcatg ggagaaaaaa gaagacacac    540

ctagggaaat tatgagtccc gcaaaagaaa catctgagaa atttacgtgg gcagcaaaag    600

gaagacctag gaagatcgca tgggagaaaa aagaaacacc tgtaaagact ggatgcgtgg    660

caagagtaac atctaataaa actaaagttt tggaaaaagg aagatctaag atgattgcat    720

gtcctacaaa agaatcatct acaaaagcaa gtgccaatga tcagaggttc ccatcagaat    780

ccaaacaaga ggaagatgaa gaatattctt gtgattctcg gagtctcttt gagagttctg    840
```

-continued

```
caaagattca agtgtgtata cctgagtcta tatatcaaaa agtaatggag ataaatagag    900

aagtagaaga gcctcctaag aagccatctg ccttcaagcc tgccattgaa atgcaaaact    960

ctgttccaaa taaagccttt gaattgaaga atgaacaaac attgagagca gatccgatgt   1020

tcccaccaga atccaaacaa aaggactatg aagaaaattc ttgggattct gagagtctct   1080

gtgagactgt ttcacagaag gatgtgtgtt tacccaaggc tacacatcaa aaagaaatag   1140

ataaaataaa tggaaaatta gaaggtaaga accgtttttt atttaaaaat cagttgaccg   1200

aatatttctc taaactgatg aggagggata tcctctagta gctgaagaaa attacctcct   1260

aaatgcaaac catggaaaaa aagagaagtg caatggtcgt aagttgtatg tctcatcagg   1320

tgttggcaac agactatatt gagagtgctg aaaaggagct gaattattag tttgaattca   1380

agatattgca agacctgaga gaaaaaaaaa aaaaaaaaaa aaaa                    1424
```

<210> SEQ ID NO 465
<211> LENGTH: 674
<212> TYPE: DNA
<213> ORGANISM: Homo sapiens

<400> SEQUENCE: 465

```
attccgagct gattacagac accaaggaag atgctgtaaa gagtcagcag ccacagccct     60

ggctagctgg ccctgtgggc atttattagt aaagttttaa tgacaaaagc tttgagtcaa    120

cacacccgtg ggtaattaac ctggtcatcc ccaccctgga gagccatcct gcccatgggt    180

gatcaaagaa ggaacatctg caggaacacc tgatgaggct gcacccttgg cggaaagaac    240

acctgacaca gctgaaagct tggtggaaaa aacacctgat gaggctgcac ccttggtgga    300

aagaacacct gacacggctg aaagcttggt ggaaaaaaca cctgatgagg ctgcatcctt    360

ggtggaggga acatctgaca aaattcaatg tttggagaaa gcgacatctg gaaagttcga    420

acagtcagca gaagaaacac ctagggaaat tacgagtcct gcaaaagaaa catctgagaa    480

atttacgtgg ccagcaaaag gaagacctag gaagatcgca tgggagaaaa aagatgactc    540

agttaaggca aaaaaaaaaa aaaaaaaaaa aaaaaaaaaa aaaaaaaaaa aaaaaaaaaa    600

aaaaaaaaaa aaaaaaaaaa aaaaaaaaaa aaaaaaaaaa aaaaaaaaaa aaaaaaaaaa    660

aaaaaaaaaa aaaa                                                      674
```

<210> SEQ ID NO 466
<211> LENGTH: 1729
<212> TYPE: DNA
<213> ORGANISM: Homo sapiens
<220> FEATURE:
<221> NAME/KEY: unsure
<222> LOCATION: (11)
<223> OTHER INFORMATION: n=A,T,C or G
<221> NAME/KEY: unsure
<222> LOCATION: (1128)
<223> OTHER INFORMATION: n=A,T,C or G

<400> SEQUENCE: 466

```
gaaagttcga ncagtcagca gaagaaacac ctagggaaat tacgagtcct gcaaaagaaa     60

catctgagaa atttacgtgg ccagcaaaag gaagacctag gaagatcgca tgggagaaaa    120

aagaagacac acctagggaa attatgagtc ccgcaaaaga aacatctgag aaatttacgt    180

gggcagcaaa aggaagacct aggaagatcg catgggagaa aaaagaaaca cctgtaaaga    240

ctggatgcgt ggcaagagta acatctaata aaactaaagt tttggaaaaa ggaagatcta    300

agatgattgc atgtcctaca aaagaatcat ctacaaaagc aagtgccaat gatcagaggt    360
```

-continued

```
tcccatcaga atccaaacaa gaggaagatg aagaatattc ttgtgattct cggagtctct    420
ttgagagttc tgcaaagatt caagtgtgta tacctgagtc tatatatcaa aaagtaatgg    480
agataaatag agaagtagaa gagcctccta agaagccatc tgccttcaag cctgccattg    540
aaatgcaaaa ctctgttcca aataaagcct ttgaattgaa gaatgaacaa acattgagag    600
cagatccgat gttcccacca gaatccaaac aaaaggacta tgaagaaaat tcttgggatt    660
ctgagagtct ctgtgagact gtttcacaga aggatgtgtg tttacccaag gctacacatc    720
aaaaagaaat agataaaata aatggaaaat tagaagagtc tcctaataaa gatggtcttc    780
tgaaggctac ctgcggaatg aaagtttcta ttccaactaa agccttagaa ttgaaggaca    840
tgcaaacttt caaagcagag cctccgggga agccatctgc cttcgagcct gccactgaaa    900
tgcaaaagtc tgtcccaaat aaagccttgg aattgaaaaa tgaacaaaca ttgagagcag    960
atgagatact cccatcagaa tccaaacaaa aggactatga agaaaattct tgggatactg   1020
agagtctctg tgagactgtt tcacagaagg atgtgtgttt acccaaggct gcgcatcaaa   1080
aagaaataga taaaataaat ggaaaattag aagggtctcc tggtaaanat ggtcttctga   1140
aggctaactg cggaatgaaa gtttctattc caactaaagc cttagaattg atggacatgc   1200
aaactttcaa agcagagcct cccgagaagc catctgcctt cgagcctgcc attgaaatgc   1260
aaaagtctgt tccaaataaa gccttggaat tgaagaatga acaaacattg agagcagatg   1320
agatactccc atcagaatcc aaacaaaagg actatgaaga aagttcttgg gattctgaga   1380
gtctctgtga gactgtttca cagaaggatg tgtgtttacc caaggctgcg catcaaaaag   1440
aaatagataa aataaatgga aaattagaag gtaagaaccg tttttttattt aaaaatcatt   1500
tgaccaaata tttctctaaa ttgatgagga aggatatcct ctagtagctg aagaaaatta   1560
cctcctaaat gcaaaccatg gaaaaaaaga gaagtgcaat ggtcataagc tatgtgtctc   1620
atcaggcatt ggcaacagac tatattgtga gtgctgaaga ggagctgaat tactagttta   1680
aattcaagat attccaagac gtgaggaaaa tgagaaaaaa aaaaaaaaa               1729
```

<210> SEQ ID NO 467
<211> LENGTH: 1337
<212> TYPE: DNA
<213> ORGANISM: Homo sapiens

<400> SEQUENCE: 467

```
aaaaagaaat agataaaata aatggaaaat tagaagggtc tcctgttaaa gatggtcttc     60
tgaaggctaa ctgcggaatg aaagtttcta ttccaactaa agccttagaa ttgatggaca    120
tgcaaacttt caaagcagag cctcccgaga agccatctgc cttcgagcct gccattgaaa    180
tgcaaaagtc tgttccaaat aaagccttgg aattgaagaa tgaacaaaca ttgagagcag    240
atgagatact cccatcagaa tccaaacaaa aggactatga agaaagttct tgggattctg    300
agagtctctg tgagactgtt tcacagaagg atgtgtgttt acccaaggct gcgcatcaaa    360
aagaaataga taaaataaat ggaaaattag aagagtctcc tgataatgat ggttttctga    420
aggctccctg cagaatgaaa gtttctattc caactaaagc cttagaattg atggacatgc    480
aaactttcaa agcagagcct cccgagaagc catctgcctt cgagcctgcc attgaaatgc    540
aaaagtctgt tccaaataaa gccttggaat tgaagaatga acaaacattg agagcagatc    600
agatgttccc ttcagaatca aaacaaaaga aggttgaaga aaattcttgg gattctgaga    660
gtctccgtga gactgtttca cagaaggatg tgtgtgtacc caaggctaca catcaaaaag    720
```

-continued

```
aaatggataa aataagtgga aaattagaag attcaactag cctatcaaaa atcttggata    780
cagttcattc ttgtgaaaga gcaagggaac ttcaaaaaga tcactgtgaa caacgtacag    840
gaaaaatgga acaaatgaaa aagaagtttt gtgtactgaa aaagaaactg tcagaagcaa    900
aagaaataaa atcacagtta gagaaccaaa aagttaaatg ggaacaagag ctctgcagtg    960
tgagattgac tttaaaccaa gaagaagaga agagaagaaa tgccgatata ttaaatgaaa   1020
aaattaggga agaattagga agaatcgaag agcagcatag gaaagagtta gaagtgaaac   1080
aacaacttga acaggctctc agaatacaag atatagaatt gaagagtgta gaaagtaatt   1140
tgaatcaggt ttctcacact catgaaaatg aaaattatct cttacatgaa aattgcatgt   1200
tgaaaaagga aattgccatg ctaaaactgg aaatagccac actgaaacac caataccagg   1260
aaaaggaaaa taaatacttt gaggacatta agattttaaa agaaaagaat gctgaacttc   1320
agatgacccc tcgtgcc                                                  1337
```

<210> SEQ ID NO 468
<211> LENGTH: 2307
<212> TYPE: DNA
<213> ORGANISM: Homo sapiens

<400> SEQUENCE: 468

```
attgagagca gatgagatac tcccatcaga atccaaacaa aaggactatg aagaaagttc     60
ttgggattct gagagtctct gtgagactgt ttcacagaag gatgtgtgtt tacccaaggc    120
tacacatcaa aaagaaatag ataaaataaa tggaaaatta gaagggtctc ctgttaaaga    180
tggtcttctg aaggctaact gcggaatgaa agtttctatt ccaactaaag ccttagaatt    240
gatggacatg caaactttca aagcagagcc tcccgagaag ccatctgcct tcgagcctgc    300
cattgaaatg caaaagtctg ttccaaataa agccttggaa ttgaagaatg aacaaacatt    360
gagagcagat gagatactcc catcagaatc caaacaaaag gactatgaag aaagttcttg    420
ggattctgag agtctctgtg agactgtttc acagaaggat gtgtgtttac ccaaggctac    480
acatcaaaaa gaaatagata aaataaatgg aaaattagaa gagtctcctg ataatgatgg    540
ttttctgaag tctccctgca gaatgaaagt ttctattcca actaaagcct tagaattgat    600
ggacatgcaa actttcaaag cagagcctcc cgagaagcca tctgccttcg agcctgccat    660
tgaaatgcaa aagtctgttc caaataaagc cttggaattg aagaatgaac aaacattgag    720
agcagatcag atgttccctt cagaatcaaa acaaaagaac gttgaagaaa attcttggga    780
ttctgagagt ctccgtgaga ctgtttcaca gaaggatgtg tgtgtaccca aggctacaca    840
tcaaaaagaa atggataaaa taagtggaaa attagaagat tcaactagcc tatcaaaaat    900
cttggataca gttcattctt gtgaaagagc aagggaactt caaaaagatc actgtgaaca    960
acgtacagga aaaatggaac aaatgaaaaa gaagttttgt gtactgaaaa agaaactgtc   1020
agaagcaaaa gaaataaaat cacagttaga gaaccaaaaa gttaaatggg aacaagagct   1080
ctgcagtgtg aggtttctca cactcatgaa aatgaaaatt atctcttaca tgaaaattgc   1140
atgttgaaaa aggaaattgc catgctaaaa ctggaaatag ccacactgaa acaccaatac   1200
caggaaaagg aaaataaata ctttgaggac attaagattt taaaagaaaa gaatgctgaa   1260
cttcagatga ccctaaaact gaaagaggaa tcattaacta aaagggcatc tcaatatagt   1320
gggcagctta aagttctgat agctgagaac acaatgctca cttctaaatt gaaggaaaaa   1380
caagacaaag aaatactaga ggcagaaatt gaatcacacc atcctagact ggcttctgct   1440
gtacaagacc atgatcaaat tgtgacatca agaaaaagtc aagaacctgc tttccacatt   1500
```

-continued

```
gcaggagatg cttgtttgca aagaaaaatg aatgttgatg tgagtagtac gatatataac   1560

aatgaggtgc tccatcaacc actttctgaa gctcaaagga aatccaaaag cctaaaaatt   1620

aatctcaatt atgcaggaga tgctctaaga gaaaatacat tggtttcaga acatgcacaa   1680

agagaccaac gtgaaacaca gtgtcaaatg aaggaagctg aacacatgta tcaaaacgaa   1740

caagataatg tgaacaaaca cactgaacag caggagtctc tagatcagaa attatttcaa   1800

ctacaaagca aaaatatgtg gcttcaacag caattagttc atgcacataa gaaagctgac   1860

aacaaaagca agataacaat tgatattcat tttcttgaga ggaaaatgca acatcatctc   1920

ctaaaagaga aaaatgagga gatatttaat tacaataacc atttaaaaaa ccgtatatat   1980

caatatgaaa aagagaaagc agaaacagaa aactcatgag agacaagcag taagaaactt   2040

cttttggaga aacaacagac cagatcttta ctcacaactc atgctaggag gccagtccta   2100

gcatcacctt atgttgaaaa tcttaccaat agtctgtgtc aacagaatac ttattttaga   2160

agaaaaattc atgatttctt cctgaagcct acagacataa aataacagtg tgaagaatta   2220

cttgttcacg aattgcataa agctgcacag gattcccatc taccctgatg atgcagcaga   2280

catcattcaa tccaaccaga atctcgc                                        2307
```

<210> SEQ ID NO 469
<211> LENGTH: 650
<212> TYPE: PRT
<213> ORGANISM: Homo sapiens
<220> FEATURE:
<221> NAME/KEY: unsure
<222> LOCATION: (310)
<223> OTHER INFORMATION: Xaa = Any Amino Acid
<221> NAME/KEY: unsure
<222> LOCATION: (429)
<223> OTHER INFORMATION: Xaa = Any Amino Acid
<221> NAME/KEY: unsure
<222> LOCATION: (522)
<223> OTHER INFORMATION: Xaa = Any Amino Acid

<400> SEQUENCE: 469

```
Met Ser Pro Ala Lys Glu Thr Ser Glu Lys Phe Thr Trp Ala Ala Lys
                5                   10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175
```

-continued

```
Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
        435                 440                 445

Gly Phe Leu Lys Ala Pro Cys Arg Met Lys Val Ser Ile Pro Thr Lys
    450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Glu Asn Ser Trp
        515                 520                 525

Asp Ser Glu Ser Leu Arg Glu Thr Val Ser Gln Lys Asp Val Cys Val
    530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
                565                 570                 575

Glu Arg Ala Arg Glu Leu Gln Lys Asp His Cys Glu Gln Arg Thr Gly
            580                 585                 590
```

-continued

Lys Met Glu Gln Met Lys Lys Lys Phe Cys Val Leu Lys Lys Lys Leu
595 600 605

Ser Glu Ala Lys Glu Ile Lys Ser Gln Leu Glu Asn Gln Lys Val Lys
610 615 620

Trp Glu Gln Glu Leu Cys Ser Val Arg Phe Leu Thr Leu Met Lys Met
625 630 635 640

Lys Ile Ile Ser Tyr Met Lys Ile Ala Cys
645 650

<210> SEQ ID NO 470
<211> LENGTH: 228
<212> TYPE: PRT
<213> ORGANISM: Homo sapiens

<400> SEQUENCE: 470

Met Ser Pro Ala Lys Glu Thr Ser Glu Lys Phe Thr Trp Ala Ala Lys
5 10 15

Gly Arg Pro Arg Lys Ile Ala Trp Glu Lys Lys Glu Thr Pro Val Lys
20 25 30

Thr Gly Cys Val Ala Arg Val Thr Ser Asn Lys Thr Lys Val Leu Glu
35 40 45

Lys Gly Arg Ser Lys Met Ile Ala Cys Pro Thr Lys Glu Ser Ser Thr
50 55 60

Lys Ala Ser Ala Asn Asp Gln Arg Phe Pro Ser Glu Ser Lys Gln Glu
65 70 75 80

Glu Asp Glu Glu Tyr Ser Cys Asp Ser Arg Ser Leu Phe Glu Ser Ser
85 90 95

Ala Lys Ile Gln Val Cys Ile Pro Glu Ser Ile Tyr Gln Lys Val Met
100 105 110

Glu Ile Asn Arg Glu Val Glu Glu Pro Pro Lys Lys Pro Ser Ala Phe
115 120 125

Lys Pro Ala Ile Glu Met Gln Asn Ser Val Pro Asn Lys Ala Phe Glu
130 135 140

Leu Lys Asn Glu Gln Thr Leu Arg Ala Asp Pro Met Phe Pro Pro Glu
145 150 155 160

Ser Lys Gln Lys Asp Tyr Glu Glu Asn Ser Trp Asp Ser Glu Ser Leu
165 170 175

Cys Glu Thr Val Ser Gln Lys Asp Val Cys Leu Pro Lys Ala Thr His
180 185 190

Gln Lys Glu Ile Asp Lys Ile Asn Gly Lys Leu Glu Gly Lys Asn Arg
195 200 205

Phe Leu Phe Lys Asn Gln Leu Thr Glu Tyr Phe Ser Lys Leu Met Arg
210 215 220

Arg Asp Ile Leu
225

<210> SEQ ID NO 471
<211> LENGTH: 154
<212> TYPE: PRT
<213> ORGANISM: Homo sapiens
<220> FEATURE:
<221> NAME/KEY: unsure
<222> LOCATION: (148)
<223> OTHER INFORMATION: Xaa = Any Amino Acid

<400> SEQUENCE: 471

Met Arg Leu His Pro Trp Arg Lys Glu His Leu Thr Gln Leu Lys Ala
5 10 15

-continued

```
Trp Trp Lys Lys His Leu Met Arg Leu His Pro Trp Trp Lys Glu His
             20                  25                  30

Leu Thr Arg Leu Lys Ala Trp Trp Lys Lys His Leu Met Arg Leu His
         35                  40                  45

Pro Trp Trp Arg Glu His Leu Thr Lys Phe Asn Val Trp Arg Lys Arg
     50                  55                  60

His Leu Glu Ser Ser Asn Ser Gln Gln Lys Lys His Leu Gly Lys Leu
 65                  70                  75                  80

Arg Val Leu Gln Lys Lys His Leu Arg Asn Leu Arg Gly Gln Gln Lys
                 85                  90                  95

Glu Asp Leu Gly Arg Ser His Gly Arg Lys Lys Met Thr Gln Leu Arg
             100                 105                 110

Gln Lys Lys Lys Lys Lys Lys Lys Lys Lys Lys Lys Lys Lys Lys Lys
        115                 120                 125

Lys Lys Lys Lys Lys Lys Lys Lys Lys Lys Lys Lys Lys Lys Lys Lys
    130                 135                 140

Lys Lys Lys Xaa Lys Lys Lys Lys Lys Lys
145                 150
```

<210> SEQ ID NO 472
<211> LENGTH: 466
<212> TYPE: PRT
<213> ORGANISM: Homo sapiens
<220> FEATURE:
<221> NAME/KEY: unsure
<222> LOCATION: (329)
<223> OTHER INFORMATION: Xaa = Any Amino Acid

<400> SEQUENCE: 472

```
Met Ser Pro Ala Lys Glu Thr Ser Glu Lys Phe Thr Trp Ala Ala Lys
                 5                  10                  15

Gly Arg Pro Arg Lys Ile Ala Trp Glu Lys Lys Glu Thr Pro Val Lys
             20                  25                  30

Thr Gly Cys Val Ala Arg Val Thr Ser Asn Lys Thr Lys Val Leu Glu
         35                  40                  45

Lys Gly Arg Ser Lys Met Ile Ala Cys Pro Thr Lys Glu Ser Ser Thr
     50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
             100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
             180                 185                 190

Gln Lys Glu Ile Asp Lys Ile Asn Gly Lys Leu Glu Glu Ser Pro Asn
        195                 200                 205
```

-continued

```
Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Asn
        275                 280                 285

Ser Trp Asp Thr Glu Ser Leu Cys Glu Thr Val Ser Gln Lys Asp Val
    290                 295                 300

Cys Leu Pro Lys Ala Ala His Gln Lys Glu Ile Asp Lys Ile Asn Gly
305                 310                 315                 320

Lys Leu Glu Gly Ser Pro Gly Lys Xaa Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Ala His Gln Lys
            420                 425                 430

Glu Ile Asp Lys Ile Asn Gly Lys Leu Glu Gly Lys Asn Arg Phe Leu
        435                 440                 445

Phe Lys Asn His Leu Thr Lys Tyr Phe Ser Lys Leu Met Arg Lys Asp
    450                 455                 460

Ile Leu
465


<210> SEQ ID NO 473
<211> LENGTH: 445
<212> TYPE: PRT
<213> ORGANISM: Homo sapiens

<400> SEQUENCE: 473

Lys Glu Ile Asp Lys Ile Asn Gly Lys Leu Glu Gly Ser Pro Val Lys
                 5                  10                  15

Asp Gly Leu Leu Lys Ala Asn Cys Gly Met Lys Val Ser Ile Pro Thr
            20                  25                  30

Lys Ala Leu Glu Leu Met Asp Met Gln Thr Phe Lys Ala Glu Pro Pro
        35                  40                  45

Glu Lys Pro Ser Ala Phe Glu Pro Ala Ile Glu Met Gln Lys Ser Val
    50                  55                  60

Pro Asn Lys Ala Leu Glu Leu Lys Asn Glu Gln Thr Leu Arg Ala Asp
 65                  70                  75                  80

Glu Ile Leu Pro Ser Glu Ser Lys Gln Lys Asp Tyr Glu Glu Ser Ser
                 85                  90                  95

Trp Asp Ser Glu Ser Leu Cys Glu Thr Val Ser Gln Lys Asp Val Cys
            100                 105                 110
```

-continued

```
Leu Pro Lys Ala Ala His Gln Lys Glu Ile Asp Lys Ile Asn Gly Lys
        115                 120                 125

Leu Glu Glu Ser Pro Asp Asn Asp Gly Phe Leu Lys Ala Pro Cys Arg
    130                 135                 140

Met Lys Val Ser Ile Pro Thr Lys Ala Leu Glu Leu Met Asp Met Gln
145                 150                 155                 160

Thr Phe Lys Ala Glu Pro Pro Glu Lys Pro Ser Ala Phe Glu Pro Ala
                165                 170                 175

Ile Glu Met Gln Lys Ser Val Pro Asn Lys Ala Leu Glu Leu Lys Asn
            180                 185                 190

Glu Gln Thr Leu Arg Ala Asp Gln Met Phe Pro Ser Glu Ser Lys Gln
        195                 200                 205

Lys Lys Val Glu Glu Asn Ser Trp Asp Ser Glu Ser Leu Arg Glu Thr
    210                 215                 220

Val Ser Gln Lys Asp Val Cys Val Pro Lys Ala Thr His Gln Lys Glu
225                 230                 235                 240

Met Asp Lys Ile Ser Gly Lys Leu Glu Asp Ser Thr Ser Leu Ser Lys
                245                 250                 255

Ile Leu Asp Thr Val His Ser Cys Glu Arg Ala Arg Glu Leu Gln Lys
            260                 265                 270

Asp His Cys Glu Gln Arg Thr Gly Lys Met Glu Gln Met Lys Lys Lys
        275                 280                 285

Phe Cys Val Leu Lys Lys Lys Leu Ser Glu Ala Lys Glu Ile Lys Ser
    290                 295                 300

Gln Leu Glu Asn Gln Lys Val Lys Trp Glu Gln Glu Leu Cys Ser Val
305                 310                 315                 320

Arg Leu Thr Leu Asn Gln Glu Glu Glu Lys Arg Arg Asn Ala Asp Ile
                325                 330                 335

Leu Asn Glu Lys Ile Arg Glu Glu Leu Gly Arg Ile Glu Glu Gln His
            340                 345                 350

Arg Lys Glu Leu Glu Val Lys Gln Gln Leu Glu Gln Ala Leu Arg Ile
        355                 360                 365

Gln Asp Ile Glu Leu Lys Ser Val Glu Ser Asn Leu Asn Gln Val Ser
    370                 375                 380

His Thr His Glu Asn Glu Asn Tyr Leu Leu His Glu Asn Cys Met Leu
385                 390                 395                 400

Lys Lys Glu Ile Ala Met Leu Lys Leu Glu Ile Ala Thr Leu Lys His
                405                 410                 415

Gln Tyr Gln Glu Lys Glu Asn Lys Tyr Phe Glu Asp Ile Lys Ile Leu
            420                 425                 430

Lys Glu Lys Asn Ala Glu Leu Gln Met Thr Pro Arg Ala
        435                 440                 445
```

<210> SEQ ID NO 474
<211> LENGTH: 3865
<212> TYPE: DNA
<213> ORGANISM: Homo sapien
<220> FEATURE:
<221> NAME/KEY: misc_feature
<222> LOCATION: (2448)...(2631)
<223> OTHER INFORMATION: 184 bp insert of B726P splice form

<400> SEQUENCE: 474

```
tccgagctga ttacagacac caaggaagat gctgtaaaga gtcagcagcc acagccctgg      60

ctagctggcc ctgtgggcat ttattagtaa agttttaatg acaaaagctt tgagtcaaca     120
```

-continued

```
cacccgtggg taattaacct ggtcatcccc accctggaga gccatcctgc ccatgggtga    180
tcaaagaagg aacatctgca ggaacacctg atgaggctgc acccttggcg gaaagaacac    240
ctgacacagc tgaaagcttg gtggaaaaaa cacctgatga ggctgcaccc ttggtggaaa    300
gaacacctga cacggctgaa agcttggtgg aaaaaacacc tgatgaggct gcatccttgg    360
tggagggaac atctgacaaa attcaatgtt tggagaaagc gacatctgga aagttcgaac    420
agtcagcaga agaaacacct agggaaatta cgagtcctgc aaaagaaaca tctgagaaat    480
ttacgtggcc agcaaaagga agacctagga agatcgcatg ggagaaaaaa gaagacacac    540
ctagggaaat tatgagtccc gcaaaagaaa catctgagaa atttacgtgg gcagcaaaag    600
gaagacctag gaagatcgca tgggagaaaa aagaaacacc tgtaaagact ggatgcgtgg    660
caagagtaac atctaataaa actaaagttt tggaaaaagg aagatctaag atgattgcat    720
gtcctacaaa agaatcatct acaaaagcaa gtgccaatga tcagaggttc ccatcagaat    780
ccaaacaaga ggaagatgaa gaatattctt gtgattctcg gagtctcttt gagagttctg    840
caaagattca agtgtgtata cctgagtcta tatatcaaaa agtaatggag ataaatagag    900
aagtagaaga gcctcctaag aagccatctg ccttcaagcc tgccattgaa atgcaaaact    960
ctgttccaaa taaagccttt gaattgaaga atgaacaaac attgagagca gatccgatgt   1020
tcccaccaga atccaaacaa aaggactatg aagaaaattc ttgggattct gagagtctct   1080
gtgagactgt ttcacagaag gatgtgtgtt tacccaaggc tacacatcaa aaagaaatag   1140
ataaaataaa tggaaaatta gaagagtctc ctaataaaga tggtcttctg aaggctacct   1200
gcggaatgaa agtttctatt ccaactaaag ccttagaatt gaaggacatg caaactttca   1260
aagcagagcc tccggggaag ccatctgcct tcgagcctgc cactgaaatg caaaagtctg   1320
tcccaaataa agccttggaa ttgaaaaatg aacaaacatt gagagcagat gagatactcc   1380
catcagaatc caaacaaaag gactatgaag aaagttcttg ggattctgag agtctctgtg   1440
agactgtttc acagaaggat gtgtgtttac ccaaggctrc rcatcaaaaa gaaatagata   1500
aataaaatgg aaaattagaa gggtctcctg ttaaagatgg tcttctgaag gctaactgcg   1560
gaatgaaagt ttctattcca actaaagcct tagaattgat ggacatgcaa actttcaaag   1620
cagagcctcc cgagaagcca tctgccttcg agcctgccat tgaaatgcaa aagtctgttc   1680
caaataaagc cttggaattg aagaatgaac aaacattgag agcagatgag atactcccat   1740
cagaatccaa acaaaaggac tatgaagaaa gttcttggga ttctgagagt ctctgtgaga   1800
ctgtttcaca gaaggatgtg tgtttaccca aggctrcrca tcaaaaagaa atagataaaa   1860
taaatggaaa attagaagag tctcctgata atgatggttt tctgaaggct ccctgcagaa   1920
tgaaagtttc tattccaact aaagccttag aattgatgga catgcaaact ttcaaagcag   1980
agcctcccga gaagccatct gccttcgagc ctgccattga aatgcaaaag tctgttccaa   2040
ataaagcctt ggaattgaag aatgaacaaa cattgagagc agatcagatg ttcccttcag   2100
aatcaaaaca aaagaasgtt gaagaaaatt cttgggattc tgagagtctc cgtgagactg   2160
tttcacagaa ggatgtgtgt gtacccaagg ctacacatca aaaagaaatg gataaaataa   2220
gtggaaaatt agaagattca actagcctat caaaaatctt ggatacagtt cattcttgtg   2280
aaagagcaag ggaacttcaa aaagatcact gtgaacaacg tacaggaaaa atggaacaaa   2340
tgaaaaagaa gttttgtgta ctgaaaaaga aactgtcaga agcaaaagaa ataaaatcac   2400
agttagagaa ccaaaaagtt aaatgggaac aagagctctg cagtgtgaga ttgactttaa   2460
```

-continued

```
accaagaaga agagaagaga agaaatgccg atatattaaa tgaaaaaatt agggaagaat   2520

taggaagaat cgaagagcag cataggaaag agttagaagt gaaacaacaa cttgaacagg   2580

ctctcagaat acaagatata gaattgaaga gtgtagaaag taatttgaat caggtttctc   2640

acactcatga aaatgaaaat tatctcttac atgaaaattg catgttgaaa aaggaaattg   2700

ccatgctaaa actggaaata gccacactga aacaccaata ccaggaaaag gaaaataaat   2760

actttgagga cattaagatt ttaaaagaaa agaatgctga acttcagatg accctaaaac   2820

tgaaagagga atcattaact aaaagggcat ctcaatatag tgggcagctt aaagttctga   2880

tagctgagaa cacaatgctc acttctaaat tgaaggaaaa acaagacaaa gaaatactag   2940

aggcagaaat tgaatcacac catcctagac tggcttctgc tgtacaagac catgatcaaa   3000

ttgtgacatc aagaaaaagt caagaacctg ctttccacat tgcaggagat gcttgtttgc   3060

aaagaaaaat gaatgttgat gtgagtagta cgatatataa caatgaggtg ctccatcaac   3120

cactttctga agctcaaagg aaatccaaaa gcctaaaaat taatctcaat tatgcmggag   3180

atgctctaag agaaaataca ttggtttcag aacatgcaca aagagaccaa cgtgaaacac   3240

agtgtcaaat gaaggaagct gaacacatgt atcaaaacga acaagataat gtgaacaaac   3300

acactgaaca gcaggagtct ctagatcaga aattatttca actacaaagc aaaaatatgt   3360

ggcttcaaca gcaattagtt catgcacata agaaagctga caacaaaagc aagataacaa   3420

ttgatattca ttttcttgag aggaaaatgc aacatcatct cctaaaagag aaaaatgagg   3480

agatatttaa ttacaataac catttaaaaa accgtatata tcaatatgaa aaagagaaag   3540

cagaaacaga aaactcatga gagacaagca gtaagaaact tcttttggag aaacaacaga   3600

ccagatcttt actcacaact catgctagga ggccagtcct agcatcacct tatgttgaaa   3660

atcttaccaa tagtctgtgt caacagaata cttattttag aagaaaaatt catgatttct   3720

tcctgaagcc tacagacata aaataacagt gtgaagaatt acttgttcac gaattgcata   3780

aagctgcaca ggattcccat ctaccctgat gatgcagcag acatcattca atccaaccag   3840

aatctcgctc tgtcactcag gctgg                                         3865
```

<210> SEQ ID NO 475
<211> LENGTH: 1002
<212> TYPE: PRT
<213> ORGANISM: Homo sapien
<220> FEATURE:
<221> NAME/KEY: VARIANT
<222> LOCATION: (1)...(1002)
<223> OTHER INFORMATION: Xaa = Any Amino Acid

<400> SEQUENCE: 475

```
Met Ser Pro Ala Lys Glu Thr Ser Glu Lys Phe Thr Trp Ala Ala Lys
 1               5                  10                  15

Gly Arg Pro Arg Lys Ile Ala Trp Glu Lys Lys Glu Thr Pro Val Lys
            20                  25                  30

Thr Gly Cys Val Ala Arg Val Thr Ser Asn Lys Thr Lys Val Leu Glu
        35                  40                  45

Lys Gly Arg Ser Lys Met Ile Ala Cys Pro Thr Lys Glu Ser Ser Thr
    50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                85                  90                  95

Ala Lys Ile Gln Val Cys Ile Pro Glu Ser Ile Tyr Gln Lys Val Met
```

-continued

```
            100                 105                 110

Glu Ile Asn Arg Glu Val Glu Glu Pro Pro Lys Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Ser
        275                 280                 285

Ser Trp Asp Ser Glu Ser Leu Cys Glu Thr Val Ser Gln Lys Asp Val
    290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
        355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
        435                 440                 445

Gly Phe Leu Lys Ala Pro Cys Arg Met Lys Val Ser Ile Pro Thr Lys
    450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Glu Asn Ser Trp
        515                 520                 525
```

-continued

```
Asp Ser Glu Ser Leu Arg Glu Thr Val Ser Gln Lys Asp Val Cys Val
    530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
                565                 570                 575

Glu Arg Ala Arg Glu Leu Gln Lys Asp His Cys Glu Gln Arg Thr Gly
            580                 585                 590

Lys Met Glu Gln Met Lys Lys Lys Phe Cys Val Leu Lys Lys Lys Leu
        595                 600                 605

Ser Glu Ala Lys Glu Ile Lys Ser Gln Leu Glu Asn Gln Lys Val Lys
    610                 615                 620

Trp Glu Gln Glu Leu Cys Ser Val Arg Leu Thr Leu Asn Gln Glu Glu
625                 630                 635                 640

Glu Lys Arg Arg Asn Ala Asp Ile Leu Asn Glu Lys Ile Arg Glu Glu
                645                 650                 655

Leu Gly Arg Ile Glu Glu Gln His Arg Lys Glu Leu Glu Val Lys Gln
            660                 665                 670

Gln Leu Glu Gln Ala Leu Arg Ile Gln Asp Ile Glu Leu Lys Ser Val
        675                 680                 685

Glu Ser Asn Leu Asn Gln Val Ser His Thr His Glu Asn Glu Asn Tyr
    690                 695                 700

Leu Leu His Glu Asn Cys Met Leu Lys Lys Glu Ile Ala Met Leu Lys
705                 710                 715                 720

Leu Glu Ile Ala Thr Leu Lys His Gln Tyr Gln Glu Lys Glu Asn Lys
                725                 730                 735

Tyr Phe Glu Asp Ile Lys Ile Leu Lys Glu Lys Asn Ala Glu Leu Gln
            740                 745                 750

Met Thr Leu Lys Leu Lys Glu Glu Ser Leu Thr Lys Arg Ala Ser Gln
        755                 760                 765

Tyr Ser Gly Gln Leu Lys Val Leu Ile Ala Glu Asn Thr Met Leu Thr
    770                 775                 780

Ser Lys Leu Lys Glu Lys Gln Asp Lys Glu Ile Leu Glu Ala Glu Ile
785                 790                 795                 800

Glu Ser His His Pro Arg Leu Ala Ser Ala Val Gln Asp His Asp Gln
                805                 810                 815

Ile Val Thr Ser Arg Lys Ser Gln Glu Pro Ala Phe His Ile Ala Gly
            820                 825                 830

Asp Ala Cys Leu Gln Arg Lys Met Asn Val Asp Val Ser Ser Thr Ile
        835                 840                 845

Tyr Asn Asn Glu Val Leu His Gln Pro Leu Ser Glu Ala Gln Arg Lys
    850                 855                 860

Ser Lys Ser Leu Lys Ile Asn Leu Asn Tyr Ala Gly Asp Ala Leu Arg
865                 870                 875                 880

Glu Asn Thr Leu Val Ser Glu His Ala Gln Arg Asp Gln Arg Glu Thr
                885                 890                 895

Gln Cys Gln Met Lys Glu Ala Glu His Met Tyr Gln Asn Glu Gln Asp
            900                 905                 910

Asn Val Asn Lys His Thr Glu Gln Gln Glu Ser Leu Asp Gln Lys Leu
        915                 920                 925

Phe Gln Leu Gln Ser Lys Asn Met Trp Leu Gln Gln Gln Leu Val His
    930                 935                 940
```

-continued

Ala His Lys Lys Ala Asp Asn Lys Ser Lys Ile Thr Ile Asp Ile His
945 950 955 960

Phe Leu Glu Arg Lys Met Gln His His Leu Leu Lys Glu Lys Asn Glu
965 970 975

Glu Ile Phe Asn Tyr Asn Asn His Leu Lys Asn Arg Ile Tyr Gln Tyr
980 985 990

Glu Lys Glu Lys Ala Glu Thr Glu Asn Ser
995 1000

<210> SEQ ID NO 476
<211> LENGTH: 356
<212> TYPE: DNA
<213> ORGANISM: Homo sapien

<400> SEQUENCE: 476
aggtctgccg gaaatgttag gcaccccaac tcaagtccca ggccccaggc atctttcctg 60
ccctgccttg cttggcccat ccagtccagg cgcctggagc aagtgctcag ctacttctcc 120
tgcactttga aagacccctc ccactcctgg cctcacattt ctctgtgtga tcccccactt 180
ctgggctctg ccaccccaca gtgggaaagg ccaccctaga aagaagtccg ctggcaccca 240
taggaagggg cctcaggagc aggaagggcc aggaccagaa ccttgcccac ggcaactgcc 300
ttcctgcctc tccccttcct cctctgctct tgatctgtgt ttcaataaat taatgt 356

<210> SEQ ID NO 477
<211> LENGTH: 1876
<212> TYPE: DNA
<213> ORGANISM: Homo sapien

<400> SEQUENCE: 477
atgacctgcg gatcaggatt tggtgggcgc gccttcagct gcatctcggc ctgcgggccg 60
cgccccggcc gctgctgcat caccgccgcc ccctaccgtg gcatctcctg ctaccgcggc 120
ctcaccgggg gcttcggcag ccacagcgtg tgcggaggct ttcgggccgg ctcctgcgga 180
cgcagcttcg gctaccgctc cgggggcgtg tgcgggccca gtcccccatg catcaccacc 240
gtgtcggtca acgagagcct cctcacgccc ctcaacctgg agatcgaccc caacgcgcag 300
tgcgtgaagc aggaggagaa ggagcagatc aagtccctca acagcaggtt cgcggccttc 360
atcgacaagg tgcgcttcct ggagcagcag aacaaactgc tggagacaaa gctgcagttc 420
taccagaacc gcgagtgttg ccagagcaac ctggagcccc tgtttgaggg ctacatcgag 480
actctgcggc gggaggccga gtgcgtggag gccgacagcg ggaggctggc ctcagagctt 540
aaccacgtgc aggaggtgct ggagggctac aagaagaagt atgaggagga ggtttctctg 600
agagcaacag ctgagaacga gtttgtggct ctgaagaagg atgtggactg cgcctacctc 660
cgcaagtcag acctggaggc caacgtggag gccctgatcc aggagatcga cttcctgagg 720
cggctgtatg aggaggagat ccgcattctc cagtcgcaca tctcagacac ctccgtggtt 780
gtcaagctgg acaacagccg ggacctgaac atggactgca tcattgccga gattaaggca 840
cagtatgacg acattgtcac ccgcagccgg gccgaggccg agtcctggta ccgcagcaag 900
tgtgaggaga tgaaggccac ggtgatcagg cacggggaga ccctgcgccg caccaaggag 960
gagatcaatg agctgaaccg catgatccaa aggctgacgg ccgaggtgga gaatgccaag 1020
tgccagaact ccaagctgga ggccgcggtg gctcagtctg agcagcaggg tgaggcagcc 1080
ctcagtgatg cccgctgcaa gctggccgag ctggagggcg ccctgcagaa ggccaagcag 1140
gacatggcct gcctgatcag ggagtaccag gaggtgatga actccaagct gggcctggac 1200

```
atcgagatcg ccacctacag gcgcctgctg gagggcgagg agcagaggct atgtgaaggc   1260

attggggctg tgaatgtctg tgtcagcagc tcccggggcg gggtcgtgtg cggggacctc   1320

tgcgtgtcag gctcccggcc agtgactggc agtgtctgca gcgctccgtg caacgggaac   1380

gtggcggtga gcaccggcct gtgtgcgccc tgcggccaat tgaacaccac ctgcggaggg   1440

ggttcctgcg gcgtgggctc ctgtggtatc agctccctgg gtgtggggtc ttgcggcagc   1500

agctgccgga aatgttaggc accccaactc aagtcccagg ccccaggcat ctttcctgcc   1560

ctgccttgct tggcccatcc agtccaggcg cctggagcaa gtgctcagct acttctcctg   1620

cactttgaaa gacccctccc actcctggcc tcacatttct ctgtgtgatc cccccacttct  1680

gggctctgcc accccacagt gggaaaggcc accctagaaa gaagtccgct ggcacccata   1740

ggaaggggcc tcaggagcag gaagggccag gaccagaacc ttgcccacgg caactgcctt   1800

cctgcctctc cccttcctcc tctgctcttg atctgtgttt caataaatta atgtagccaa   1860

aaaaaaaaaa aaaaaa                                                   1876
```

<210> SEQ ID NO 478
<211> LENGTH: 505
<212> TYPE: PRT
<213> ORGANISM: Homo sapien

<400> SEQUENCE: 478

```
Met Thr Cys Gly Ser Gly Phe Gly Gly Arg Ala Phe Ser Cys Ile Ser
 1               5                  10                  15

Ala Cys Gly Pro Arg Pro Gly Arg Cys Cys Ile Thr Ala Ala Pro Tyr
            20                  25                  30

Arg Gly Ile Ser Cys Tyr Arg Gly Leu Thr Gly Gly Phe Gly Ser His
        35                  40                  45

Ser Val Cys Gly Gly Phe Arg Ala Gly Ser Cys Gly Arg Ser Phe Gly
    50                  55                  60

Tyr Arg Ser Gly Gly Val Cys Gly Pro Ser Pro Pro Cys Ile Thr Thr
65                  70                  75                  80

Val Ser Val Asn Glu Ser Leu Leu Thr Pro Leu Asn Leu Glu Ile Asp
                85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
    210                 215                 220

Leu Glu Ala Asn Val Glu Ala Leu Ile Gln Glu Ile Asp Phe Leu Arg
225                 230                 235                 240

Arg Leu Tyr Glu Glu Glu Ile Arg Ile Leu Gln Ser His Ile Ser Asp
```

-continued

```
            245                 250                 255

Thr Ser Val Val Val Lys Leu Asp Asn Ser Arg Asp Leu Asn Met Asp
            260                 265                 270

Cys Ile Ile Ala Glu Ile Lys Ala Gln Tyr Asp Asp Ile Val Thr Arg
        275                 280                 285

Ser Arg Ala Glu Ala Glu Ser Trp Tyr Arg Ser Lys Cys Glu Glu Met
    290                 295                 300

Lys Ala Thr Val Ile Arg His Gly Glu Thr Leu Arg Arg Thr Lys Glu
305                 310                 315                 320

Glu Ile Asn Glu Leu Asn Arg Met Ile Gln Arg Leu Thr Ala Glu Val
            325                 330                 335

Glu Asn Ala Lys Cys Gln Asn Ser Lys Leu Glu Ala Ala Val Ala Gln
            340                 345                 350

Ser Glu Gln Gln Gly Glu Ala Ala Leu Ser Asp Ala Arg Cys Lys Leu
        355                 360                 365

Ala Glu Leu Glu Gly Ala Leu Gln Lys Ala Lys Gln Asp Met Ala Cys
    370                 375                 380

Leu Ile Arg Glu Tyr Gln Glu Val Met Asn Ser Lys Leu Gly Leu Asp
385                 390                 395                 400

Ile Glu Ile Ala Thr Tyr Arg Arg Leu Leu Glu Gly Glu Glu Gln Arg
            405                 410                 415

Leu Cys Glu Gly Ile Gly Ala Val Asn Val Cys Val Ser Ser Ser Arg
            420                 425                 430

Gly Gly Val Val Cys Gly Asp Leu Cys Val Ser Gly Ser Arg Pro Val
        435                 440                 445

Thr Gly Ser Val Cys Ser Ala Pro Cys Asn Gly Asn Val Ala Val Ser
    450                 455                 460

Thr Gly Leu Cys Ala Pro Cys Gly Gln Leu Asn Thr Thr Cys Gly Gly
465                 470                 475                 480

Gly Ser Cys Gly Val Gly Ser Cys Gly Ile Ser Ser Leu Gly Val Gly
            485                 490                 495

Ser Cys Gly Ser Ser Cys Arg Lys Cys
            500                 505


<210> SEQ ID NO 479
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 479

ggtccattcc tttcctcgcg tngggggtttc tctgtgtcag cgagcctcgg tacactgatt      60

tccgatcaaa agaatcatca tctttacctt gacttttcag ggaattactg aactttcttc     120

tcagaagata gggcacagcc attgccttgg cctcacttga agggtctgca tttgggtcct     180

ctggtctctt gccaagtttc ccagccactc gagggagaaa t                         221


<210> SEQ ID NO 480
<211> LENGTH: 36
<212> TYPE: DNA
<213> ORGANISM: Artificial Sequence
<220> FEATURE:
<223> OTHER INFORMATION: PCR primer

<400> SEQUENCE: 480
```

-continued

```
cggcgaattc accatgggaa caagagctct gcagtg                              36


<210> SEQ ID NO 481
<211> LENGTH: 62
<212> TYPE: DNA
<213> ORGANISM: Artificial Sequence
<220> FEATURE:
<223> OTHER INFORMATION: PCR primer

<400> SEQUENCE: 481

cggcaagctt ttaatggtga tggtgatgat gtataacttc tgtttctgct ttctcttttt     60

ca                                                                   62


<210> SEQ ID NO 482
<211> LENGTH: 972
<212> TYPE: DNA
<213> ORGANISM: Homo sapiens

<400> SEQUENCE: 482

atgggaacaa gagctctgca gtgtgaggtt tctcacactc atgaaaatga aaattatctc     60

ttacatgaaa attgcatgtt gaaaaaggaa attgccatgc taaaactgga aatagccaca    120

ctgaaacacc aataccagga aaaggaaaat aaatactttg aggacattaa gattttaaaa    180

gaaaagaatg ctgaacttca gatgacccta aaactgaaag aggaatcatt aactaaaagg    240

gcatctcaat atagtgggca gcttaaagtt ctgatagctg agaacacaat gctcacttct    300

aaattgaagg aaaaacaaga caaagaaata ctagaggcag aaattgaatc acaccatcct    360

agactggctt ctgctgtaca agaccatgat caaattgtga catcaagaaa aagtcaagaa    420

cctgctttcc acattgcagg agatgcttgt ttgcaaagaa aaatgaatgt tgatgtgagt    480

agtacgatat ataacaatga ggtgctccat caaccacttt ctgaagctca aaggaaatcc    540

aaaagcctaa aaattaatct caattatgcc ggagatgctc taagagaaaa tacattggtt    600

tcagaacatg cacaaagaga ccaacgtgaa acacagtgtc aaatgaagga agctgaacac    660

atgtatcaaa acgaacaaga taatgtgaac aaacacactg aacagcagga gtctctagat    720

cagaaattat ttcaactaca aagcaaaaat atgtggcttc aacagcaatt agttcatgca    780

cataagaaag ctgacaacaa aagcaagata acaattgata ttcattttct tgagaggaaa    840

atgcaacatc atctcctaaa agagaaaaat gaggagatat ttaattacaa taaccattta    900

aaaaaccgta tatatcaata tgaaaaagag aaagcagaaa cagaagttat acatcatcac    960

catcaccatt aa                                                        972


<210> SEQ ID NO 483
<211> LENGTH: 323
<212> TYPE: PRT
<213> ORGANISM: Homo sapiens

<400> SEQUENCE: 483

Met Gly Thr Arg Ala Leu Gln Cys Glu Val Ser His Thr His Glu Asn
                  5                  10                  15

Glu Asn Tyr Leu Leu His Glu Asn Cys Met Leu Lys Lys Glu Ile Ala
             20                  25                  30

Met Leu Lys Leu Glu Ile Ala Thr Leu Lys His Gln Tyr Gln Glu Lys
         35                  40                  45

Glu Asn Lys Tyr Phe Glu Asp Ile Lys Ile Leu Lys Glu Lys Asn Ala
     50                  55                  60
```

-continued

```
Glu Leu Gln Met Thr Leu Lys Leu Lys Glu Glu Ser Leu Thr Lys Arg
 65                  70                  75                  80

Ala Ser Gln Tyr Ser Gly Gln Leu Lys Val Leu Ile Ala Glu Asn Thr
                 85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
        115                 120                 125

His Asp Gln Ile Val Thr Ser Arg Lys Ser Gln Glu Pro Ala Phe His
    130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
        195                 200                 205

Arg Glu Thr Gln Cys Gln Met Lys Glu Ala Glu His Met Tyr Gln Asn
    210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
        275                 280                 285

Lys Asn Glu Glu Ile Phe Asn Tyr Asn Asn His Leu Lys Asn Arg Ile
    290                 295                 300

Tyr Gln Tyr Glu Lys Glu Lys Ala Glu Thr Glu Val Ile His His His
305                 310                 315                 320

His His His


<210> SEQ ID NO 484
<211> LENGTH: 1518
<212> TYPE: DNA
<213> ORGANISM: Homo sapiens

<400> SEQUENCE: 484

atgacctgcg gatcaggatt tggtgggcgc gccttccgct gcatctcggc ctgcgggccg      60

cggcccggcc gctgctgcat caccgccgcc ccctaccgtg gcatctcctg ctaccgcggc     120

ctcaccgggg gcttcggcag ccacagcgtg tgcggaggct ttcgggccgg ctcctgcgga     180

cgcagcttcg gctaccgctc cgggggcgtg tgcgggccca gtcccccatg catcaccacc     240

gtgtcggtca acgagagcct cctcacgccc ctcaacctgg agatcgaccc caacgcgcag     300

tgcgtgaagc aggaggagaa ggagcagatc aagtccctca acagcaggtt cgcggccttc     360

atcgacaagg tgcgcttcct ggagcagcag aacaaactgc tggagacaaa gctgcagttc     420

taccagaacc gcgagtgttg ccagagcaac ctggagcccc tgtttgaggg ctacatcgag     480

actctgcggc gggaggccga gtgcgtggag gccgacagcg ggaggctggc ctcagagctt     540

aaccacgtgc aggaggtgct ggagggctac aagaagaagt atgaggagga ggtttctctg     600

agagcaacag ctgagaacga gtttgtggct ctgaagaagg atgtggactg cgcctacctc     660
```

-continued

```
cgcaagtcag acctggaggc caacgtggag gccctgatcc aggagatcga cttcctgagg    720

cggctgtatg aggaggagat ccgcattctc cagtcgcaca tctcagacac ctccgtggtt    780

gtcaagctgg acaacagccg ggacctgaac atggactgca tcattgccga gattaaggca    840

cagtatgacg acattgtcac ccgcagccgg gccgaggccg agtcctggta ccgcagcaag    900

tgtgaggaga tgaaggccac ggtgatcagg cacggggaga ccctgcgccg caccaaggag    960

gagatcaatg agctgaaccg catgatccaa aggctgacgg ccgaggtgga gaatgccaag   1020

tgccagaact ccaagctgga ggccgcggtg gcccagtctg agcagcaggg tgaggcagcc   1080

ctcagtgatg cccgctgcaa gctggccgag ctggagggcg ccctgcagaa ggccaagcag   1140

gacatggcct gcctgatcag ggagtaccag gaggtgatga actccaagct gggcctggac   1200

atcgagatcg ccacctacag gcgcctgctg gagggcgagg agcagaggct atgtgaaggc   1260

attggggctg tgaatgtctg tgtcagcagc tcccggggcg gggtcgtgtg cggggacctc   1320

tgcgtgtcag gctcccggcc agtgactggc agtgtctgca gcgctccgtg caacgggaac   1380

gtggcggtga gcaccggcct gtgtgcgccc tgcggccaat tgaacaccac ctgcggaggg   1440

ggttcctgcg gcgtgggctc ctgtggtatc agctccctgg gtgtggggtc ttgcggcagc   1500

agctgccgga aatgttag                                                 1518
```

<210> SEQ ID NO 485
<211> LENGTH: 505
<212> TYPE: PRT
<213> ORGANISM: Homo sapiens

<400> SEQUENCE: 485

```
Met Thr Cys Gly Ser Gly Phe Gly Gly Arg Ala Phe Arg Cys Ile Ser
                  5                  10                  15

Ala Cys Gly Pro Arg Pro Gly Arg Cys Cys Ile Thr Ala Ala Pro Tyr
             20                  25                  30

Arg Gly Ile Ser Cys Tyr Arg Gly Leu Thr Gly Gly Phe Gly Ser His
         35                  40                  45

Ser Val Cys Gly Gly Phe Arg Ala Gly Ser Cys Gly Arg Ser Phe Gly
     50                  55                  60

Tyr Arg Ser Gly Gly Val Cys Gly Pro Ser Pro Pro Cys Ile Thr Thr
 65                  70                  75                  80

Val Ser Val Asn Glu Ser Leu Leu Thr Pro Leu Asn Leu Glu Ile Asp
                 85                  90                  95

Pro Asn Ala Gln Cys Val Lys Gln Glu Glu Lys Glu Gln Ile Lys Ser
            100                 105                 110

Leu Asn Ser Arg Phe Ala Ala Phe Ile Asp Lys Val Arg Phe Leu Glu
        115                 120                 125

Gln Gln Asn Lys Leu Leu Glu Thr Lys Leu Gln Phe Tyr Gln Asn Arg
    130                 135                 140

Glu Cys Cys Gln Ser Asn Leu Glu Pro Leu Phe Glu Gly Tyr Ile Glu
145                 150                 155                 160

Thr Leu Arg Arg Glu Ala Glu Cys Val Glu Ala Asp Ser Gly Arg Leu
                165                 170                 175

Ala Ser Glu Leu Asn His Val Gln Glu Val Leu Glu Gly Tyr Lys Lys
            180                 185                 190

Lys Tyr Glu Glu Glu Val Ser Leu Arg Ala Thr Ala Glu Asn Glu Phe
        195                 200                 205

Val Ala Leu Lys Lys Asp Val Asp Cys Ala Tyr Leu Arg Lys Ser Asp
```

-continued

```
    210                 215                 220

Leu Glu Ala Asn Val Glu Ala Leu Ile Gln Glu Ile Asp Phe Leu Arg
225                 230                 235                 240

Arg Leu Tyr Glu Glu Glu Ile Arg Ile Leu Gln Ser His Ile Ser Asp
                245                 250                 255

Thr Ser Val Val Val Lys Leu Asp Asn Ser Arg Asp Leu Asn Met Asp
            260                 265                 270

Cys Ile Ile Ala Glu Ile Lys Ala Gln Tyr Asp Asp Ile Val Thr Arg
        275                 280                 285

Ser Arg Ala Glu Ala Glu Ser Trp Tyr Arg Ser Lys Cys Glu Glu Met
    290                 295                 300

Lys Ala Thr Val Ile Arg His Gly Glu Thr Leu Arg Arg Thr Lys Glu
305                 310                 315                 320

Glu Ile Asn Glu Leu Asn Arg Met Ile Gln Arg Leu Thr Ala Glu Val
                325                 330                 335

Glu Asn Ala Lys Cys Gln Asn Ser Lys Leu Glu Ala Ala Val Ala Gln
            340                 345                 350

Ser Glu Gln Gln Gly Glu Ala Ala Leu Ser Asp Ala Arg Cys Lys Leu
        355                 360                 365

Ala Glu Leu Glu Gly Ala Leu Gln Lys Ala Lys Gln Asp Met Ala Cys
    370                 375                 380

Leu Ile Arg Glu Tyr Gln Glu Val Met Asn Ser Lys Leu Gly Leu Asp
385                 390                 395                 400

Ile Glu Ile Ala Thr Tyr Arg Arg Leu Leu Glu Gly Glu Glu Gln Arg
                405                 410                 415

Leu Cys Glu Gly Ile Gly Ala Val Asn Val Cys Val Ser Ser Ser Arg
            420                 425                 430

Gly Gly Val Val Cys Gly Asp Leu Cys Val Ser Gly Ser Arg Pro Val
        435                 440                 445

Thr Gly Ser Val Cys Ser Ala Pro Cys Asn Gly Asn Val Ala Val Ser
    450                 455                 460

Thr Gly Leu Cys Ala Pro Cys Gly Gln Leu Asn Thr Thr Cys Gly Gly
465                 470                 475                 480

Gly Ser Cys Gly Val Gly Ser Cys Gly Ile Ser Ser Leu Gly Val Gly
                485                 490                 495

Ser Cys Gly Ser Ser Cys Arg Lys Cys
            500                 505


<210> SEQ ID NO 486
<211> LENGTH: 827
<212> TYPE: DNA
<213> ORGANISM: Homo sapiens

<400> SEQUENCE: 486

gcattctcca gtcgcacatc tcagacacct ccgtggttgt caagctggac aacagccggg     60

acctgaacat ggactgcatc attgccgaga ttaaggcaca gtatgacgac attgtcaccc    120

gcagccgggc cgaggccgag tcctggtacc gcagcaagtg tgaggagatg aaggccacgg    180

tgatcaggca cggggagacc ctgcgccgca ccaaggagga gatcaatgag ctgaaccgca    240

tgatccaaag gctgacggcc gaggtggaga atgccaagtg ccagaactcc aagctggagg    300

ccgcggtggc ccagtctgag cagcagggtg aggcagccct cagtgatgcc cgctgcaagc    360

tggccgagct ggagggcgcc ctgcagaagg ccaagcagga catggcctgc ctgatcaggg    420

agtaccagga ggtgatgaac tccaagctgg gcctggacat cgagatcgcc acctacaggc    480
```

-continued gcctgctgga gggcgaggag cagaggctat gtgaaggcat tggggctgtg aatgtctgtg 540
tcagcagctc ccggggcggg gtcgtgtgcg gggacctctg cgtgtcaggc tcccggccag 600
tgactggcag tgtctgcagc gctccgtgca acgggaacgt ggcggtgagc accggcctgt 660
gtgcgccctg cggccaattg aacaccacct gcggaggggg ttcctgcggc gtgggctcct 720
gtggtatcag ctccctgggt gtggggtctt gcggcagcag ctgccggaaa tgttaggcac 780
cccaactcaa gtcccaggcc ccaggcatct ttcctgccct gccttgc 827

<210> SEQ ID NO 487
<211> LENGTH: 235
<212> TYPE: PRT
<213> ORGANISM: Homo sapiens

<400> SEQUENCE: 487

```
Met Asp Cys Ile Ile Ala Glu Ile Lys Ala Gln Tyr Asp Asp Ile Val
                  5                  10                  15

Thr Arg Ser Arg Ala Glu Ala Glu Ser Trp Tyr Arg Ser Lys Cys Glu
             20                  25                  30

Glu Met Lys Ala Thr Val Ile Arg His Gly Glu Thr Leu Arg Arg Thr
         35                  40                  45

Lys Glu Glu Ile Asn Glu Leu Asn Arg Met Ile Gln Arg Leu Thr Ala
     50                  55                  60

Glu Val Glu Asn Ala Lys Cys Gln Asn Ser Lys Leu Glu Ala Ala Val
 65                  70                  75                  80

Ala Gln Ser Glu Gln Gln Gly Glu Ala Ala Leu Ser Asp Ala Arg Cys
                 85                  90                  95

Lys Leu Ala Glu Leu Glu Gly Ala Leu Gln Lys Ala Lys Gln Asp Met
            100                 105                 110

Ala Cys Leu Ile Arg Glu Tyr Gln Glu Val Met Asn Ser Lys Leu Gly
        115                 120                 125

Leu Asp Ile Glu Ile Ala Thr Tyr Arg Arg Leu Leu Glu Gly Glu Glu
    130                 135                 140

Gln Arg Leu Cys Glu Gly Ile Gly Ala Val Asn Val Cys Val Ser Ser
145                 150                 155                 160

Ser Arg Gly Gly Val Val Cys Gly Asp Leu Cys Val Ser Gly Ser Arg
                165                 170                 175

Pro Val Thr Gly Ser Val Cys Ser Ala Pro Cys Asn Gly Asn Val Ala
            180                 185                 190

Val Ser Thr Gly Leu Cys Ala Pro Cys Gly Gln Leu Asn Thr Thr Cys
        195                 200                 205

Gly Gly Gly Ser Cys Gly Val Gly Ser Cys Gly Ile Ser Ser Leu Gly
    210                 215                 220

Val Gly Ser Cys Gly Ser Ser Cys Arg Lys Cys
225                 230                 235
```

<210> SEQ ID NO 488
<211> LENGTH: 9
<212> TYPE: PRT
<213> ORGANISM: Homo sapiens

<400> SEQUENCE: 488

```
Ser Leu Thr Lys Arg Ala Ser Gln Tyr
                  5
```

<210> SEQ ID NO 489

-continued

<211> LENGTH: 27
<212> TYPE: DNA
<213> ORGANISM: Homo sapiens

<400> SEQUENCE: 489
tcattaacta aaagggcatc tcaatat 27

<210> SEQ ID NO 490
<211> LENGTH: 3288
<212> TYPE: DNA
<213> ORGANISM: Homo sapiens

<400> SEQUENCE: 490
atgaagttgc tgatggtcct catgctggcg gccctctccc agcactgcta cgcaggctct 60
ggctgcccct tattggagaa tgtgatttcc aagacaatca atccacaagt gtctaagact 120
gaatacaaag aacttcttca agagttcata gacgacaatg ccactacaaa tgccatagat 180
gaattgaagg aatgttttct taaccaaacg gatgaaactc tgagcaatgt tgaggtgttt 240
atgcaattaa tatatgacag cagtctttgt gatttattta tgagtcccgc aaaagaaaca 300
tctgagaaat ttacgtgggc agcaaaagga agacctagga agatcgcatg ggagaaaaaa 360
gaaacacctg taaagactgg atgcgtggca agagtaacat ctaataaaac taaagttttg 420
gaaaaaggaa gatctaagat gattgcatgt cctacaaaag aatcatctac aaaagcaagt 480
gccaatgatc agaggttccc atcagaatcc aaacaagagg aagatgaaga atattcttgt 540
gattctcgga gtctctttga gagttctgca aagattcaag tgtgtatacc tgagtctata 600
tatcaaaaag taatggagat aaatagagaa gtagaagagc ctcctaagaa gccatctgcc 660
ttcaagcctg ccattgaaat gcaaaactct gttccaaata aagcctttga attgaagaat 720
gaacaaacat tgagagcaga tccgatgttc ccaccagaat ccaaacaaaa ggactatgaa 780
gaaaattctt gggattctga gagtctctgt gagactgttt cacagaagga tgtgtgttta 840
cccaaggcta cacatcaaaa agaaatagat aaaataaatg gaaaattaga agagtctcct 900
aataaagatg gtcttctgaa ggctacctgc ggaatgaaag tttctattcc aactaaagcc 960
ttagaattga aggacatgca aactttcaaa gcagagcctc cggggaagcc atctgccttc 1020
gagcctgcca ctgaaatgca aaagtctgtc ccaaataaag ccttggaatt gaaaaatgaa 1080
caaacattga gagcagatga gatactccca tcagaatcca aacaaaagga ctatgaagaa 1140
agttcttggg attctgagag tctctgtgag actgtttcac agaaggatgt gtgtttaccc 1200
aaggctrcrc atcaaaaaga aatagataaa ataaatggaa aattagaagg gtctcctgtt 1260
aaagatggtc ttctgaaggc taactgcgga atgaaagttt ctattccaac taaagcctta 1320
gaattgatgg acatgcaaac tttcaaagca gagcctcccg agaagccatc tgccttcgag 1380
cctgccattg aaatgcaaaa gtctgttcca aataaagcct tggaattgaa gaatgaacaa 1440
acattgagag cagatgagat actcccatca gaatccaaac aaaaggacta tgaagaaagt 1500
tcttgggatt ctgagagtct ctgtgagact gtttcacaga aggatgtgtg tttacccaag 1560
gctrcrcatc aaaaagaaat agataaaata aatggaaaat tagaagagtc tcctgataat 1620
gatggttttc tgaaggctcc ctgcagaatg aaagtttcta ttccaactaa agccttagaa 1680
ttgatggaca tgcaaacttt caaagcagag cctcccgaga agccatctgc cttcgagcct 1740
gccattgaaa tgcaaaagtc tgttccaaat aaagccttgg aattgaagaa tgaacaaaca 1800
ttgagagcag atcagatgtt cccttcagaa tcaaaacaaa agaasgttga agaaaattct 1860
tgggattctg agagtctccg tgagactgtt tcacagaagg atgtgtgtgt acccaaggct 1920

-continued acacatcaaa aagaaatgga taaaataagt ggaaaattag aagattcaac tagcctatca 1980
aaaatcttgg atacagttca ttcttgtgaa agagcaaggg aacttcaaaa agatcactgt 2040
gaacaacgta caggaaaaat ggaacaaatg aaaaagaagt tttgtgtact gaaaaagaaa 2100
ctgtcagaag caaaagaaat aaaatcacag ttagagaacc aaaaagttaa atgggaacaa 2160
gagctctgca gtgtgagatt gactttaaac caagaagaag agaagagaag aaatgccgat 2220
atattaaatg aaaaaattag ggaagaatta ggaagaatcg aagagcagca taggaaagag 2280
ttagaagtga aacaacaact tgaacaggct ctcagaatac aagatataga attgaagagt 2340
gtagaaagta atttgaatca ggtttctcac actcatgaaa atgaaaatta tctcttacat 2400
gaaaattgca tgttgaaaaa ggaaattgcc atgctaaaac tggaaatagc cacactgaaa 2460
caccaatacc aggaaaagga aaataaatac tttgaggaca ttaagatttt aaaagaaaag 2520
aatgctgaac ttcagatgac cctaaaactg aaagaggaat cattaactaa aagggcatct 2580
caatatagtg ggcagcttaa agttctgata gctgagaaca caatgctcac ttctaaattg 2640
aaggaaaaac aagacaaaga aatactagag gcagaaattg aatcacacca tcctagactg 2700
gcttctgctg tacaagacca tgatcaaatt gtgacatcaa gaaaaagtca agaacctgct 2760
ttccacattg caggagatgc ttgtttgcaa agaaaaatga atgttgatgt gagtagtacg 2820
atatataaca atgaggtgct ccatcaacca ctttctgaag ctcaaaggaa atccaaaagc 2880
ctaaaaatta atctcaatta tgcmggagat gctctaagag aaaatacatt ggtttcagaa 2940
catgcacaaa gagaccaacg tgaaacacag tgtcaaatga aggaagctga acacatgtat 3000
caaaacgaac aagataatgt gaacaaacac actgaacagc aggagtctct agatcagaaa 3060
ttatttcaac tacaaagcaa aaatatgtgg cttcaacagc aattagttca tgcacataag 3120
aaagctgaca acaaaagcaa gataacaatt gatattcatt ttcttgagag gaaaatgcaa 3180
catcatctcc taaaagagaa aaatgaggag atatttaatt acaataacca tttaaaaaac 3240
cgtatatatc aatatgaaaa agagaaagca gaaacagaaa actcatga 3288

<210> SEQ ID NO 491
<211> LENGTH: 2232
<212> TYPE: DNA
<213> ORGANISM: Homo sapiens

<400> SEQUENCE: 491
atgaagttgc tgatggtcct catgctggcg gccctctccc agcactgcta cgcaggctct 60
ggctgcccct tattggagaa tgtgatttcc aagacaatca atccacaagt gtctaagact 120
gaatacaaag aacttcttca agagttcata gacgacaatg ccactacaaa tgccatagat 180
gaattgaagg aatgttttct taaccaaacg gatgaaactc tgagcaatgt tgaggtgttt 240
atgcaattaa tatatgacag cagtctttgt gatttattta tgagtcccgc aaaagaaaca 300
tctgagaaat ttacgtgggc agcaaaagga agacctagga agatcgcatg ggagaaaaaa 360
gaaacacctg taaagactgg atgcgtggca agagtaacat ctaataaaac taaagttttg 420
gaaaaaggaa gatctaagat gattgcatgt cctacaaaag aatcatctac aaaagcaagt 480
gccaatgatc agaggttccc atcagaatcc aaacaagagg aagatgaaga atattcttgt 540
gattctcgga gtctctttga gagttctgca aagattcaag tgtgtatacc tgagtctata 600
tatcaaaaag taatggagat aaatagagaa gtagaagagc ctcctaagaa gccatctgcc 660
ttcaagcctg ccattgaaat gcaaaactct gttccaaata aagcctttga attgaagaat 720

-continued

```
gaacaaacat tgagagcaga tccgatgttc ccaccagaat ccaaacaaaa ggactatgaa    780

gaaaattctt gggattctga gagtctctgt gagactgttt cacagaagga tgtgtgttta    840

cccaaggcta cacatcaaaa agaaatagat aaaataaatg gaaaattaga agagtctcct    900

aataaagatg gtcttctgaa ggctacctgc ggaatgaaag tttctattcc aactaaagcc    960

ttagaattga aggacatgca aactttcaaa gcagagcctc cggggaagcc atctgccttc   1020

gagcctgcca ctgaaatgca aaagtctgtc ccaaataaag ccttggaatt gaaaaatgaa   1080

caaacattga gagcagatga gatactccca tcagaatcca aacaaaagga ctatgaagaa   1140

agttcttggg attctgagag tctctgtgag actgtttcac agaaggatgt gtgtttaccc   1200

aaggctrcrc atcaaaaaga aatagataaa ataaatggaa aattagaagg gtctcctgtt   1260

aaagatggtc ttctgaaggc taactgcgga atgaaagttt ctattccaac taaagcctta   1320

gaattgatgg acatgcaaac tttcaaagca gagcctcccg agaagccatc tgccttcgag   1380

cctgccattg aaatgcaaaa gtctgttcca aataaagcct tggaattgaa gaatgaacaa   1440

acattgagag cagatgagat actcccatca gaatccaaac aaaaggacta tgaagaaagt   1500

tcttgggatt ctgagagtct ctgtgagact gtttcacaga aggatgtgtg tttacccaag   1560

gctrcrcatc aaaaagaaat agataaaata aatggaaaat tagaagagtc tcctgataat   1620

gatggttttc tgaaggctcc ctgcagaatg aaagtttcta ttccaactaa agccttagaa   1680

ttgatggaca tgcaaacttt caaagcagag cctcccgaga agccatctgc cttcgagcct   1740

gccattgaaa tgcaaaagtc tgttccaaat aaagccttgg aattgaagaa tgaacaaaca   1800

ttgagagcag atcagatgtt cccttcagaa tcaaaacaaa agaasgttga agaaaattct   1860

tgggattctg agagtctccg tgagactgtt tcacagaagg atgtgtgtgt acccaaggct   1920

acacatcaaa aagaaatgga taaaataagt ggaaaattag aagattcaac tagcctatca   1980

aaaatcttgg atacagttca ttcttgtgaa agagcaaggg aacttcaaaa agatcactgt   2040

gaacaacgta caggaaaaat ggaacaaatg aaaaagaagt tttgtgtact gaaaaagaaa   2100

ctgtcagaag caaaagaaat aaaatcacag ttagagaacc aaaaagttaa atgggaacaa   2160

gagctctgca gtgtgaggtt tctcacactc atgaaaatga aaattatctc ttacatgaaa   2220

attgcatgtt ga                                                       2232
```

<210> SEQ ID NO 492
<211> LENGTH: 1233
<212> TYPE: DNA
<213> ORGANISM: Homo sapiens

<400> SEQUENCE: 492

```
atgaagttgc tgatggtcct catgctggcg gccctctccc agcactgcta cgcaggctct     60

ggctgcccct tattggagaa tgtgatttcc aagacaatca atccacaagt gtctaagact    120

gaatacaaag aacttcttca agagttcata gacgacaatg ccactacaaa tgccatagat    180

gaattgaagg aatgttttct taaccaaacg gatgaaactc tgagcaatgt tgaggtgttt    240

atgcaattaa tatatgacag cagtctttgt gatttattta tgggaacaag agctctgcag    300

tgtgaggttt ctcacactca tgaaaatgaa aattatctct tacatgaaaa ttgcatgttg    360

aaaaaggaaa ttgccatgct aaaactggaa atagccacac tgaaacacca ataccaggaa    420

aaggaaaata aatactttga ggacattaag attttaaaag aaaagaatgc tgaacttcag    480

atgaccctaa aactgaaaga ggaatcatta actaaaaggg catctcaata tagtgggcag    540

cttaaagttc tgatagctga gaacacaatg ctcacttcta aattgaagga aaaacaagac    600
```

-continued

```
aaagaaatac tagaggcaga aattgaatca caccatccta gactggcttc tgctgtacaa    660

gaccatgatc aaattgtgac atcaagaaaa agtcaagaac ctgctttcca cattgcagga    720

gatgcttgtt tgcaaagaaa aatgaatgtt gatgtgagta gtacgatata taacaatgag    780

gtgctccatc aaccactttc tgaagctcaa aggaaatcca aaagcctaaa aattaatctc    840

aattatgccg gagatgctct aagagaaaat acattggttt cagaacatgc acaaagagac    900

caacgtgaaa cacagtgtca aatgaaggaa gctgaacaca tgtatcaaaa cgaacaagat    960

aatgtgaaca aacacactga acagcaggag tctctagatc agaaattatt tcaactacaa   1020

agcaaaaata tgtggcttca acagcaatta gttcatgcac ataagaaagc tgacaacaaa   1080

agcaagataa caattgatat tcattttctt gagaggaaaa tgcaacatca tctcctaaaa   1140

gagaaaaatg aggagatatt taattacaat aaccatttaa aaaaccgtat atatcaatat   1200

gaaaaagaga aagcagaaac agaagttata taa                                1233
```

```
<210> SEQ ID NO 493
<211> LENGTH: 1095
<212> TYPE: PRT
<213> ORGANISM: Homo sapiens
<220> FEATURE:
<221> NAME/KEY: variant
<222> LOCATION: (1)...(1095)
<223> OTHER INFORMATION: Xaa = Any amino acid

<400> SEQUENCE: 493

Met Lys Leu Leu Met Val Leu Met Leu Ala Ala Leu Ser Gln His Cys
                5                   10                  15

Tyr Ala Gly Ser Gly Cys Pro Leu Leu Glu Asn Val Ile Ser Lys Thr
            20                  25                  30

Ile Asn Pro Gln Val Ser Lys Thr Glu Tyr Lys Glu Leu Leu Gln Glu
        35                  40                  45

Phe Ile Asp Asp Asn Ala Thr Thr Asn Ala Ile Asp Glu Leu Lys Glu
    50                  55                  60

Cys Phe Leu Asn Gln Thr Asp Glu Thr Leu Ser Asn Val Glu Val Phe
65                  70                  75                  80

Met Gln Leu Ile Tyr Asp Ser Ser Leu Cys Asp Leu Phe Met Ser Pro
                85                  90                  95

Ala Lys Glu Thr Ser Glu Lys Phe Thr Trp Ala Ala Lys Gly Arg Pro
            100                 105                 110

Arg Lys Ile Ala Trp Glu Lys Lys Glu Thr Pro Val Lys Thr Gly Cys
        115                 120                 125

Val Ala Arg Val Thr Ser Asn Lys Thr Lys Val Leu Glu Lys Gly Arg
    130                 135                 140

Ser Lys Met Ile Ala Cys Pro Thr Lys Glu Ser Ser Thr Lys Ala Ser
145                 150                 155                 160

Ala Asn Asp Gln Arg Phe Pro Ser Glu Ser Lys Gln Glu Glu Asp Glu
                165                 170                 175

Glu Tyr Ser Cys Asp Ser Arg Ser Leu Phe Glu Ser Ser Ala Lys Ile
            180                 185                 190

Gln Val Cys Ile Pro Glu Ser Ile Tyr Gln Lys Val Met Glu Ile Asn
        195                 200                 205

Arg Glu Val Glu Glu Pro Pro Lys Lys Pro Ser Ala Phe Lys Pro Ala
    210                 215                 220

Ile Glu Met Gln Asn Ser Val Pro Asn Lys Ala Phe Glu Leu Lys Asn
225                 230                 235                 240
```

-continued

```
Glu Gln Thr Leu Arg Ala Asp Pro Met Phe Pro Pro Glu Ser Lys Gln
                245                 250                 255

Lys Asp Tyr Glu Glu Asn Ser Trp Asp Ser Glu Ser Leu Cys Glu Thr
            260                 265                 270

Val Ser Gln Lys Asp Val Cys Leu Pro Lys Ala Thr His Gln Lys Glu
        275                 280                 285

Ile Asp Lys Ile Asn Gly Lys Leu Glu Glu Ser Pro Asn Lys Asp Gly
    290                 295                 300

Leu Leu Lys Ala Thr Cys Gly Met Lys Val Ser Ile Pro Thr Lys Ala
305                 310                 315                 320

Leu Glu Leu Lys Asp Met Gln Thr Phe Lys Ala Glu Pro Pro Gly Lys
                325                 330                 335

Pro Ser Ala Phe Glu Pro Ala Thr Glu Met Gln Lys Ser Val Pro Asn
            340                 345                 350

Lys Ala Leu Glu Leu Lys Asn Glu Gln Thr Leu Arg Ala Asp Glu Ile
        355                 360                 365

Leu Pro Ser Glu Ser Lys Gln Lys Asp Tyr Glu Glu Ser Ser Trp Asp
    370                 375                 380

Ser Glu Ser Leu Cys Glu Thr Val Ser Gln Lys Asp Val Cys Leu Pro
385                 390                 395                 400

Lys Ala Xaa His Gln Lys Glu Ile Asp Lys Ile Asn Gly Lys Leu Glu
                405                 410                 415

Gly Ser Pro Val Lys Asp Gly Leu Leu Lys Ala Asn Cys Gly Met Lys
            420                 425                 430

Val Ser Ile Pro Thr Lys Ala Leu Glu Leu Met Asp Met Gln Thr Phe
        435                 440                 445

Lys Ala Glu Pro Pro Glu Lys Pro Ser Ala Phe Glu Pro Ala Ile Glu
    450                 455                 460

Met Gln Lys Ser Val Pro Asn Lys Ala Leu Glu Leu Lys Asn Glu Gln
465                 470                 475                 480

Thr Leu Arg Ala Asp Glu Ile Leu Pro Ser Glu Ser Lys Gln Lys Asp
                485                 490                 495

Tyr Glu Glu Ser Ser Trp Asp Ser Glu Ser Leu Cys Glu Thr Val Ser
            500                 505                 510

Gln Lys Asp Val Cys Leu Pro Lys Ala Xaa His Gln Lys Glu Ile Asp
        515                 520                 525

Lys Ile Asn Gly Lys Leu Glu Glu Ser Pro Asp Asn Asp Gly Phe Leu
    530                 535                 540

Lys Ala Pro Cys Arg Met Lys Val Ser Ile Pro Thr Lys Ala Leu Glu
545                 550                 555                 560

Leu Met Asp Met Gln Thr Phe Lys Ala Glu Pro Pro Glu Lys Pro Ser
                565                 570                 575

Ala Phe Glu Pro Ala Ile Glu Met Gln Lys Ser Val Pro Asn Lys Ala
            580                 585                 590

Leu Glu Leu Lys Asn Glu Gln Thr Leu Arg Ala Asp Gln Met Phe Pro
        595                 600                 605

Ser Glu Ser Lys Gln Lys Xaa Val Glu Glu Asn Ser Trp Asp Ser Glu
    610                 615                 620

Ser Leu Arg Glu Thr Val Ser Gln Lys Asp Val Cys Val Pro Lys Ala
625                 630                 635                 640

Thr His Gln Lys Glu Met Asp Lys Ile Ser Gly Lys Leu Glu Asp Ser
                645                 650                 655
```

-continued

Thr Ser Leu Ser Lys Ile Leu Asp Thr Val His Ser Cys Glu Arg Ala
660 665 670

Arg Glu Leu Gln Lys Asp His Cys Glu Gln Arg Thr Gly Lys Met Glu
675 680 685

Gln Met Lys Lys Lys Phe Cys Val Leu Lys Lys Lys Leu Ser Glu Ala
690 695 700

Lys Glu Ile Lys Ser Gln Leu Glu Asn Gln Lys Val Lys Trp Glu Gln
705 710 715 720

Glu Leu Cys Ser Val Arg Leu Thr Leu Asn Gln Glu Glu Glu Lys Arg
725 730 735

Arg Asn Ala Asp Ile Leu Asn Glu Lys Ile Arg Glu Glu Leu Gly Arg
740 745 750

Ile Glu Glu Gln His Arg Lys Glu Leu Glu Val Lys Gln Gln Leu Glu
755 760 765

Gln Ala Leu Arg Ile Gln Asp Ile Glu Leu Lys Ser Val Glu Ser Asn
770 775 780

Leu Asn Gln Val Ser His Thr His Glu Asn Glu Asn Tyr Leu Leu His
785 790 795 800

Glu Asn Cys Met Leu Lys Lys Glu Ile Ala Met Leu Lys Leu Glu Ile
805 810 815

Ala Thr Leu Lys His Gln Tyr Gln Glu Lys Glu Asn Lys Tyr Phe Glu
820 825 830

Asp Ile Lys Ile Leu Lys Glu Lys Asn Ala Glu Leu Gln Met Thr Leu
835 840 845

Lys Leu Lys Glu Glu Ser Leu Thr Lys Arg Ala Ser Gln Tyr Ser Gly
850 855 860

Gln Leu Lys Val Leu Ile Ala Glu Asn Thr Met Leu Thr Ser Lys Leu
865 870 875 880

Lys Glu Lys Gln Asp Lys Glu Ile Leu Glu Ala Glu Ile Glu Ser His
885 890 895

His Pro Arg Leu Ala Ser Ala Val Gln Asp His Asp Gln Ile Val Thr
900 905 910

Ser Arg Lys Ser Gln Glu Pro Ala Phe His Ile Ala Gly Asp Ala Cys
915 920 925

Leu Gln Arg Lys Met Asn Val Asp Val Ser Ser Thr Ile Tyr Asn Asn
930 935 940

Glu Val Leu His Gln Pro Leu Ser Glu Ala Gln Arg Lys Ser Lys Ser
945 950 955 960

Leu Lys Ile Asn Leu Asn Tyr Ala Gly Asp Ala Leu Arg Glu Asn Thr
965 970 975

Leu Val Ser Glu His Ala Gln Arg Asp Gln Arg Glu Thr Gln Cys Gln
980 985 990

Met Lys Glu Ala Glu His Met Tyr Gln Asn Glu Gln Asp Asn Val Asn
995 1000 1005

Lys His Thr Glu Gln Gln Glu Ser Leu Asp Gln Lys Leu Phe Gln Leu
1010 1015 1020

Gln Ser Lys Asn Met Trp Leu Gln Gln Gln Leu Val His Ala His Lys
1025 1030 1035 1040

Lys Ala Asp Asn Lys Ser Lys Ile Thr Ile Asp Ile His Phe Leu Glu
1045 1050 1055

Arg Lys Met Gln His His Leu Leu Lys Glu Lys Asn Glu Glu Ile Phe
1060 1065 1070

Asn Tyr Asn Asn His Leu Lys Asn Arg Ile Tyr Gln Tyr Glu Lys Glu

-continued

```
        1075                1080                1085

Lys Ala Glu Thr Glu Asn Ser
    1090                1095


<210> SEQ ID NO 494
<211> LENGTH: 743
<212> TYPE: PRT
<213> ORGANISM: Homo sapiens
<220> FEATURE:
<221> NAME/KEY: variant
<222> LOCATION: (1)...(743)
<223> OTHER INFORMATION: Xaa = Any amino acid

<400> SEQUENCE: 494

Met Lys Leu Leu Met Val Leu Met Leu Ala Ala Leu Ser Gln His Cys
                  5                  10                  15

Tyr Ala Gly Ser Gly Cys Pro Leu Leu Glu Asn Val Ile Ser Lys Thr
             20                  25                  30

Ile Asn Pro Gln Val Ser Lys Thr Glu Tyr Lys Glu Leu Leu Gln Glu
        35                  40                  45

Phe Ile Asp Asp Asn Ala Thr Thr Asn Ala Ile Asp Glu Leu Lys Glu
     50                  55                  60

Cys Phe Leu Asn Gln Thr Asp Glu Thr Leu Ser Asn Val Glu Val Phe
 65                  70                  75                  80

Met Gln Leu Ile Tyr Asp Ser Ser Leu Cys Asp Leu Phe Met Ser Pro
                 85                  90                  95

Ala Lys Glu Thr Ser Glu Lys Phe Thr Trp Ala Ala Lys Gly Arg Pro
            100                 105                 110

Arg Lys Ile Ala Trp Glu Lys Lys Glu Thr Pro Val Lys Thr Gly Cys
        115                 120                 125

Val Ala Arg Val Thr Ser Asn Lys Thr Lys Val Leu Glu Lys Gly Arg
    130                 135                 140

Ser Lys Met Ile Ala Cys Pro Thr Lys Glu Ser Ser Thr Lys Ala Ser
145                 150                 155                 160

Ala Asn Asp Gln Arg Phe Pro Ser Glu Ser Lys Gln Glu Glu Asp Glu
                165                 170                 175

Glu Tyr Ser Cys Asp Ser Arg Ser Leu Phe Glu Ser Ser Ala Lys Ile
            180                 185                 190

Gln Val Cys Ile Pro Glu Ser Ile Tyr Gln Lys Val Met Glu Ile Asn
        195                 200                 205

Arg Glu Val Glu Glu Pro Pro Lys Lys Pro Ser Ala Phe Lys Pro Ala
    210                 215                 220

Ile Glu Met Gln Asn Ser Val Pro Asn Lys Ala Phe Glu Leu Lys Asn
225                 230                 235                 240

Glu Gln Thr Leu Arg Ala Asp Pro Met Phe Pro Pro Glu Ser Lys Gln
                245                 250                 255

Lys Asp Tyr Glu Glu Asn Ser Trp Asp Ser Glu Ser Leu Cys Glu Thr
            260                 265                 270

Val Ser Gln Lys Asp Val Cys Leu Pro Lys Ala Thr His Gln Lys Glu
        275                 280                 285

Ile Asp Lys Ile Asn Gly Lys Leu Glu Glu Ser Pro Asn Lys Asp Gly
    290                 295                 300

Leu Leu Lys Ala Thr Cys Gly Met Lys Val Ser Ile Pro Thr Lys Ala
305                 310                 315                 320

Leu Glu Leu Lys Asp Met Gln Thr Phe Lys Ala Glu Pro Pro Gly Lys
                325                 330                 335
```

-continued

```
Pro Ser Ala Phe Glu Pro Ala Thr Glu Met Gln Lys Ser Val Pro Asn
            340                 345                 350

Lys Ala Leu Glu Leu Lys Asn Glu Gln Thr Leu Arg Ala Asp Glu Ile
        355                 360                 365

Leu Pro Ser Glu Ser Lys Gln Lys Asp Tyr Glu Glu Ser Ser Trp Asp
    370                 375                 380

Ser Glu Ser Leu Cys Glu Thr Val Ser Gln Lys Asp Val Cys Leu Pro
385                 390                 395                 400

Lys Ala Xaa His Gln Lys Glu Ile Asp Lys Ile Asn Gly Lys Leu Glu
                405                 410                 415

Gly Ser Pro Val Lys Asp Gly Leu Leu Lys Ala Asn Cys Gly Met Lys
            420                 425                 430

Val Ser Ile Pro Thr Lys Ala Leu Glu Leu Met Asp Met Gln Thr Phe
        435                 440                 445

Lys Ala Glu Pro Pro Glu Lys Pro Ser Ala Phe Glu Pro Ala Ile Glu
    450                 455                 460

Met Gln Lys Ser Val Pro Asn Lys Ala Leu Glu Leu Lys Asn Glu Gln
465                 470                 475                 480

Thr Leu Arg Ala Asp Glu Ile Leu Pro Ser Glu Ser Lys Gln Lys Asp
                485                 490                 495

Tyr Glu Glu Ser Ser Trp Asp Ser Glu Ser Leu Cys Glu Thr Val Ser
            500                 505                 510

Gln Lys Asp Val Cys Leu Pro Lys Ala Xaa His Gln Lys Glu Ile Asp
        515                 520                 525

Lys Ile Asn Gly Lys Leu Glu Glu Ser Pro Asp Asn Asp Gly Phe Leu
    530                 535                 540

Lys Ala Pro Cys Arg Met Lys Val Ser Ile Pro Thr Lys Ala Leu Glu
545                 550                 555                 560

Leu Met Asp Met Gln Thr Phe Lys Ala Glu Pro Pro Glu Lys Pro Ser
                565                 570                 575

Ala Phe Glu Pro Ala Ile Glu Met Gln Lys Ser Val Pro Asn Lys Ala
            580                 585                 590

Leu Glu Leu Lys Asn Glu Gln Thr Leu Arg Ala Asp Gln Met Phe Pro
        595                 600                 605

Ser Glu Ser Lys Gln Lys Xaa Val Glu Glu Asn Ser Trp Asp Ser Glu
    610                 615                 620

Ser Leu Arg Glu Thr Val Ser Gln Lys Asp Val Cys Val Pro Lys Ala
625                 630                 635                 640

Thr His Gln Lys Glu Met Asp Lys Ile Ser Gly Lys Leu Glu Asp Ser
                645                 650                 655

Thr Ser Leu Ser Lys Ile Leu Asp Thr Val His Ser Cys Glu Arg Ala
            660                 665                 670

Arg Glu Leu Gln Lys Asp His Cys Glu Gln Arg Thr Gly Lys Met Glu
        675                 680                 685

Gln Met Lys Lys Lys Phe Cys Val Leu Lys Lys Lys Leu Ser Glu Ala
    690                 695                 700

Lys Glu Ile Lys Ser Gln Leu Glu Asn Gln Lys Val Lys Trp Glu Gln
705                 710                 715                 720

Glu Leu Cys Ser Val Arg Phe Leu Thr Leu Met Lys Met Lys Ile Ile
                725                 730                 735

Ser Tyr Met Lys Ile Ala Cys
            740
```

-continued

<210> SEQ ID NO 495
<211> LENGTH: 410
<212> TYPE: PRT
<213> ORGANISM: Homo sapiens

<400> SEQUENCE: 495

Met Lys Leu Leu Met Val Leu Met Leu Ala Ala Leu Ser Gln His Cys
5 10 15

Tyr Ala Gly Ser Gly Cys Pro Leu Leu Glu Asn Val Ile Ser Lys Thr
20 25 30

Ile Asn Pro Gln Val Ser Lys Thr Glu Tyr Lys Glu Leu Leu Gln Glu
35 40 45

Phe Ile Asp Asp Asn Ala Thr Thr Asn Ala Ile Asp Glu Leu Lys Glu
50 55 60

Cys Phe Leu Asn Gln Thr Asp Glu Thr Leu Ser Asn Val Glu Val Phe
65 70 75 80

Met Gln Leu Ile Tyr Asp Ser Ser Leu Cys Asp Leu Phe Met Gly Thr
85 90 95

Arg Ala Leu Gln Cys Glu Val Ser His Thr His Glu Asn Glu Asn Tyr
100 105 110

Leu Leu His Glu Asn Cys Met Leu Lys Lys Glu Ile Ala Met Leu Lys
115 120 125

Leu Glu Ile Ala Thr Leu Lys His Gln Tyr Gln Glu Lys Glu Asn Lys
130 135 140

Tyr Phe Glu Asp Ile Lys Ile Leu Lys Glu Lys Asn Ala Glu Leu Gln
145 150 155 160

Met Thr Leu Lys Leu Lys Glu Glu Ser Leu Thr Lys Arg Ala Ser Gln
165 170 175

Tyr Ser Gly Gln Leu Lys Val Leu Ile Ala Glu Asn Thr Met Leu Thr
180 185 190

Ser Lys Leu Lys Glu Lys Gln Asp Lys Glu Ile Leu Glu Ala Glu Ile
195 200 205

Glu Ser His His Pro Arg Leu Ala Ser Ala Val Gln Asp His Asp Gln
210 215 220

Ile Val Thr Ser Arg Lys Ser Gln Glu Pro Ala Phe His Ile Ala Gly
225 230 235 240

Asp Ala Cys Leu Gln Arg Lys Met Asn Val Asp Val Ser Ser Thr Ile
245 250 255

Tyr Asn Asn Glu Val Leu His Gln Pro Leu Ser Glu Ala Gln Arg Lys
260 265 270

Ser Lys Ser Leu Lys Ile Asn Leu Asn Tyr Ala Gly Asp Ala Leu Arg
275 280 285

Glu Asn Thr Leu Val Ser Glu His Ala Gln Arg Asp Gln Arg Glu Thr
290 295 300

Gln Cys Gln Met Lys Glu Ala Glu His Met Tyr Gln Asn Glu Gln Asp
305 310 315 320

Asn Val Asn Lys His Thr Glu Gln Gln Glu Ser Leu Asp Gln Lys Leu
325 330 335

Phe Gln Leu Gln Ser Lys Asn Met Trp Leu Gln Gln Gln Leu Val His
340 345 350

Ala His Lys Lys Ala Asp Asn Lys Ser Lys Ile Thr Ile Asp Ile His
355 360 365

Phe Leu Glu Arg Lys Met Gln His His Leu Leu Lys Glu Lys Asn Glu
370 375 380

-continued

```
Glu Ile Phe Asn Tyr Asn Asn His Leu Lys Asn Arg Ile Tyr Gln Tyr
385                 390                 395                 400

Glu Lys Glu Lys Ala Glu Thr Glu Val Ile
                405                 410
```

<210> SEQ ID NO 496
<211> LENGTH: 20
<212> TYPE: PRT
<213> ORGANISM: Homo sapiens

<400> SEQUENCE: 496

```
Ile Asp Glu Leu Lys Glu Cys Phe Leu Asn Gln Thr Asp Glu Thr Leu
 1               5                  10                  15

Ser Asn Val Glu
            20
```

<210> SEQ ID NO 497
<211> LENGTH: 15
<212> TYPE: PRT
<213> ORGANISM: Homo sapiens

<400> SEQUENCE: 497

```
Thr Thr Asn Ala Ile Asp Glu Leu Lys Glu Cys Phe Leu Asn Gln
 1               5                  10                  15
```

<210> SEQ ID NO 498
<211> LENGTH: 21
<212> TYPE: PRT
<213> ORGANISM: Homo sapiens

<400> SEQUENCE: 498

```
Ser Gln His Cys Tyr Ala Gly Ser Gly Cys Pro Leu Leu Glu Asn Val
 1               5                  10                  15

Ile Ser Lys Thr Ile
            20
```

<210> SEQ ID NO 499
<211> LENGTH: 20
<212> TYPE: PRT
<213> ORGANISM: Homo sapiens

<400> SEQUENCE: 499

```
Glu Tyr Lys Glu Leu Leu Gln Glu Phe Ile Asp Asp Asn Ala Thr Thr
 1               5                  10                  15

Asn Ala Ile Asp
            20
```

<210> SEQ ID NO 500
<211> LENGTH: 9
<212> TYPE: PRT
<213> ORGANISM: Homo sapiens

<400> SEQUENCE: 500

```
Lys Leu Leu Met Val Leu Met Leu Ala
 1               5
```

<210> SEQ ID NO 501
<211> LENGTH: 13
<212> TYPE: PRT
<213> ORGANISM: Homo sapiens

<400> SEQUENCE: 501

-continued

```
Gln Glu Phe Ile Asp Asp Asn Ala Thr Thr Asn Ala Ile
 1               5                  10


<210> SEQ ID NO 502
<211> LENGTH: 13
<212> TYPE: PRT
<213> ORGANISM: Homo sapiens

<400> SEQUENCE: 502

Leu Lys Glu Cys Phe Leu Asn Gln Thr Asp Glu Thr Leu
 1               5                  10


<210> SEQ ID NO 503
<211> LENGTH: 93
<212> TYPE: PRT
<213> ORGANISM: Homo sapiens

<400> SEQUENCE: 503

Met Lys Leu Leu Met Val Leu Met Leu Ala Ala Leu Ser Gln His Cys
 1               5                  10                  15

Tyr Ala Gly Ser Gly Cys Pro Leu Leu Glu Asn Val Ile Ser Lys Thr
            20                  25                  30

Ile Asn Pro Gln Val Ser Lys Thr Glu Tyr Lys Glu Leu Leu Gln Glu
        35                  40                  45

Phe Ile Asp Asp Asn Ala Thr Thr Asn Ala Ile Asp Glu Leu Lys Glu
    50                  55                  60

Cys Phe Leu Asn Gln Thr Asp Glu Thr Leu Ser Asn Val Glu Val Phe
65                  70                  75                  80

Met Gln Leu Ile Tyr Asp Ser Ser Leu Cys Asp Leu Phe
                85                  90


<210> SEQ ID NO 504
<211> LENGTH: 1964
<212> TYPE: DNA
<213> ORGANISM: Homo sapiens

<400> SEQUENCE: 504

gcatgctcga cgccccatgt gctgaaaggg cgaggagcct cctgcggcgg cccctgtgtc      60

cctgcctcta cctgcgcacc tgcatgtgtt caaccccccgg gagaacacct ggcggcccct     120

gacccaggtg cccgaggagg ccccgcttcg gggctgcggt ctctgcacca tgcacaacta     180

cctgtttctg gcggggggca tccgtggctc cggtgccaag gccgtctgct ccaacgaggt     240

cttctgctac aaccctctga ccaacatctg gagccaggtt cggcccatgc agcaggcccg     300

agcccagctc aagctggtgg ccctggacgg gctgctctat gccatcggtg gcgaatgcct     360

gtacagcatg gagtgctacg acccgcgaac agacgcctgg accccacgcg cgccactccc     420

cgcaggcacc ttccctgtgg cccacgaggc tgtggcctgc cgtggggaca tctacgtcac     480

cgggggtcac ctcttctacc gcctgctcag gtacagcccc gtgaaggatg cttgggacga     540

gtgcccatac agtgccagcc accggcgttc cagcgacatc gttgcactgg ggggcttcct     600

gtaccgcttc gacctgctgc ggggcgtggg cgccgccgtg atgcgctaca acacagtgac     660

cggctcctgg agcagggctg cctccctgcc cctgcccgcc cccgccccac tgcgctgcac     720

caccctgggc aacaccattt actgcctcaa cccccaggtc actgccacct tcacggtctc     780

tggggggact gcccagttcc aggccaagga gctgcagccc ttccccttgg ggagcaccgg     840

ggtcctcagt ccattcatcc tgactctgcc ccctgaggac cggctgcaga cctcactctg     900

agtggcaggc agagaaccaa agctgcttcg ctgctctcca gggagaccct cctgggatgg     960
```

-continued

```
gcctgagagg ccggggctca gggaaggggc tgggatcgga acttcctgct cttgtttctg   1020

gacaactttc cccttctgct ttaaaggttg tcgattattt tgaagcccag actccctcag   1080

cctctttctg cccctcactc cacacccaga ctgtttcctg actcaattcc gtacctactt   1140

acagaccctc tcagcttgct gacacccccc tgtctgtggg actccctatt ccctagagcc   1200

agggactgat gcgtctccac agacaaggac ttggctcgct ggagctctgc tgagccgaga   1260

gaggaggggg tagaaaacat tcacacttcc tatgctctgt cagcaggaca gggagcaaaa   1320

acgtccccag gcaacgccct cgcctctggg actttctgcc tgtcctaagg cctccccagg   1380

taccaacccc gtagctatct gggtctgttt ggcactgtgg attctcaagg gcctagaacc   1440

cttgcctctg aaactggtcc gctggtgcag ccctgctgtc tgcagctcct gcccataccc   1500

ccagcccaca ccaggccagg cccactccgg gctcaccacc ctctgcagcc ttgtggggct   1560

ctcccagccc ctccagaagc ccaccccact tctcgccaac ccccgatctc taaatgaggc   1620

ctgagcgtca ccctagttct gccccttttt agctgtgtag acttggacga gacatttgac   1680

ttccctttct ccttgtctat aaaatgtgga cagtggacgt ctgtcaccca agagagttgt   1740

gggagacaag atcacagcta tgagcacctc gcacggtgtc caggatgcac agcacaatcc   1800

atgatgcgtt ttctcccctt acgcactttg aaacccatgc tagaaaagtg aatacatctg   1860

actgtgctcc actccaacct ccagcctgga tgtccctgtc tgggcccttt ttctgttttt   1920

tattctatgt tcagcaccac tggcaccaaa tacattttaa ttca                    1964
```

<210> SEQ ID NO 505
<211> LENGTH: 732
<212> TYPE: DNA
<213> ORGANISM: Homo sapiens

<400> SEQUENCE: 505

```
atgcacaact acctgtttct ggcgggggc atccgtggct ccggtgccaa ggccgtctgc     60

tccaacgagg tcttctgcta caaccctctg accaacatct ggagccaggt tcggcccatg    120

cagcaggccc gagcccagct caagctggtg gccctggacg ggctgctcta tgccatcggt    180

ggcgaatgcc tgtacagcat ggagtgctac gacccgcgaa cagacgcctg gaccccacgc    240

gcgccactcc ccgcaggcac cttccctgtg gcccacgagg ctgtggcctg ccgtggggac    300

atctacgtca ccgggggtca cctcttctac cgcctgctca ggtacagccc cgtgaaggat    360

gcttgggacg agtgcccata cagtgccagc caccggcgtt ccagcgacat cgttgcactg    420

gggggcttcc tgtaccgctt cgacctgctg cggggcgtgg gcgccgccgt gatgcgctac    480

aacacagtga ccggctcctg gagcagggct gcctccctgc ccctgcccgc ccccgcccca    540

ctgcgctgca ccaccctggg caacaccatt tactgcctca acccccaggt cactgccacc    600

ttcacggtct ctgggggac tgcccagttc caggccaagg agctgcagcc cttccccttg    660

gggagcaccg gggtcctcag tccattcatc ctgactctgc cccctgagga ccggctgcag    720

acctcactct ga                                                        732
```

<210> SEQ ID NO 506
<211> LENGTH: 729
<212> TYPE: DNA
<213> ORGANISM: Homo sapiens

<400> SEQUENCE: 506

```
atgcacaact acctgtttct ggcgggggc atccgtggct ccggtgccaa ggccgtctgc     60
```

-continued

```
tccaacgagg tcttctgcta caaccctctg accaacatct ggagccaggt tcggcccatg    120

cagcaggccc gagcccagct caagctggtg gccctggacg ggctgctcta tgccatcggt    180

ggcgaatgcc tgtacagcat ggagtgctac gacccgcgaa cagacgcctg gaccccacgc    240

gcgccactcc ccgcaggcac cttccctgtg gcccacgagg ctgtggcctg ccgtggggac    300

atctacgtca ccgggggtca cctcttctac cgcctgctca ggtacagccc cgtgaaggat    360

gcttgggacg agtgcccata cagtgccagc caccggcgtt ccagcgacat cgttgcactg    420

gggggcttcc tgtaccgctt cgacctgctg cggggcgtgg gcgccgccgt gatgcgctac    480

aacacagtga ccggctcctg gagcagggct gcctccctgc ccctgcccgc ccccgcccca    540

ctgcgctgca ccaccctggg caacaccatt tactgcctca acccccaggt cactgccacc    600

ttcacggtct ctggggggac tgcccagttc caggccaagg agctgcagcc cttccccttg    660

gggagcaccg gggtcctcag tccattcatc ctgactctgc cccctgagga ccggctgcag    720

acctcactc                                                            729
```

```
<210> SEQ ID NO 507
<211> LENGTH: 243
<212> TYPE: PRT
<213> ORGANISM: Homo sapiens

<400> SEQUENCE: 507

Met His Asn Tyr Leu Phe Leu Ala Gly Gly Ile Arg Gly Ser Gly Ala
                5                   10                  15

Lys Ala Val Cys Ser Asn Glu Val Phe Cys Tyr Asn Pro Leu Thr Asn
            20                  25                  30

Ile Trp Ser Gln Val Arg Pro Met Gln Gln Ala Arg Ala Gln Leu Lys
        35                  40                  45

Leu Val Ala Leu Asp Gly Leu Leu Tyr Ala Ile Gly Gly Glu Cys Leu
    50                  55                  60

Tyr Ser Met Glu Cys Tyr Asp Pro Arg Thr Asp Ala Trp Thr Pro Arg
65                  70                  75                  80

Ala Pro Leu Pro Ala Gly Thr Phe Pro Val Ala His Glu Ala Val Ala
                85                  90                  95

Cys Arg Gly Asp Ile Tyr Val Thr Gly Gly His Leu Phe Tyr Arg Leu
            100                 105                 110

Leu Arg Tyr Ser Pro Val Lys Asp Ala Trp Asp Glu Cys Pro Tyr Ser
        115                 120                 125

Ala Ser His Arg Arg Ser Ser Asp Ile Val Ala Leu Gly Gly Phe Leu
    130                 135                 140

Tyr Arg Phe Asp Leu Leu Arg Gly Val Gly Ala Ala Val Met Arg Tyr
145                 150                 155                 160

Asn Thr Val Thr Gly Ser Trp Ser Arg Ala Ala Ser Leu Pro Leu Pro
                165                 170                 175

Ala Pro Ala Pro Leu Arg Cys Thr Thr Leu Gly Asn Thr Ile Tyr Cys
            180                 185                 190

Leu Asn Pro Gln Val Thr Ala Thr Phe Thr Val Ser Gly Gly Thr Ala
        195                 200                 205

Gln Phe Gln Ala Lys Glu Leu Gln Pro Phe Pro Leu Gly Ser Thr Gly
    210                 215                 220

Val Leu Ser Pro Phe Ile Leu Thr Leu Pro Pro Glu Asp Arg Leu Gln
225                 230                 235                 240

Thr Ser Leu
```

-continued

<210> SEQ ID NO 508
<211> LENGTH: 158
<212> TYPE: PRT
<213> ORGANISM: Homo sapiens

<400> SEQUENCE: 508

```
Met His Asn Tyr Leu Phe Leu Ala Gly Gly Ile Arg Gly Ser Gly Ala
                  5                  10                  15

Lys Ala Val Cys Ser Asn Glu Val Phe Cys Tyr Asn Pro Leu Thr Asn
             20                  25                  30

Ile Trp Ser Gln Val Arg Pro Met Gln Gln Ala Arg Ala Gln Leu Lys
         35                  40                  45

Leu Val Ala Leu Asp Gly Leu Leu Tyr Ala Ile Gly Gly Glu Cys Leu
     50                  55                  60

Tyr Ser Met Glu Cys Tyr Asp Pro Arg Thr Asp Ala Trp Thr Pro Arg
 65                  70                  75                  80

Ala Pro Leu Pro Ala Gly Thr Phe Pro Val Ala His Glu Ala Val Ala
                 85                  90                  95

Cys Arg Gly Asp Ile Tyr Val Thr Gly Gly His Leu Phe Tyr Arg Leu
            100                 105                 110

Leu Arg Tyr Ser Pro Val Lys Asp Ala Trp Asp Glu Cys Pro Tyr Ser
        115                 120                 125

Ala Ser His Arg Arg Ser Ser Asp Ile Val Ala Leu Gly Gly Phe Leu
    130                 135                 140

Tyr Arg Phe Asp Leu Leu Arg Gly Val Gly Ala Ala Val Met
145                 150                 155
```

<210> SEQ ID NO 509
<211> LENGTH: 85
<212> TYPE: PRT
<213> ORGANISM: Homo sapiens

<400> SEQUENCE: 509

```
Arg Tyr Asn Thr Val Thr Gly Ser Trp Ser Arg Ala Ala Ser Leu Pro
                  5                  10                  15

Leu Pro Ala Pro Ala Pro Leu Arg Cys Thr Thr Leu Gly Asn Thr Ile
             20                  25                  30

Tyr Cys Leu Asn Pro Gln Val Thr Ala Thr Phe Thr Val Ser Gly Gly
         35                  40                  45

Thr Ala Gln Phe Gln Ala Lys Glu Leu Gln Pro Phe Pro Leu Gly Ser
     50                  55                  60

Thr Gly Val Leu Ser Pro Phe Ile Leu Thr Leu Pro Pro Glu Asp Arg
 65                  70                  75                  80

Leu Gln Thr Ser Leu
                 85
```

<210> SEQ ID NO 510
<211> LENGTH: 732
<212> TYPE: DNA
<213> ORGANISM: Homo sapiens

<400> SEQUENCE: 510

```
atgcgacccc agggccccgc cgcctccccg cagcggctcc gcggcctcct gctgctcctg     60

ctgctgcagc tgcccgcgcc gtcgagcgcc tctgagatcc ccaaggggaa gcaaaaggcg    120

cagctccggc agagggaggt ggtggacctg tataatggaa tgtgcttaca agggccagca    180

ggagtgcctg gtcgagacgg gagccctggg gccaatgtta ttccgggtac acctgggatc    240
```

-continued ccaggtcggg atggattcaa aggagaaaag ggggaatgtc tgagggaaag ctttgaggag 300
tcctggacac ccaactacaa gcagtgttca tggagttcat tgaattatgg catagatctt 360
gggaaaattg cggagtgtac atttacaaag atgcgttcaa atagtgctct aagagttttg 420
ttcagtggct cacttcggct aaaatgcaga aatgcatgct gtcagcgttg gtatttcaca 480
ttcaatggag ctgaatgttc aggacctctt cccattgaag ctataattta tttggaccaa 540
ggaagccctg aaatgaattc aacaattaat attcatcgca cttcttctgt ggaaggactt 600
tgtgaaggaa ttggtgctgg attagtggat gttgctatct gggttggcac ttgttcagat 660
tacccaaaag gagatgcttc tactggatgg aattcagttt ctcgcatcat tattgaagaa 720
ctaccaaaat aa 732

<210> SEQ ID NO 511
<211> LENGTH: 729
<212> TYPE: DNA
<213> ORGANISM: Homo sapiens

<400> SEQUENCE: 511
atgcgacccc agggccccgc cgcctccccg cagcggctcc gcggcctcct gctgctcctg 60
ctgctgcagc tgcccgcgcc gtcgagcgcc tctgagatcc ccaaggggaa gcaaaaggcg 120
cagctccggc agagggaggt ggtggacctg tataatggaa tgtgcttaca agggccagca 180
ggagtgcctg gtcgagacgg gagccctggg gccaatgtta ttccgggtac acctgggatc 240
ccaggtcggg atggattcaa aggagaaaag ggggaatgtc tgagggaaag ctttgaggag 300
tcctggacac ccaactacaa gcagtgttca tggagttcat tgaattatgg catagatctt 360
gggaaaattg cggagtgtac atttacaaag atgcgttcaa atagtgctct aagagttttg 420
ttcagtggct cacttcggct aaaatgcaga aatgcatgct gtcagcgttg gtatttcaca 480
ttcaatggag ctgaatgttc aggacctctt cccattgaag ctataattta tttggaccaa 540
ggaagccctg aaatgaattc aacaattaat attcatcgca cttcttctgt ggaaggactt 600
tgtgaaggaa ttggtgctgg attagtggat gttgctatct gggttggcac ttgttcagat 660
tacccaaaag gagatgcttc tactggatgg aattcagttt ctcgcatcat tattgaagaa 720
ctaccaaaa 729

<210> SEQ ID NO 512
<211> LENGTH: 837
<212> TYPE: DNA
<213> ORGANISM: Homo sapiens

<400> SEQUENCE: 512
atgcagcctg cggcggcctc ggagcgcggc ggagcagacg ctgaccacgt tcctctcctc 60
ggtctcctcc gcctccagct ccgcgctgcc cggcagccgg gagccatgcg accccagggc 120
cccgccgcct ccccgcagcg gctccgcggc ctcctgctgc tcctgctgct gcagctgccc 180
gcgccgtcga gcgcctctga gatccccaag gggaagcaaa aggcgcagct ccggcagagg 240
gaggtggtgg acctgtataa tggaatgtgc ttacaagggc cagcaggagt gcctggtcga 300
gacgggagcc ctggggccaa tgttattccg ggtacacctg ggatcccagg tcgggatgga 360
ttcaaaggag aaaaggggga atgtctgagg gaaagctttg aggagtcctg gacacccaac 420
tacaagcagt gttcatggag ttcattgaat tatggcatag atcttgggaa aattgcggag 480
tgtacattta caaagatgcg ttcaaatagt gctctaagag ttttgttcag tggctcactt 540

-continued

```
cggctaaaat gcagaaatgc atgctgtcag cgttggtatt tcacattcaa tggagctgaa    600

tgttcaggac ctcttcccat tgaagctata atttatttgg accaaggaag ccctgaaatg    660

aattcaacaa ttaatattca tcgcacttct tctgtggaag gactttgtga aggaattggt    720

gctggattag tggatgttgc tatctgggtt ggcacttgtt cagattaccc aaaaggagat    780

gcttctactg gatggaattc agtttctcgc atcattattg aagaactacc aaaataa       837
```

<210> SEQ ID NO 513
<211> LENGTH: 837
<212> TYPE: DNA
<213> ORGANISM: Homo sapiens

<400> SEQUENCE: 513

```
atgcagcctg cggcggcctc ggagcgcggc ggagcagacg ctgaccacgt tcctctcctc     60

ggtctcctcc gcctccagct ccgcgctgcc cggcagccgg gagccatgcg accccagggc    120

cccgccgcct ccccgcagcg gctccgcggc ctcctgctgc tcctgctgct gcagctgccc    180

gcgccgtcga gcgcctctga gatccccaag gggaagcaaa aggcgcagct ccggcagagg    240

gaggtggtgg acctgtataa tggaatgtgc ttacaagggc cagcaggagt gcctggtcga    300

gacgggagcc ctggggccaa tgttattccg ggtacacctg ggatcccagg tcgggatgga    360

ttcaaaggag aaaaggggga atgtctgagg gaaagctttg aggagtcctg gacacccaac    420

tacaagcagt gttcatggag ttcattgaat tatggcatag atcttgggaa aattgcggag    480

tgtacattta caaagatgcg ttcaaatagt gctctaagag ttttgttcag tggctcactt    540

cggctaaaat gcagaaatgc atgctgtcag cgttggtatt tcacattcaa tggagctgaa    600

tgttcaggac ctcttcccat tgaagctata atttatttgg accaaggaag ccctgaaatg    660

aattcaacaa ttaatattca tcgcacttct tctgtggaag gactttgtga aggaattggt    720

gctggattag tggatgttgc tatctgggtt ggcacttgtt cagattaccc aaaaggagat    780

gcttctactg gatggaattc agtttctcgc atcattattg aagaactacc aaaataa       837
```

<210> SEQ ID NO 514
<211> LENGTH: 243
<212> TYPE: PRT
<213> ORGANISM: Homo sapiens

<400> SEQUENCE: 514

```
Met Arg Pro Gln Gly Pro Ala Ala Ser Pro Gln Arg Leu Arg Gly Leu
                  5                  10                  15

Leu Leu Leu Leu Leu Leu Gln Leu Pro Ala Pro Ser Ser Ala Ser Glu
             20                  25                  30

Ile Pro Lys Gly Lys Gln Lys Ala Gln Leu Arg Gln Arg Glu Val Val
         35                  40                  45

Asp Leu Tyr Asn Gly Met Cys Leu Gln Gly Pro Ala Gly Val Pro Gly
     50                  55                  60

Arg Asp Gly Ser Pro Gly Ala Asn Val Ile Pro Gly Thr Pro Gly Ile
 65                  70                  75                  80

Pro Gly Arg Asp Gly Phe Lys Gly Glu Lys Gly Glu Cys Leu Arg Glu
                 85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
        115                 120                 125

Thr Lys Met Arg Ser Asn Ser Ala Leu Arg Val Leu Phe Ser Gly Ser
```

-continued

```
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val Glu Gly Leu Cys Glu Gly Ile Gly Ala Gly Leu
        195                 200                 205

Val Asp Val Ala Ile Trp Val Gly Thr Cys Ser Asp Tyr Pro Lys Gly
    210                 215                 220

Asp Ala Ser Thr Gly Trp Asn Ser Val Ser Arg Ile Ile Ile Glu Glu
225                 230                 235                 240

Leu Pro Lys


<210> SEQ ID NO 515
<211> LENGTH: 278
<212> TYPE: PRT
<213> ORGANISM: Homo sapiens

<400> SEQUENCE: 515

Met Gln Pro Ala Ala Ala Ser Glu Arg Gly Gly Ala Asp Ala Asp His
                  5                  10                  15

Val Pro Leu Leu Gly Leu Leu Arg Leu Gln Leu Arg Ala Ala Arg Gln
             20                  25                  30

Pro Gly Ala Met Arg Pro Gln Gly Pro Ala Ala Ser Pro Gln Arg Leu
         35                  40                  45

Arg Gly Leu Leu Leu Leu Leu Leu Leu Gln Leu Pro Ala Pro Ser Ser
     50                  55                  60

Ala Ser Glu Ile Pro Lys Gly Lys Gln Lys Ala Gln Leu Arg Gln Arg
 65                  70                  75                  80

Glu Val Val Asp Leu Tyr Asn Gly Met Cys Leu Gln Gly Pro Ala Gly
                 85                  90                  95

Val Pro Gly Arg Asp Gly Ser Pro Gly Ala Asn Val Ile Pro Gly Thr
            100                 105                 110

Pro Gly Ile Pro Gly Arg Asp Gly Phe Lys Gly Glu Lys Gly Glu Cys
        115                 120                 125

Leu Arg Glu Ser Phe Glu Glu Ser Trp Thr Pro Asn Tyr Lys Gln Cys
    130                 135                 140

Ser Trp Ser Ser Leu Asn Tyr Gly Ile Asp Leu Gly Lys Ile Ala Glu
145                 150                 155                 160

Cys Thr Phe Thr Lys Met Arg Ser Asn Ser Ala Leu Arg Val Leu Phe
                165                 170                 175

Ser Gly Ser Leu Arg Leu Lys Cys Arg Asn Ala Cys Cys Gln Arg Trp
            180                 185                 190

Tyr Phe Thr Phe Asn Gly Ala Glu Cys Ser Gly Pro Leu Pro Ile Glu
        195                 200                 205

Ala Ile Ile Tyr Leu Asp Gln Gly Ser Pro Glu Met Asn Ser Thr Ile
    210                 215                 220

Asn Ile His Arg Thr Ser Ser Val Glu Gly Leu Cys Glu Gly Ile Gly
225                 230                 235                 240

Ala Gly Leu Val Asp Val Ala Ile Trp Val Gly Thr Cys Ser Asp Tyr
                245                 250                 255

Pro Lys Gly Asp Ala Ser Thr Gly Trp Asn Ser Val Ser Arg Ile Ile
```

-continued

```
            260                 265                 270

Ile Glu Glu Leu Pro Lys
        275


<210> SEQ ID NO 516
<211> LENGTH: 197
<212> TYPE: PRT
<213> ORGANISM: Homo sapiens

<400> SEQUENCE: 516

Met Arg Pro Gln Gly Pro Ala Ala Ser Pro Gln Arg Leu Arg Gly Leu
                  5                  10                  15

Leu Leu Leu Leu Leu Leu Gln Leu Pro Ala Pro Ser Ser Ala Ser Glu
            20                  25                  30

Ile Pro Lys Gly Lys Gln Lys Ala Gln Leu Arg Gln Arg Glu Val Val
        35                  40                  45

Asp Leu Tyr Asn Gly Met Cys Leu Gln Gly Pro Ala Gly Val Pro Gly
     50                  55                  60

Arg Asp Gly Ser Pro Gly Ala Asn Val Ile Pro Gly Thr Pro Gly Ile
 65                  70                  75                  80

Pro Gly Arg Asp Gly Phe Lys Gly Glu Lys Gly Glu Cys Leu Arg Glu
                 85                  90                  95

Ser Phe Glu Glu Ser Trp Thr Pro Asn Tyr Lys Gln Cys Ser Trp Ser
            100                 105                 110

Ser Leu Asn Tyr Gly Ile Asp Leu Gly Lys Ile Ala Glu Cys Thr Phe
        115                 120                 125

Thr Lys Met Arg Ser Asn Ser Ala Leu Arg Val Leu Phe Ser Gly Ser
    130                 135                 140

Leu Arg Leu Lys Cys Arg Asn Ala Cys Cys Gln Arg Trp Tyr Phe Thr
145                 150                 155                 160

Phe Asn Gly Ala Glu Cys Ser Gly Pro Leu Pro Ile Glu Ala Ile Ile
                165                 170                 175

Tyr Leu Asp Gln Gly Ser Pro Glu Met Asn Ser Thr Ile Asn Ile His
            180                 185                 190

Arg Thr Ser Ser Val
        195


<210> SEQ ID NO 517
<211> LENGTH: 232
<212> TYPE: PRT
<213> ORGANISM: Homo sapiens

<400> SEQUENCE: 517

Met Gln Pro Ala Ala Ala Ser Glu Arg Gly Gly Ala Asp Ala Asp His
                  5                  10                  15

Val Pro Leu Leu Gly Leu Leu Arg Leu Gln Leu Arg Ala Ala Arg Gln
            20                  25                  30

Pro Gly Ala Met Arg Pro Gln Gly Pro Ala Ala Ser Pro Gln Arg Leu
        35                  40                  45

Arg Gly Leu Leu Leu Leu Leu Leu Leu Gln Leu Pro Ala Pro Ser Ser
     50                  55                  60

Ala Ser Glu Ile Pro Lys Gly Lys Gln Lys Ala Gln Leu Arg Gln Arg
 65                  70                  75                  80

Glu Val Val Asp Leu Tyr Asn Gly Met Cys Leu Gln Gly Pro Ala Gly
                 85                  90                  95

Val Pro Gly Arg Asp Gly Ser Pro Gly Ala Asn Val Ile Pro Gly Thr
```

-continued

```
            100                 105                 110

Pro Gly Ile Pro Gly Arg Asp Gly Phe Lys Gly Glu Lys Gly Glu Cys
        115                 120                 125

Leu Arg Glu Ser Phe Glu Glu Ser Trp Thr Pro Asn Tyr Lys Gln Cys
    130                 135                 140

Ser Trp Ser Ser Leu Asn Tyr Gly Ile Asp Leu Gly Lys Ile Ala Glu
145                 150                 155                 160

Cys Thr Phe Thr Lys Met Arg Ser Asn Ser Ala Leu Arg Val Leu Phe
                165                 170                 175

Ser Gly Ser Leu Arg Leu Lys Cys Arg Asn Ala Cys Cys Gln Arg Trp
            180                 185                 190

Tyr Phe Thr Phe Asn Gly Ala Glu Cys Ser Gly Pro Leu Pro Ile Glu
        195                 200                 205

Ala Ile Ile Tyr Leu Asp Gln Gly Ser Pro Glu Met Asn Ser Thr Ile
    210                 215                 220

Asn Ile His Arg Thr Ser Ser Val
225                 230


<210> SEQ ID NO 518
<211> LENGTH: 46
<212> TYPE: PRT
<213> ORGANISM: Homo sapiens

<400> SEQUENCE: 518

Glu Gly Leu Cys Glu Gly Ile Gly Ala Gly Leu Val Asp Val Ala Ile
                  5                  10                  15

Trp Val Gly Thr Cys Ser Asp Tyr Pro Lys Gly Asp Ala Ser Thr Gly
             20                  25                  30

Trp Asn Ser Val Ser Arg Ile Ile Ile Glu Glu Leu Pro Lys
         35                  40                  45


<210> SEQ ID NO 519
<211> LENGTH: 26
<212> TYPE: PRT
<213> ORGANISM: Homo sapiens

<400> SEQUENCE: 519

Cys Ser Asp Tyr Pro Lys Gly Asp Ala Ser Thr Gly Trp Asn Ser Val
                  5                  10                  15

Ser Arg Ile Ile Ile Glu Glu Leu Pro Lys
             20                  25


<210> SEQ ID NO 520
<211> LENGTH: 60
<212> TYPE: DNA
<213> ORGANISM: Homo sapiens

<400> SEQUENCE: 520

aaaaatgagg agatatttaa ttacaataac catttaaaaa accgtatata tcaatatgaa     60


<210> SEQ ID NO 521
<211> LENGTH: 60
<212> TYPE: DNA
<213> ORGANISM: Homo sapiens

<400> SEQUENCE: 521

atgcaacatc atctcctaaa agagaaaaat gaggagatat ttaattacaa taaccattta     60


<210> SEQ ID NO 522
```

-continued

<211> LENGTH: 60
<212> TYPE: DNA
<213> ORGANISM: Homo sapiens

<400> SEQUENCE: 522
gacaacaaaa gcaagataac aattgatatt cattttcttg agaggaaaat gcaacatcat 60

<210> SEQ ID NO 523
<211> LENGTH: 60
<212> TYPE: DNA
<213> ORGANISM: Homo sapiens

<400> SEQUENCE: 523
aaaaatatgt ggcttcaaca gcaattagtt catgcacata agaaagctga caacaaaagc 60

<210> SEQ ID NO 524
<211> LENGTH: 63
<212> TYPE: DNA
<213> ORGANISM: Homo sapiens

<400> SEQUENCE: 524
gatcagaaat tatttcaact acaaagcaaa aatatgtggc ttcaacagca attagttcat 60
gca 63

<210> SEQ ID NO 525
<211> LENGTH: 60
<212> TYPE: DNA
<213> ORGANISM: Homo sapiens

<400> SEQUENCE: 525
actgaacagc aggagtctct agatcagaaa ttatttcaac tacaaagcaa aaatatgtgg 60

<210> SEQ ID NO 526
<211> LENGTH: 63
<212> TYPE: DNA
<213> ORGANISM: Homo sapiens

<400> SEQUENCE: 526
gctcaaagga aatccaaaag cctaaaaatt aatctcaatt atgccggaga tgctctaaga 60
gaa 63

<210> SEQ ID NO 527
<211> LENGTH: 60
<212> TYPE: DNA
<213> ORGANISM: Homo sapiens

<400> SEQUENCE: 527
agtacgatat ataacaatga ggtgctccat caaccacttt ctgaagctca aaggaaatcc 60

<210> SEQ ID NO 528
<211> LENGTH: 60
<212> TYPE: DNA
<213> ORGANISM: Homo sapiens

<400> SEQUENCE: 528
agaaaaatga atgttgatgt gagtagtacg atatataaca atgaggtgct ccatcaacca 60

<210> SEQ ID NO 529
<211> LENGTH: 60
<212> TYPE: DNA
<213> ORGANISM: Homo sapiens

<400> SEQUENCE: 529

-continued attgcaggag atgcttgttt gcaaagaaaa atgaatgttg atgtgagtag tacgatatat 60

<210> SEQ ID NO 530
<211> LENGTH: 60
<212> TYPE: DNA
<213> ORGANISM: Homo sapiens

<400> SEQUENCE: 530
aaaagtcaag aacctgcttt ccacattgca ggagatgctt gtttgcaaag aaaaatgaat 60

<210> SEQ ID NO 531
<211> LENGTH: 60
<212> TYPE: DNA
<213> ORGANISM: Homo sapiens

<400> SEQUENCE: 531
gaaaataaat actttgagga cattaagatt ttaaaagaaa agaatgctga acttcagatg 60

<210> SEQ ID NO 532
<211> LENGTH: 60
<212> TYPE: DNA
<213> ORGANISM: Homo sapiens

<400> SEQUENCE: 532
ctgaaacacc aataccagga aaaggaaaat aaatactttg aggacattaa gattttaaaa 60

<210> SEQ ID NO 533
<211> LENGTH: 63
<212> TYPE: DNA
<213> ORGANISM: Homo sapiens

<400> SEQUENCE: 533
aattgcatgt tgaaaaagga aattgccatg ctaaaactgg aaatagccac actgaaacac 60
caa 63

<210> SEQ ID NO 534
<211> LENGTH: 21
<212> TYPE: PRT
<213> ORGANISM: Homo sapiens

<400> SEQUENCE: 534

```
Asn Cys Met Leu Lys Lys Glu Ile Ala Met Leu Lys Leu Glu Ile Ala
                  5                   10                  15

Thr Leu Lys His Gln
             20
```

<210> SEQ ID NO 535
<211> LENGTH: 20
<212> TYPE: PRT
<213> ORGANISM: Homo sapiens

<400> SEQUENCE: 535

```
Leu Lys His Gln Tyr Gln Glu Lys Glu Asn Lys Tyr Phe Glu Asp Ile
                  5                   10                  15

Lys Ile Leu Lys
             20
```

<210> SEQ ID NO 536
<211> LENGTH: 20
<212> TYPE: PRT
<213> ORGANISM: Homo sapiens -continued

<400> SEQUENCE: 536

Glu Asn Lys Tyr Phe Glu Asp Ile Lys Ile Leu Lys Glu Lys Asn Ala
1               5                   10                  15

Glu Leu Gln Met
            20

<210> SEQ ID NO 537
<211> LENGTH: 20
<212> TYPE: PRT
<213> ORGANISM: Homo sapiens

<400> SEQUENCE: 537

Lys Ser Gln Glu Pro Ala Phe His Ile Ala Gly Asp Ala Cys Leu Gln
1               5                   10                  15

Arg Lys Met Asn
            20

<210> SEQ ID NO 538
<211> LENGTH: 20
<212> TYPE: PRT
<213> ORGANISM: Homo sapiens

<400> SEQUENCE: 538

Ile Ala Gly Asp Ala Cys Leu Gln Arg Lys Met Asn Val Asp Val Ser
1               5                   10                  15

Ser Thr Ile Tyr
            20

<210> SEQ ID NO 539
<211> LENGTH: 20
<212> TYPE: PRT
<213> ORGANISM: Homo sapiens

<400> SEQUENCE: 539

Arg Lys Met Asn Val Asp Val Ser Ser Thr Ile Tyr Asn Asn Glu Val
1               5                   10                  15

Leu His Gln Pro
            20

<210> SEQ ID NO 540
<211> LENGTH: 20
<212> TYPE: PRT
<213> ORGANISM: Homo sapiens

<400> SEQUENCE: 540

Ser Thr Ile Tyr Asn Asn Glu Val Leu His Gln Pro Leu Ser Glu Ala
1               5                   10                  15

Gln Arg Lys Ser
            20

<210> SEQ ID NO 541
<211> LENGTH: 21
<212> TYPE: PRT
<213> ORGANISM: Homo sapiens

<400> SEQUENCE: 541

Ala Gln Arg Lys Ser Lys Ser Leu Lys Ile Asn Leu Asn Tyr Ala Gly
1               5                   10                  15

Asp Ala Leu Arg Glu
            20

-continued

<210> SEQ ID NO 542
<211> LENGTH: 20
<212> TYPE: PRT
<213> ORGANISM: Homo sapiens

<400> SEQUENCE: 542

Thr Glu Gln Gln Glu Ser Leu Asp Gln Lys Leu Phe Gln Leu Gln Ser
1 5 10 15

Lys Asn Met Trp
20

<210> SEQ ID NO 543
<211> LENGTH: 21
<212> TYPE: PRT
<213> ORGANISM: Homo sapiens

<400> SEQUENCE: 543

Asp Gln Lys Leu Phe Gln Leu Gln Ser Lys Asn Met Trp Leu Gln Gln
1 5 10 15

Gln Leu Val His Ala
20

<210> SEQ ID NO 544
<211> LENGTH: 20
<212> TYPE: PRT
<213> ORGANISM: Homo sapiens

<400> SEQUENCE: 544

Lys Asn Met Trp Leu Gln Gln Gln Leu Val His Ala His Lys Lys Ala
1 5 10 15

Asp Asn Lys Ser
20

<210> SEQ ID NO 545
<211> LENGTH: 20
<212> TYPE: PRT
<213> ORGANISM: Homo sapiens

<400> SEQUENCE: 545

Asp Asn Lys Ser Lys Ile Thr Ile Asp Ile His Phe Leu Glu Arg Lys
1 5 10 15

Met Gln His His
20

<210> SEQ ID NO 546
<211> LENGTH: 20
<212> TYPE: PRT
<213> ORGANISM: Homo sapiens

<400> SEQUENCE: 546

Met Gln His His Leu Leu Lys Glu Lys Asn Glu Glu Ile Phe Asn Tyr
1 5 10 15

Asn Asn His Leu
20

<210> SEQ ID NO 547
<211> LENGTH: 20
<212> TYPE: PRT
<213> ORGANISM: Homo sapiens

<400> SEQUENCE: 547

-continued

```
Lys Asn Glu Glu Ile Phe Asn Tyr Asn Asn His Leu Lys Asn Arg Ile
                5                   10                  15

Tyr Gln Tyr Glu
            20
```